United States Patent
Silverman et al.

(10) Patent No.: US 9,533,947 B2
(45) Date of Patent: *Jan. 3, 2017

(54) BENZAMIDE COMPOUNDS AND RELATED METHODS OF USE

(71) Applicants: Northwestern University, Evanston, IL (US); The General Hospital Corporation, Boston, MA (US)

(72) Inventors: Richard B. Silverman, Winnetka, IL (US); Hua Wang, Evanston, IL (US); Mohammad Khanfar, Evanston, IL (US); Aleksey G. Kazantsev, Boston, MA (US)

(73) Assignees: Northwestern University, Evanston, IL (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/292,087

(22) Filed: May 30, 2014

(65) Prior Publication Data

US 2015/0025235 A1  Jan. 22, 2015

Related U.S. Application Data

(63) Continuation of application No. 14/139,763, filed on Dec. 23, 2013.

(Continued)

(51) Int. Cl.
| | |
|---|---|
| C07C 311/16 | (2006.01) |
| C07D 213/75 | (2006.01) |
| C07D 213/81 | (2006.01) |
| C07D 213/82 | (2006.01) |
| C07D 213/85 | (2006.01) |
| C07D 207/04 | (2006.01) |
| C07D 317/48 | (2006.01) |
| C07D 237/20 | (2006.01) |
| C07D 271/113 | (2006.01) |
| C07C 255/60 | (2006.01) |
| C07C 257/18 | (2006.01) |
| C07C 323/49 | (2006.01) |
| C07D 217/04 | (2006.01) |
| C07D 207/16 | (2006.01) |
| C07D 295/26 | (2006.01) |
| C07D 305/06 | (2006.01) |
| C07C 311/21 | (2006.01) |
| C07C 311/29 | (2006.01) |
| C07C 317/44 | (2006.01) |
| C07C 317/48 | (2006.01) |
| C07D 213/76 | (2006.01) |
| C07D 213/80 | (2006.01) |
| C07D 223/04 | (2006.01) |
| C07D 239/42 | (2006.01) |
| C07D 261/14 | (2006.01) |

(Continued)

(52) U.S. Cl.
CPC .......... *C07C 311/16* (2013.01); *C07C 235/60* (2013.01); *C07C 255/60* (2013.01); *C07C 257/18* (2013.01); *C07C 311/21* (2013.01); *C07C 311/29* (2013.01); *C07C 311/46* (2013.01); *C07C 311/47* (2013.01); *C07C 317/22* (2013.01); *C07C 317/34* (2013.01); *C07C 317/40* (2013.01); *C07C 317/44* (2013.01); *C07C 317/48* (2013.01); *C07C 323/20* (2013.01); *C07C 323/42* (2013.01); *C07C 323/49* (2013.01); *C07C 323/62* (2013.01); *C07D 207/16* (2013.01); *C07D 213/75* (2013.01); *C07D 213/76* (2013.01); *C07D 213/80* (2013.01); *C07D 213/81* (2013.01); *C07D 213/82* (2013.01); *C07D 213/85* (2013.01); *C07D 217/04* (2013.01); *C07D 223/04* (2013.01); *C07D 237/20* (2013.01); *C07D 239/42* (2013.01); *C07D 261/14* (2013.01); *C07D 271/113* (2013.01); *C07D 277/46* (2013.01); *C07D 295/26* (2013.01); *C07D 305/06* (2013.01); *C07D 311/16* (2013.01); *C07D 403/12* (2013.01); *C07D 413/12* (2013.01); *C07D 417/12* (2013.01); *C07B 2200/07* (2013.01); *C07C 2101/02* (2013.01)

(58) Field of Classification Search
CPC .... C07C 323/62; C07C 323/49; C07C 323/42; C07C 323/20; C07C 317/48; C07C 317/44; C07C 317/40; C07C 317/34; C07C 317/22; C07C 311/16; C07C 311/29; C07C 311/21; C07C 311/46; C07C 311/47; C07D 213/75; C07D 213/81; C07D 213/82; C07D 213/85; C07D 213/76; C07D 213/80; C07D 217/40; C07D 207/16; C07D 295/26; C07D 305/06; C07D 403/12; C07D 417/12; C07D 271/113; C07D 261/14; C07D 239/42; C07D 237/20; C07D 223/04; C07D 413/12; C07D 311/16; C07D 277/46
See application file for complete search history.

(56) References Cited

FOREIGN PATENT DOCUMENTS

WO   WO 2004110986 A1 * 12/2004
WO       2011097600 A1    8/2011
(Continued)

OTHER PUBLICATIONS

RN 366453-93-2, available Nov. 2001.*
(Continued)

*Primary Examiner* — Blessing M Fubara
(74) *Attorney, Agent, or Firm* — Reinhart Boerner Van Deuren s.c.

(57) ABSTRACT

Benzamide compounds and derivatives thereof, as can be used for selective inhibition of the SIRT2 enzyme and/or therapeutic use in the treatment of Huntington's disease.

5 Claims, 3 Drawing Sheets

Related U.S. Application Data

(60) Provisional application No. 61/745,056, filed on Dec. 21, 2012.

(51) Int. Cl.

| | | |
|---|---|---|
| *C07D 277/46* | (2006.01) |
| *C07D 403/12* | (2006.01) |
| *C07D 413/12* | (2006.01) |
| *C07D 417/12* | (2006.01) |
| *C07D 311/16* | (2006.01) |
| *C07C 311/46* | (2006.01) |
| *C07C 317/40* | (2006.01) |
| *C07C 323/62* | (2006.01) |
| *C07C 311/47* | (2006.01) |
| *C07C 317/22* | (2006.01) |
| *C07C 317/34* | (2006.01) |
| *C07C 323/20* | (2006.01) |
| *C07C 323/42* | (2006.01) |
| *C07C 235/60* | (2006.01) |

(56) References Cited

FOREIGN PATENT DOCUMENTS

| WO | 2011115892 A1 | 9/2011 |
| WO | 2012167023 A2 | 12/2012 |

OTHER PUBLICATIONS

RN 1297070-00-8, available May 19, 2011.*
Wu, Fang et al. "Novel Gamma-Secretase Inhibitors Uncover a Common Nucleotide-Binding Site in JAK3, SIRT2, and PS1", FASEB Journal, vol. 24(7), pp. 2464-2474 (2010).
International Search Report for PCT/US2013/077625, dated Apr. 23, 2014.

* cited by examiner

Figure 3

Preliminary SAR
C2-8 Scaffold

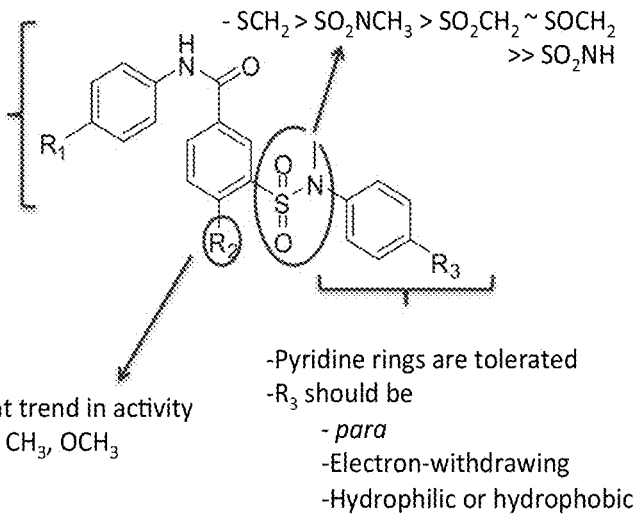

- 6-membered heterocyclic rings are tolerated but not 5-membered rings
- $R_1$ should be
  - *para*
  - Electron-withdrawing
  - Hydrophilic or hydrophobic
  - Small group (F) at *ortho* is tolerated

- Nitrogen should be methylated
- Sulfonamide is not essential
- $SCH_2 > SO_2NCH_3 > SO_2CH_2 \sim SOCH_2 \gg SO_2NH$

- No apparent trend in activity
- H, F, Cl, Br, $CH_3$, $OCH_3$

- Pyridine rings are tolerated
- $R_3$ should be
  - *para*
  - Electron-withdrawing
  - Hydrophilic or hydrophobic Preliminary SAR
AK-1 Scaffold

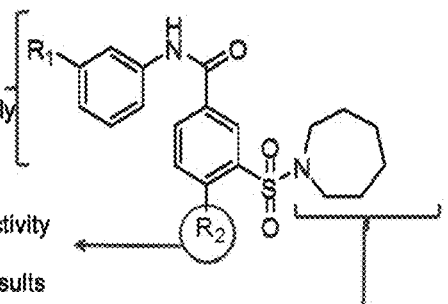

- Heterocycles are not tolerated
- $R_1$ should be
  - *meta*
  - Electron-withdrawing or mildly electron-donating ($CH_3$)
  - Hydrophilic, hydrophobic

- No apparent trend in activity
- H, F, Cl, Br, $CH_3$
- $OCH_3$: contradicting results

ized small-molecule sulfobenzoic acid derived inhibitors of
BENZAMIDE COMPOUNDS AND RELATED METHODS OF USE This application is a continuation of and claims priority benefit of application Ser. No. 14/139,763 filed Dec. 23, 2013 which claimed priority from application Ser. No. 61/745,056 filed Dec. 21, 2012—each of which is incorporated herein by reference in its entirety.

This invention was made with government support under grant number 5 U01 NS066912 awarded by the National Institutes of Health. The government has certain rights in the invention.

BACKGROUND OF THE INVENTION

Huntington's disease (HD) is an autosomal dominant inherited neurodegenerative disorder that is characterized by progressive motor dysfunction, emotional disturbances, dementia, and weight loss. There currently is no treatment for delaying the onset of the disease or for slowing the progression of HD. Management of HD is focused on symptom reduction, and the only drug approved by the FDA is tetrabenazine, which is indicated to suppress involuntary movements (chorea) but does not slow the disease progression. The disease is caused by an elongated CAG trinucleotide repeat expansion located within exon 1 of the IT-15 gene encoding huntingtin, a 350-kDa protein of unknown function. The CAG repeat is translated into a polyglutamine (polyQ) stretch. In HD patients, huntingtin is expressed with 38-180 glutamine residues, whereas in healthy individuals the protein is synthesized with 8-37 glutamine residues. The accumulation of ubiquitinated polyQ-containing huntingtin aggregates in neuronal inclusions causes the death of affected neurons and has emerged as a pathologic hallmark of HD Inhibiting polyQ aggregation has exhibited some efficacy in vivo in both *Drosophila* and mouse models of HD, which suggests that inhibition of neuronal polyQ aggregation might be therapeutic in HD patients.

Sirtuins comprise a family of protein deacetylase enzymes that have been shown to impact longevity in a number of eukaryotic species. The role for sirtuins as therapeutic targets in age-dependent neurodegenerative disorders has recently emerged, primarily as a result of their functions as regulators of metabolism and subsequent effects on longevity. SIRT2, one of the seven human sirtuins so far identified, belongs to the class III histone deacetylases (HDAC), which couple hydrolysis of acetyllysine residues with NAD hydrolysis. Known substrates of SIRT2 include α-tubulin, FOXO1, FOXO3a, P523, and histones 3 and 4. (See, e.g., Taylor, D. M.; Maxwell, M. M.; Luthi-Carter, R.; Kazantsev, A. G. Biological and potential therapeutic roles of sirtuin deacetylases. *Cell Mol. Life Sci.* 2008, 65, 24, 4000 4018; and North, B. J.; Marshall, B. L.; Borra, M. T.; Denu, J. M.; Verdin, E. The human Sir2 ortholog, SIRT2, is an NAD+-dependent tubulin deacetylase. *Mol. Cell* 2003, 11, 2, 437 444.) SIRT2 level is sharply increased during neurodevelopment, remains strikingly high in mature brain, and accumulates in the aged CNS. Chemical inhibition of SIRT2 changes protein inclusion body characteristics and increases neuronal survival in animal models of Parkinson's disease. It also achieves neuroprotection in cellular and invertebrate models of HD and leads to increased acetylation of its substrate α-tubulin, a major component of microtubules, subsequently leading to neuroprotective transcriptional modulation of metabolic pathways and to reduction of polyQ inclusions in HD primary neurons by decreasing sterol biosynthesis.

Cell-based high-throughput and in silico screening identified small-molecule sulfobenzoic acid derived inhibitors of polyQ aggregation and SIRT2 (FIG. 1). C2-8 inhibited polyQ aggregation in brain slices from R6/2 HD transgenic mice at sub-micromolar concentrations, reversed the effects of neurodegeneration in a fruit fly model of HD, crossed the blood brain bather following oral administration, inhibited huntingtin (htt) aggregation in vivo in the striatum by 25-30% in R6/2 mice, effectively suppressed aggregation in a cell-based model with an $EC_{50}$=50 nM, significantly reduced striatal neuron loss in R6/2 mice and improved their clinical phenotype, markedly reduced htt aggregation by 50% in the 140 CAG knock-in model of HD, which is much more analogous to human HD, and was not toxic in acute and chronic tolerability studies. (See, e.g., Chopra, V.; Fox, J. H.; Lieberman, G.; Dorsey, K.; Matson, W.; Waldmeier, P.; Housman, D. E.; Kazantsev, A.; Young, A. B.; Hersch, S. A small-molecule therapeutic lead for Huntington's disease: preclinical pharmacology and efficacy of C2-8 in the R6/2 transgenic mouse. *Proc. Natl. Acad. Sci. USA* 2007, 104, 42, 16685-16689.) AK-1 was neuroprotective in *C. elegans* and *Drosophila* HD models and inhibited polyQ aggregation in primary rat striatal neurons expressing the mutant huntingtin fragment delivered by a lentivirus and selectively inhibited SIRT2 at low micromolar concentrations ($IC_{50}$=12.5 μM). (See, e.g., Taylor, D. M.; Balabadra, U.; Xiang, Z.; Woodman, B.; Meade, S.; Amore, A.; Maxwell, M. M.; Reeves, S.; Bates, G. P.; Luthi-Carter, R.; Lowden, P. A.; Kazantsev, A. G. A brain-permeable small molecule reduces neuronal cholesterol by inhibiting activity of sirtuin 2 deacetylase. *ACS Chem. Biol.* 2011, 6, 6, 540-546.) In silico screening of a ChemBridge diverse library identified AK-7, the first brain-permeable selective SIRT2 inhibitor ($IC_{50}$=15.5 μM) that reduces cholesterol in neuronal models and protects an in vitro model of HD. (Id.)

Notwithstanding the excellent pharmacologic properties of such sulfobenzoic acid derivatives, further lead optimization of the scaffold is required for CNS drug development to achieve increased potency and metabolic stability, en route to preclinical efficacy testing in HD. For instance, C2-8, AK-1, and AK-7 are characterized by the low aqueous solubility, high c log P, and low plasma and microsomal metabolic stability. As a result, there remains an on-going need for medicinal chemistry modification to, for instance: (1) enhance potency and favorable pharmacokinetic properties; (2) enhance the water solubility (lower the log P) and lower the molecular weight; (3) probe chemical space to define a structure activity relationship (SAR).

SUMMARY OF THE INVENTION

In light of the foregoing, it is an object of the present invention to provide one or more inhibitor compounds and/or related methods of use, thereby overcoming various deficiencies and shortcomings of the prior art, including those outlined above. It will be understood by those skilled in the art that one or more aspects of this invention can meet certain objectives, while one or more aspects can meet certain other objectives. Each objective may not apply equally, in all its respects, to every aspect of this invention. As such, various objectives can be viewed in the alternative with respect to any one aspect of this invention.

In part, the present invention can be directed to a compound selected from compounds of a formula

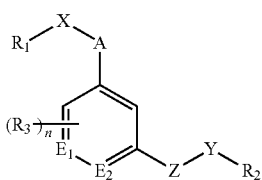

wherein $R_1$ and $R_2$ can be independently selected from but not limited to cycloalkyl, cycloheteroalkyl, aryl, arylalkyl, heteroaryl and heteroarylalkyl moieties; $E_1$ and $E_2$ can be independently selected from but not limited to CH and a heteroatom; A can be selected from but not limited to divalent moieties such as alkylene, carbonyl, amino, carboxamido (—C(O)NH—), imidocarbyl (—C(NH)—) and a tautomer thereof with X; X can be selected from but not limited to divalent oxy, amino, carbonyl, alkylene and heteroatom-substituted alkylene moieties; Y can be selected from but not limited to divalent oxy, amino, alkylene and heteroatom-substituted alkylene moieties; and Z can be selected from sulfonyl, sulfinyl, thio, amino, alkylene and heteroatom-substituted alkylene moieties, and wherein each of $R_1$, $R_2$, A, X, Y and Z can be optionally substituted with 1-10 substituents independently selected from but not limited to halogen, cyano, nitro, hydroxy, amino, alkyl, cycloalkyl, cycloheteroalkyl, aryl, arylalkyl, alkoxy, alkenyl, haloalkyl, aminoalkyl, hydroxyalkyl, alkylene, formyl, alkylsulfonyl, alkylsulfonyl, haloalkylsulfonyl, haloalkylsulfinyl, alkylamido, alkylsulfonamido, alkylthio, alkylcarbonyl, alkoxycarbonyl and combinations of such substituents; $R_3$ can be selected from but not limited to any of the aforementioned substituents and combinations thereof; and n can be an integer from 0-4, and salts of such compounds.

Without limitation, such compounds can be selected from

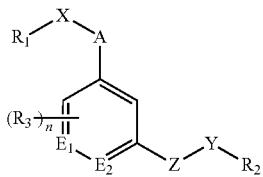

I and salts thereof. With respect to any such compound, $R_1$ and $R_2$ can be independently selected from phenyl, mono- and multi-substituted phenyl, benzyl, mono- and multi-substituted benzyl, heteroarylalkyl, mon- and multi-substituted heteroarylalkyl, cycloheteroalkyl and mono- and multi-substituted cycloheteroalkyl moieties—such substituents as can be independently selected from those discussed herein or inferred therefrom; $E_1$ and $E_2$ can be independently selected from CH and N, optionally providing at least one of $E_1$ and $E_2$ is CH; $R_3$ can be selected from but not limited to halo (e.g., F, Cl and Br), $C_1$-$C_6$ alkyl and alkoxy moieties; n is an integer and can be 0-4; A can be selected from carbonyl, amino, alkylamino, carboxamido (—C(O)NH—), imidocarbyl (—C(NH)—) and a tautomer thereof (—N=C (NH$_2$)—) with X; X can be selected from methylene, carbonyl, amino, alkylamino and aza-substituted ethylene (—NHCH$_2$—) moieties; Y can be selected from oxy, amino, alkyl-, cycloalkyl- and arylalkylamino, allylamino, alkylene, alkyl-substituted alkylene and aza-substituted alkylene moieties; and Z can be selected from sulfonyl, sulfinyl, thio, oxy, amino, alkylamino, cycloalkylamino, methylene and alkyl-substituted methylene moieties. For instance, where Z is sulfonyl, $E_1$ can be CH, $E_2$ can be N and Y can be an alkylamine moiety. However and without limitation, where A is carbonyl, Z is sulfonyl and $R_1$ and $R_2$ are phenyl or substituted phenyl, optional exceptions to such compounds can be considered and provided where X is an amino or methylamino moiety, and Y is an amino, alkylamino, allylamino or benzylamino moiety.

In certain embodiments, such compounds can be of a formula

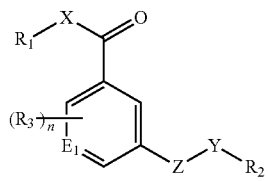

II and salts thereof. Except as provided above, with respect to any such compound, $R_1$, $R_2$ and $R_3$, $E_1$, and X, Y and Z can be independently selected from moieties of the sort described above or discussed elsewhere herein. For instance, without limitation, $R_1$ and $R_2$ can be, independently, pheny or heteroaryl, $E_1$ can be CH or N, Z can be O and Y can be an alkylene or alkyl-substituted alkylene (e.g., —CH(CH$_3$)—) moiety.

In certain such embodiments, such compounds can be of a formula

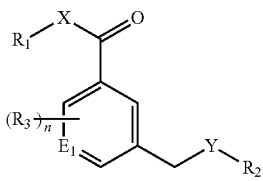

III wherein X can be without limitation, amino or alkylamino and Z can be methylene, and salts thereof. Except as provided above, with respect to any such compound, $R_1$, $R_2$ and $E_1$ can be independently selected from moieties of the sort described above or discussed elsewhere herein; Y can be selected from oxy, alkylene, alkyl-substituted alkylene, amino and substituted amino moieties; and $R_3$ can optionally be a substituted benzyl moiety, such substituents as can be selected, for instance, from 1-3 halo and/or cyano substituents and combinations thereof.

Without limitation, Y can be a substituted amino moiety and $R_2$ can be selected from phenyl, substituted phenyl, benzyl, substituted benzyl, heteroaryl, substituted heteroaryl and heteroarylalkyl and substituted heteroarylalkyl moieties. In certain embodiments, the amino substituent can be selected from alkyl and cycloalkyl moieties. Regardless of $R_2$ identity, the amino substituent can be selected from methyl, ethyl, isopropyl, and cyclopropyl moieties.

In certain other embodiments, where Y, $R_1$ and $R_2$ can be as described above, such an amino substituent can be a divalent alkylene moiety, whereby such an $R_3$ substituent and such an alkylene moiety together provide a cycloheteroalkyl (e.g., without limitation, a hydroisoquinolinyl moiety). Alternatively, such a divalent alkylene amino substituent and $R_2$ substituent can together provide such a cycloheteroalkyl moiety.

Without limitation, such compounds can be selected from

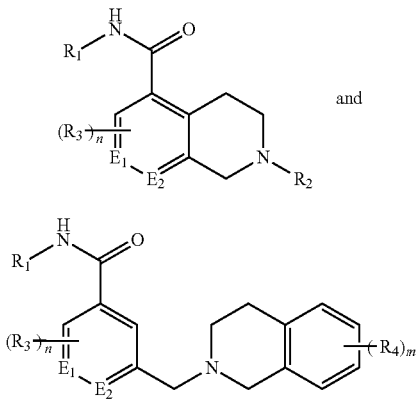

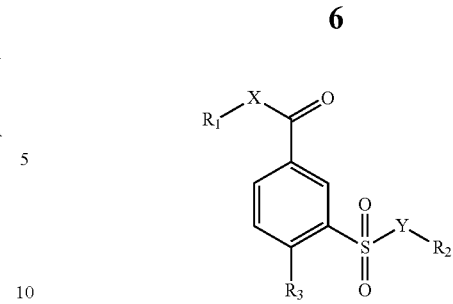

wherein each of $R_1$ and $R_2$ can be independently selected from phenyl, benzyl, heteroarylalkyl and heteroaryl moieties; each of $E_1$ and $E_2$ can be independently selected from CH and N; and wherein each of $R_1$ and $R_2$ can be optionally substituted with 1-5 substituents independently selected from but not limited to halo, cyano, nitro, hydroxy, amino, alkyl, cycloalkyl, cycloheteroalkyl, aryl, arylalkyl, alkoxy, alkenyl, haloalkyl, aminoalkyl, hydroxyalkyl, alkylsulfonyl, alkylsulfonyl, haloalkylsulfonyl, haloalkylsulfinyl, alkylamido, alkylsulfonamido, alkylthio, alkylcarbonyl, alkoxycarbonyl and combinations of such substituents; each of $R_3$ and $R_4$ can be independently selected from such substituents and combinations thereof; and each of n and m can be an integer independently selected from 0-4, and salts of such compounds.

In certain embodiments, such a compound can be selected from compounds A wherein $R_1$ is phenyl, such compound of a formula

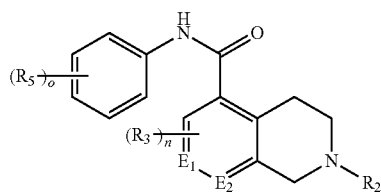

wherein $R_5$ can be selected from such $R_1$ substituents and combinations thereof; and o can be an integer selected from 0-4. In certain such embodiments, at least one of $E_1$ and $E_2$ can be CH, and n can be 0. Regardless, o can be 1-2, and, independently, $R_2$ can be selected from benzyl and mono- and disubstituted benzyl moieties. In certain other embodiments, such a compound can be selected from compounds B, wherein m can, optionally, be 1-2, and, independently, $R_1$ can be selected from phenyl and mono- and disubstituted phenyl moieties. Regardless, at least one of $E_2$ and $E_1$ can be CH, and n can be 0.

In certain other embodiments, such compounds can be of a formula and salts thereof. Without limitation, in certain such compounds, $R_1$ can be selected from phenyl, 2-, 3-, and 5-pyridinyl, 2-pyrimidinyl, 3-pyridazinyl, 2-thiazolyl, methylene-2-thiazolyl, 2-oxadiazolyl, 5-isoxazolyl, 2-nicotintate and 2-nicotinamide moieties; $R_2$ can be selected from phenyl and 2-pyridinyl moieties; and $R_3$ and Y can be moieties selected from those discussed above or described elsewhere herein including but not limited to (for Y) amino and alkylamino moieties. Regardless, $R_1$ and $R_2$ can be unsubstituted, monosubstituted or multi-substituted, as described elsewhere herein. Without limitation, any such $R_1$ and $R_2$ substituent(s) as can be independently selected from one or more halo (F, Cl, Br), cyano, $C_1$-$C_6$ alkyl, substituted alkyl (e.g., $CF_3$, etc.) and alkoxy, methylsulfinyl, hydroxy, methylsulfonyl, amino, alkylamino, dialkylamino, methylcarbonyl (aceto), acetamido, nitro, aminoalkyl, methylthio and 1-hydroxyethyl substituents and combinations of such substituents.

Alternatively, in certain other embodiments, such compounds can be of a formula

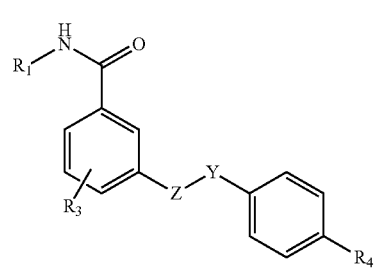

and salts thereof. Without limitation, $R_1$, $R_3$, Y and Z can be as described above or discussed elsewhere herein. Likewise, $R_4$ can be selected from H and $R_2$ substituents of the sort described above or discussed elsewhere herein. Without limitation, Z can be O, amino or alkylamino, and Y can be an alkyl-substituted methylene moiety providing a chiral center. Such a methylene substituent can be methyl. Regardless, such a compound can be selected from the (R) and (S) enantiomers.

In certain such embodiments, such compounds can be of a formula

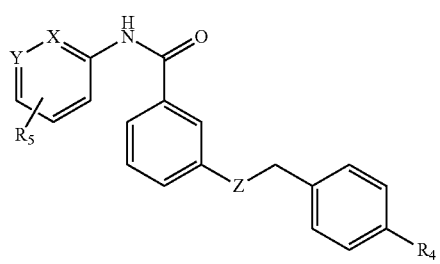

and salts thereof, wherein X and Y can be independently selected from CH and N to provide phenyl, pyridinyl and pyridinazinyl moieties; Z can be selected from moieties of the sort discussed above or described elsewhere herein; and $R_5$ can be H or an $R_1$ substituent of the sort described herein. Without limitation, Z can be selected from amino, alkylamino, thio, sulfinyl and sulfonyl moieties. More specifically, in certain non-limiting embodiments, such compounds can be of a formula

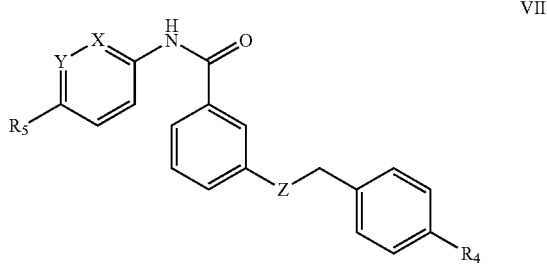

VII wherein $R_5$ can have a para-relationship with respect to the carboxamido moiety.

In part, the present invention can also be directed to compounds of a formula

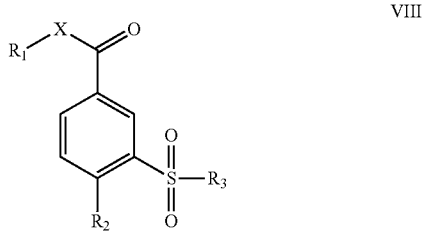

VIII and salts thereof. With respect to any such compound, $R_1$ can be selected from moieties discussed above or described elsewhere herein, including but not limited to phenyl, benzyl and heteroaryl moieties; $R_2$ can be selected from H, halo, $C_1$-$C_6$ alkyl and alkoxy moieties; and $R_3$ can be selected from $N(R_4)(R_5)$ moieties where each of $R_4$ and $R_5$ can be independently selected from H, alkyl and arylalkyl moieties and moieties where $R_4$ and $R_5$ together form alkylene or heteroatom-substituted alkylene moieties to provide an $R_3$ moiety selected from

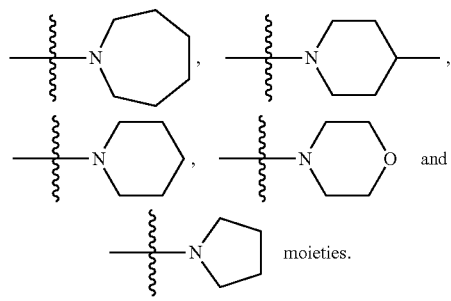

moieties.

Regardless, $R_1$ can be optionally substituted with 1-10 substituents selected from but not limited to halo, cyano, nitro, hydroxy, amino, alkyl, alkoxy, alkenyl, haloalkyl, aminoalkyl, hydroxyalkyl, alkylsulfonyl, alkylsulfinyl, haloalkylsulfonyl, haloalkylsulfinyl, alkylamido, alkylsulfonamido, alkylthio, alkylcarbonyl, alkoxycarbonyl and combinations of such substituents. However and without limitation, where $R_3$ is hexamethyleneimino (a seven-membered ring), X is an amino moiety and $R_2$ is H, optional exceptions to such compounds can be considered and provided where $R_1$ is a nitro- or bromosubstituted phenyl moiety.

In certain embodiments, such a compound can be of a formula,

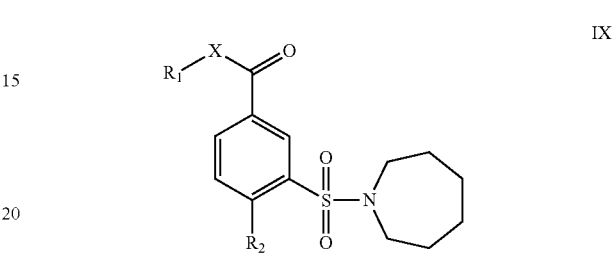

IX wherein, except as provided above, each of X, $R_1$ and $R_2$ can be as discussed above or described elsewhere herein. In certain such embodiments, depending on $R_1$, X can be selected from amino and aza-substituted ethylene moieties.

As discussed above, it will be understood by those skilled in the art that certain compounds of this invention can comprise an acid salt, hydrate and/or solvate of any such compound. Without limitation, certain embodiments can be partially or fully protonated, comprising a primary, secondary and/or tertiary amine, whereby the counter ion(s) can be a conjugate base of a protic acid. Regardless, any such compound(s) can be provided as part of a pharmaceutical composition comprising a pharmaceutically-acceptable carrier component for use in conjunction with a method or medicament of this invention.

In part, the present invention can also be directed to a method of affecting, inhibiting and/or otherwise modulating activity of a sirtuin enzyme. Such a method can comprise contacting, whether in vitro or in vivo, a sirtuin enzyme with an effective amount of any one or more of the present compounds or compositions, including but not limited to those compounds illustrated by the following examples, figures, accompanying synthetic schemes and/or incorporated references. More specifically, as discussed below, the present invention can provide a method for selective inhibition of SIRT2.

BRIEF DESCRIPTION OF THE DRAWINGS

FIG. 3. Without limitation as to any compound or composition of this invention, a summary of preliminary SARs developed herein, from the C2-8 and AK-1 scaffolds of the prior art, in accordance with certain non-limiting embodiments thereof.

DETAILED DESCRIPTION OF CERTAIN EMBODIMENTS

Figure 1:
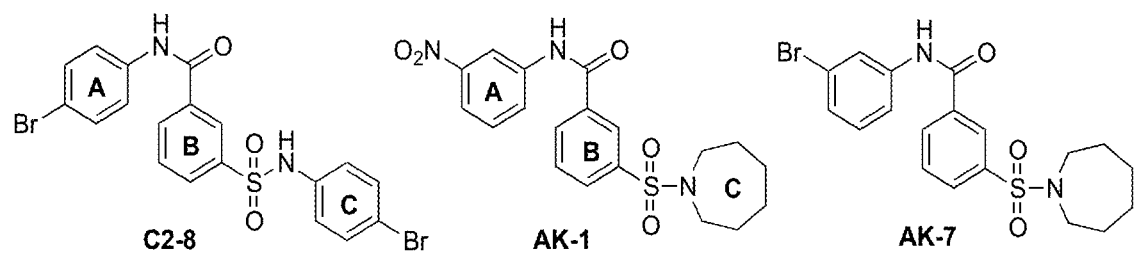
FIG. 1. Small molecule sulfobenzoic acid inhibitors of polyQ aggregation (Prior Art).

Throughout, where compounds or compositions are described as having, including, or comprising specific components, or where processes are described as having, including, or comprising specific process steps, it is contemplated that compounds of the present teachings also consist essentially of, or consist of, the recited moieties and/or substituents thereof, that compositions of the present teachings also consist essentially of, or consist of, the recited components, and that the processes of the present teachings also consist essentially of, or consist of, the recited process steps.

Where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

Throughout, structures may or may not be presented with chemical names. Where any question arises as to nomenclature, the structure prevails.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which can be optionally substituted as described herein.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can be optionally substituted as described herein.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group, but can be substituted with other substituents (e.g., halo, as described below, amino, cyano, etc.) of the sort described herein.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_sH_{2s+1-t}X^0_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O-alkyl group can be substituted as described herein. For example, an —O-haloalkyl group is considered within the definition of "alkoxy" as used herein.

As used herein, "alkylthio" refers to an —S-alkyl group (which, in some cases, can be expressed as $-S(O)_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "arylalkyl" refers to an -alkyl-aryl group, where the arylalkyl group is covalently linked to the defined chemical structure via the alkyl group. An arylalkyl group is within the definition of a $-Y-C_{6-14}$ aryl group, where Y is defined as a divalent alky group that can be optionally substituted as described herein. An example of an arylalkyl group is a benzyl group (—CH$_2$—C$_6$H$_5$). An arylalkyl group can be optionally substituted, i.e., the aryl group and/or the alkyl group, can be substituted as disclosed herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C$_{2-40}$ alkenyl group), for example, 2 to 20 carbon atoms (i.e., C$_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., C$_{2-40}$ alkynyl group), for example, 2 to 20 carbon atoms (i.e., C$_{2-20}$ alkynyl group). In some embodiments, alkynyl groups can be substituted as described herein. An alkynyl group is generally not substituted with another alkynyl group, an alkyl group, or an alkenyl group.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., C$_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C$_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C$_6$F$_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below.

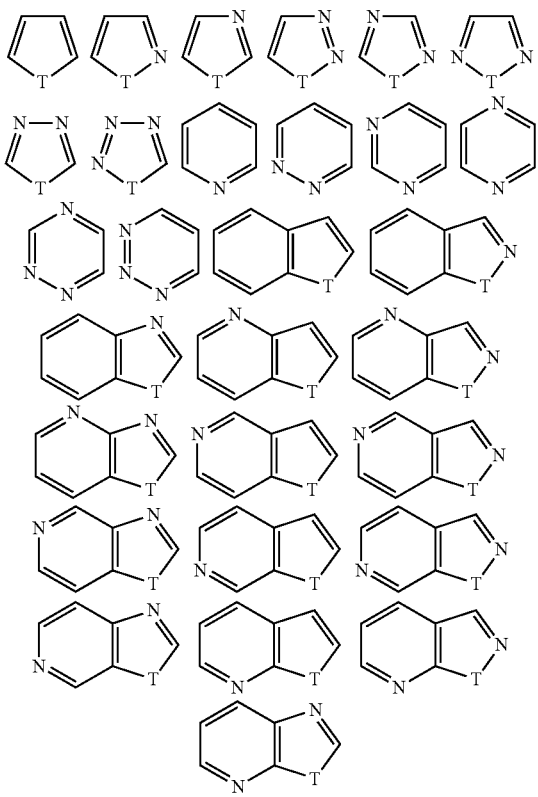

where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent moiety" defined herein as a linking group capable of forming a covalent bond with two other moieties. For example, compounds of the present teachings can include a divalent $C_{1-20}$ alkyl group (e.g., a methylene or, more generally, alkylene), a divalent $C_{2-20}$ alkenyl group (e.g., a vinylyl group), a divalent $C_{2-20}$ alkynyl group (e.g., an ethynylyl group). a divalent $C_{6-14}$ aryl group (e.g., a phenylyl group) and heteroatom-substituted variations of any such group, including but not limited to heteroatom-substituted alkylene (e.g., aza-substituted ethylene); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

Syntheses of 3-sulfonamide benzoate derivatives began from the commercially available benzoic acid or 3-methoxybenzoic acid (1-2) using procedures described in the literature (Scheme 1). (See, e.g., Nie, Z.; Perretta, C.; Lu, J.; Su, Y.; Margosiak, S.; Gajiwala, K. S.; Cortez, J.; Nikulin, V.; Yager, K. M.; Appelt, K.; Chu, S. Structure-based design, synthesis, and study of potent inhibitors of beta-ketoacyl-acyl carrier protein synthase III as potential antimicrobial agents. *J. Med. Chem.* 2005, 48, 5, 1596-1609; and Wrobel, J.; Green, D.; Jetter, J.; Kao, W.; Rogers, J.; Perez, M. C.; Hardenburg, J.; Deecher, D. C.; Lopez, F. J.; Arey, B. J.; Shen, E. S. Synthesis of (bis)sulfonic acid, (bis)benzamides as follicle-stimulating hormone (FSH) antagonists. *Bioorg. Med. Chem.* 2002, 1, 3, 639-656.) The synthetic route started by sulfonylation of benzoic acid analogs to produce 3 and 4, which were coupled with primary or secondary anilines (for 5-20) or with azepane (for 21 and 22) in pyridine to generate the corresponding sulfonamide derivatives. The carboxylic acid was then coupled with aniline or other heterocyclic rings using N-(3-dimethylaminopropyl)-N'-ethylcarbodiimide hydrochloride (EDCI) and 4-(dimethylamino)pyridine (DMAP) to generate the final compounds (23-152). DMAP was removed in the last step of the 23-42 syntheses to overcome polymerization that has been observed. The commercially available aminothioanisole derivatives (153 and 154) were used to synthesize the corresponding sulfoxides (155 and 156) using self-catalyzed selective oxidation, and sulfones (157 and 158) using sodium tungstate and an excess of hydrogen peroxide (Scheme 2). (See, e.g., Beller, M.; Shi, F.; Tse, M. K.; Kaiser, H. M. Self-catalyzed oxidation of sulfides with hydrogen peroxide: A green and practical process for the synthesis of sulfoxides. *Adv. Synth. Cata.* 2007, 349, 16, 2425-2430; and Biava, M.; Porretta, G. C.; Poce, G.; Supino, S.; Forli, S.; Rovini, M.; Cappelli, A.; Manetti, F.; Botta, M.; Sautebin, L.; Rossi, A.; Pergola, C.; Ghelardini, C.; Vivoli, E.; Makovec, F.; Anzellotti, P.; Patrignani, P.; Anzini, M. Cyclooxygenase-2 inhibitors. 1,5-diarylpyrrol-3-acetic esters with enhanced inhibitory activity toward cyclooxygenase-2 and improved cyclooxygenase-2/cyclooxygenase-1 selectivity. *J. Med. Chem.* 2007, 50, 22, 5403-5411.

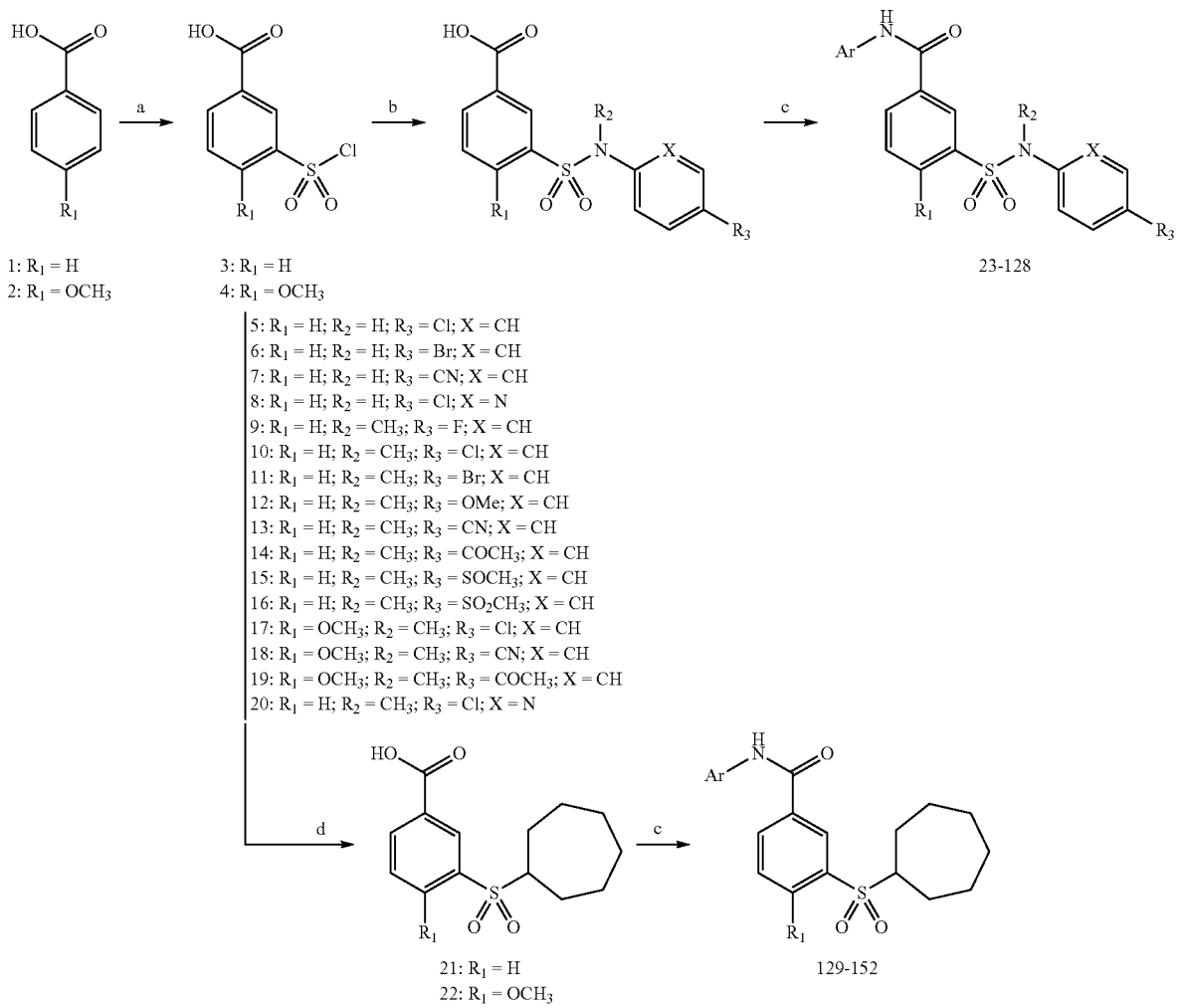

Scheme 1. General synthetic routes to new analogs of C2-8, AK-1, and AK-7

1: $R_1$ = H
2: $R_1$ = $OCH_3$

3: $R_1$ = H
4: $R_1$ = $OCH_3$

5: $R_1$ = H; $R_2$ = H; $R_3$ = Cl; X = CH
6: $R_1$ = H; $R_2$ = H; $R_3$ = Br; X = CH
7: $R_1$ = H; $R_2$ = H; $R_3$ = CN; X = CH
8: $R_1$ = H; $R_2$ = H; $R_3$ = Cl; X = N
9: $R_1$ = H; $R_2$ = $CH_3$; $R_3$ = F; X = CH
10: $R_1$ = H; $R_2$ = $CH_3$; $R_3$ = Cl; X = CH
11: $R_1$ = H; $R_2$ = $CH_3$; $R_3$ = Br; X = CH
12: $R_1$ = H; $R_2$ = $CH_3$; $R_3$ = OMe; X = CH
13: $R_1$ = H; $R_2$ = $CH_3$; $R_3$ = CN; X = CH
14: $R_1$ = H; $R_2$ = $CH_3$; $R_3$ = $COCH_3$; X = CH
15: $R_1$ = H; $R_2$ = $CH_3$; $R_3$ = $SOCH_3$; X = CH
16: $R_1$ = H; $R_2$ = $CH_3$; $R_3$ = $SO_2CH_3$; X = CH
17: $R_1$ = $OCH_3$; $R_2$ = $CH_3$; $R_3$ = Cl; X = CH
18: $R_1$ = $OCH_3$; $R_2$ = $CH_3$; $R_3$ = CN; X = CH
19: $R_1$ = $OCH_3$; $R_2$ = $CH_3$; $R_3$ = $COCH_3$; X = CH
20: $R_1$ = H; $R_2$ = $CH_3$; $R_3$ = Cl; X = N 23-128

21: $R_1$ = H
22: $R_1$ = $OCH_3$ 129-152

[a]Reagents and conditions: (a) $ClSO_3H$, 65° c.; (b) aniline, pyridine, EtOAc; (c) Ar—$NH_2$, EDCl, DMAP, $CH_2Cl_2$; (d) $BBr_3$, $CH_2Cl_2$, -80° C. → rt, 12 h; (e) azepane, pyridine, EtOAc Scheme 2[a]. Oxidation of aminothioanisole to generate the corresponding sulfoxide and sulfone derivatives

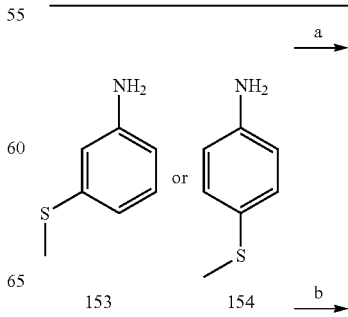

153    154

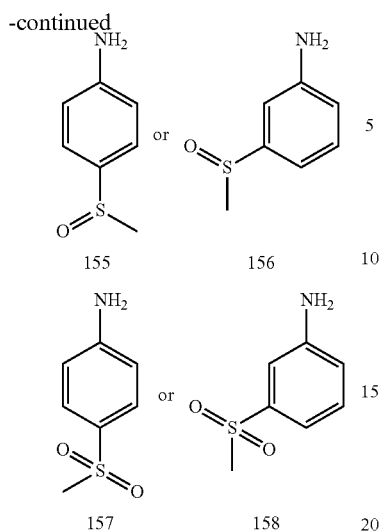

*Reagents and conditions: (a) H₂O₂ (30%, 1 equiv), 70° C., 1 h; (b) H₂O₂ (30%), AcOH, Na₂WO₄, 65° C., 1 h.

The N-methyl-4-(methylthio)aniline (161) and 5-chloro-N-methylpyridin-2-amine (162) were synthesized from the corresponding commercially available demethylated derivatives (159 and 160, respectively) using the Chan-Lam selective monomethylation procedure, which involves copper (II)-promoted coupling of anilines and methylboronic acid (Scheme 3). (See, e.g., Gonzalez, I.; Mosquera, J.; Guerrero, C.; Rodriguez, R.; Cruces, J. Selective monomethylation of anilines by Cu(OAc)-2-promoted cross-coupling with MeB(OH)₂. *Org. Lett.* 2009, 11, 8, 1677-1680.) Subsequently, 161 was oxidized to the sulfoxide (163) and sulfone (164) intermediates as described above.

The sulfonamide moiety was replaced by sulfone, sulfoxide, or thioether moieties as described in Scheme 4. Commercially available 3-mercaptobenzoic acid and 3-benzyl bromide derivatives were coupled to yield 3-(benzylthio) benzoic acid derivatives (165-167), which were subjected to oxidation with excess H₂O₂ in acetic acid to generate the corresponding sulfone (168-170), or with one equivalent of H₂O₂ to form the sulfoxide intermediates (184 and 185). Subsequently, the sulfone, sulfoxide, and thioether derivatives were coupled with aniline, pyridine, or pyridazine amines using EDCI and DMAP to form the final compounds (171-183, 186-189).

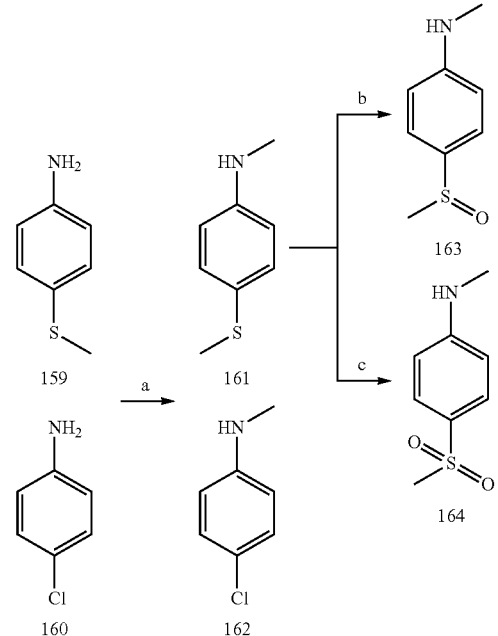

*Reagents and conditions: (a) MeB(OH)₂ (2.5 equiv), Cu(OAc)₂ (2.5 equiv), pyridine, dioxane, reflux. (b) H₂O₂ (30%, 1 equiv), 70° C., 1 h; (c) H₂O₂ (30%), AcOH, Na₂WO₄, 65° C., 1 h.

The phenolic analogs (35, 57, 58, 71, 85, 152) were generated from their parent anisole compounds (29, 55, 59, 70, 84, 151, respectively) using one molarity of boron tribromide (BBr₃) in DCM as described in the literature. Reduction of the acetyl group of 103, 104, and 107 was performed using sodium borohydride (NaBH₄) in anhydrous methanol to generate the secondary alcohol derivatives 126, 127, and 128, respectively. (See, e.g., Watts, P.; Wiles, C.; Haswell, S. J. Clean and selective oxidation of aromatic alcohols using silica-supported Jones' reagent in a pressure-driven flow reactor. *Tetrahedron Lett.* 2006, 47, 30, 5261-5264.)

Scheme 4. *The synthetic routes of sulfone, sulfoxide, and thioether derivatives.

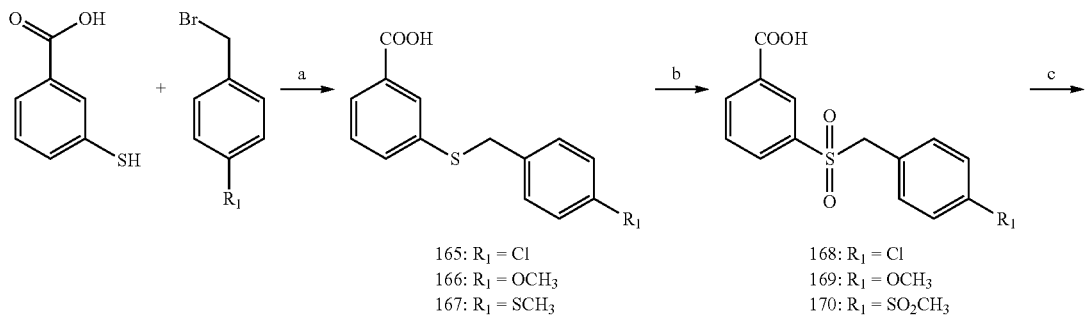

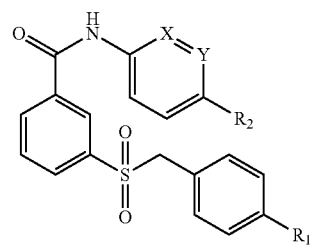

171: $R_1$ = Cl; $R_2$ = Cl; X = CH; Y = CH
172: $R_1$ = Cl; $R_2$ = Br; X = CH; Y = CH
173: $R_1$ = Cl; $R_2$ = Cl; X = N; Y = CH
174: $R_1$ = Cl; $R_2$ = CN; X = CH; Y = CH
175: $R_1$ = Cl; $R_2$ = SOCH$_3$; X = CH; Y = CH
176: $R_1$ = Cl; $R_2$ = CN; X = N; Y = CH
177: $R_1$ = Cl; $R_2$ = SO$_2$CH$_3$; X = CH; Y = CH
178: $R_1$ = Cl; $R_2$ = COCH$_3$; X = CH; Y = CH
179: $R_1$ = Cl; $R_2$ = Cl; X = N; Y = N
180: $R_1$ = OCH$_3$; $R_2$ = CN; X = CH; Y = CH

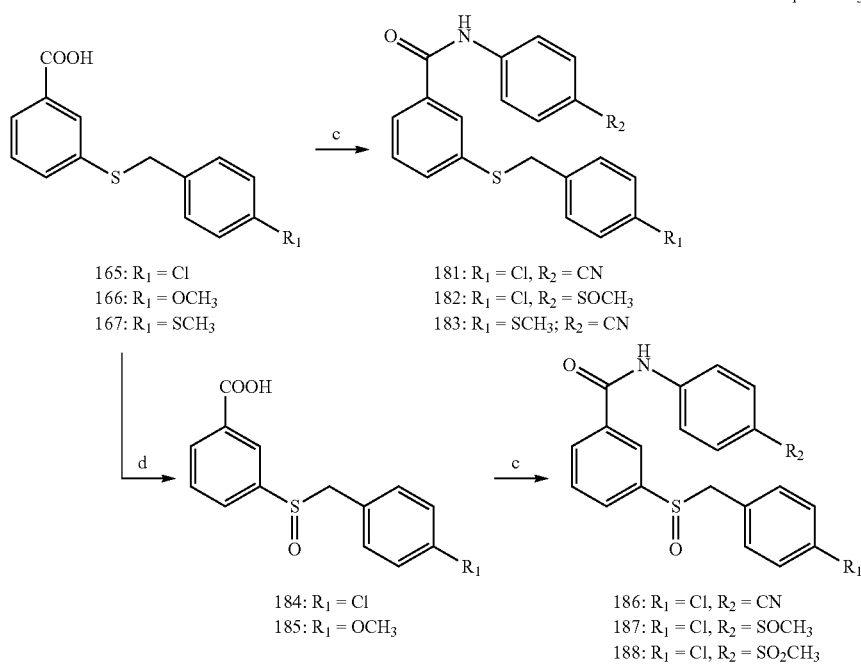

165: $R_1$ = Cl
166: $R_1$ = OCH$_3$
167: $R_1$ = SCH$_3$

181: $R_1$ = Cl, $R_2$ = CN
182: $R_1$ = Cl, $R_2$ = SOCH$_3$
183: $R_1$ = SCH$_3$; $R_2$ = CN

184: $R_1$ = Cl
185: $R_1$ = OCH$_3$

186: $R_1$ = Cl, $R_2$ = CN
187: $R_1$ = Cl, $R_2$ = SOCH$_3$
188: $R_1$ = Cl, $R_2$ = SO$_2$CH$_3$
189: $R_1$ = OCH$_3$, $R_2$ = CN $^a$Reagents and conditions: (a) (i) KOH, CH$_3$CH$_2$OH, H$_2$O, reflux, 2 h; (ii) 20% aq NaOH, reflux, 1 h; (b) H$_2$O$_2$ (30%), 65° C., 1 h; Ar—NH$_2$, EDCl, DMAP, CH$_2$Cl$_2$; (d) H$_2$O$_2$ (30%, 1 equiv), 70° C., 1 h.

To evaluate the potency and selectivity of the synthesized compounds robust, sensitive, and quantitative, biochemical sirtuin deacetylation assays were employed. (SIRT2 then SIRT1 and SIRT3 for selectivity). Sirtuin activity was assessed using the Fluor-de-Lys assay with recombinant active enzymes SIRT1, SIRT2, and the catalytically active fragment of SIRT3, as described in the literature. (See, Outeiro, T. F.; Kontopoulos, E.; Altmann, S. M.; Kufareva, I.; Strathearn, K. E.; Amore, A. M.; Volk, C. B.; Maxwell, M. M.; Rochet, J. C.; McLean, P. J.; Young, A. B.; Abagyan, R.; Feany, M. B.; Hyman, B. T.; Kazantsev, A. G. Sirtuin 2 inhibitors rescue alpha-synuclein-mediated toxicity in models of Parkinson's disease. *Science* 2007, 317, 5837, 516-519.) Compounds were tested at a single 10 μM dose in the primary SIRT2 assay and counter-screened in SIRT1 and SIRT3 assays as described. AK-1 was included as the reference compound with each assay. Hits demonstrating SIRT2 inhibition activity equal to or better than AK-1 in the SIRT2 assay were selected for dose-response studies, which were performed with five doses in the primary SIRT2 assay in at least two independent experiments, including a direct side-by-side comparison of SIRT2 inhibition by AK-1. Those compounds also were subjected to SIRT1 and SIRT3 assays to determine sirtuin selectivity. The dose-response assays identified 47, 64, 90, 102, 106, 115, and 126 as significantly more potent SIRT2 inhibitors than AK-1, while a number of analogs, 51, 52, 59, 61, 71, 103, 109, 117, and 174 had either equal or just slightly better potency.

High potency and selectivity in in vitro biochemical assays do not ensure compound cell permeability and bioactivity. To that end, a confirmatory test of SIRT2 inhibition activity was performed in live cells. This scaffold showed a high degree of selectivity; most of the compounds were totally inactive in SIRT1 and SIRT3 inhibitory assays.

Compounds 43, 56, 106, and 115 showed minimal SIRT1 inhibition, while 41, 106, and 58 displayed minimal SIRT3 inhibition. The only compound that significantly inhibited SIRT1 was 31, a 2-thiazole derivative that was totally inactive as a SIRT2 and SIRT3 inhibitor but inhibited SIRT1 by 65% at 10 μM.

Figure 2A:
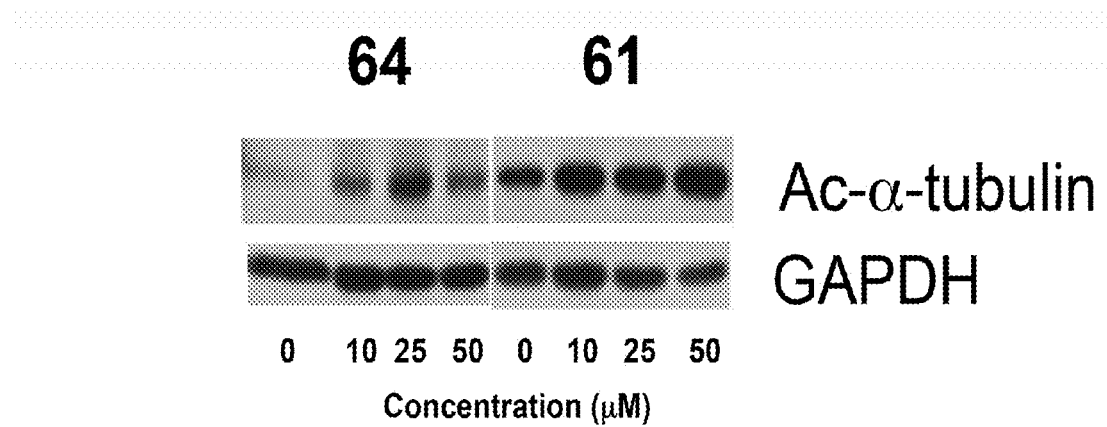
FIGS. 2A-B. Cell-based assay for evaluating the bioactivity of SIRT2 inhibitors. A) Extracts from neuronal N2a cells treated with 61 and 64 for 6 h were resolved on SDS-PAGE and analyzed by Western analysis using antibodies specific to acetylated α-tubulin, and normalized to GADPH and total α-tubulin (not shown) levels. B) Compound dose-dependent increase of α-tubulin acetylation, normalized to GADPH levels, and quantified from Western blots in A).
Figure 2B:
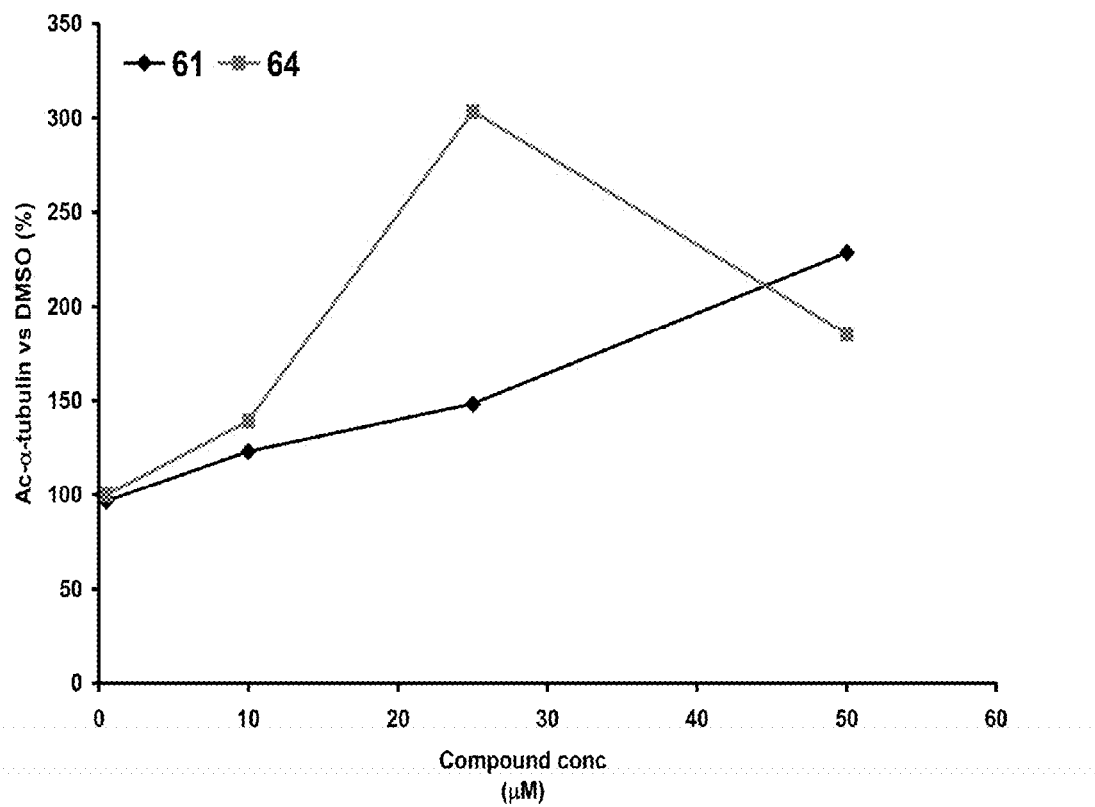

To assess SIRT2 inhibition activity in cells, an increase in α-tubulin K40 acetylation (α-tubulin is a substrate for SIRT2) in neuronal N2a and in wild type and HD ST14 1 cell lines was measured. In this bioactivity test, extracts from compound-treated cells were resolved on SDS-PAGE and subjected to Western analysis using primary antibodies specific to K40 acetylated α-tubulin. Trichostatin A (TSA), a potent HDAC inhibitor, was used as a positive control. To normalize the levels of acetylated α-tubulin we used total α-tubulin and GADPH proteins, detected by Western reactive antibodies specific to total α-tubulin and GADPH. All compounds that showed confirmed SIRT2 inhibitory activities were selected for cell-based acetylation assays. Sixteen compounds were tested, and all of them, except 115, increased α-tubulin K40 acetylation in the two cell lines in a dose-dependent manner. Analog 115 did not show any significant increase in α-tubulin acetylation in either cell line. FIGS. 2A-B show the bioactivity of 61 and 64 in N2a cells at three tested concentrations (10, 25, and 50 μM). Toxicity of the compounds was monitored in both cell lines, and most of them were non-toxic up to 50 μM in a 6 h treatment. Compound 90 was toxic at 50 μM in N2a cells and partially toxic at 25 μM, but no toxicity was observed in WT st14a cells up to an 18 h treatment.

Because of low aqueous solubility (high lipophilicity) and metabolic instability, the initial stage of structural modification involved water solubility enhancement that would potentially improve the ADMET properties. Lipinski's Rule of Five and Veber's rules were adopted for the synthesis criteria, limiting the range for molecular weight to ≤500, calculated octanol-water partition coefficient (C log P) to ≤5, the number of hydrogen bond donors (OH's and NH's) and hydrogen bond acceptors (N's and O's) to ≤10, the number of rotatable bonds≤10, the polar surface area<90 Å$^2$. The ideal C log P value for BBB penetration is 2≤log P≤4; therefore, most of the compounds that were synthesized were in that range. The syntheses are straightforward, mostly only 3-5 steps. Syntheses of such analogs were not conducted at random; an initial structural hypothesis was proposed, which drove the synthetic effort. The synthesized compounds were tested for enhancement of solubility and activity, and the hypotheses were refined and adjusted according to the evolving results.

The following structural modification strategies were applied to the C2-8 and AK-1 scaffolds to improve their solubility: (1) the A, B, and C phenyl rings (FIG. 1) of C2-8 and AK-1 were replaced with five- and six-membered heterocyclic ring(s), e.g., pyridine, pyrimidine, pyridazine, thiazole, oxazole, isoxazole, and oxadiazole rings—to increase aqueous solubility in drug design. Heterocyclic rings were found to be tolerated on ring A of C2-8 but not on ring C, as described, below; (2) hydrophobic groups: halogens of C2-8 and AK-1 were replaced with more polar and hydrophilic groups, such as hydroxyl, methoxyl, amino, cyano, carboxyl, acetyl, methylsulfoxide, methylsulfone, and acetamide groups. Four hydrophilic groups were found to increase or at least maintain the SIRT2 inhibitory activities: the cyano, sulfoxide, sulfone, and acetyl groups, specifically on ring A of C2-8; (3) the sulfonamide was replaced with sulfone, sulfoxide, and sulfide, and phenylamide planarity was disrupted by introduction of a methylene group between them. Replacing the N—CH$_3$ group with a CH$_2$ moiety was tolerated and a good strategy to overcome the metabolic instability by demethylation, as described below; (4) the active derivatives from the above-mentioned strategies were combined into one compound. The structures of the new compounds are summarized along with their SIRT2 inhibitory activities at 10 μM in Table 1 and Table 2, below.

An understanding of the SAR of the sulfobenzoic acid derivatives is not only useful for the synthesis of more active analogs, but also for selecting optimal approaches for increasing solubility without significant loss in activity. With respect to certain non-limiting embodiments of this invention, FIG. 3 summarizes several SAR conclusions from the SIRT2 inhibition assays. Although C2-8 and AK-1 both contain a 3-sulfonyl benzoate scaffold, the SAR shows that their analogs have a few structurally distinct features, which differentiate the two scaffolds.

On the basis of the SIRT2 inhibitory activities of analogs synthesized here and those tested in previous screening studies, a SAR of the C2-8 scaffold can be summarized as follows: (1) $R_1$ on ring A of C2-8 should be at the para position; however, small groups (e.g., F) at the ortho position are tolerated; (2) $R_1$ should be electron withdrawing, but both hydrophobic and hydrophilic substituents are tolerated; (3) Six-membered heterocyclic rings in place of benzene ring A are tolerated, but not five-membered heterocyclic rings; (4) The sulfonamide nitrogen must be methylated but the N-methyl group is not essential for activity. Sulfide is more potent than sulfoxide and sulfone in the order described in FIG. 3; (5) $R_3$ is optimal at the para position; pyridinyl modification of ring C is tolerated; (6) $R_3$ should be electron withdrawing, and both hydrophobic and hydrophilic substituents are tolerated; (7) There is no apparent trend for $R_2$ on ring B; H, F, Cl, Br, CH$_3$, OCH$_3$ groups are tolerated at this position.

A SAR for the AK-1 scaffold also has been studied and can be summarized as follows: (1) AK-1 derivatives have optimum activities when $R_1$ is at the meta position, not para, which is favored for C2-8 analogs; (2) $R_1$ should have electron-withdrawing or weakly electron-donating properties; (3) Similar to C2-8, both hydrophobic and hydrophilic substituents are tolerated at $R_1$; (4) Five- and six-membered heterocyclic rings in place of benzene ring A were inactive; (5) Hexamethyleneimine (seven-membered ring) is better than smaller cyclic ring amines AK-1 analogs that contain a 4-methylpiperidine group were more potent than those containing a piperidine group. These results suggest that ring C may be involved in a hydrophobic interaction in a binding pocket; (6) There is no apparent trend for $R_2$ on ring B; H, F, Cl, Br, CH$_3$ groups are tolerated at this position, and OCH$_3$ gave opposite results.

In vitro ADME studies were carried out at Apredica, Inc. (Watertown, Mass.). The solubility of 51 and 59 in PBS was moderately increased by two- and four-fold, respectively, compared to AK-1. The plasma protein binding for both compounds is high; 99.8% for 51 and 99.1% for 59. Microsomal stability is still low; neither compound was stable in mouse and human microsomes after 60 minutes (0% remaining for 51 and 16% for 59). The efflux ratio is 0.7 and 1.7 for 51 and 59 respectively, which suggests that they are not substrates for P-glycoprotein or other active transporters.

In an attempt to better understand the microsome instability of these compounds, 51 and 59 were submitted for metabolite identification studies at Apredica, Inc. The N-demethylated metabolite of 51 was detected, which we had already tested (26) and found to be inactive in the SIRT2 assay. This rapid metabolism of 51 to an inactive metabolite explains why this compound appears to have low concentration in blood and in brain homogenate. Other active compounds became inactive when the N-methyl group was removed. In an attempt to overcome this metabolic inactivation, the sulfonamide moiety was replaced with sulfone, sulfoxide, and thioether analogs as shown in Scheme 4 and Table 3. The replacement of the N—$CH_3$ group with $CH_2$ (171-180) was tolerated in 174, 175, and 176 compared to the parent analog (64, 59, and 71, respectively). Other sulfone derivatives were less potent than the corresponding sulfonamide analogs.

The major metabolite from 59 is the corresponding sulfone (61; the sulfoxide is oxidized to sulfone). Unlike the loss in activity when the N—$CH_3$ group is demethylated, oxidation of the sulfoxide to the sulfone produces a more potent compound in both the SIRT2 and cell-based tubulin deacetylation assays. One of the most potent compounds in that series, however, is the corresponding nitrile (64), which avoids potential sulfur oxidation because there is no sulfoxide group. Compound 71, with a cyanopyridine analog is also more potent than 59; 174, with a cyano in place of the sulfoxide and a $CH_2$ group in place of the N—$CH_3$ group also is more potent than 59.

The other significant result from the metabolism identification study was that no amide hydrolysis products were detected in microsomal incubations and limited hydrolysis was detected in plasma (half-lives>2 h). This supports the stability of the amide linkage. Detailed ADME studies results with 51 and 59 and the experimental procedures are provided, below.

As mentioned earlier, one of the few hydrophilic functional groups used to enhance solubility that was found to be active in SIRT2 inhibition is the acetyl group. However, it is well known that it is susceptible to reduction to the corresponding secondary alcohol by aldo-keto reductases. To test if the secondary alcohol derivatives maintain SIRT2 inhibitory activity, the acetyl analogs 103, 104, and 107 were reduced to their corresponding alcohols 126, 127, and 128. Compound 126 maintained inhibitory activity (45%) with SIRT2, comparable to 103 (40%)

As demonstrated, starting with C2-8 and AK-1 as lead compounds, structural alteration enhanced water solubility and metabolic stability. Synthesis of 187 representative, non-limiting compounds allowed formulation of a SAR for these two classes of compounds. No sulfonamide is necessary; sulfide, sulfoxide, and sulfone can substitute. Substituents on the aromatic ring include cyano, acetyl, 1-hydroxyethyl, methylthio.

More specifically, seven new analogs were found to be much more potent SIRT2 inhibitors than AK-1 with high selectivity over SIRT1 and SIRT3. Nine new analogs were as potent or slightly more potent than AK-1 with high SIRT1 and SIRT3 selectivity. These compounds were subjected to a secondary screen for SIRT2 inhibition in live cells, which measured an increase in α-tubulin K40 acetylation (α-tubulin is a substrate for SIRT2) in neuronal N2a and in wild type and HD ST14 1 cell lines. Fifteen compounds increased α-tubulin K40 acetylation in both cell lines in a dose-dependent manner, and most of them were non-toxic in both cell lines up to 50 µM in a 6 h treatment.

Methods of the present invention can also, as would be understood by those skilled in the art, be extended to or include methods using or in conjunction with a pharmaceutical composition comprising an inhibitor compound of the sort described herein in a physiologically or otherwise suitable formulation. In some embodiments, the present invention includes one or more such inhibitors, as outlined above or discussed more fully below, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or non-aqueous solutions, dispersions, suspensions or emulsions. The resulting compositions can be, in conjunction with the various methods described herein, for administration or contact with a human/animal sirtuin enzyme expressed or otherwise present therein. Whether or not in conjunction with a pharmaceutical composition, "contacting" means that a sirtuin enzyme and one or more inhibitor compounds are brought together for purpose of binding and/or complexing such an inhibitor compound to the enzyme. Amounts of a compound effective to affect or otherwise inhibit a sirtuin enzyme may be determined empirically, and making such determinations is within the skill in the art. Inhibition, affecting or otherwise modulating sirtuin enzyme activity includes both reduction and/or mitigation, such results as can be confirmed through an increase in substrate acetylation.

It is understood by those skilled in the art that dosage amount will vary with the activity of a particular inhibitor compound, disease state, route of administration, duration of treatment and like factors well-known in the medical and pharmaceutical arts. In general, a suitable dose will be an amount which is the lowest dose effective to produce a therapeutic or prophylactic effect. If desired, an effective dose of such a compound, pharmaceutically acceptable salt thereof or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mac Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more sirtuin inhibitor compounds for the manufacture of a medicament for therapeutic use in the treatment of Huntington's disease or the prevention thereof.

EXAMPLES OF THE INVENTION

The following non-limiting examples and data illustrate various aspects and features relating to the compounds/compositions and/or methods of the present invention, including various benzamide compounds as are available through the synthetic methodologies described herein. In comparison with the prior art, the present compounds, compositions, and/or methods provide results and data which are surprising, unexpected and contrary thereto. While the utility of the invention is illustrated for the use of several compounds, components, moieties and/or substituents thereof, it will be understood by those skilled in the art that comparable results are obtainable with various other compounds, components, moieties and/or substituents, as are commensurate with the scope of this invention.

General Experimental Procedures. $^1$H NMR and $^{13}$C NMR spectra were recorded on a Bruker Avance III (500 MHz $^1$H, 125 MHz $^{13}$C) with a DCH Cryo-Probe. Chemical shift values (δ) are reported in parts per million (ppm) relative to CDCl$_3$ [δ 7.26 ppm (1H), 77.16 ppm (13C)]. The proton spectra are reported as follows: δ (multiplicity, number of protons). Multiplicities are indicated by s (singlet), d (doublet), t (triplet), q (quartet), p (pentet), h (heptet), m (multiplet), and br (broad). The HREIMS experiments were conducted on a 6200-TOF LCMS (Agilent, Santa Clara, Calif.) equipped with a multimode source (mixed source that can ionize the samples alternatively by ESI or APCI). Electrospray mass spectra (ESMS) were obtained using an LCQ-Advantage with methanol as the solvent in the positive ion mode. Analytical HPLC analyses were performed on a Beckman HPLC system using a Vydac C18 column (4.6× 150, 5 μm Phenomenex) and isocratic elution (CH$_3$CN: H$_2$O; 60:40) with UV detection set at 305 and 220 nm to verify the purity of tested compounds. Except for compounds 28, 75, and 147 a purity of >95% has been established for all final tested compounds. Compound 28, 75, and 147 achieved 89%, 90%, and 88% purity level, respectively. Except as otherwise indicated, all reactions were magnetically stirred and monitored by analytical thin-layer chromatography using Whatman precoated silica gel flexible plates (0.25 mm) with F254 indicator or Merck precoated silica gel plates with F254 indicator. Visualization was accomplished by UV light (256 nm). Flash column chromatography was performed using silica gel 60 (mesh 230-400) supplied by E. Merck. Yields refer to chromatographically and spectrographically pure compounds, unless otherwise noted. Commercial grade reagents and solvents were used without further purification except as indicated below.

General Chemical Reaction Procedures.

(A) Chlorosulfonation of benzoic acid derivatives. A mixture of 1 (5 g, 40.94 mmol) or 2 (5 g, 32.86 mmol) in chlorosulfonic acid (20 mL) was heated to 65° C. in an oil bath for 4 h, after which time TLC indicated complete conversion of the starting material to the intermediates, 3-(chlorosulfonyl)benzoic acid (3) and 3-(chlorosulfonyl)-4-methoxybenzoic acid (4), respectively. The reaction mixture was slowly poured over ice and filtered. The solid was dried in vacuo to yield intermediates 3 (7.90 g, 87%) and 4 (6.40 g, 86%), which were carried forward without further purification.

(B) Formation of the sulfonamide bonds. Sulfonyl chloride derivative 1 or 2 (3.99 mmol) was added gradually to a mixture of substituted amine (4.39 mmol) and pyridine (2 mL) in EtOAc with stirring at 0° C. The reaction mixture was stirred at room temperature until the TLC indicated complete conversion of sulfonyl chloride to the sulfonamide intermediate. The reaction mixture was dissolved in DCM and extracted (2×) with 10% NaOH. After the aqueous layer was acidified with 2 N HCl, the precipitate was collected by filtration, washed with H$_2$O, and dried in vacuo to give the desired products (5-22), which were carried forward without further purification.

(C) Formation of the amide bond. To a stirred solution of amine (0.169 mmol), corresponding carboxylic acid (5-22, 0.154 mmol), and with or without DMAP (0.154 mmol) in DCM (10 mL) at room temperature was added EDCI (0.308 mmol). The reaction mixture was stirred overnight and then concentrated in vacuo. The crude material was purified by flash chromatography (EtOAc/hexane) to afford the desired product (23-152).

(D) Self-catalyzed selective oxidation of methylthio aniline to methylsulfonyl aniline. Aminothioanisoles 153, 154, or 161 (1.0 g, 7.18 mmol) and H$_2$O$_2$ (0.74 mL, 30 wt % in H$_2$O, 7.18 mmol) were stiffed at 70° C. for 1 h. The mixture was then cooled to room temperature and extracted with DCM (20 mL×2). After drying with anhydrous Na$_2$SO$_4$, the organic mixture was removed in vacuo, and a brownish solid of the desired product (155, 156, and 163) was obtained.

(E) Oxidation of methylthio aniline to methylsulfonyl aniline. A mixture of Na$_2$WO$_4$ (0.067 g), 1 drop of acetic acid, and H$_2$O (5 mL) was placed in a flask and heated to 65° C. Methylthioaniline 153, 154, or 161 (500 mg, 3.59 mmol) was added, followed by dropwise addition of H$_2$O$_2$ (1.1 mL, 10.77 mmol). The mixture was stirred at 65° C. for 1.5 h and, after cooling, 80 mL of 1 N HCl and 50 mL of DCM were added. The layers were separated, and the aqueous phase was washed with additional DCM. The aqueous phase was basified with 25% NaOH and extracted with DCM. The organic phase was washed with brine and dried over Na$_2$SO$_4$. The solvent was removed to give methylsulfonyl aniline derivatives 157, 158 and 164.

(F) N-Methylation of aniline. Copper (II) acetate (0.550 g, 3.03 mmol) was added to a solution of aniline (1.22 mmol) and pyridine (0.34 mL, 4.24 mmol) in dioxane (15 mL). The mixture was stirred for 15 min, methyl boronic acid (0.181 g, 3.03 mmol) was added, and the reaction was refluxed until aniline was totally consumed (TLC analysis, 1.5-18 h). The reaction mixture was allowed to reach room temp, filtered through Celite, and the solvent was evaporated. The residue was purified by flash chromatography (0→50% EtOAc/hexanes) to afford N-methylaniline.

(G) Synthesis of 3-(benzylthio)benzoic acid derivatives. A mixture of 3-mercaptobenzoic acid (1 g, 7.25 mmol), KOH (0.89 g, 0.016 mmol), and benzyl bromide (7.97 mmol) in ethanol:water (16 mL/2 mL) was heated under reflux for 20 h. Aqueous KOH solution (20%, 10 mL) was added, and the mixture was heated under reflux for a further 4 h. The reaction mixture was allowed to cool, water was added, and the solution was acidified with 2 N HCl. The precipitate was filtered off and dried in vacuo to give the desired products (165-167), which were carried forward without further purification.

(H) Oxidation of 3-(benzylthio)benzoic acid to the corresponding 3-(benzylsulfinyl)benzoic acid derivatives. To a solution of a 3-(benzylthio)benzoic acid derivative (165, 166, or 167, 1.79 mmol) in AcOH (20 mL) was added dropwise 30% H$_2$O$_2$ (1.79 mmol) at 60° C. After being stirred for 60 min at 65° C., the reaction mixture was poured into ice water (50 mL). The precipitate was collected and washed with water to give 168-170.

(I) Oxidation of 3-(benzylthio)benzoic acid to the corresponding 3-(benzylsulfonyl)benzoic acid derivatives. To a solution of a 3-(benzylthio)benzoic acid derivative (165, 166, or 167, 1.79 mmol) in AcOH (20 mL) was added dropwise 30% H$_2$O$_2$ (5.37 mmol) at 60° C. After being stirred for 90 min at 70° C., the reaction mixture was poured into ice water (50 mL). The precipitate was collected and washed with water to give 184 and 185.

(J) Demethylation of anisole compounds. To a 10-mL flask were added 29, 55, 59, 70, 84, or 151 (0.089 mmol) and 2 mL of anhydrous DCM. An argon atmosphere was established and maintained. This mixture was cooled in a Dry Ice/acetone bath and boron tribromide (1 M in DCM, 0.107 mmol) was added via syringe through a septum. After the mixture was stirred overnight at room temperature, it was poured into ice water and extracted with dichloromethane. The extract was dried (MgSO$_4$) and concentrated. The crude material was purified by flash chromatography (EtOAc/hexane) to afford the desired products (35, 57, 58, 71, 85, 152).

(K) Reduction of acetyl analogs to the secondary alcohol derivatives. Sodium borohydride (0.50 mmol) was added to a stirred solution of 103, 104, or 107 (0.118 mmol) in anhydrous methanol (5 mL). After being stirred overnight, the reaction mixture was concentrated in vacuo and the residue dissolved in DCM (25 mL). The organic layer was subsequently washed with distilled water (2×20 mL), the organic extract dried over MgSO$_4$ and concentrated in vacuo to afford the respective secondary alcohol analogs (126, 127, and 128).

N-(4-Cyanophenyl)-3-(N-(4-fluorophenyl)-N-methylsulfamoyl)benzamide (47)

Compound 47 was prepared according to procedure C from 4-aminobenzonitrile (21.5 mg, 0.182 mmol) and 9 (50 mg, 0.162 mmol) to afford 39 mg of 46 (58%). $^1$H NMR (500 MHz, CDCl$_3$) δ 3.17 (s, 3H), 6.99-7.05 (m, 4H), 7.61-7.83 (m, 4H), 7.81 (d, J=8.8 Hz, 2H), 7.99 (s, 1H), 8.17 (dt, J=1.6, 7.4 Hz, 1H), 8.27 (s, 1H). $^{13}$C NMR (126 MHz, CDCl$_3$) δ 38.57, 107.88, 116.02, 116.20, 118.69, 120.19, 125.66, 128.61, 128.68, 129.85, 131.11, 132.41, 133.37, 135.19, 136.74, 136.76, 136.91, 141.56, 160.74, 162.72, 164.21. LC-TOF (M+H$^+$) calcd for C$_{21}$H$_{16}$FN$_3$O$_3$S 410.0975. found 410.0969.

3-(N-(4-Chlorophenyl)-N-methylsulfamoyl)-N-(6-chloropyridazin-3-yl)benzamide (51)

Compound 51 was prepared according to procedure C from 3-amino-6-chloropyridazine (37.6 mg, 0.29 mmol) and 10 (84.7 mg, 0.26 mmol) to afford 80.7 mg of 51 (71%). $^1$H NMR (500 MHz, Acetone) δ 3.27 (s, 3H), 7.21 (d, J=8.7 Hz, 2H), 7.38 (d, J=8.7 Hz, 2H), 7.73 (dd, J=1.2, 7.9 Hz, 1H), 7.78 (t, J=7.8 Hz, 1H), 7.86 (d, J=9.3 Hz, 1H), 8.37 (s, 1H), 8.45 (dd, J=1.2, 7.9 Hz, 1H), 8.61 (d, J=9.3 Hz, 1H). $^{13}$C NMR (126 MHz, Acetone) δ 38.57, 122.78, 128.06, 129.02, 129.82, 130.53, 130.62, 132.19, 133.35, 133.43, 135.60, 137.98, 141.20, 153.00, 156.24, 166.03; LC-TOF (M+H$^+$) calcd for C$_{18}$H$_{14}$C$_{12}$N$_4$O$_3$S 437.0242. found 437.0239.

3-(N-(4-Chlorophenyl)-N-methylsulfamoyl)-N-(4-(methylsulfinyl)phenyl)benzamide (59)

Compound 59 was prepared according to procedure C from 4-aminobenzonitrile (45.0 mg, 0.29 mmol) and 10 (84.7 mg, 0.26 mmol) to afford 109.5 mg of 59 (91%). $^1$H NMR (500 MHz, CDCl$_3$) δ 2.74 (s, 3H), 3.20 (s, 3H), 7.04 (d, J=8.8 Hz, 2H), 7.29 (d, J=8.8 Hz, 2H), 7.58-7.64 (m, 4H), 7.85 (d, J=7.0 Hz, 2H), 8.13 (s, 1H), 8.20 (d, J=7.4 Hz, 1H), 9.23 (s, 1H). $^{13}$C NMR (126 MHz, CDCl$_3$) δ 38.32, 43.68, 121.15, 121.26, 124.73, 126.07, 128.00, 129.31, 129.59, 130.81, 132.58, 133.59, 135.61, 136.69, 139.51, 140.25, 140.84, 164.58. LC-TOF (M+H$^+$) calcd for C$_{21}$H$_{19}$ClN$_2$O$_4$S$_2$ 463.0553. found 463.0544.

3-(N-(4-Chlorophenyl)-N-methylsulfamoyl)-N-(4-(methylsulfonyl)phenyl)benzamide (61)

Compound 61 was prepared according to procedure C from 4-(methylsulfonyl)aniline (157, 29.0 mg, 0.169 mmol) and 10 (50 mg, 0.154 mmol) to afford 56.1 mg of 71 (76%). $^1$H NMR (500 MHz, CDCl$_3$) δ 3.07 (s, 3H), 3.19 (s, 3H), 7.03 (d, J=8.7 Hz, 2H), 7.30 (d, J=8.7 Hz, 2H), 7.59-7.65 (m, 2H), 7.85 (d, J=8.8 Hz, 2H), 7.89 (d, J=8.8 Hz, 2H), 8.04 (s, 1H), 8.17 (d, J=7.5 Hz, 1H), 8.42 (s, 1H). $^{13}$C NMR (126 MHz, CDCl$_3$) δ 38.30, 44.63, 114.08, 120.43, 125.83, 127.96, 128.70, 129.33, 129.82, 131.07, 132.39, 133.64, 135.19, 135.82, 136.87, 139.44, 142.43, 164.27. LC-TOF (M+H$^+$) calcd for C$_{21}$H$_{19}$ClN$_2$O$_5$S$_2$ 479.0502. found 479.0497.

3-(N-(4-Chlorophenyl)-N-methylsulfamoyl)-N-(4-cyanophenyl)benzamide (64)

Compound 64 was prepared according to procedure C from 4-aminobenzonitrile (20.0 mg, 0.169 mmol) and 10 (50 mg, 0.154 mmol) to afford 45.3 mg of 69 (76%). $^1$H NMR (500 MHz, CDCl$_3$) δ 3.20 (s, 3H), 7.04 (d, J=8.8 Hz, 2H), 7.30 (d, J=8.9 Hz, 2H), 7.62-7.69 (m, 4H), 7.87 (dd, J=1.9, 8.9 Hz, 2H), 8.08 (s, 1H), 8.21 (dt, J=1.6, 7.4 Hz, 1H). $^{13}$C NMR (126 MHz, CDCl$_3$) δ 42.17, 110.96, 122.83, 124.42, 130.33, 131.80, 131.87, 131.93, 133.15, 133.20, 133.26, 133.44, 134.76, 136.46, 137.07, 137.51, 139.48, 140.57, 143.35, 146.48, 169.13. LC-TOF (M+H$^+$) calcd for C$_{21}$H$_{16}$ClN$_3$O$_3$S 426.0679. found 426.0673.

3-(N-(4-Chlorophenyl)-N-methylsulfamoyl)-N-(5-cyanopyridin-2-yl)benzamide (71)

Compound 71 was prepared according to procedure C from 4'-aminoacetophenone (22.3 mg, 0.165 mmol) and 10 (50 mg, 0.154 mmol) to afford 33.5 mg of 71 (51%). $^1$H NMR (500 MHz, CDCl$_3$) δ 3.20 (s, 3H), 7.05 (d, J=8.8 Hz, 2H), 7.31 (d, J=8.8 Hz, 2H), 7.67 (t, J=7.8 Hz, 1H), 7.73 (dt, J=1.3, 8.0 Hz, 1H), 8.03 (dd, J=2.2, 8.7 Hz, 1H), 8.09 (t, J=1.6 Hz, 1H), 8.18 (dt, J=1.3, 8.0 Hz, 1H), 8.50 (d, J=8.7 Hz, 1H), 8.62 (d, J=1.7 Hz, 1H), 8.76 (s, 1H). $^{13}$C NMR (126 MHz, CDCl$_3$) δ 38.29, 105.76, 113.85, 116.59, 126.23, 127.86, 129.39, 129.94, 131.63, 131.93, 133.72, 134.33, 137.44, 139.48, 141.88, 151.75, 153.49, 163.97. LC-TOF (M+H$^+$) calcd for C$_{20}$H$_{15}$ClN$_4$O$_3$S 427.0632. found 427.0624.

N-(4-Cyanophenyl)-3-(N-(4-methoxyphenyl)-N-methylsulfamoyl)benzamide (90)

Compound 90 was prepared according to procedure C from 4-aminobenzonitrile (20.2 mg, 0.171 mmol) and 12 (50 mg, 0.156 mmol) to afford 44.7 mg of 90 (68%). $^1$H NMR (500 MHz, DMSO) δ 3.15 (s, 3H), 3.73 (s, 3H), 6.88 (d, J=9.0 Hz, 2H), 7.0 (d, J=9.0 Hz, 2H), 7.66 (dt, J=1.2, 8.1 Hz, 1H), 7.76 (t, J=7.8 Hz, 1H), 7.85 (d, J=8.8 Hz, 2H), 7.97 (d, J=8.8 Hz, 2H), 8.14 (t, J=1.7 Hz, 1H), 8.27 (dt, J=1.2, 8.0 Hz, 1H), 10.89 (brs, 1H). $^{13}$C NMR (126 MHz, DMSO) δ 38.41, 55.28, 105.68, 114.11, 118.98, 120.43, 126.68, 127.88, 129.58, 130.61, 132.35, 133.15, 133.31, 135.11, 136.54, 143.12, 158.30, 164.57. LC-TOF (M+H$^+$) calcd for C$_{22}$H$_{19}$N$_3$O$_4$S 422.1175. found 422.1167.

3-(N-(4-Acetylphenyl)-N-methylsulfamoyl)-N-(4-chlorophenyl)benzamide (102)

Compound 102 was prepared according to procedure C from 4-chloroaniline (21.6 mg, 0.169 mmol) and 14 (50 mg, 0.150 mmol) to afford 59.1 mg of 102 (89%). $^1$H NMR (500 MHz, CDCl$_3$) δ 2.57 (s, 3H), 3.20 (s, 3H), 7.19 (d, J=8.7 Hz, 2H), 7.31 (d, J=8.7 Hz, 2H), 7.56-7.60 (m, 4H), 7.88 (d, J=8.6 Hz, 2H), 8.01 (s, 1H), 8.13 (dt, J=1.9, 6.6 Hz, 1H), 8.27 (s, 1H). $^{13}$C NMR (126 MHz, CDCl$_3$) δ 26.67, 37.88, 121.72, 125.61, 125.88, 129.12, 129.21, 129.74, 130.06, 130.53, 132.37, 135.60, 135.75, 136.02, 136.75, 145.12, 163.99, 197.13. LC-TOF (M+H$^+$) calcd for C$_{22}$H$_{19}$ClN$_2$O$_4$S 443.0832. found 443.0826.

3-(N-(4-Acetylphenyl)-N-methylsulfamoyl)-N-(5-chloropyridin-2-yl)benzamide (103)

Compound 103 was prepared according to procedure C from 2-amino-5-chloropyridine (21.7 mg, 0.169 mmol) and 14 (50 mg, 0.150 mmol) to afford 45.8 mg of 103 (67%). $^1$H NMR (500 MHz, CDCl$_3$) δ 2.61 (s, 3H), 3.25 (s, 3H), 7.25 (d, J=8.7 Hz, 2H), 7.63 (t, J=7.8 Hz, 1H), 7.71 (dt, J=1.3, 8.0 Hz, 1H), 7.74 (dd, J=2.6, 8.9 Hz, 1H), 7.94 (d, J=8.7 Hz, 2H), 8.01 (t, J=1.6 Hz, 1H), 8.15 (dt, J=1.4, 7.9 Hz, 1H), 8.25 (d, J=2.3 Hz, 1H), 8.31 (d, J=8.9 Hz, 1H), 8.44 (brs, 1H). $^{13}$C NMR (126 MHz, CDCl$_3$) δ 26.69, 37.85, 114.84, 125.81, 125.95, 127.52, 129.25, 129.83, 131.01, 131.93, 134.92, 135.66, 137.13, 138.21, 145.16, 146.67, 149.22, 163.55, 196.92. LC-TOF (M+H$^+$) calcd for C$_{21}$H$_{18}$ClN$_3$O$_4$S 444.0785. found 444.0782.

3-(N-(4-Acetylphenyl)-N-methylsulfamoyl)-N-(4-cyanophenyl)benzamide (106)

Compound 106 was prepared according to procedure C from 4-aminobenzonitrile (20.2 mg, 0.169 mmol) and 14 (50 mg, 0.150 mmol) to afford 47.5 mg of 106 (73%). $^1$H NMR (500 MHz, CDCl$_3$) δ 2.60 (s, 3H), 3.25 (s, 3H), 7.22 (d, J=8.7 Hz, 2H), 7.61-7.69 (m, 4H), 7.80 (d, J=8.8 Hz, 2H), 7.91 (d, J=8.7 Hz, 2H), 8.02 (s, 1H), 8.16 (dt, J=1.6, 7.4 Hz, 1H), 8.24 (s, 1H). $^{13}$C NMR (126 MHz, CDCl$_3$) δ 26.71, 37.96, 107.97, 118.68, 120.18, 125.63, 125.97, 129.27, 129.99, 131.00, 132.46, 133.42, 135.29, 135.74, 137.05, 141.52, 145.10, 164.07, 197.09. LC-TOF (M+H$^+$) calcd for C$_{23}$H$_{19}$N$_3$O$_4$S 434.1175. found 434.1169.

N-(4-Acetylphenyl)-3-(N-(4-acetylphenyl)-N-methylsulfamoyl)benzamide (109)

Compound 109 was prepared according to procedure C from 6-amino-3-pyridinecarbonitrile (20.1 mg, 0.169 mmol) and 10 (50 mg, 0.154 mmol) to afford 60.8 mg of 109 (90%). $^1$H NMR (500 MHz, CDCl$_3$) δ 2.48 (s, 3H), 2.49 (s, 3H), 3.15 (s, 3H), 7.14 (d, J=7.1 Hz, 2H), 7.48-7.49 (m, 2H), 7.72 (d, J=7.3 Hz, 2H), 7.80 (d, J=7.1 Hz, 2H), 7.87 (d, J=7.3 Hz, 2H), 8.08-8.10 (m, 2H). $^{13}$C NMR (126 MHz, CDCl$_3$) δ 30.28, 30.45, 41.75, 123.81, 129.81, 130.45, 133.20, 133.43, 133.58, 134.43, 136.42, 136.80, 139.34, 139.80, 140.66, 146.81, 149.26, 169.05, 201.87, 202.11. LC-TOF (M+H$^+$) calcd for C$_{24}$H$_{22}$N$_2$O$_5$S 451.1328. found 451.1327.

N-(4-Cyanophenyl)-3-(N-methyl-N-(4-(methylsulfonyl)phenyl)sulfamoyl)benzamide (115)

Compound 115 was prepared according to procedure C from 4-aminobenzonitrile (16.0 mg, 0.149 mmol) and 16 (50 mg, 0.135 mmol) to afford 41.8 mg of 117 (66%). $^1$H NMR (500 MHz, CDCl$_3$) δ 3.09 (s, 3H), 3.28 (s, 3H), 7.38 (d, J=8.5 Hz, 2H), 7.64-7.68 (m, 4H), 7.88-7.92 (m, 4H), 8.17 (s, 1H), 8.21 (d, J=6.9 Hz, 1H). $^{13}$C NMR (126 MHz, CDCl$_3$) δ 37.81, 44.31, 107.21, 118.87, 120.42, 120.50, 126.39, 126.48, 128.40, 129.73, 130.53, 132.75, 133.17, 135.73, 136.60, 138.64, 142.37, 145.97, 164.83. LC-TOF (M+H$^+$) calcd for C$_{22}$H$_{19}$N$_3$O$_5$S$_2$ 470.0844. found 470.0840.

N-(4-Chlorophenyl)-3-(N-methyl-N-(4-(methylsulfonyl)phenyl)sulfamoyl)benzamide (117)

Compound 117 was prepared according to procedure C from 6-chloroaniline (18.9 mg, 0.149 mmol) and 16 (50 mg, 0.135 mmol) to afford 56.9 mg of 117 (88%). $^1$H NMR (500 MHz, CDCl$_3$) δ 3.08 (s, 3H), 3.26 (s, 3H), 7.33-7.37 (m, 4H), 7.60-7.65 (m, 4H), 7.89 (d, J=8.8 Hz, 2H), 8.06 (s, 1H), 8.15 (dd, J=1.6, 7.3 Hz, 1H). $^{13}$C NMR (126 MHz, CDCl$_3$) δ 37.88, 44.44, 121.61, 121.71, 125.91, 126.47, 128.46, 129.17, 129.89, 130.08, 130.45, 132.41, 136.06, 136.76, 138.85, 145.97, 163.86. LC-TOF (M+H$^+$) calcd for C$_{21}$H$_{19}$ClN$_2$O$_5$S$_2$ 479.0502. found 479.0503.

N-(4-Cyanophenyl)-3-(N-(4-(1-hydroxyethyl)phenyl)-N-methylsulfamoyl)benzamide (126)

Compound 126 was prepared according to procedure K from 103 (25 mg, 0.058 mmol) to afford 23.1 mg of 126 (93%). $^1$H NMR (500 MHz, CDCl$_3$) δ 1.46 (d, J=6.3 Hz, 3H), 3.20 (s, 3H), 4.89 (q, J=6.3 Hz, 1H), 7.05 (d, J=8.5 Hz, 2H), 7.32 (d, J=8.5 Hz, 2H), 7.64-7.68 (m, 3H), 7.75 (d, J=7.9 Hz, 1H), 7.81 (d, J=8.7 Hz, 2H), 7.93 (t, J=1.5 Hz, 1H), 8.18 (d, J=7.8 Hz, 1H), 8.24 (s, 1H). $^{13}$C NMR (126 MHz, CDCl$_3$) δ 25.34, 38.38, 69.70, 107.88, 118.68, 120.19, 125.67, 126.20, 126.78, 129.83, 131.14, 132.36, 133.35, 134.97, 137.19, 139.95, 141.56, 145.55, 164.17. LC-TOF (M+Na$^+$) calcd for C$_{23}$H$_{21}$N$_3$O$_4$S 458.1150. found 458.1141.

3-((4-Chlorobenzyl)sulfonyl)-N-(4-cyanophenyl)benzamide (174)

Compound 174 was prepared according to procedure C from 4-aminobenzonitrile (34.3 mg, 0.29 mmol) and 168 (80.8 mg, 0.26 mmol) to afford 89.6 mg of 174 (84%). $^1$H NMR (500 MHz, CDCl$_3$) δ 4.36 (s, 2H), 7.07 (d, J=8.4 Hz, 2H), 7.29 (d, J=8.4 Hz, 2H), 7.67 (t, J=8.3 Hz, 1H), 7.70 (d, J=8.7 Hz, 2H), 7.80 (d, J=7.9 Hz, 1H), 7.85 (d, J=8.7 Hz, 2H), 8.13 (t, J=1.6 Hz, 1H), 8.25 (d, J=7.9 Hz, 1H). $^{13}$C NMR (126 MHz, CDCl$_3$) δ 62.02, 107.80, 118.76, 120.16, 120.25, 125.96, 126.52, 129.09, 130.01, 131.99, 132.17, 133.37, 133.75, 135.41, 135.55, 138.11, 141.74, 163.98. LC-TOF (M+H$^+$) calcd for C$_{21}$H$_{15}$ClN$_2$O$_3$S 411.0570. found 411.0560.

As discussed above, Tables 1-10 are presented and followed by details relating to the synthesis and characterization of compounds prepared. Inhibition assays and related testing of such compounds are conducted according to well-known literature protocols including those found in Silverman, et al., *Biorg. Med. Chem. Lett.* 22 (2012) 2789-2793 and the references cited therein, such references and tests incorporated herein by reference.

TABLE 1

C2-8 Derivatives and Their SIRT2 Inhibitory Activities at 10 μM.

| Cmpd No. | Cmpd ID | R₁ | R₂ | R₃ | X | Y | % of SIRT2 inhibition at 10 μM |
|---|---|---|---|---|---|---|---|
| 23 | MAK-33 | 2-(5-chloropyridine) | 4-chlorophenyl | H | NH | NH | 0 |
| 24 | MAK-64 | 4-cyanophenyl | 4-chlorophenyl | H | NH | NH | 0 |
| 25 | MAK-68 | 4-chlorophenyl | 4-chlorophenyl | H | NHCH₂ | NH | 0 |
| 26 | MAK-77 | 3-(6-chloropyridazine) | 4-chlorophenyl | H | NH | NH | 0 |
| 27 | MAK-86 | 2-pyridine | 4-chlorophenyl | H | NHCH₂ | NH | 2 |
| 28 | MAK-103 | 2-(5-methoxypyridine) | 4-chlorophenyl | H | NH | NH | 22 |
| 29 |  | 4-chlorophenyl | 4-chlorophenyl | OCH₃ | NH | NH | 15 |
| 30 | MAK-56 | 4-chlorophenyl | 4-chlorophenyl | H | NHCH₂ | NHCH₂ | 0 |
| 31 | MAK-7 | 2-thiazole | 4-chlorophenyl | H | NH | NH | 0 |
| 32 | MAK-8 | methylene-2-thiazole | 4-chlorophenyl | H | NH | NH | 0 |
| 33 | MAK-9 | 2-(4-methylthiazole) | 4-chlorophenyl | H | NH | NH | 0 |
| 34 | MAK-10 | 2-(5-chlorothiazole) | 4-chlorophenyl | H | NH | NH | 15 |
| 35 | MAK-23 | 4-chlorophenyl | 4-chlorophenyl | OH | NH | NH | 11 |
| 36 | MAK-66 | 2-(5-trifluoromethyl-1,3,4-oxadiazole) | 4-chlorophenyl | H | NH | NH | 0 |
| 37 | MAK-98 | 2-(5-bromothiazole) | 4-chlorophenyl | H | NH | NH | 0 |
| 38 | MAK-13 | 2-(5-chlorothiazole) | 4-bromophenyl | H | NH | NH | 16 |
| 39 | MAK-14 | 2-thiazole | 4-bromophenyl | H | NH | NH | 0 |
| 40 | MAK-63-B | 4-cyanophenyl | 4-cyanophenyl | H | NH | NH | 0 |
| 41 | MAK-48 | 2-(5-chloropyridine) | 2-(5-chloropyridine) | H | NH | NH | 1 |
| 42 | MAK-71 | 4-chlorophenyl | 2-(5-chloropyridine) | H | NH | NH | 0 |
| 43 | MAK-116 | 2-(5-chloropyridine) | 4-fluorophenyl | H | NH | NCH₃ | 0 |
| 44 | MAK-118 | 3-(6-chloropyridazine) | 4-fluorophenyl | H | NH | NCH₃ | 0 |
| 45 | MAK-160 | 4-(methylsulfinyl)phenyl | 4-fluorophenyl | H | NH | NCH₃ | 15 |
| 46 | MAK-220 | 4-(methylsulfonyl)phenyl | 4-fluorophenyl | H | NH | NCH₃ | 18 |
| 47 | MAK-221 | 4-cyanophenyl | 4-fluorophenyl | H | NH | NCH₃ | 36 |
| 48 | MAK-233 | 2-(5-cyanopyridin) | 4-fluorophenyl | H | NH | NCH₃ | 16 |
| 49 | MAK-37 | 2-(4-chloropyridine) | 4-chlorophenyl | H | NH | NCH₃ | 32 |
| 50 | MAK-38 | 2-(4-bromopyridine) | 4-chlorophenyl | H | NH | NCH₃ | 0 |
| 51 | MAK-73 | 3-(6-chloropyridazine) | 4-chlorophenyl | H | NH | NCH₃ | 25 |
| 52 | MAK-65 | 2-(5-chloropyrimidine) | 4-chlorophenyl | H | NH | NCH₃ | 29 |
| 53 | MAK-83 | 2-pyridine | 4-chlorophenyl | H | NHCH₂ | NCH₃ | 0 |
| 54 | MAK-92 | 2-(5-fluoropyridine) | 4-chlorophenyl | H | NH | NCH₃ | 33 |
| 55 | MAK-99 | 2-(5-methoxypyridine) | 4-chlorophenyl | H | NH | NCH₃ | 8 |
| 56 | MAK-101 | 2-(5-trifluoromethylpyridine) | 4-chlorophenyl | H | NH | NCH₃ | 33 |
| 57 | MAK-102 | 2-(5-methylpyridine) | 4-chlorophenyl | H | NH | NCH₃ | 29 |
| 58 | MAK-106 | 2-(5-hydroxypyridine) | 4-chlorophenyl | H | NH | NCH₃ | 12 |
| 59 | MAK-107 | 4-(methylsulfinyl)pehnyl | 4-chlorophenyl | H | NH | NCH₃ | 37 |
| 60 | MAK-115 | 4-((trifluoromethyl)sulfonyl)phenyl | 4-chlorophenyl | H | NH | NCH₃ | 23 |
| 61 | MAK-126 | 4-(methylsulfinyl)phenyl | 4-chlorophanyl | H | NH | NCH₃ | 37 |
| 62 | MAK-130 | 3-pyridine | 4-chlorophenyl | H | NHCH₂ | NCH₃ | 3 |
| 63 | MAK-135 | 3-(6-methoxypyridazine) | 4-chlorophenyl | H | NH | NCH₃ | 0 |
| 64 | MAK-142 | 4-cyanophenyl | 4-chlorophenyl | H | NH | NCH₃ | 71 |
| 65 | MAK-147 | 2-(methylnicotinate) | 4-chlorophenyl | H | NH | NCH₃ | 25 |
| 65-b | MAK-173 | 2-nicotinate | 4-chlorophenyl | H | NH | NCH₃ | 19 |
| 66 | MAK-134 | 2-(5-cyanopyrimidine) | 4-chlorophenyl | H | NH | NCH₃ | 27 |
| 67 | MAK-146 | 2-nicotinamide | 4-chlorophenyl | H | NH | NCH₃ | 19 |
| 68 | MAK-148 | 5-(2-aminopyridine) | 4-chlorophenyl | H | NH | NCH₃ | 13 |
| 69 | MAK-149 | 4-chlorophenyl | 4-chlorophenyl | OCH₃ | NH | NCH₃ | 34 |
| 70 | MAK-153 | 4-chlorophenyl | 4-chlorophenyl | OH | NH | NCH₃ | 11 |
| 71 | MAK-164 | 2-(5-cyanopyridine) | 4-chlorophanyl | H | NH | NCH₃ | 34 |
| 72 | MAK-169 | 4-sulfonamide | 4-chlorophanyl | H | NH | NCH₃ | 1 |
| 73 | MAK-180 | 4-(dimethylamino)phenyl | 4-chlorophenyl | H | NH | NCH₃ | 7 |
| 74 | MAK-197 | 4-acetamidophenyl | 4-chlorophenyl | H | NH | NCH₃ | 26 |

TABLE 1-continued

C2-8 Derivatives and Their SIRT2 Inhibitory Activities at 10 μM.

| Cmpd No. | Cmpd ID | R₁ | R₂ | R₃ | X | Y | % of SIRT2 inhibition at 10 μM |
|---|---|---|---|---|---|---|---|
| 75 | MAK-72 | 2-(5-trifluoromethyl-1,3,4-oxadiazole) | 4-chlorophenyl | H | NH | NCH₃ | 0 |
| 76 | MAK-96 | 5-(3,4-dimethylisoxazole) | 4-chlorophenyl | H | NH | NCH₃ | 21 |
| 77 | MAK-136 | 5-(4-bromo-3-methylisoxazole) | 4-chlorophenyl | H | NH | NCH₃ | 0 |
| 78 | MAK-139 | 5-(3-methylisoxazole) | 4-chlorophenyl | H | NH | NCH₃ | 1 |
| 79 | MAK-141 | 2-(5-bromothiazole) | 4-chlorophenyl | H | NH | NCH₃ | 6 |
| 80 | MAK-143 | 2-(5-methylhiazole) | 4-chlorophenyl | H | NH | NCH₃ | 3 |
| 81 | MAK-82 | 2-(5-chloropyridine) | 4-bromophenyl | H | NH | NCH₃ | 12 |
| 82 | MAK-93 | 2-(5-fluoropyridine) | 4-bromophenyl | H | NH | NCH₃ | 31 |
| 83 | MAK-100 | 2-(5-methoxypyridine) | 4-bromophenyl | H | NH | NCH₃ | 20 |
| 84 | MAK-108 | 2-(5-hydroxypyridine) | 4-bromophenyl | H | NH | NCH₃ | 0 |
| 85 | MAK-120 | 3-(6-chloropyridazine) | 4-bromophenyl | H | NH | NCH₃ | 16 |
| 86 | MAK-144 | 3-(6-chloropyridazine) | 4-bromophenyl | H | NH | NCH₃ | 13 |
| 87 | MAK-132 | 2-(5-chlorothiazole) | 4-bromophenyl | H | NH | NCH₃ | 0 |
| 88 | MAK-127 | 2-(5-chloropyridine) | 4-methoxyphenyl | H | NH | NCH₃ | 23 |
| 89 | MAK-128 | 3-(6-chloropyridazine) | 4-methoxyphenyl | H | NH | NCH₃ | 5 |
| 90 | MAK-174 | 4-cyanophenyl | 4-methoxyphenyl | H | NH | NCH₃ | 53 |
| 91 | MAK-175 | 4-(methylsulfonyl)phenyl | 4-methoxyphenyl | H | NH | NCH₃ | 21 |
| 92 | MAK-185 | 2-(5-cyanopyridin) | 4-methoxyphenyl | H | NH | NCH₃ | 21 |
| 93 | MAK-152 | 4-chlorophenyl | 4-cyanophenyl | H | NH | NCH₃ | 38 |
| 94 | MAK-154 | 2-(5-chloropyridine) | 4-cyanophenyl | H | NH | NCH₃ | 31 |
| 95 | MAK-158 | 3-(6-chloropyridazine) | 4-cyanophenyl | H | NH | NCH₃ | 10 |
| 96 | MAK-161 | 4-(methylsulfinyl)phnyl | 4-cyanophenyl | H | NH | NCH₃ | 39 |
| 97 | MAK-177 | 4-cyanophenyl | 4-cyanophenyl | H | NH | NCH₃ | 31 |
| 98 | MAK-178 | 4-(methylsulfonyl)phenyl | 4-cyanophenyl | H | NH | NCH₃ | 16 |
| 99 | MAK-182 | 2-(5-cyanopyridine) | 4-cyanophenyl | H | NH | NCH₃ | 10 |
| 100 | MAK-194 | 4-acetophenyl | 4-cyanophenyl | H | NH | NCH₃ | 26 |
| 101 | MAK-204 | 4-acetamidophenyl | 4-cyanophenyl | H | NH | NCH₃ | 3 |
| 102 | MAK-155 | 4-chlorophenyl | 4-acetophenyl | H | NH | NCH₃ | 60 |
| 103 | MAK-156 | 2-(5-chloropyridine) | 4-acetophenyl | H | NH | NCH₃ | 40 |
| 104 | MAK-159 | 3-(6-chloropyridazine) | 4-acetophenyl | H | NH | NCH₃ | 20 |
| 105 | MAK-163 | 4-(methylsulfinyl)phnyl | 4-acetophenyl | H | NH | NCH₃ | 59 |
| 106 | MAK-171 | 4-cyanophenyl | 4-acetophenyl | H | NH | NCH₃ | 51 |
| 107 | MAK-172 | 4-(methylsulfonyl)phenyl | 4-acetophenyl | H | NH | NCH₃ | 21 |
| 108 | MAK-183 | 2-(5-cyanopyridine) | 4-acetophenyl | H | NH | NCH₃ | 23 |
| 109 | MAK-193 | 4-acetophenyl | 4-acetophenyl | H | NH | NCH₃ | 38 |
| 110 | MAK-198 | 4-acetamidophenyl | 4-acetophenyl | H | NH | NCH₃ | 0 |
| 111 | MAK-209 | 4-cyanophenyl | 4-(methylsulfinyl)phenyl | H | NH | NCH₃ | 19 |
| 112 | MAK-214 | 4-(methylsulfinyl)phenyl | 4-(methylsulfinyl)phenyl | H | NH | NCH₃ | 0 |
| 113 | MAK-218 | 4-chlorophenyl | 4-(methylsulfinyl)phenyl | H | NH | NCH₃ | 19 |
| 114 | MAK-219 | 4-fluorophenyl | 4-(methylsulfinyl)phenyl | H | NH | NCH₃ | 5 |
| 115 | MAK-213 | 4-cyanophenyl | 4-(methylsulfonyl)phenyl | H | NH | NCH₃ | 33 |
| 116 | MAK-215 | 4-(methylsulfinyl)phenyl | 4-(methylsulfonyl)phenyl | H | NH | NCH₃ | 1 |
| 117 | MAK-216 | 4-chlorophenyl | 4-(methylsulfonyl)phenyl | H | NH | NCH₃ | 23 |
| 118 | MAK-217 | 2-(5-cyanopyridine) | 4-(methylsulfonyl)phenyl | H | NH | NCH₃ | 3 |
| 119 | MAK-199 | 4-cyanophenyl | 4-cyanophenyl | OCH₃ | NH | NCH₃ | 8 |
| 120 | MAK-202 | 4-(methylsulfinyl)phenyl | 4-cyanophenyl | OCH₃ | NH | NCH₃ | 0 |
| 121 | MAK-206 | 4-cyanophenyl | 4-acetophenyl | OCH₃ | NH | NCH₃ | 22 |

TABLE 1-continued

C2-8 Derivatives and Their SIRT2 Inhibitory Activities at 10 μM.

| Cmpd No. | Cmpd ID | R1 | R2 | R3 | X | Y | % of SIRT2 inhibition at 10 μM |
|---|---|---|---|---|---|---|---|
| 122 | MAK-207 | 4-(methylsulfonyl)phenyl | 4-acetophenyl | OCH3 | NH | NCH3 | 5 |
| 123 | MAK-167 | 4-chlorophanyl | 2-(5-chloropyridine) | H | NH | NCH3 | 17 |
| 124 | MAK-259 | 4-cyanophenyl | 2-(5-chloropyridine) | H | NH | NCH3 | 67 |
| 125 | MAK-260 | 4-(methylsulfinyl)phenyl | 2-(5-chloropyridine) | H | NH | NCH3 | 19 |
| 126 | MAK-237 | 4-cyanophenyl | 4-(1-hydroxyethyl)phenyl | H | NH | NCH3 | 45 |
| 127 | NAK-261 | 4-chlorophenyl | 4-(1-hydroxyethyl)phenyl | H | NH | NCH3 | 16 |
| 128 | MAK-262 | 2-(5-chloropyridine) | 4-(1-hydroxyethyl)phenyl | H | NH | NCH3 | 10 |

TABLE 2

AK-1 Derivatives and Their SIRT2 Inhibitory Activities at 10 μM.

| Cmpd No. | Cmpd ID | R1 | R2 | X | % of SIRT2 Inhibition at 10 μM |
|---|---|---|---|---|---|
| 129 | MAK-40 | 3-(5-chloropyridine) | H | NH | 2 |
| 130 | MAK-39 | 3-(5-bromopyridine) | H | NH | 0 |
| 131 | MAK-58 | 3-bromophenyl | H | NHCH2 | 9 |
| 132 | MAK-60 | 3-chlorophenyl | H | NHCH2 | 0 |
| 133 | MAK-69 | 3-cyanophenyl | H | NH | 9 |
| 134 | MAK-70 | 3-(6-chloropyridizine) | H | NH | 0 |
| 135 | MAK-78 | 2-(5-chloropyridine) | H | NH | 0 |
| 136 | MAK-87 | 2-pyridine | H | NHCH2 | 0 |
| 137 | MAK-113 | 3-(trifluoromethyl)phenyl | H | NH | 0 |
| 138 | MAK-114 | 3-(methylsulfinyl)phenyl | H | NH | 4 |
| 139 | MAK-121 | 3-(methylsulfonyl)phenyl | H | NH | 10 |
| 140 | MAK-131 | 3-pyridine | H | NH | 0 |
| 141 | MAK-170 | 3-sulfonamide | H | NH | 1 |
| 142 | MAK-16 | 2-(5-chlorothiazole) | H | NH | 0 |
| 143 | MAK-17 | 2-(4-methylthiazole) | H | NH | 11 |
| 144 | MAK-18 | methylene-2-thiazole | H | NH | 0 |
| 145 | MAK-29 | 2-thiazole | H | NH | 0 |
| 146 | MAK-67 | 2-(5-trifluoromethyl-1,3,4-oxadiazole) | H | NH | 0 |
| 147 | MAK-75 | 2-(4-methyloxazole) | H | NH | 0 |
| 148 | MAK-94 | 2-(5-bromothiazole) | H | NH | 0 |
| 149 | MAK-95 | 5-(3,4-dimethylisoxazole) | H | NH | 23 |
| 150 | MAK-140 | 5-(3-methylisoxazole) | H | NH | 0 |
| 151 | MAK-57 | 3-bromophenyl | OCH3 | NH | 5 |
| 152 | MAK-59 | 3-bromophenyl | OH | NH | 0 |

TABLE 3

The Structures of Sulfone, Sulfoxide, and Thioether derivatives of C2-8 scaffold.

| Comd No. | Comd ID | R1 | R2 | X | Y | Z | % of SIRT2 Inhibition at 10 μM |
|---|---|---|---|---|---|---|---|
| 171 | MAK-88 | Cl | Cl | CH | CH | SO2 | 0 |
| 172 | MAK-89 | Cl | Br | CH | CH | SO2 | 0 |
| 173 | MAK-90 | Cl | Cl | N | CH | SO2 | 2 |
| 174 | MAK-91 | Cl | CN | CH | CH | SO2 | 40 |
| 175 | MAK-162 | Cl | SOCH3 | CH | CH | SO2 | 31 |
| 176 | MAK-166 | Cl | CN | N | CH | SO2 | 36 |
| 177 | MAK-208 | Cl | SO2CH3 | CH | CH | SO2 | 17 |
| 178 | MAK-211 | Cl | COCH3 | CH | CH | SO2 | 23 |
| 179 | MAK-212 | Cl | Cl | N | N | SO2 | 0 |
| 180 | MAK-244 | OCH3 | CN | CH | CH | SO2 | 50 |
| 181 | MAK-245 | Cl | CN | CH | CH | S | 81 |
| 182 | MAK-248 | Cl | SOCH3 | CH | CH | S | 60 |
| 183 | MAK-241 | SCH3 | CN | CH | CH | S | 83 |
| 186 | MAK-249 | Cl | CN | CH | CH | SO | 47 |
| 187 | MAK-250 | Cl | SOCH3 | CH | CH | SO | 24 |
| 188 | MAK-253 | Cl | SO2CH3 | CH | CH | SO | 18 |
| 189 | MAK-247 | OCH3 | CN | CH | CH | SO | 21 |

TABLE 4

Microsomal Stability Screen of Selected Active Compounds.

| Compd No. | Compd ID | Test conc (μM) | Test species | Mean remaining parent with NADPH (%) | Mean remaining parent NADPH-free (%) | Comment |
|---|---|---|---|---|---|---|
| | Verapamil | 1 | Human | 17% | 111% | metabolized control |
| | Warfarin | 1 | Human | 100% | 103% | non-metabolized control |
| 47 | MAK-221 | 1 | Human | 16% | 89% | |
| 51 | MAK-73 | 1 | Human | 0% | 78% | |
| 59 | MAK-107 | 1 | Human | 16% | 99% | |
| 61 | MAK-126 | 1 | Human | 2% | 112% | |
| 64 | MAK-142 | 1 | Human | 2% | 102% | |
| 71 | MAK-164 | 1 | Human | 2% | 91% | |
| 90 | MAK-174 | 1 | Human | 2% | 106% | |
| 102 | MAK-155 | 1 | Human | 12% | 94% | |
| 103 | MAK-156 | 1 | Human | 12% | 82% | |
| 106 | MAK-171 | 1 | Human | 12% | 104% | |
| 126 | MAK-237 | 1 | Human | 24% | 93% | |
| 174 | MAK-91 | 1 | Human | 89% | 93% | |
| | Verapamil | 1 | Mouse | 2% | 110% | metabolized control |
| | Warfarin | 1 | Mouse | 102% | 101% | non-metabolized control |
| 47 | MAK-221 | 1 | Mouse | 28% | 89% | |
| 51 | MAK-73 | 1 | Mouse | 0% | 71% | |
| 59 | MAK-107 | 1 | Mouse | 16% | 99% | |
| 61 | MAK-126 | 1 | Mouse | 4% | 100% | |
| 64 | MAK-142 | 1 | Mouse | 4% | 102% | |
| 71 | MAK-164 | 1 | Mouse | 1% | 96% | |
| 90 | MAK-174 | 1 | Mouse | 2% | 90% | |
| 102 | MAK-155 | 1 | Mouse | 0% | 108% | |
| 103 | MAK-156 | 1 | Mouse | 0% | 91% | |
| 106 | MAK-171 | 1 | Mouse | 2% | 117% | |
| 126 | MAK-237 | 1 | Mouse | 40% | 83% | |
| 174 | MAK-91 | 1 | Mouse | 68% | 100% | |

TABLE 5

Microsomal Intrinsic Clearance of Selected Active Compound.

| Compd No. | Compd ID | Test conc (μM) | Test species | NADPH-dependent $CL_{int}^{a}$ | NADPH-dependent $T1/2^{b}$ (min) | NADPH-free $CL_{int}^{a}$ | NADPH-free $T_{1/2}^{b}$ (min) | Comment | % remaining 60 min |
|---|---|---|---|---|---|---|---|---|---|
| | Verapamil | 1 | Human | 209 | 11 | 0 | >180 | Metabolized Control | 96% |
| | Warfarin | 1 | Human | 0 | >180 | 0 | >180 | Non-metabolized control | 102% |
| 64 | MAK-142 | 1 | Human | 222 | 10.4 | 17 | 133 | | 1.4% |
| 106 | MAK-171 | 1 | Human | 158 | 14.7 | 14 | 163 | | 14% |
| 126 | MAK-237 | 1 | Human | 234 | 9.9 | 17 | 133 | | 4.4% |
| 182 | MAK-248 | 1 | Human | 241 | 9.6 | 39 | 59 | | 5.3% |
| | Verapamil | 1 | Mouse | 649 | 3.6 | 1 | >180 | Metabolized Control | 98% |
| | Warfarin | 1 | Mouse | 0 | >180 | 0 | >180 | Non-metabolized control | 99% |
| 64 | MAK-142 | 1 | Mouse | 406 | 5.7 | 11 | >180 | | 1.3% |
| 106 | MAK-171 | 1 | Mouse | 435 | 5.3 | 19 | 123 | | 3.8% |
| 126 | MAK-237 | 1 | Mouse | 552 | 4.2 | 22 | 104 | | 0.6% |
| 182 | MAK-248 | 1 | Mouse | 445 | 5.2 | 58 | 40 | | 0.8% |

[a]Microsomal Intrinsic Clearance (μl min$^{-1}$ mg$^{-1}$).
[b]Half-life (min).

TABLE 6

Plasma Half Life of Selected Active Compounds.

| Compd No. | Compd ID | Test conc (μM) | Test species | Plasma $T_{1/2}^{a}$ | Fraction remaining, last time point (%) | Comment |
|---|---|---|---|---|---|---|
| | Propantheline | 5 | Mouse | 18 | 3.4% | Metabolized control |
| | Warfarin | 5 | Mouse | >180 | 98% | Stable control |
| 64 | MAK-142 | 5 | Mouse | 212 | 73% | |
| 106 | MAK-171 | 5 | Mouse | >180 | 93% | |
| 182 | MAK-248 | 5 | Mouse | 89 | 62% | |

[a]Half-life (min)

TABLE 7

Caco-2 Permeability of Selected Active Compounds.

| Compd No. | Compd ID | Test conc (μM) | Assay duration (h) | Mean A->B Papp$^{a}$ | Mean B->A Papp$^{a}$ | Efflux ratio | Comment |
|---|---|---|---|---|---|---|---|
| | Ranitidine | 10 | 2 | 0.4 | 2.6 | 6.6 | Low permeability control |
| | Warfarin | 10 | 2 | 42.1 | 14.1 | 0.3 | High permeability control |
| 51 | MAK-73 | 10 | 2 | 23.2 | 15.1 | 0.7 | |
| 59 | MAK-107 | 10 | 2 | 25.7 | 44.5 | 1.7 | |
| 64 | MAK-142 | 10 | 2 | 19.9 | 4.4 | 0.2 | |
| 106 | MAK-171 | 10 | 2 | 13.9 | 7.9 | 0.6 | |
| 126 | MAK-237 | 10 | 2 | 32.9 | 23.1 | 0.7 | |

[a] Apparent permeability
$P_{app}$(B->A)/Papp(A->B) ($10^{-6}$ cm s$^{-1}$)

TABLE 8

PBS Express solubility of Selected Active Compounds.

| Compd No. | Compd ID | Medium | Solubility limit (μM)[a] 45 min | 16 h | Comment |
|---|---|---|---|---|---|
| | Tamoxifen | PBS | 15.6 | 15.6 | Low solubility control |
| | Reserpine | PBS | 15.6 | 15.6 | Low solubility control |
| | Verapamil | PBS | >500 | >500 | High solubility control |
| 47 | MAK-221 | PBS | 3.9 | 7.8 | |
| 51 | MAK-73 | PBS | 15.625 | 3.91 | |
| 59 | MAK-107 | PBS | 15.6 | 15.6 | |
| 61 | MAK-126 | PBS | 15.625 | 15.625 | |
| 64 | MAK-142 | PBS | 7.8125 | 7.8125 | |
| 71 | MAK-164 | PBS | 31.25 | 62.5 | |
| 90 | MAK-174 | PBS | 15.625 | 15.625 | |
| 102 | MAK-155 | PBS | 7.8125 | 7.8125 | |
| 103 | MAK-156 | PBS | 15.625 | 15.625 | |
| 106 | MAK-171 | PBS | 15.625 | 15.625 | |
| 126 | MAK-237 | PBS | 62.5 | 62.5 | |
| 174 | MAK-91 | PBS | 62.5 | 62.5 | |
| 182 | MAK-248 | PBS | 15.6 | 15.6 | |

[a]Solubility limit is highest concentration with no detectable precipitate.

TABLE 9

Plasma Protein Binding of Selected Active Compounds.

| Compd No. | Compd ID | Test conc (μM) | Assay duration (h) | Mean fraction bound (%) | Comment |
|---|---|---|---|---|---|
| | Propranol | 5 | 4 | 82.9% | Low binding control |
| | Warfarin | 5 | 4 | 99.7% | High binding control |
| 51 | MAK-73 | 5 | 4 | 99.8% | |
| 59 | MAK-107 | 5 | 4 | 99.1% | |

Analytical Data ($^1$H, $^{13}$C, and MS) for all Compounds Synthesized in this Study.

3-(N-(4-chlorophenyl)sulfamoyl)benzoic acid (5)

Compound 5 was prepared according to procedure B to afford 1169 mg of white powder (94%). $^1$H NMR (500 MHz, DMSO) δ 7.10 (d, 2H, J=8.9 Hz), 7.32 (d, 2H, 8.8 Hz), 7.70 (t, 1H, J=7.9 Hz), 7.95 (dt, 1H, J=7.9, 1.4 Hz), 8.15 (dt, 1H, J=1.2, 7.9 Hz), 8.30 (t, 1H, J=7.9 Hz), 10.60 (s, 1H). $^{13}$C NMR (126 MHz, CDCl$_3$) δ 122.67, 128.28, 129.13, 129.28, 130.50, 131.13, 131.81, 133.93, 135.37, 139.69, 167.20.

3-(N-(4-bromophenyl)sulfamoyl)benzoic acid (6)

Compound 6 was prepared according to procedure B to afford 1379 mg of white powder (96%). $^1$H NMR (500 MHz, CDCl$_3$) δ 7.99 (d, J=8.8 Hz, 2H), 7.33 (d, J=8.8 Hz, 2H), 7.53 (t, J=7.8 Hz, 1H), 7.90 (d, J=7.8 Hz, 1H), 8.20 (d, J=7.8 Hz, 1H), 8.47 (s, 1H). $^{13}$C NMR (126 MHz, CDCl$_3$) δ 118.03, 122.74, 128.27, 129.13, 131.06, 131.76, 132.20, 133.91, 135.99, 139.73, 167.05.

3-(N-(4-cyanophenyl)sulfamoyl)benzoic acid (7)

Compound 7 was prepared according to procedure B to afford 941 mg of white powder (78%). $^1$H NMR (500 MHz, CDCl$_3$) δ 7.22 (dd, J=2.1, 8.8 Hz, 2H), 7.48-7.53 (m, 3H), 7.95 (d, J=7.7 Hz, 1H), 8.20 (d, J=7.7 Hz, 1H), 8.50 (s, 1H). $^{13}$C NMR (126 MHz, CDCl$_3$) δ 106.95, 118.71, 119.21, 128.16, 129.17, 130.43, 133.52, 134.26, 139.51, 141.75, 169.13.

3-(N-(5-chloropyridin-2-yl)sulfamoyl)benzoic acid (8)

Compound 8 was prepared according to procedure B to afford 536 mg of white powder (43%). $^1$H NMR (500 MHz, CDCl$_3$) δ 7.47-7.51 (m, 1H), 7.85 (t, J=7.8 Hz, 1H), 7.97-8.01 (m, 1H), 8.21-8.24 (m, 3H), 8.46 (s, 1H).

3-(N-(4-fluorophenyl)-N-methylsulfamoyl)benzoic acid (9)

Compound 9 was prepared according to procedure B to afford 1000 mg of white powder (81%). $^1$H NMR (500 MHz, CDCl$_3$) δ 3.21 (s, 3H), 7.00-7.08 (m, 4H), 7.61 (t, J=7.8 Hz, 1H), 7.74 (d, J=8.1 Hz, 1H), 8.33 (d, J=1.1 Hz, 1H), 8.35 (s, 1H). $^{13}$C NMR (126 MHz, CDCl$_3$) δ 38.56, 115.95, 116.13, 128.52, 128.59, 129.34, 129.38, 130.24, 132.73, 134.30, 136.93, 136.95, 137.24, 160.73, 162.71, 169.85.

3-(N-(4-chlorophenyl)-N-methylsulfamoyl)benzoic acid (10)

Compound 10 was prepared according to procedure B to afford 1222 mg of white powder (94%). $^1$H NMR (500 MHz, CDCl$_3$) δ 3.21 (s, 3H), 7.04 (d, J=8.8 Hz, 2H), 7.29 (d, J=8.8 Hz, 2H), 7.61 (t, J=7.8 Hz, 1H), 7.72 (dt, J=1.5, 7.9 Hz, 1H), 8.33 (dt, J=1.5, 7.9 HZ, 1H), 8.37 (t, J=1.5 Hz, 1H). $^{13}$C NMR (126 MHz, CDCl$_3$) δ 38.28, 127.84, 129.29, 129.32, 129.40, 130.26, 132.72, 133.50, 134.37, 137.19, 139.56, 170.12.

3-(N-(4-bromophenyl)-N-methylsulfamoyl)benzoic acid (11)

Compound 11 was prepared according to procedure B to afford 1432 mg of white powder (97%). $^1$H NMR (500 MHz, CDCl$_3$) δ 3.23 (s, 3H), 7.00 (d, J=8.7 Hz, 2H), 7.47 (d, J=7.8 Hz, 2H), 7.63 (t, J=7.8 Hz, 1H), 7.74 (d, J=7.9 Hz, 1H), 8.36 (d, J=7.9 Hz, 1H), 8.39 (s, 1H). $^{13}$C NMR (126 MHz, CDCl$_3$) δ 38.22, 121.48, 128.13, 129.30, 129.40, 130.27, 132.27, 132.67, 134.37, 137.16, 140.11, 169.77.

3-(N-(4-methoxyphenyl)-N-methylsulfamoyl)benzoic acid (12)

Compound 12 was prepared according to procedure B to afford 1038 mg of white powder (81%). $^1$H NMR (500 MHz, CDCl$_3$) δ 3.20 (s, 3H), 3.81 (s, 3H), 6.82 (d, J=8.9 Hz, 2H), 6.98 (d, J=8.9 Hz, 2H), 2H), 7.59 (t, J=7.8 Hz, 1H), 7.74 (d, J=7.9 Hz, 1H), 8.32 (d, J=7.8 Hz, 1H), 8.38 (s, 1H). $^{13}$C NMR (126 MHz, CDCl$_3$) δ 38.71, 55.50, 114.28, 128.14, 129.21, 129.43, 130.07, 132.89, 133.63, 134.10, 137.62, 158.95, 170.00.

3-(N-(4-cyanophenyl)-N-methylsulfamoyl)benzoic acid (13)

Compound 12 was prepared according to procedure B to afford 669 mg of white powder (53%). $^1$H NMR (500 MHz, DMSO) δ 3.21 (s, 3H), 7.39 (d, J=8.8 Hz, 2H), 7.74-7.75 (m, 2H), 7.86 (d, J=8.8 Hz, 2H), 7.95 (d, J=0.9 Hz, 1H), 8.24-8.26 (m, 1H). $^{13}$C NMR (126 MHz, DMSO) δ 37.27, 109.37, 118.30, 126.19, 127.67, 130.23, 131.24, 131.84, 133.10, 134.08, 135.85, 144.89, 165.73.

3-(N-(4-acetylphenyl)-N-methylsulfamoyl)benzoic acid (14)

Compound 14 was prepared according to procedure B to afford 625 mg of white powder (47%). $^1$H NMR (500 MHz, DMSO) δ 2.57 (s, 3H), 3.21 (s, 3H), 7.31 (d, J=8.7 Hz, 2H), 7.72-7.76 (m, 2H), 7.94 (d, j=8.7 Hz, 2H), 7.98 (s, 1H), 8.23-8.25 (m, 1H). $^{13}$C NMR (126 MHz, DMSO) δ 26.70, 37.49, 125.52, 127.70, 128.97, 130.13, 131.27, 131.70, 133.94, 134.97, 136.15, 144.82, 165.69, 197.01.

3-(N-methyl-N-(4-(methylsulfinyl)phenyl)sulfamoyl)benzoic acid (15)

Compound 15 was prepared according to procedure B to afford 1029 mg of white powder (73%). $^1$H NMR (500 MHz, CDCl$_3$) δ 2.78 (s, 3H), 3.22 (s, 3H), 7.31 (d, J=8.4 Hz, 2H), 7.59-7.62 (m, 3H), 7.73 (d, J=7.7 Hz, 1H), 8.11 (s, 1H), 8.28 (d, J=7.5 HZ, 1H). $^{13}$C NMR (126 MHz, CDCl$_3$) δ 37.87, 43.45, 124.41, 127.15, 129.01, 129.18, 131.30, 134.29, 136.15, 143.57, 143.94, 166.99.

3-(N-methyl-N-(4-(methylsulfonyl)phenyl)sulfamoyl)benzoic acid (16)

Compound 15 was prepared according to procedure B to afford 1149 mg of white powder (78%). $^1$H NMR (500 MHz, CDCl$_3$) δ 3.08 (s, 3H), 3.24 (s, 3H), 7.37-7.35 (d, J=8.7 Hz, 2H), 7.59 (t, J=7.8 Hz, 1H), 7.73 (d, J=7.9 Hz, 1H), 7.90 (d, J=8.7 Hz, 2H), 8.16 (s, 1H), 8.29 (d, J=7.9 Hz, 1H). $^{13}$C NMR (126 MHz, CDCl$_3$) δ 37.73, 44.48, 126.35, 128.38, 128.97, 129.39, 131.48, 131.68, 134.48, 136.42, 138.58, 146.18, 166.65.

3-(N-(4-acetylphenyl)-N-methylsulfamoyl)-4-methoxybenzoic acid (19)

Compound 19 was prepared according to procedure B to afford 957 mg of white powder (66%). $^1$H NMR (500 MHz, CDCl$_3$) δ 2.58 (s, 3H), 3.39 (s, 3H), 3.76 (s, 3H), 6.98 (d, J=8.6 Hz, 1H), 7.35 (d, J=8.9 Hz, 2H), 7.89 (d, J=8.9 Hz, 2H), 8.21 (dd, J=2.2, 8.6 Hz, 1H), 8.59 (d, J=2.1 Hz, 1). $^{13}$C NMR (126 MHz, CDCl$_3$) δ 26.58, 37.65, 56.25, 111.84, 122.86, 123.55, 126.21, 129.14, 133.99, 137.00, 146.01, 160.10, 166.99, 197.46.

3-(N-(5-chloropyridin-2-yl)-N-methylsulfamoyl)benzoic acid (20)

Compound 15 was prepared according to procedure B to afford 482 mg of white powder (37%). $^1$H NMR (500 MHz, CDCl$_3$) δ 3.27 (s, 3H), 7.54-7.74 (m, 4H), 8.21-8.30 (m, 3H). $^{13}$C NMR (126 MHz, CDCl$_3$) δ 35.76, 121.33, 121.53, 128.91, 129.26, 129.53, 131.30, 134.33, 137.20, 137.22, 137.62, 146.64, 151.55, 166.96.

3-(azepan-1-ylsulfonyl)benzoic acid (21)

Compound 21 was prepared according to procedure B to afford 622 mg of white powder (55%). $^1$H NMR (500 MHz, CDCl$_3$) δ 1.61 (m, 4H), 1.74 (m, 4H), 3.32 (t, 4H, J=5.9 Hz), 7.66 (t, 1H, J=7.8 Hz), 8.05 (dt, 1H, J=1.3, 7.9 Hz), 8.30 (d, 1H, J=7.8 Hz), 8.52 (d, 1H, J=1.3 Hz). $^{13}$C NMR (126 MHz, CDCl$_3$) δ 26.85, 29.16, 48.33, 128.49, 129.47, 130.24, 131.88, 133.61, 140.56, 170.10.

3-(azepan-1-ylsulfonyl)-4-methoxybenzoic acid (22)

Compound 22 was prepared according to procedure B to afford 650 mg of white powder (52%). $^1$H NMR (500 MHz, CDCl$_3$) δ 1.64 (m, 4H), 1.77 (brs, 4H), 3.39 (t, J=5.9 Hz, 4H), 4.03 (s, 3H), 7.07 (d, J=8.8 Hz, 1H), 8.25 (dd, J=2.3, 8.8 Hz, 1H), 8.65 (d, J=2.3 Hz, 1H). $^{13}$C NMR (126 MHz, CDCl$_3$) δ 26.84, 29.23, 48.60, 56.43, 111.86, 121.13, 121.27, 127.49, 128.55, 133.83, 135.88, 136.29, 156.71, 160.74, 168.71, 170.19.

N-(4-chlorobenzyl)-3-(N-(4-chlorophenyl)sulfamoyl)benzamide (25)

Compound 25 was prepared according to procedure C to afford 58 mg of white powder (87%). $^1$H NMR (500 MHz, DMSO) δ 4.46 (d, J=4.8 Hz, 2H), 7.10 (d, J=7.7 Hz, 2H), 7.21-7.34 (m, 4H), 7.39 (d, J=7.5 Hz, 2H), 7.68 (t, J=7.5 Hz, 1H), 7.88 (d, J=7.4 Hz, 1H), 8.11 (d, J=7.4 Hz, 1H), 8.30 (s, 1H), 9.35 (s, 1H), 10.57 (s, 1H). $^{13}$C NMR (126 MHz, DMSO) δ 42.11, 121.72, 125.76, 128.24, 128.37, 129.13, 129.19, 129.65, 131.37, 131.43, 135.01, 136.33, 138.24, 139.49, 164.64. LCQ (M+H$^+$) calcd for C$_{20}$H$_{16}$C$_{12}$N$_2$O$_3$S 435. found 435.

3-(N-(4-chlorophenyl)sulfamoyl)-N-(6-chloropyridazin-3-yl)benzamide (26)

Compound 26 was prepared according to procedure C to afford 43 mg of white powder (66%). $^1$H NMR (500 MHz, CDCl$_3$) δ 7.07 (d, J=8.8 Hz, 2H), 7.19 (d, J=8.8 Hz, 2H), 7.59-7.65 (m, 2H), 7.90 (d, J=7.9 Hz, 1H), 8.20 (d, J=7.9 Hz, 1H), 8.48 (s, 1H). 8.66 (d, J=9.5 Hz, 1H). $^{13}$C NMR (126 MHz, CDCl$_3$) δ 122.20, 122.72, 126.03, 129.32, 129.58, 130.28, 130.60, 131.08, 132.19, 134.22, 135.33, 140.18, 152.39, 154.94, 165.34. LCQ (M+H$^+$) calcd for C$_{17}$H$_{12}$Cl$_2$N$_4$O$_3$S 423. found 423.

3-(N-(4-chlorophenyl)sulfamoyl)-N-(pyridin-2-ylmethyl)benzamide (27)

Compound 27 was prepared according to procedure C to afford 60 mg of white powder (97%). $^1$H NMR (500 MHz, CDCl$_3$) δ 4.77 (d, 4.9 Hz, 2H), 7.11 (d, J=8.7 Hz, 2H), 7.18 (d, J=8.7 Hz, 2H), 7.22 (dd, J=5.2, 7.2 Hz, 1H), 7.34 (d, 7.8 Hz, 1H), 7.49 (t, J=7.8 Hz, 1H), 7.69 (dt, J=1.6, 7.7 Hz, 1H), 7.78 (d, J=7.9 Hz, 1H), 8.05 (d, J=7.9 Hz, 1H), 8.27 (t, J=4.8 Hz, 1H), 8.47 (d, J=4.7 Hz, 1H), 8.52 (s, 1H). $^{13}$C NMR (126 MHz, CDCl$_3$) δ 44.92, 122.57, 122.78, 123.43, 125.93, 129.30, 129.41, 130.13, 131.01, 131.55, 135.25, 135.27, 137.24, 139.70, 148.76, 155.68, 165.90. LCQ (M+H$^+$) calcd for C$_{19}$H$_{16}$ClN$_3$O$_3$S 402. found 402.

3-(N-(4-chlorophenyl)sulfamoyl)-N-(5-methoxypyridin-2-yl)benzamide (28)

Compound 28 was prepared according to procedure C to afford 57 mg of white powder (89%). $^1$H NMR (500 MHz, CDCl$_3$) δ 3.87 (s, 3H), 7.05 (d, J=8.8 Hz, 2H), 7.22 (d, J=8.8 Hz, 2H), 7.34 (dd, J=3.0, 9.1 Hz, 1H), 7.57 (t, J=7.8 Hz, 1H), 7.84 (d, J=8.0 Hz, 1H), 7.98 (d, J=2.8 Hz, 1H), 8.12 (d, J=7.9 HZ, 1H), 8.30 (d, J=9.1 Hz, 1H), 8.43 (s, 1H), 8.88 (brs, 1H). $^{13}$C NMR (126 MHz, CDCl$_3$) δ 53.44, 115.18, 123.57, 123.71, 125.72, 129.60, 129.69, 130.47, 131.63, 131.94, 134.37, 134.53, 135.61, 139.63, 144.55, 153.29, 163.45. LCQ (M+H$^+$) calcd for C$_{19}$H$_{16}$ClN$_3$O$_4$S 418. found 418.

N-(4-chlorobenzyl)-3-(N-(4-chlorobenzyl)sulfamoyl)benzamide (30)

Compound 30 was prepared according to procedure C to afford 54.7 mg of white powder (79%). $^1$H NMR (500 MHz, CDCl$_3$) δ 4.01 (s, 2H), 4.53 (s, 2H), 7.08 (d, J=8.3 Hz, 2H), 7.15 (d, J=8.3 Hz, 2H), 7.25 (m, 4H), 7.52 (t, J=7.9 Hz, 1H), 7.87 (d, J=7.9 Hz, 1H), 7.99 (d, J=7.9 Hz, 1H), 8.14 (s, 1H). $^{13}$C NMR (126 MHz, CDCl$_3$) δ 43.26, 46.21, 125.32, 128.55, 128.71, 129.13, 129.38, 129.65, 131.34, 133.22, 133.42, 134.98, 135.14, 136.58, 140.78, 166.55. LCQ (M+H$^+$) calcd for C$_{21}$H$_{18}$Cl$_2$N$_2$O$_3$S 449. found 449.

3-(N-(4-chlorophenyl)sulfamoyl)-N-(thiazol-2-yl)benzamide (31)

Compound 31 was prepared according to procedure C to afford 49 mg of white powder (80%). $^1$H NMR (500 MHz, CDCl$_3$) δ 6.98 (d, 2H, J=8.8 Hz), 7.17 (d, 2H, J=8.8 Hz), 7.54 (t, 1H, 7.9 Hz), 7.78 (d, 1H, 8.1 Hz), 7.81 (d, 1H, 8.1 Hz), 7.99 (d, 1H, 8.4 Hz), 8.13 (d, 1H 7.9 Hz), 8.47 (s, 1H). $^{13}$C NMR (126 MHz, CDCl$_3$) δ 114.26, 122.82, 126.20, 129.44, 129.70, 130.68, 131.15, 132.38, 133.49, 135.47, 137.07, 140.27, 159.45, 164.17. LCQ (M+H$^+$) calcd for C$_{16}$H$_{12}$ClN$_3$O$_3$S$_2$ 394. found 394.

3-(N-(4-chlorophenyl)sulfamoyl)-N-(thiazol-2-ylmethyl)benzamide (32)

Compound 32 was prepared according to procedure C to afford 51 mg of white powder (81%). $^1$H NMR (500 MHz, CDCl$_3$) δ 4.89 (s, 2H), 7.04 (d, J=8.8 Hz, 2H), 7.17 (d, J=8.8 Hz, 2H), 7.36 (d, J=3.3 Hz, 1H), 7.50 (t, J=7.8 Hz, 1H), 7.72 (d, J=3.3 Hz, 1H), 7.78 (dd, J=0.6, 7.9 Hz, 1H), 8.06 (dd, J=0.6, 7.9 Hz, 1H), 8.31 (s, 1H). $^{13}$C NMR (126 MHz, CDCl$_3$) δ 40.69, 120.26, 122.90, 125.55, 129.26, 129.28, 130.27, 130.58, 131.73, 134.58, 134.62, 135.41, 139.81, 141.79, 166.14, 166.22, 167.50. LCQ (M+H$^+$) calcd for C$_{16}$H$_{12}$ClN$_3$O$_3$S$_2$ 408. found 408.

3-(N-(4-chlorophenyl)sulfamoyl)-N-(4-methylthiazol-2-yl)benzamide (33)

Compound 33 was prepared according to procedure C to afford 59 mg of white powder (94%). $^1$H NMR (500 MHz, CDCl$_3$) δ 2.14 (s, 2H), 6.54 (d, 1H, J=0.9 Hz), 7.08 (d, 2H, J=8.8 Hz), 7.16 (d, 2H, J=8.8 Hz), 7.47 (t, 1H, J=7.9 Hz), 7.84, (d, 1H, J=7.9 Hz), 8.12 (d, 1H, J=7.9 Hz), 8.58 (s, 1H). $^{13}$C NMR (126 MHz, CDCl$_3$) δ 108.71, 123.89, 126.41, 129.37, 129.42, 129.51, 131.03, 131.17, 132.58, 134.08, 134.90, 139.73, 160.30, 162.98, 164.86. LCQ (M+H$^+$) calcd for C$_{16}$H$_{12}$ClN$_3$O$_3$S$_2$ 408. found 408.

3-(N-(4-chlorophenyl)sulfamoyl)-N-(5-chlorothiazol-2-yl)benzamide (34)

Compound 34 was prepared according to procedure C to afford 50 mg of white powder (75%). $^1$H NMR (500 MHz, DMSO) δ 7.12 (d, 2H, J=8.8 Hz), 7.31 (d, 2H, J=8.8 Hz), 7.65 (s, 1H), 7.75 (t, 1H, J=7.9 Hz), 7.96, (d, 1H, J=7.9 Hz), 8.32 (d, 1H, J=7.9 Hz), 8.47 (t, 1H, J=1.5 Hz). $^{13}$C NMR (126 MHz, CDCl$_3$) δ 121.34, 122.69, 126.07, 129.32, 129.61, 130.60, 131.14, 132.16, 135.28, 140.27, 153.53, 164.26. LCQ (M+H$^+$) calcd for C$_{16}$H$_{12}$ClN$_3$O$_3$S$_2$ 428. found 428.

N-(4-chlorophenyl)-3-(N-(4-chlorophenyl)sulfamoyl)-4-hydroxybenzamide (35)

Compound 35 was prepared according to procedure J to afford 17 mg of white powder (45%). $^1$H NMR (500 MHz, DMSO) 67.12 (d, J=8.8 Hz, 1H), 7.25 (d, J=9.0 Hz, 2H), 7.29 (d, J=9.0 Hz, 2H), 7.36 (d, J=8.7 Hz, 2H), 7.82 (d, J=8.8 Hz, 2H), 8.08 (dd, J=2.3, 8.6 Hz, 1H), 8.37 (d, J=2.3 Hz, 1H), 9.80 (brs, 1H). $^{13}$C NMR (126 MHz, Acetone) δ 118.15, 122.55, 122.97, 125.52, 126.99, 128.91, 129.40, 129.89, 130.11, 130.72, 135.25, 137.43, 139.02, 158.61, 164.61. LCQ (M+H$^+$) calcd for C$_{19}$H$_{14}$Cl$_2$N$_2$O$_4$S 437. found 437.

3-(N-(4-chlorophenyl)sulfamoyl)-N-(5-(trifluoromethyl)-1,3,4-oxadiazol-2-yl)benzamide (36)

Compound 36 was prepared according to procedure C to afford 22 mg of white powder (32%). $^1$H NMR (500 MHz, CDCl$_3$) δ 7.02 (d, J=8.7 Hz, 2H), 7.15 (d, J=8.7 Hz, 2H), 7.43 (t, J=7.8 Hz, 1H), 7.69 (d, J=7.7 Hz, 1H), 8.44 (d, J=6.1 Hz, 1H), 8.64 (s, 1H). $^{13}$C NMR (126 MHz, CDCl$_3$) δ 121.50, 123.27, 127.41, 128.74, 129.29, 129.81, 130.88, 133.79, 135.20, 138.83, 169.46, 171.58, 172.30. LCQ (M+H$^+$) calcd for C$_{16}$H$_{10}$ClF$_3$N$_4$O$_4$S 447. found 447.

N-(5-bromothiazol-2-yl)-3-(N-(4-chlorophenyl)sulfamoyl)benzamide (37)

Compound 37 was prepared according to procedure C to afford 64 mg of white powder (88%). $^1$H NMR (500 MHz, DMSO) δ 7.11 (d, J=8.7 Hz, 2H), 7.30 (d, J=8.7 Hz, 2H), 7.69 (s, 1H), 7.74 (t, J=7.9 Hz, 1H), 7.96 (d, J=7.4 Hz, 1H), 8.31 (d, J=7.4 Hz, 1H), 8.46 (s, 1H). $^{13}$C NMR (126 MHz, DMSO) δ 102.44, 121.66, 126.74, 128.37, 129.23, 129.92, 130.36, 132.48, 136.26, 139.72, 158.64, 158.72, 163.95. LCQ (M+H$^+$) calcd for C$_{16}$H$_{11}$BrClN$_3$O$_3$S$_2$ 472. found 472.

3-(N-(4-bromophenyl)sulfamoyl)-N-(5-chlorothiazol-2-yl)benzamide (38))

Compound 38 was prepared according to procedure C to afford 61 mg of white powder (84%). $^1$H NMR (500 MHz, DMSO) δ 6.96 (d, 2H, J=8.8 Hz), 7.33 (d, 2H, J=8.8 Hz), 7.54 (s, 1H), 7.65 (t, 1H, J=7.9 Hz), 7.987, (d, 1H, J=7.9 Hz), 8.21 (d, 1H, J=7.9 Hz), 8.37 (s, 1H). $^{13}$C NMR (126 MHz, CDCl$_3$) δ 118.37, 121.47, 122.99, 126.16, 129.75, 131.27, 132.32, 132.39, 132.91, 134.91, 135.93, 140.35, 156.75, 163.96. LCQ (M+H$^+$) calcd for C$_{16}$H$_{11}$BrClN$_3$O$_3$S$_2$ 472. found 472.

3-(N-(4-bromophenyl)sulfamoyl)-N-(thiazol-2-yl)benzamide (39)

Compound 39 was prepared according to procedure C to afford 49 mg of white powder (72%). $^1$H NMR (500 MHz, CDCl$_3$) δ 7.09 (d, 2H, J=8.8 Hz), 7.11 (d, 1H, 4.1 Hz), 7.18 (d, 2H, J=8.8 Hz), 7.51 (t, 1H, 7.9 Hz), 7.68 (d, 1H, 4.1 Hz), 7.86 (d, 1H, J=7.9 Hz), 8.25 (d, 1H, 7.9 Hz), 9.11 (s, 1H). $^{13}$C NMR (126 MHz, CDCl$_3$) δ 114.06, 118.71, 123.66, 127.65, 128.84, 129.86, 131.07, 132.25, 132.39, 133.14, 135.70, 140.19, 162.12, 163.78. LCQ (M+H$^+$) calcd for C$_{16}$H$_{12}$BrN$_3$O$_3$S$_2$ 452. found 452.

N-(4-cyanophenyl)-3-(N-(4-cyanophenyl)sulfamoyl)benzamide (40)

Compound 40 was prepared according to procedure C to afford 42 mg of white powder (67%). $^1$H NMR (500 MHz, CDCl$_3$) δ 7.14 (d, J=5.8 Hz, 2H), 7.23-7.26 (m, 1H), 7.42 (d, J=6.0 Hz, 2H), 7.50-7.58 (m, 3H), 7.80 (d, J=6.0 Hz, 2H), 7.89 (d, J=5.9 Hz, 1H), 8.04 (d, J=5.9 Hz, 1H), 8.32 (d, J=5.2 Hz, 1H). $^{13}$C NMR (126 MHz, CDCl$_3$) δ 110.85, 111.11, 122.48, 122.78, 123.08, 124.42, 130.01, 133.49, 134.08, 136.21, 137.07, 137.43, 139.64, 143.93, 145.60, 146.47, 169.15. LCQ (M+H$^+$) calcd for C$_{21}$H$_{14}$N$_4$O$_3$S 403. found 403.

N-(5-chloropyridin-2-yl)-3-(N-(5-chloropyridin-2-yl)sulfamoyl)benzamide (41)

Compound 42 was prepared according to procedure C to afford 34 mg of white powder (52%). $^1$H NMR (500 MHz, DMSO) δ 7.11 (d, J=8.8 Hz, 1H), 7.72, (t, J=7.9 Hz, 1H), 7.82 (dd, J=2.7, 8.9 Hz, 1H), 8.00 (dd, J=2.7, 8.9 Hz, 1H), 8.11 (d, J=7.9 Hz, 1H), 8.21 (s, 1H), 8.22 (m, 2H), 8.26 (d, J=7.8 Hz, 1H), 8.48 (m, 2H), 11.39 (s, 1H). $^{13}$C NMR (126 MHz, DMSO) δ 113.33, 116.09, 125.94, 126.87, 129.41, 130.21, 132.35, 134.74, 137.95, 138.55, 140.44, 146.09, 146.20, 146.39, 149.86, 150.60, 164.78. LCQ (M+H$^+$) calcd C$_{17}$H$_{12}$Cl$_2$N$_4$O$_3$S 423. found 423.

N-(4-chlorophenyl)-3-(N-(5-chloropyridin-2-yl)sulfamoyl)benzamide (42)

Compound 42 was prepared according to procedure C to afford 48 mg of white powder (74%). $^1$H NMR (500 MHz, DMSO) δ 7.07 (d, J=8.8 Hz, 1H), 7.72 (t, J=7.9 Hz, 1H), 7.78 (dd, J=1.8, 8.9 Hz, 1H), 7.99 (dd, J=1.8, 8.9 Hz, 1H), 8.10 (d, J=7.9 Hz, 1H), 8.18-8.25 (m, 3H), 8.47 (d, J=1.9 Hz, 2H), 11.33 (s, 1H). $^{13}$C NMR (126 MHz, DMSO) δ 113.58, 115.35, 115.88, 122.11, 125.84, 126.80, 129.33, 130.21, 132.07, 134.63, 137.95, 138.31, 143.03, 146.38, 150.57, 164.87. LCQ (M+H$^+$) calcd C$_{17}$H$_{12}$Cl$_2$N$_4$O$_3$S 422. found 422.

N-(5-chloropyridin-2-yl)-3-(N-(4-fluorophenyl)-N-methylsulfamoyl)benzamide (43)

Compound 43 was prepared according to procedure C to afford 41 mg of white powder (63%). $^1$H NMR (500 MHz, CDCl$_3$) δ 3.20 (s, 3H), 7.00-7.08 (m, 4H), 7.63 (t, J=7.8 Hz, 1H), 7.69 (d, J=7.9 Hz, 1H), 7.74 (dd, J=2.6, 8.9 Hz, 1H), 8.10 (s, 1H), 8.16 (d, J=7.7 Hz, 1H), 8.25 (d, J=2.4 Hz, 1H), 8.34 (d, J=8.9 Hz, 1H). 8.65 (s, 1H). $^{13}$C NMR (126 MHz, CDCl$_3$) δ 38.54, 114.92, 115.99, 116.17, 126.17, 127.47, 128.51, 128.57, 129.68, 131.27, 131.69, 134.88, 136.86, 136.89, 137.36, 138.21, 146.69, 149.30, 160.72, 162.70, 163.74. LCQ (M+H$^+$) calcd C$_{19}$H$_{15}$ClFN$_3$O$_3$S 420. found 420.

N-(6-chloropyridazin-3-yl)-3-(N-(4-fluorophenyl)-N-methylsulfamoyl)benzamide (44)

Compound 44 was prepared according to procedure C to afford 38 mg of white powder (59%). $^1$H NMR (500 MHz, CDCl$_3$) δ 3.21 (s, 3H), 7.00-7.09 (m, 4H), 7.60 (d, J=9.3 Hz, 1H), 7.65 (t, J=7.8 Hz, 1H), 7.73 (d, J=7.9 Hz, 1H), 8.19 (s, 1H), 8.22 (d, J=7.7 Hz, 1H), 8.63 (d, J=7.7 Hz, 1H), 9.43 (s, 1H). $^{13}$C NMR (126 MHz, CDCl$_3$) δ 38.57, 116.01, 116.19, 121.50, 126.70, 128.53, 128.59, 129.78, 130.17, 131.73, 131.77, 134.03, 136.83, 136.85, 137.64, 152.87, 154.28, 160.73, 162.71, 164.48. LCQ (M+H$^+$) calcd C$_{18}$H$_{14}$ClFN$_4$O$_3$S 421. found 421.

3-(N-(4-fluorophenyl)-N-methylsulfamoyl)-N-(4-(methylsulfinyl)phenyl)benzamide (45)

Compound 45 was prepared according to procedure C to afford 52 mg of white powder (75%). $^1$H NMR (500 MHz, CDCl$_3$) δ 2.74 (s, 3H), 3.20 (s, 3H), 7.00-7.08 (m, 4H), 7.59-7.67 (m, 4H), 7.82 (d, J=8.7 HZ, 2H), 8.07 (t, J=1.6 Hz, 1H), 8.18 (dt, 1.6, 7.7 Hz, 1H), 8.55 (s, 1H). $^{13}$C NMR (126 MHz, CDCl$_3$) δ 38.58, 43.81, 115.98, 116.16, 121.11, 124.78, 125.90, 128.62, 128.69, 129.63, 130.96, 132.29, 135.47, 136.88, 136.90, 136.96, 140.36, 140.83, 160.72, 162.69, 164.26. LCQ (M+H$^+$) calcd C$_{21}$H$_{19}$FN$_2$O$_4$S$_2$ 447. found 447.

3-(N-(4-fluorophenyl)-N-methylsulfamoyl)-N-(4-(methylsulfonyl)phenyl)benzamide (46)

Compound 46 was prepared according to procedure C to afford 56 mg of white powder (79%). $^1$H NMR (500 MHz, CDCl$_3$) δ 3.08 (s, 3H), 3.21 (s, 3H), 7.00-7.08 (m, 4H), 7.62-7.68 (m, 2H), 7.93 (s, 4H), 8.12 (s, 1H), 8.22 (dd, J=1.3, 7.5 Hz, 1H). $^{13}$C NMR (126 MHz, CDCl$_3$) δ 38.65, 44.66, 114.06, 116.04, 116.22, 120.42, 120.51, 126.06, 128.65, 128.72, 128.79, 129.42, 129.71, 131.02, 132.77, 135.41, 135.45, 136.76, 136.79, 136.82, 143.12, 164.86. LCQ (M+H$^+$) calcd C$_{21}$H$_{19}$FN$_2$O$_5$S$_2$ 463. found 463.

N-(5-cyanopyridin-2-yl)-3-(N-(4-fluorophenyl)-N-methylsulfamoyl)benzamide (48)

Compound 48 was prepared according to procedure C to afford 34 mg of white powder (54%). $^1$H NMR (500 MHz, CDCl$_3$) δ 3.21 (s, 3H), 7.01-7.09 (m, 4H), 7.67 (t, J=7.8 Hz, 1H), 7.74 (d, J=8.0 Hz, 1H), 8.03 (dd, J=2.2, 8.7 Hz, 1H), 8.09 (s, 1H), 8.18 (d, J=7.8 Hz, 1H), 8.50 (8.8 Hz, 1H), 8.62 (d, J=1.6 Hz, 1H), 8.76 (s, 1H). $^{13}$C NMR (126 MHz, CDCl$_3$) δ 38.58, 105.76, 113.85, 116.06, 116.24, 116.58, 126.27, 128.54, 128.61, 129.89, 131.68, 131.85, 134.29, 136.83, 136.86, 137.54, 141.88, 151.73, 153.49, 160.79, 162.76, 163.99. LCQ (M+H$^+$) calcd C$_{20}$H$_{15}$FN$_4$O$_3$S 411. found 411.

3-(N-(4-chlorophenyl)-N-methylsulfamoyl)-N-(5-chloropyridin-2-yl)benzamide (49)

Compound 49 was prepared according to procedure C to afford 32 mg of white powder (47%). $^1$H NMR (500 MHz, CDCl$_3$) δ 3.19 (s, 3H), 7.04 (d, J=8.7 Hz, 2H), 7.29 (d, J=8.7 Hz, 2H), 7.64 (m, 2H), 7.73 (dd, J=2.5, 8.9 Hz, 1H), 8.02 (s, 1H), 8.17 (d, J=7.7 Hz, 1H), 8.24 (d, J=2.5 Hz, 1H), 8.33 (d, J=8.9 Hz, 1H), 8.96 (s, 1H). $^{13}$C NMR (126 MHz, CDCl$_3$) δ 38.27, 115.07, 126.29, 127.37, 127.85, 129.66, 131.16, 131.91, 133.55, 135.04, 137.17, 138.12, 139.55, 146.70, 149.49, 162.62, 163.94. LCQ (M+H$^+$) calcd C$_{19}$H$_{15}$Cl$_2$N$_3$O$_3$S 435. found 435.

N-(5-bromopyridin-2-yl)-3-(N-(4-chlorophenyl)-N-methylsulfamoyl)benzamide (50)

Compound 50 was prepared according to procedure C to afford 30 mg of white powder (40%). $^1$H NMR (500 MHz, CDCl$_3$) δ 3.17 (s, 3H), 7.02 (d, J=8.7 Hz, 2H), 7.27 (d, J=8.7 Hz, 2H), 7.63 (m, 2H), 7.84 (dd, J=2.5, 8.9 Hz, 1H), 8.0 (s, 1H), 8.16 (d, J=7.7 Hz, 1H), 8.26 (d, J=8.8 Hz, 1H), 8.31 (d, J=2.2 Hz, 1H), 9.13 (s, 1H). $^{13}$C NMR (126 MHz, CDCl$_3$) δ 38.26, 115.67, 126.38, 127.85, 129.28, 129.61, 131.12, 131.99, 133.50, 135.09, 137.09, 139.55, 140.84, 148.91, 149.97, 162.63, 164.09. LCQ (M+H$^+$) calcd C$_{19}$H$_{15}$BrClN$_3$O$_3$S 479. found 479.

3-(N-(4-chlorophenyl)-N-methylsulfamoyl)-N-(pyridin-2-ylmethyl)benzamide (53)

Compound 53 was prepared according to procedure C to afford 60 mg of white powder (94%). $^1$H NMR (500 MHz, CDCl$_3$) δ 3.19 (s, 3H), 4.77 (d, J=4.7 Hz, 2H), 7.05 (d, J=8.7 Hz, 2H), 7.26 (d, J=7.3 Hz, 1H), 7.29 (d, J=8.7 Hz, 2H), 7.33 (d, J=7.9 Hz, 1H), 7.59 (t, J=7.8 Hz, 1H), 7.64 (d, J=7.9 Hz, 1H), 8.08 (s, 1H), 8.15 (d, J=7.7 Hz, 1H), 8.58 (d, J=4.8 Hz, 1H). $^{13}$C NMR (126 MHz, CDCl$_3$) δ 38.25, 44.76, 122.19, 122.65, 126.00, 127.90, 129.23, 129.39, 130.48, 131.88, 133.38, 135.47, 136.77, 136.96, 139.69, 149.10, 155.39, 165.53. LCQ (M+H$^+$) calcd C$_{20}$H$_{18}$ClN$_3$O$_3$S 416. found 416.

3-(N-(4-chlorophenyl)-N-methylsulfamoyl)-N-(5-fluoropyridin-2-yl)benzamide (54)

Compound 54 was prepared according to procedure C to afford 50 mg of white powder (77%). $^1$H NMR (500 MHz, CDCl$_3$) δ 3.17 (s, 3H), 7.02 (d, J=8.9 Hz, 2H), 7.45 (d, J=8.9 Hz, 2H), 7.50-54 (m, 1H), 7.59 (t, J=7.9 Hz, 1H), 7.64 (d, J=7.9 Hz, 1H), 8.06 (d, J=3.0 Hz, 1H), 8.14-8.16 (m, 2H), 8.35 (dd, J=4.1, 9.2 Hz, 1H), 9.08 (s, 1H). $^{13}$C NMR (126 MHz, CDCl$_3$) δ 38.23, 115.34, 115.37, 125.37, 125.53, 126.36, 127.81, 127.84, 129.28, 129.63, 131.08, 131.85, 133.48, 135.13, 135.41, 135.62, 137.13, 139.55, 147.37, 147.39, 155.59, 157.59, 163.89. LCQ (M+H$^+$) calcd C$_{19}$H$_{15}$ClFN$_3$O$_3$S 420. found 416.

3-(N-(4-chlorophenyl)-N-methylsulfamoyl)-N-(5-methoxypyridin-2-yl)benzamide (55)

Compound 55 was prepared according to procedure C to afford 55 mg of white powder (82%). $^1$H NMR (500 MHz, CDCl$_3$) δ 3.19 (s, 3H), 3.87 (s, 3H), 7.04 (d, J=8.7 Hz, 2H), 7.30 (d, J=8.7 Hz, 2H), 7.32 (dd, J=3.0, 9.1 Hz, 1H), 7.60 (t, J=7.8 Hz, 1H), 7.64 (dt, J=1.4, 7.9 Hz, 1H), 7.95 (d, J=3.0 Hz, 1H), 8.14-8.16 (m, 2H), 8.28 (d, J=9.1 Hz, 1H), 8.67 (s, 1H). $^{13}$C NMR (126 MHz, CDCl$_3$) δ 38.25, 55.94, 114.82, 123.33, 126.09, 127.84, 129.29, 129.59, 130.91, 131.69, 133.51, 134.60, 135.47, 137.16, 139.56, 144.53, 153.21, 163.40. LCQ (M+H$^+$) calcd C$_{20}$H$_{18}$ClN$_3$O$_4$S 432. found 432.

3-(N-(4-chlorophenyl)-N-methylsulfamoyl)-N-(5-(trifluoromethyl)pyridin-2-yl)benzamide (56)

Compound 56 was prepared according to procedure C to afford 57 mg of white powder (79%). $^1$H NMR (500 MHz, CDCl$_3$) δ 3.19 (s, 3H), 7.04 (d, J=8.8 Hz, 2H), 7.28 (d, J=8.8 Hz, 2H), 7.63 (t, J=7.8 Hz, 1H), 7.68 (dt, J=1.4, 7.9 Hz, 1H), 7.99 (dd, J=2.1, 8.6 Hz, 1H), 8.16 (s, 1H), 8.19 (dd, J=1.4, 7.7 Hz, 1H), 8.49 (d, J=8.8 Hz, 1H), 8.50 (s, 1H), 9.15 (s, 1H). $^{13}$C NMR (126 MHz, CDCl$_3$) δ 38.24, 113.75, 122.63, 122.90, 123.16, 123.43, 126.46, 127.85, 129.31, 129.76, 131.40, 131.92, 133.57, 134.72, 135.98, 136.01, 137.28, 139.51, 145.34, 145.38, 153.74, 164.28. LCQ (M+H$^+$) calcd C$_{20}$H$_{15}$ClF$_3$N$_3$O$_3$S 470. found 470.

3-(N-(4-chlorophenyl)-N-methylsulfamoyl)-N-(5-methylpyridin-2-yl)benzamide (57)

Compound 57 was prepared according to procedure C to afford 51 mg of white powder (80%). $^1$H NMR (500 MHz, CDCl$_3$) δ 2.27 (s, 3H), 3.16 (s, 3H), 7.02 (d, J=8.8 Hz, 2H), 7.27 (d, J=8.8 Hz, 2H), 7.56 (t, 7.9 Hz, 1H), 7.62 (dt, J=1.3, 8.0 Hz, 1H), 7.93 (s, 1H), 8.15 (d, J=7.7 Hz, 1H), 8.20 (s, 1H), 8.23 (d, J=7.7 Hz, 1H), 9.50 (s, 1H). $^{13}$C NMR (126 MHz, CDCl$_3$) δ 17.86, 38.22, 114.24, 126.47, 127.83, 129.24, 129.47, 129.85, 130.85, 131.88, 133.39, 135.64, 137.07, 139.20, 139.59, 147.68, 149.11, 164.19. LCQ (M+H$^+$) calcd C$_{20}$H$_{18}$ClN$_3$O$_3$S 416. found 416.

3-(N-(4-chlorophenyl)-N-methylsulfamoyl)-N-(5-hydroxypyridin-2-yl)benzamide (58)

Compound 58 was prepared according to procedure J from 55 to afford 51 mg of white powder (90%). $^1$H NMR (500 MHz, CDCl$_3$) δ 3.20 (s, 3H), 7.04 (d, J=8.8 Hz, 2H), 7.28-7.30 (m, 3H), 7.60-7.62 (m, 2H), 7.91 (d, J=2.8 Hz, 1H), 8.18 (d, J=7.8 Hz, 1H), 8.23 (s, 1H). $^{13}$C NMR (126 MHz, CDCl$_3$) δ 38.28, 115.44, 125.35, 126.25, 127.91, 129.28, 129.56, 130.88, 131.81, 133.50, 135.18, 135.41, 137.05, 139.55, 143.74, 150.81, 163.53. LCQ (M+H$^+$) calcd C$_{19}$H$_{16}$ClN$_3$O$_4$S 418. found 418.

3-(N-(4-chlorophenyl)-N-methylsulfamoyl)-N-(4-((trifluoromethyl)sulfonyl)phenyl)benzamide (60)

Compound 60 was prepared according to procedure C to afford 62 mg of white powder (75%). $^1$H NMR (500 MHz, CDCl$_3$) δ 3.21 (s, 3H), 7.02 (d, J=8.7 Hz, 2H), 7.29 (d, J=8.7 Hz, 2H), 7.62-7.6745 (m, 2H), 8.01-8.06 (m, 5H), 8.21 (d, J=7.3 Hz, 1H). $^{13}$C NMR (126 MHz, CDCl$_3$) δ 38.35, 114.14, 120.36, 120.45, 125.40, 125.90, 128.02, 129.38, 129.91, 131.19, 132.31, 132.81, 133.17, 133.78, 135.04, 135.07, 136.73, 139.33, 145.57, 145.67, 164.73, 164.81. LCQ (M+H$^+$) calcd C$_{21}$H$_{16}$ClF$_3$N$_2$O$_5$S$_2$ 533. found 533.

3-(N-(4-chlorophenyl)-N-methylsulfamoyl)-N-(pyridin-2-ylmethyl)benzamide (62)

Compound 62 was prepared according to procedure C to afford 60 mg of white powder (93%). $^1$H NMR (500 MHz, CDCl$_3$) δ 3.08 (s, 3H), 4.60 (d, J=5.9 Hz, 2H), 6.95 (d, J=8.7 Hz, 2H), 7.21 (d, J=8.7 Hz, 2H), 7.24-7.25 (m, 1H), 7.49-7.55 (m, 2H), 7.70 (d, J=7.8 Hz, 1H), 8.07 (s, 1H), 8.13 (d, J=7.3 Hz, 1H), 8.30 (t, J=5.8 Hz, 1H), 8.37 (brs, 1H), 8.46 (brs, 1H). $^{13}$C NMR (126 MHz, CDCl$_3$) δ 38.19, 41.50, 123.78, 125.96, 127.86, 127.89, 129.17, 129.42, 130.44, 132.42, 133.39, 134.15, 135.08, 136.11, 136.32, 139.46, 148.44, 149.03, 165.92. LCQ (M+H$^+$) calcd C$_{20}$H$_{18}$ClN$_3$O$_3$S 416. found 416.

3-(N-(4-chlorophenyl)-N-methylsulfamoyl)-N-(6-methoxypyridazin-3-yl)benzamide (63)

Compound 63 was prepared according to procedure C to afford 57 mg of white powder (86%). $^1$H NMR (500 MHz, CDCl$_3$) δ 3.18 (s, 3H), 4.00 (s, 3H), 7.03 (d, J=7.8 Hz, 2H), 7.10 (d, J=9.6 Hz, 1H), 7.28 (d, J=8.7 Hz, 2H), 7.59 (t, J=7.8 Hz, 1H), 7.63 (dd, J=1.4, 7.9 Hz, 1H), 8.29 (s, 1H), 8.35 (d, J=7.7 Hz, 1H), 8.49 (d, J=9.5 Hz, 1H), 10.30 (brs, 1H). $^{13}$C NMR (126 MHz, CDCl$_3$) δ 38.23, 54.72, 119.78, 124.04, 127.08, 127.80, 129.19, 129.24, 129.41, 131.20, 132.00, 133.39, 134.87, 137.29, 139.56, 151.73, 163.12, 164.71. LCQ (M+H$^+$) calcd C$_{19}$H$_{17}$ClN$_4$O$_4$S 433. found 433.

methyl 6-(3-(N-(4-chlorophenyl)-N-methylsulfamoyl)benzamido)nicotinate (65)

Compound 65 was prepared according to procedure C to afford 46 mg of white powder (65%). $^1$H NMR (500 MHz, CDCl$_3$) δ 3.20 (s, 3H), 3.95 (s, 3H), 7.05 (d, J=8.8 Hz, 2H), 7.30 (d, J=8.8 Hz, 2H), 7.64 (t, J=7.8 Hz, 1H), 7.70 (d, J=7.9 Hz, 1H), 8.13 (s, 1H), 8.18 (d, J=7.7 Hz, 1H), 8.38 (dd, J=2.2, 8.8 Hz, 1H), 8.43 (d, J=8.7 Hz, 1H), 8.84 (s, 1H), 8.91 (d, J=1.6 Hz, 1H). $^{13}$C NMR (126 MHz, CDCl$_3$) δ 38.27, 52.35, 113.18, 122.67, 126.22, 127.84, 129.34, 129.78, 131.40, 131.81, 133.62, 134.77, 137.37, 139.49, 140.02, 150.09, 153.94, 163.93, 165.23. LCQ (M+H$^+$) calcd C$_{21}$H$_{18}$ClN$_3$O$_5$S 460. found 460.

6-(3-(N-(4-chlorophenyl)-N-methylsulfamoyl)benzamido)nicotinic acid (65-b)

Compound 65-b was prepared by stirring 65 (20 mg, 0.043 mmol) in EtOH/H$_2$O (1:1, 4 mL) and K$_2$CO$_3$ (11.9 mg, 0.086 mmol) overnight at room temperature. Reaction mixture was then neutralized to PH 3.0, extracted with EtOAc and then dried over MgSO$_3$ to generate 17 mg of 65-b (90%). $^1$H NMR (500 MHz, CDCl$_3$) δ 3.20 (s, 3H), 7.05 (d, J=8.8 Hz, 2H), 7.30 (d, J=8.8 Hz, 2H), 7.64 (t, J=7.8 Hz, 1H), 7.70 (d, J=7.9 Hz, 1H), 8.13 (s, 1H), 8.18 (d, J=7.7 Hz, 1H), 8.38 (dd, J=2.2, 8.8 Hz, 1H), 8.43 (d, J=8.7 Hz, 1H), 8.84 (s, 1H), 8.91 (d, J=1.6 Hz, 1H). $^{13}$C NMR (126 MHz, CDCl$_3$) δ 38.27, 52.35, 113.18, 122.67, 126.22, 127.84, 129.34, 129.78, 131.40, 131.81, 133.62, 134.77, 137.37, 139.49, 140.02, 150.09, 153.94, 163.93, 165.23. LCQ (M−H$^+$) calcd C$_{20}$H$_{16}$ClN$_3$O$_5$S 444. found 444.

6-(3-(N-(4-chlorophenyl)-N-methylsulfamoyl)benzamido)nicotinamide (67)

Compound 67 was prepared according to procedure C to afford 34 mg of white powder (50%). $^1$H NMR (500 MHz, DMSO) δ 3.19 (s, 3H), 7.18 (d, J=8.8 Hz, 2H), 7.43 (d, J=8.8 Hz, 2H), 7.54 (brs, 1H), 7.61 (d, J=7.7 Hz, 1H), 7.72 (t, J=7.8 Hz, 1H), 8.12 (s, 1H), 8.24-8.36 (m, 4H), 8.90 (s, 1H), 11.50 (s, 1H). $^{13}$C NMR (126 MHz, DMSO) δ 37.92, 113.50, 125.73, 126.96, 128.02, 128.95, 129.65, 130.65, 131.75, 132.88, 134.85, 136.00, 137.63, 139.74, 147.73, 153.86, 164.77, 165.87. LCQ (M+H$^+$) calcd C$_{20}$H$_{17}$ClN$_4$O$_4$S 445. found 445.

N-(6-aminopyridin-3-yl)-3-(N-(4-chlorophenyl)-N-methylsulfamoyl)benzamide (68)

Compound 68 was prepared according to procedure C to afford 20 mg of white powder (31%). $^1$H NMR (500 MHz, CDCl$_3$) δ 3.09 (s, 3H), 6.37 (d, J=8.8 Hz, 1H), 6.97 (d, J=8.8 Hz, 2H), 7.22 (d, J=8.8 Hz, 2H), 7.46-7.47 (m, 2H), 7.66 (dd, J=2.4, 8.8 Hz, 1H), 8.06 (d, J=2.2 Hz, 1H), 8.10 (d, J=6.4 Hz, 1H), 8.14 (s, 1H), 9.29 (s, 1H). $^{13}$C NMR (126 MHz, CDCl$_3$) δ 38.24, 108.63, 125.65, 126.20, 127.95, 129.23, 129.43, 130.48, 132.39, 132.74, 133.39, 135.46, 136.36, 139.49, 141.13, 156.06, 164.71. LCQ (M+H$^+$) calcd C$_{19}$H$_{17}$ClN$_4$O$_3$S 417. found 417.

N-(4-chlorophenyl)-3-(N-(4-chlorophenyl)-N-methylsulfamoyl)-4-methoxybenzamide (69)

Compound 69 was prepared according to procedure C to afford 62 mg of white powder (86%). $^1$H NMR (500 MHz, CDCl$_3$) δ 3.36 (s, 3H), 3.87 (s, 3H), 7.11 (d, J=8.8 Hz, 1H), 8.8 Hz, 2H), 7.27 (d, J=8.8 Hz, 2H), 7.32 (d, J=8.8 Hz, 2H), 7.64 (d, J=8.8 Hz, 2H), 8.21 (dd, J=2.3, 8.7 Hz, 1H), 8.26 (d, J=2.3 Hz, 1H). $^{13}$C NMR (126 MHz, CDCl$_3$) δ 38.99, 56.31, 112.54, 121.77, 125.91, 126.85, 127.59, 128.97, 129.21, 129.50, 129.97, 132.89, 135.71, 136.71, 139.81, 159.28, 164.14. LCQ (M+H$^+$) calcd C$_{21}$H$_{18}$Cl$_2$N$_2$O$_4$S 465. found 465.

N-(4-chlorophenyl)-3-(N-(4-chlorophenyl)-N-methylsulfamoyl)-4-hydroxybenzamide (70)

Compound 70 was prepared according to procedure J from 69 to afford 33 mg of white powder (83%). $^1$H NMR (500 MHz, CDCl$_3$) δ 3.25 (s, 3H), 7.05-7.09 (m, 3H), 7.31-7.33 (m, 4H), 7.57 (d, J=2.4 Hz, 1H), 7.59 (d, J=2.4 Hz, 1H), 7.90 (d, J=2.3 Hz, 1H), 8.06 (dd, J=2.3, 8.7 Hz, 1H), 8.47 (s, 1H). $^{13}$C NMR (126 MHz, CDCl$_3$) δ 38.53, 119.25, 119.54, 121.61, 121.72, 126.66, 126.69, 127.92, 128.29, 129.06, 129.58, 129.67, 129.70, 134.35, 135.06, 136.37, 136.45, 138.78, 158.25, 163.93. LCQ (M+H$^+$) calcd C$_{20}$H$_{16}$C$_{12}$N$_2$O$_4$S 451. found 451.

3-(N-(4-chlorophenyl)-N-methylsulfamoyl)-N-(4-sulfamoylphenyl)benzamide (72)

Compound 72 was prepared according to procedure C to afford 53 mg of white powder (71%). $^1$H NMR (500 MHz, CDCl$_3$) δ 3.19 (s, 3H), 6.98 (d, J=8.8 Hz, 2H), 7.03 (d, J=8.8 Hz, 2H), 7.24 (d, J=8.8 Hz, 2H), 7.28 (d, J=8.8 Hz, 2H), 7.48 (t, J=7.8 Hz, 1H), 7.54-7.64 (m, 3H), 7.70 (brs, 2H), 8.11 (s, 1H). $^{13}$C NMR (126 MHz, CDCl$_3$) δ 38.33, 99.99, 120.05, 126.05, 127.96, 128.01, 129.25, 129.32, 129.68, 130.95, 132.63, 133.51, 133.62, 136.68, 139.44, 164.70, 188.28. LCQ (M+H$^+$) calcd C$_{20}$H$_{18}$ClN$_3$O$_5$S$_2$ 480. found 480.

3-(N-(4-chlorophenyl)-N-methylsulfamoyl)-N-(4-(dimethylamino)phenyl)benzamide (73)

Compound 73 was prepared according to procedure C to afford 58 mg of white powder (85%). $^1$H NMR (500 MHz, CDCl$_3$) δ 3.18 (s, 6H), 3.20 (s, 3H), 7.03 (d, J=8.7 Hz, 2H), 7.28 (d, J=8.7 Hz, 2H), 7.60-7.67 (m, 4H), 7.89 (d, J=8.7 Hz, 2H), 8.18 (s, 1H), 8.21 (d, J=6.2 Hz, 1H). $^{13}$C NMR (126 MHz, CDCl$_3$) δ 38.24, 46.33, 122.12, 122.22, 126.43, 127.95, 129.23, 129.45, 130.77, 132.42, 133.52, 135.50, 136.68, 139.45, 165.02. LCQ (M+H$^+$) calcd C$_{22}$H$_{22}$ClN$_3$O$_3$S 444. found 444.

N-(4-acetamidophenyl)-3-(N-(4-chlorophenyl)-N-methylsulfamoyl)benzamide (74)

Compound 74 was prepared according to procedure C to afford 49 mg of white powder (70%). $^1$H NMR (500 MHz, DMSO) δ 2.04 (s, 3H), 3.17 (s, 3H), 7.16 (d, J=8.5 Hz, 2H), 7.43 (d, J=8.5 Hz, 2H), 7.57 (d, J=8.7 Hz, 2H), 7.62 (d, J=7.8 Hz, 1H), 7.66 (d, J=8.7 Hz, 2H), 7.74 (t, J=7.8 Hz, 1H), 8.15 (s, 1H), 8.29 (d, J=7.7 Hz, 1H), 9.96 (s, 1H), 10.46 (s, 1H). $^{13}$C NMR (126 MHz, DMSO) δ 23.91, 37.85, 119.10, 121.09, 126.43, 127.95, 128.95, 129.61, 130.06, 131.74, 132.33, 133.75, 135.57, 135.72, 136.01, 139.72, 163.38, 168.03. LCQ (M+H$^+$) calcd C$_{22}$H$_{20}$ClN$_3$O$_4$S 458. found 458.

3-(N-(4-chlorophenyl)-N-methylsulfamoyl)-N-(3,4-dimethylisoxazol-5-yl)benzamide (76)

Compound 76 was prepared according to procedure C to afford 24 mg of white powder (37%). $^1$H NMR (500 MHz, CDCl$_3$) δ 1.92 (s, 3H), 2.20 (s, 3H), 3.18 (s, 3H), 7.03 (d, J=8.7 Hz, 2H), 7.26 (d, J=8.7 Hz, 2H), 7.58-7.64 (m, 2H), 8.21 (s, 1H). $^{13}$C NMR (126 MHz, CDCl$_3$) δ 7.32, 10.67, 38.32, 104.29, 126.49, 127.93, 129.27, 129.64, 131.35, 132.79, 133.56, 133.86, 136.89, 139.41, 155.98, 162.16, 163.22. LCQ (M+H$^+$) calcd C$_{19}$H$_{18}$ClN$_3$O$_4$S 420. found 420.

N-(4-bromo-3-methylisoxazol-5-yl)-3-(N-(4-chlorophenyl)-N-methylsulfamoyl)benzamide (77)

Compound 77 was prepared according to procedure C to afford 37 mg of white powder (49%). $^1$H NMR (500 MHz, MeOD) δ 2.22 (s, 3H), 3.23 (s, 3H), 7.14 (d, J=8.8 Hz, 2H), 7.33 (d, J=8.8 Hz, 2H), 7.47 (d, J=7.9 Hz, 1H), 7.53 (t, J=7.8 Hz, 1H), 8.30 (d, J=7.6 Hz, 1H), 8.36 (s, 1H). $^{13}$C NMR (126 MHz, MeOD) δ 11.38, 38.68, 128.99, 129.28, 129.48, 130.05, 130.16, 134.07, 134.27, 137.15, 141.69, 141.94, 147.63, 161.26, 170.32, 170.32. LCQ (M+H$^+$) calcd C$_{18}$H$_{15}$BrClN$_3$O$_4$S 484. found 484.

3-(N-(4-chlorophenyl)-N-methylsulfamoyl)-N-(3-methylisoxazol-5-yl)benzamide (78)

Compound 78 was prepared according to procedure C to afford 37 mg of white powder (49%). $^1$H NMR (500 MHz, CDCl$_3$) δ 2.22 (s, 3H), 3.21 (s, 3H), 6.40 (s, 1H), 7.04 (d, J=8.8 Hz, 2H), 7.30 (d, J=8.8 Hz, 2H), 7.63 (t, J=7.8 Hz, 1H), 7.67 (d, J=7.9 Hz, 1H), 8.21 (d, J=7.9 Hz, 1H), 8.26 (s, 1H), 9.96 (s, 1H). $^{13}$C NMR (126 MHz, CDCl$_3$) δ 11.93, 38.44, 90.67, 126.25, 127.96, 129.37, 129.82, 131.56, 132.67, 133.69, 133.79, 137.25, 139.37, 160.17, 161.77, 161.88. LCQ (M+H$^+$) calcd C$_{18}$H$_{16}$ClN$_3$O$_4$S 406. found 406.

N-(5-bromothiazol-2-yl)-3-(N-(4-chlorophenyl)-N-methylsulfamoyl)benzamide (79)

Compound 79 was prepared according to procedure C to afford 50 mg of white powder (67%). $^1$H NMR (500 MHz, CDCl$_3$) δ 3.20 (s, 3H), 7.00 (s, 1H), 7.04 (d, J=8.8 Hz, 2H), 7.29 (d, J=8.8 Hz, 2H), 7.66 (t, J=7.8 Hz, 1H), 7.73 (d, J=8.0 Hz, 1H), 8.19 (d, J=7.8 Hz, 1H), 8.25 (s, 1H), 11.84 (brs, 1H). $^{13}$C NMR (126 MHz, CDCl$_3$) δ 38.35, 104.38, 126.95, 127.85, 129.35, 129.82, 131.91, 132.13, 133.05, 133.58, 137.76, 137.83, 139.44, 159.55, 163.86. LCQ (M+H$^+$) calcd C$_{17}$H$_{13}$BrClN$_3$O$_3$S$_2$ 486. found 486.

3-(N-(4-chlorophenyl)-N-methylsulfamoyl)-N-(4-methylthiazol-2-yl)benzamide (80)

Compound 80 was prepared according to procedure C to afford 43 mg of white powder (66%). $^1$H NMR (500 MHz, CDCl$_3$) δ 2.05 (s, 3H), 3.17 (s, 3H), 6.60 (d, J=1.0 Hz, 1H), 7.01 (d, J=8.8 Hz, 2H), 7.26 (d, J=8.8 Hz, 2H), 7.55 (t, J=7.8 Hz, 1H), 7.64 (d, J=6.6 Hz, 1H), 8.09 (d, J=8.9 Hz, 1H), 8.22 (s, 1H). $^{13}$C NMR (126 MHz, CDCl$_3$) δ 16.49, 38.22, 109.00, 127.00, 127.73, 129.25, 129.56, 131.45, 131.95, 133.38, 133.70, 137.52, 139.47, 146.22, 159.15, 163.93. LCQ (M+H$^+$) calcd C$_{18}$H$_{16}$ClN$_3$O$_3$S$_2$ 421. found 421.

3-(N-(4-bromophenyl)-N-methylsulfamoyl)-N-(5-chloropyridin-2-yl)benzamide (81)

Compound 81 was prepared according to procedure C to afford 42 mg of white powder (57%). $^1$H NMR (500 MHz, CDCl$_3$) δ 3.21 (s, 3H), 7.01 (d, J=8.7 Hz, 2H), 7.47 (d, J=8.7 Hz, 2H), 7.65 (t, J=7.8 Hz, 1H), 7.70 (d, J=7.9 Hz, 1H), 7.77 (dd, J=2.5, 8.9 Hz, 1H), 8.12 (s, 1H), 8.18 (d, J=7.7 Hz, 1H), 8.29 (d, J=2.4 Hz, 1H), 8.35 (d, J=7.7 Hz, 1H), 8.62 (s, 1H). $^{13}$C NMR (126 MHz, CDCl$_3$) δ 38.22, 114.92, 121.63, 126.11, 127.51, 128.16, 129.78, 131.25, 131.81, 132.33, 134.94, 137.28, 138.23, 140.08, 146.76, 149.31, 163.70. LCQ (M+H$^+$) calcd C$_{19}$H$_{15}$BrClN$_3$O$_3$S 480. found 480.

3-(N-(4-bromophenyl)-N-methylsulfamoyl)-N-(5-fluoropyridin-2-yl)benzamide (82)

Compound 82 was prepared according to procedure C to afford 49 mg of white powder (69%). $^1$H NMR (500 MHz, CDCl$_3$) δ 3.19 (s, 3H), 6.99 (d, J=8.9 Hz, 2H), 7.26 (d, J=8.9 Hz, 2H), 7.47-7.51 (m, 1H), 7.63 (t, J=7.9 Hz, 1H), 7.68 (d, J=7.9 Hz, 1H), 8.06 (d, J=3.0 Hz, 1H), 8.15-8.18 (m, 2H), 8.37 (dd, J=4.1, 9.2 Hz, 1H), 8.59 (s, 1H). $^{13}$C NMR (126 MHz, CDCl$_3$) δ 38.18, 115.04, 115.07, 121.59, 125.36, 125.51, 126.05, 128.08, 128.13, 129.73, 131.14, 131.76, 132.24, 132.30, 135.03, 135.57, 135.77, 137.21, 140.07, 147.13, 147.15, 155.67, 157.68, 163.54. LCQ (M+H$^+$) calcd C$_{19}$H$_{15}$BrFN$_3$O$_3$S 464. found 464.

3-(N-(4-bromophenyl)-N-methylsulfamoyl)-N-(5-methoxypyridin-2-yl)benzamide (83)

Compound 83 was prepared according to procedure C to afford 52 mg of white powder (71%). $^1$H NMR (500 MHz, CDCl$_3$) δ 3.18 (s, 3H), 3.85 (s, 3H), 6.98 (d, J=8.8 Hz, 2H), 7.32 (dd, J=3.0, 9.1 Hz, 1H), 7.44 (d, J=8.8 Hz, 2H), 7.59 (t, J=7.8 Hz, 1H), 7.63 (dt, J=1.4, 7.9 Hz, 1H), 7.91 (d, J=3.0 Hz, 1H), 8.15-8.16 (m, 2H), 8.28 (d, J=9.0 Hz, 1H), 8.91 (s, 1H). $^{13}$C NMR (126 MHz, CDCl$_3$) δ 38.17, 55.92, 114.94, 121.48, 123.35, 126.17, 128.10, 128.13, 128.16, 129.56, 130.87, 131.74, 132.25, 134.54, 135.52, 137.10, 140.11, 144.61, 153.17, 163.52. LCQ (M+H$^+$) calcd C$_{20}$H$_{18}$BrN$_3$O$_4$S 476. found 476.

3-(N-(4-bromophenyl)-N-methylsulfamoyl)-N-(5-hydroxypyridin-2-yl)benzamide (84)

Compound 84 was prepared according to procedure J from 83 to afford 36 mg of white powder (88%). $^1$H NMR (500 MHz, CDCl$_3$) δ 3.20 (s, 3H), 6.98 (d, J=8.8 Hz, 2H), 2.27 (dd, J=3.1, 8.9 Hz, 1H), 7.44 (d, J=8.8 Hz, 2H), 7.60-7.62 (m, 2H), 7.91 (d, J=1.9 Hz, 1H), 8.17-8.22 (m, 2H). $^{13}$C NMR (126 MHz, CDCl$_3$) δ 38.22, 115.41, 121.51, 123.53, 125.36, 126.21, 128.21, 129.59, 130.89, 131.83, 132.27, 134.51, 135.18, 135.42, 137.06, 140.10, 143.83, 150.69, 163.50. LCQ (M+H$^+$) calcd C$_{19}$H$_{16}$BrN$_3$O$_4$S 462. found 462.

3-(N-(4-bromophenyl)-N-methylsulfamoyl)-N-(6-chloropyridazin-3-yl)benzamide (85)

Compound 85 was prepared according to procedure C to afford 37 mg of white powder (50%). $^1$H NMR (500 MHz, CDCl$_3$) δ 3.21 (s, 3H), 6.99 (d, J=8.7 Hz, 2H), 7.45 (d, J=8.7

Hz, 2H), 7.60 (d, J=9.3 Hz, 1H), 7.66 (d, J=7.6 Hz, 1H), 7.71 (d, J=7.9 Hz, 1H), 8.21 (s, 1H), 8.22 (d, J=1.3 Hz, 1H), 8.63 (d, J=9.4 Hz, 1H), 9.37 (s, 1H). $^{13}$C NMR (126 MHz, CDCl$_3$) δ 38.27, 121.48, 121.60, 126.66, 128.16, 129.88, 130.19, 131.75, 131.79, 132.34, 134.10, 137.60, 140.03, 152.91, 154.27, 164.44. LCQ (M+H$^+$) calcd C$_{18}$H$_{14}$BrClN$_4$O$_3$S 481. found 481.

3-(N-(4-bromophenyl)-N-methylsulfamoyl)-N-(6-chloropyridazin-3-yl)benzamide (86)

Compound 86 was prepared according to procedure C to afford 34 mg of white powder (46%). $^1$H NMR (500 MHz, CDCl$_3$) δ 3.21 (s, 3H), 6.99 (d, J=8.7 Hz, 2H), 7.45 (d, J=8.7 Hz, 2H), 7.60 (d, J=9.3 Hz, 1H), 7.66 (d, J=7.6 Hz, 1H), 7.71 (d, J=7.9 Hz, 1H), 8.21 (s, 1H), 8.22 (d, J=1.3 Hz, 1H), 8.63 (d, J=9.4 Hz, 1H), 9.37 (s, 1H). $^{13}$C NMR (126 MHz, CDCl$_3$) δ 38.27, 121.48, 121.60, 126.66, 128.16, 129.88, 130.19, 131.75, 131.79, 132.34, 134.10, 137.60, 140.03, 152.91, 154.27, 164.44. LCQ (M+H$^+$) calcd C$_{18}$H$_{14}$BrClN$_4$O$_3$S 481. found 481.

3-(N-(4-bromophenyl)-N-methylsulfamoyl)-N-(5-chlorothiazol-2-yl)benzamide (87)

Compound 87 was prepared according to procedure C to afford 52 mg of white powder (69%). $^1$H NMR (500 MHz, CDCl$_3$) δ 3.20 (s, 3H), 6.87 (s, 1H), 6.99 (d, J=8.8 Hz, 2H), 7.44 (d, J=8.8 Hz, 2H), 7.66 (t, J=7.8 Hz, 1H), 7.72 (d, J=7.9 Hz, 1H), 8.19 (d, J=7.7 Hz, 1H), 8.25 (s, 1H). $^{13}$C NMR (126 MHz, CDCl$_3$) δ 38.26, 121.54, 126.94, 128.10, 129.80, 131.85, 132.11, 132.30, 133.09, 134.41, 137.78, 139.94, 157.14, 163.85. LCQ (M+H$^+$) calcd C$_{17}$H$_{13}$BrClN$_3$O$_3$S$_2$ 486. found 486.

N-(5-chloropyridin-2-yl)-3-(N-(4-methoxyphenyl)-N-methylsulfamoyl)benzamide (88)

Compound 88 was prepared according to procedure C to afford 36 mg of white powder (54%). $^1$H NMR (500 MHz, CDCl$_3$) δ 3.18 (s, 3H), 3.79 (s, 3H), 6.82 (d, J=8.9 Hz, 2H), 6.98 (d, J=8.9 Hz, 2H), 7.61 (t, J=7.8 Hz, 1H), 7.71-7.74 (m, 2H), 8.98 (s, 1H), 8.16 (d, J=7.8 Hz, 1H), 8.20 (d, J=2.4 Hz, 1H), 8.33 (d, J=8.9 Hz, 1H), 8.75 (s, 1H). $^{13}$C NMR (126 MHz, CDCl$_3$) δ 38.67, 55.45, 114.27, 115.02, 126.21, 127.37, 128.12, 129.58, 131.35, 131.71, 133.55, 134.75, 137.51, 138.18, 146.60, 149.44, 158.98, 164.01. LCQ (M+H$^+$) calcd C$_{20}$H$_{18}$ClN$_3$O$_4$S 432. found 432.

N-(6-chloropyridazin-3-yl)-3-(N-(4-methoxyphenyl)-N-methylsulfamoyl)benzamide (89)

Compound 88 was prepared according to procedure C to afford 43 mg of white powder (64%). $^1$H NMR (500 MHz, CDCl$_3$) δ 3.19 (s, 3H), 3.81 (s, 3H), 6.83 (d, J=9.0 Hz, 2H), 6.99 (d, J=9.0 Hz, 2H), 7.59 (d, J=9.3 Hz, 1H), 7.65 (t, J=7.8 Hz, 1H), 7.75 (d, J=7.9 Hz, 1H), 8.14 (s, 1H), 8.23 (d, J=7.9 Hz, 1H), 8.63 (d, J=9.3 Hz, 1H), 9.46 (s, 1H). $^{13}$C NMR (126 MHz, CDCl$_3$) δ 38.67, 55.48, 114.27, 121.53, 126.61, 128.10, 129.66, 130.11, 131.76, 131.81, 133.48, 133.87, 137.75, 152.77, 154.35, 158.99, 164.67. LCQ (M+H$^+$) calcd C$_{19}$H$_{17}$ClN$_4$O$_4$S 433. found 433.

3-(N-(4-methoxyphenyl)-N-methylsulfamoyl)-N-(4-(methylsulfonyl)phenyl)benzamide (91)

Compound 91 was prepared according to procedure C to afford 53 mg of white powder (72%). $^1$H NMR (500 MHz, CDCl$_3$) δ 3.09 (s, 3H), 3.20 (s, 3H), 3.79 (s, 3H), 6.83 (d, J=8.9 Hz, 2H), 6.99 (d, J=8.9 Hz, 2H), 7.64 (t, J=7.8 Hz, 1H), 7.72 (d, J=7.9 Hz, 1H), 7.94 (s, 4H), 8.05 (d, J=1.5 Hz, 1H), 8.22 (dd, J=1.4, 7.8 Hz, 1H). $^{13}$C NMR (126 MHz, CDCl$_3$) δ 38.74, 44.64, 55.48, 114.28, 120.32, 120.40, 125.90, 128.28, 128.63, 129.62, 131.05, 132.70, 133.44, 135.19, 135.39, 136.92, 143.15, 159.02, 164.92. LCQ (M+H$^+$) calcd C$_{22}$H$_{22}$N$_2$O$_6$S$_2$ 475. found 475.

N-(5-cyanopyridin-2-yl)-3-(N-(4-methoxyphenyl)-N-methylsulfamoyl)benzamide (92)

Compound 92 was prepared according to procedure C to afford 33 mg of white powder (50%). $^1$H NMR (500 MHz, CDCl$_3$) δ 3.19 (s, 3H), 3.82 (s, 3H), 6.83 (d, J=9.0 Hz, 2H), 6.99 (d, J=9.0 Hz, 2H), 7.66 (t, J=7.8 Hz, 1H), 7.77 (d, J=7.9 Hz, 1H), 8.02 (dd, J=2.1, 8.7 Hz, 1H), 8.05 (s, 1H), 8.18 (d, J=7.9 Hz, 1H). 8.50 (d, J=8.7 Hz, 1H), 8.61 (s, 1H), 8.73 (s, 1H). $^{13}$C NMR (126 MHz, CDCl$_3$) δ 38.70, 55.47, 113.86, 114.32, 116.62, 126.18, 128.14, 129.80, 131.76, 131.84, 133.49, 134.09, 137.73, 141.84, 151.68, 153.56, 159.05. LCQ (M+H$^+$) calcd C$_{21}$H$_{18}$N$_4$O$_4$S 423. found 423.

N-(4-chlorophenyl)-3-(N-(4-cyanophenyl)-N-methylsulfamoyl)benzamide (93)

Compound 93 was prepared according to procedure C to afford 50 mg of white powder (76%). $^1$H NMR (500 MHz, CDCl$_3$) δ 3.24 (s, 3H), 7.28 (d, J=8.8 Hz, 2H), 7.35 (d, J=8.8 Hz, 2H), 7.60-7.64 (m, 6H), 8.06 (s, 1H), 8.15-8.17 (m, 1H), 8.25 (brs, 1H). $^{13}$C NMR (126 MHz, CDCl$_3$) δ 37.77, 110.95, 118.04, 121.55, 121.65, 125.70, 126.40, 129.23, 129.91, 130.15, 130.17, 130.51, 132.46, 133.07, 135.96, 135.99, 136.04, 136.75, 145.04, 163.85. LCQ (M+H$^+$) calcd C$_{21}$H$_{16}$ClN$_3$O$_3$S 426. found 426.

N-(5-chloropyridin-2-yl)-3-(N-(4-cyanophenyl)-N-methylsulfamoyl)benzamide (94)

Compound 94 was prepared according to procedure C to afford 45 mg of white powder (69%). $^1$H NMR (500 MHz, CDCl$_3$) δ 3.24 (s, 3H), 7.29 (d, J=8.7 Hz, 2H), 7.65 (d, J=8.7 Hz, 2H), 7.70 (dt, J=1.5, 8.0 Hz, 1H), 7.75 (dd, J=2.6, 8.9 Hz, 1H), 8.05 (s, 1H), 8.17 (dt, J=1.5, 7.7 Hz, 1H), 8.30 (d, J=2.4 Hz, 1H), 8.33 (d, J=9.0 Hz, 1H), 8.56 (brs, 1H). $^{13}$C NMR (126 MHz, CDCl$_3$) δ 37.68, 111.03, 114.87, 118.08, 126.08, 126.26, 127.61, 129.93, 130.92, 131.97, 133.06, 135.12, 137.04, 138.29, 145.05, 146.78, 149.20, 163.43. LCQ (M+H$^+$) calcd C$_{20}$H$_{15}$ClN$_4$O$_3$S 427. found 427.

N-(6-chloropyridazin-3-yl)-3-(N-(4-cyanophenyl)-N-methylsulfamoyl)benzamide (95)

Compound 95 was prepared according to procedure C to afford 38 mg of white powder (57%). $^1$H NMR (500 MHz, CDCl$_3$) δ 3.29 (s, 3H), 7.30 (d, J=8.7 Hz, 2H), 7.61-7.67 (m, 5H), 8.27-8.29 (m, 2H), 8.66 (d, J=9.3 Hz, 1H). $^{13}$C NMR (126 MHz, CDCl$_3$) δ 37.71, 110.75, 118.09, 121.95, 126.27, 126.92, 129.84, 130.27, 131.25, 132.35, 133.06, 134.46, 137.16, 145.07, 152.58, 154.74, 164.76. LCQ (M+H$^+$) calcd C$_{19}$H$_{14}$ClN$_5$O$_3$S 428. found 428.

3-(N-(4-cyanophenyl)-N-methylsulfamoyl)-N-(4-(methylsulfinyl)phenyl)benzamide (96)

Compound 96 was prepared according to procedure C to afford 53 mg of white powder (76%). $^1$H NMR (500 MHz, CDCl$_3$) δ 2.73 (s, 3H), 3.24 (s, 3H), 7.28 (d, J=8.7 Hz, 2H), 7.55-7.58 (m, 4H), 7.62 (d, J=8.7 Hz, 2H), 7.83 (d, J=8.7 Hz, 2H), 8.19-8.21 (m, 1H), 8.22 (s, 1H), 9.34 (s, 1H). $^{13}$C NMR (126 MHz, CDCl$_3$) δ 37.77, 43.59, 110.78, 118.14, 121.45, 124.76, 126.33, 126.39, 129.65, 130.49, 132.68, 133.06, 135.84, 136.69, 140.18, 140.86, 145.10, 164.38. LCQ (M+H$^+$) calcd C$_{22}$H$_{19}$N$_3$O$_4$S$_2$ 454. found 454.

N-(4-cyanophenyl)-3-(N-(4-cyanophenyl)-N-methyl-sulfamoyl)benzamide (97)

Compound 97 was prepared according to procedure C to afford 34 mg of white powder (53%). $^1$H NMR (500 MHz, CDCl$_3$) δ 3.28 (s, 3H), 7.30 (d, J=8.8 HZ, 2H), 7.62-7.69 (m, 6H), 7.89 (d, J=7.4 Hz, 2H), 8.19-8.22 (m, 2H). $^{13}$C NMR (126 MHz, CDCl$_3$) δ 37.68, 107.21, 110.71, 118.01, 118.85, 120.39, 126.33, 126.37, 129.66, 130.50, 132.74, 133.03, 133.17, 135.78, 136.54, 142.40, 145.04, 164.90. LCQ (M+H$^+$) calcd C$_{22}$H$_{16}$N$_4$O$_3$S 417. found 417.

3-(N-(4-cyanophenyl)-N-methylsulfamoyl)-N-(4-(methylsulfonyl)phenyl)benzamide (98)

Compound 98 was prepared according to procedure C to afford 58 mg of white powder (80%). $^1$H NMR (500 MHz, CDCl$_3$) δ 3.09 (s, 3H), 3.27 (s, 3H), 7.31 (d, J=8.7 Hz, 2H), 7.62-7.66 (m, 4H), 7.93-7.99 (m, 4H), 8.21-8.24 (m, 2H). $^{13}$C NMR (126 MHz, CDCl$_3$) δ 37.66, 44.52, 110.67, 118.01, 120.50, 126.36, 126.43, 128.51, 129.63, 130.51, 132.71, 133.02, 135.25, 135.74, 136.57, 143.31, 145.06, 165.00. LCQ (M+H$^+$) calcd C$_{22}$H$_{19}$N$_3$O$_5$S$_2$ 470. found 470. MAK-182.

3-(N-(4-cyanophenyl)-N-methylsulfamoyl)-N-(5-cyanopyridin-2-yl)benzamide (99)

Compound 99 was prepared according to procedure C to afford 26 mg of white powder (41%). $^1$H NMR (500 MHz, CDCl$_3$) δ 3.26 (s, 3H), 7.30 (d, J=8.7 Hz, 2H), 7.64-7.72 (m, 4H), 8.05 (dd, J=2.2, 8.8 Hz, 1H), 8.15 (s, 1H), 8.23 (d, J=7.6 Hz, 1H), 8.52 (d, J=8.8 Hz, 1H), 8.64 (d, J=1.6 Hz, 1H). $^{13}$C NMR (126 MHz, CDCl$_3$) δ 37.72, 105.61, 110.97, 114.09, 114.14, 116.56, 118.08, 126.32, 126.39, 130.00, 131.25, 132.39, 133.09, 134.58, 134.62, 137.06, 141.95, 145.03, 151.68, 153.76, 153.85, 164.06, 164.13. LCQ (M+H$^+$) calcd C$_{21}$H$_{15}$N$_5$O$_3$S 418. found 418.

N-(4-acetylphenyl)-3-(N-(4-cyanophenyl)-N-methyl-sulfamoyl)benzamide (100)

Compound 100 was prepared according to procedure C to afford 43 mg of white powder (79%). $^1$H NMR (500 MHz, CDCl$_3$) δ 2.43 (s, 3H), 3.25 (s, 3H), 7.29 (d, J=8.6 Hz, 2H), 7.60-7.65 (m, 4H), 7.83 (d, J=8.8 Hz, 2H), 7.98 (d, J=8.7 Hz, 2H), 8.17 (s, 1H), 8.21 (dd, J=1.7, 6.6 Hz, 1H). $^{13}$C NMR (126 MHz, CDCl$_3$) δ 26.49, 37.74, 110.79, 118.05, 119.71, 119.80, 126.15, 126.40, 129.71, 129.74, 130.48, 132.75, 133.06, 133.13, 135.96, 136.55, 142.43, 145.04, 164.55, 197.65. LCQ (M+H$^+$) calcd C$_{23}$H$_{19}$N$_3$O$_4$S 434. found 434.

N-(4-acetamidophenyl)-3-(N-(4-cyanophenyl)-N-methylsulfamoyl)benzamide (101)

Compound 101 was prepared according to procedure C to afford 37 mg of white powder (54%). $^1$H NMR (500 MHz, DMSO) δ 2.04 (s, 3H), 3.24 (s, 3H), 7.41 (d, J=8.3 Hz, 2H), 7.57 (d, J=8.7 Hz, 2H), 7.63-7.67 (m, 3H), 7.74 (t, J=7.8 Hz, 1H), 7.86 (d, J=8.3 Hz, 2H), 8.17 (s, 1H), 8.29 (d, J=7.7 Hz, 1H), 9.96 (s, 1H), 10.46 (s, 1H). $^{13}$C NMR (126 MHz, DMSO) δ 23.91, 37.34, 109.19, 118.33, 119.10, 121.09, 125.95, 126.32, 129.78, 129.88, 132.57, 133.12, 133.71, 135.59, 135.82, 136.03, 144.95, 163.29, 168.04. LCQ (M+H$^+$) calcd C$_{23}$H$_{20}$N$_4$O$_4$S 449. found 449.

3-(N-(4-acetylphenyl)-N-methylsulfamoyl)-N-(6-chloropyridazin-3-yl)benzamide (104)

Compound 104 was prepared according to procedure C to afford 33 mg of white powder (48%). $^1$H NMR (500 MHz, CDCl$_3$) δ 2.61 (s, 3H), 3.28 (s, 3H), 7.26 (d, J=8.7 Hz, 2H), 7.61-7.69 (m, 3H), 7.92 (d, J=8.7 Hz, 2H), 8.25-8.28 (m, 2H), 8.65 (d, J=9.4 Hz, 1H). $^{13}$C NMR (126 MHz, CDCl$_3$) δ 26.69, 37.94, 122.00, 125.88, 126.90, 129.33, 129.78, 130.26, 131.40, 132.29, 134.39, 135.57, 137.36, 145.28, 152.56, 154.82, 164.99, 197.58. LCQ (M+H$^+$) calcd C$_{20}$H$_{17}$ClN$_4$O$_4$S 445. found 445.

3-(N-(4-acetylphenyl)-N-methylsulfamoyl)-N-(4-(methylsulfinyl)phenyl)benzamide (105)

Compound 105 was prepared according to procedure C to afford 54 mg of white powder (74%). $^1$H NMR (500 MHz, CDCl$_3$) δ 2.59 (s, 3H), 2.74 (s, 3H), 3.25 (s, 3H), 7.24 (d, J=8.7 Hz, 2H), 7.56-7.61 (m, 4H), 7.81 (d, J=8.7 Hz, 2H), 7.91 (d, J=8.7 Hz, 2H), 8.14 (s, 1H), 8.18 (d, J=7.3 Hz, 1H), 8.80 (s, 1H). $^{13}$C NMR (126 MHz, CDCl$_3$) δ 26.68, 37.93, 43.74, 121.19, 124.76, 125.89, 126.01, 129.23, 129.67, 130.69, 132.42, 135.61, 136.94, 140.49, 140.65, 145.18, 164.26, 197.09. LCQ (M+H$^+$) calcd C$_{23}$H$_{22}$N$_2$O$_5$S$_2$ 471. found 471.

3-(N-(4-acetylphenyl)-N-methylsulfamoyl)-N-(4-(methylsulfonyl)phenyl)benzamide (107)

Compound 107 was prepared according to procedure C to afford 49 mg of white powder (66%). $^1$H NMR (500 MHz, CDCl$_3$) δ 2.59 (s, 3H), 3.07 (s, 3H), 3.25 (s, 3H), 7.23 (d, J=8.7 Hz, 2H), 7.59-7.65 (m, 2H), 7.83-7.85 (m, 2H), 7.89-7.92 (m, 4H), 8.07 (s, 1H), 8.17 (dt, J=1.7, 7.3 Hz, 1H), 8.42 (s, 1H). $^{13}$C NMR (126 MHz, CDCl$_3$) δ 26.69, 37.95, 44.64, 120.37, 125.82, 125.95, 128.74, 129.25, 129.90, 130.95, 132.39, 135.26, 135.70, 135.90, 137.06, 142.41, 145.10, 164.18, 197.11. LCQ (M+H$^+$) calcd C$_{23}$H$_{22}$N$_2$O$_6$S$_2$ 487. found 487.

3-(N-(4-acetylphenyl)-N-methylsulfamoyl)-N-(5-cyanopyridin-2-yl)benzamide (108)

Compound 108 was prepared according to procedure C to afford 49 mg of white powder (66%). $^1$H NMR (500 MHz, CDCl$_3$) δ 2.61 (s, 3H), 3.26 (s, 3H), 7.26 (d, J=8.7 Hz, 2H), 7.66 (t, J=7.8 Hz, 1H), 7.74 (d, J=7.9 Hz, 2H), 8.01-8.04 (m, 2H), 8.18 (d, J=7.8 Hz, 1H), 8.48 (d, J=8.8 Hz, 1H), 8.59 (d, J=1.9 Hz, 1H), 8.68 (s, 1H). $^{13}$C NMR (126 MHz, CDCl$_3$) δ 26.73, 37.90, 105.79, 113.85, 116.56, 125.86, 126.11, 129.30, 130.01, 131.42, 132.08, 134.35, 135.72, 137.32, 141.89, 145.13, 151.67, 153.46, 163.88, 196.95. LCQ (M+H$^+$) calcd C$_{22}$H$_{18}$N$_4$O$_4$S 435. found 435.

N-(4-acetamidophenyl)-3-(N-(4-acetylphenyl)-N-methylsulfamoyl)benzamide (110)

Compound 110 was prepared according to procedure C to afford 53 mg of white powder (74%). NMR (500 MHz, DMSO) δ 2.04 (s, 3H), 2.56 (s, 3H), 3.24 (s, 3H), 7.33 (d, J=8.3 Hz, 2H), 7.56 (d, J=8.7 Hz, 2H), 7.63-7.66 (m, 3H), 7.73 (t, J=7.8 Hz, 1H), 7.93 (d, J=8.3 Hz, 2H), 8.17 (s, 1H), 8.28 (d, J=7.7 Hz, 1H), 9.96 (s, 1H), 10.46 (s, 1H). $^{13}$C NMR (126 MHz, DMSO) δ 23.91, 26.72, 37.58, 119.09, 121.06, 125.34, 126.33, 129.01, 129.69, 129.89, 132.43, 133.73, 134.83, 135.58, 135.80, 136.26, 144.90, 163.37, 168.03, 197.00. LCQ (M+H$^+$) calcd C$_{23}$H$_{22}$N$_4$O$_5$S 467. found 467.

N-(4-cyanophenyl)-3-(N-methyl-N-(4-(methylsulfinyl)phenyl)sulfamoyl)benzamide (111)

Compound 111 was prepared according to procedure C to afford 46 mg of white powder (66%). $^1$H NMR (500 MHz, CDCl$_3$) δ 2.75 (s, 3H), 3.26 (s, 3H), 7.31-7.34 (m, 2H), 7.60-7.69 (m, 6H), 7.89 (d, J=8.3 Hz, 2H), 8.16 (s, 1H), 8.21 (d, J=6.5 Hz, 1H). $^{13}$C NMR (126 MHz, CDCl$_3$) δ 38.04, 43.37, 107.13, 118.87, 120.40, 124.53, 126.43, 127.27, 129.58, 130.63, 132.61, 133.14, 135.65, 136.64, 142.46, 143.73, 143.78, 164.97. LCQ (M+H$^+$) calcd C$_{22}$H$_{19}$N$_3$O$_4$S$_2$ 454. found 454.

3-(N-methyl-N-(4-(methylsulfinyl)phenyl)sulfamoyl)-N-(4-(methylsulfinyl)phenyl)benzamide (112)

Compound 112 was prepared according to procedure C to afford 60 mg of white powder (80%). $^1$H NMR (500 MHz, CDCl$_3$) δ 2.72 (s, 3H), 2.73 (s, 3H), 3.23 (s, 3H), 7.27 (d, J=8.8 Hz, 2H), 7.53-7.58 (m, 6H), 7.87 (d, J=8.7 Hz, 2H), 8.21 (d, J=7.5 Hz, 1H), 8.24 (s, 1H), 9.71 (s, 1H). $^{13}$C NMR (126 MHz, CDCl$_3$) δ 38.14, 43.68, 43.73, 121.39, 124.51, 124.64, 126.61, 127.21, 129.45, 130.56, 132.62, 135.80, 136.65, 140.06, 141.11, 143.70, 144.26, 164.59. LCQ (M+H$^+$) calcd C$_{22}$H$_{22}$N$_2$O$_5$S$_3$ 491. found 491.

N-(4-chlorophenyl)-3-(N-methyl-N-(4-(methylsulfinyl)phenyl)sulfamoyl)benzamide (113)

Compound 113 was prepared according to procedure C to afford 51 mg of white powder (71%). $^1$H NMR (500 MHz, CDCl$_3$) δ 2.71 (s, 3H), 3.23 (s, 3H), 7.28 (d, J=8.6 Hz, 2H), 7.34 (d, J=8.8 Hz, 2H), 7.58-7.64 (m, 6H), 8.04 (s, 1H), 8.11 (s, 1H), 8.14 (dd, J=1.5, 7.5 Hz, 1H). $^{13}$C NMR (126 MHz, CDCl$_3$) δ 38.11, 43.82, 121.63, 124.47, 125.82, 127.19, 129.18, 129.78, 130.09, 130.64, 132.17, 135.83, 136.00, 136.91, 143.56, 144.65, 163.82. LCQ (M+H$^+$) calcd C$_{21}$H$_{19}$ClN$_2$O$_4$S$_2$ 463. found 463.

N-(4-fluorophenyl)-3-(N-methyl-N-(4-(methylsulfinyl)phenyl)sulfamoyl)benzamide (114)

Compound 114 was prepared according to procedure C to afford 57 mg of white powder (83%). $^1$H NMR (500 MHz, CDCl$_3$) δ 2.71 (s, 3H), 3.23 (s, 3H), 7.06-7.09 (m, 2H), 7.28 (d, J=8.7 Hz, 2H), 7.58-7.64 (m, 6H), 8.05 (s, 1H), 8.14 (s, 1H), 8.15 (s, 1H). $^{13}$C NMR (126 MHz, CDCl$_3$) δ 38.11, 43.81, 115.76, 115.94, 122.29, 122.36, 124.47, 125.83, 127.19, 129.74, 130.55, 132.19, 133.40, 133.42, 135.93, 136.86, 143.58, 144.62, 163.87. LCQ (M+H$^+$) calcd C$_{21}$H$_{19}$FN$_2$O$_4$S$_2$ 447. found 447.

3-(N-methyl-N-(4-(methylsulfonyl)phenyl)sulfamoyl)-N-(4-(methylsulfinyl)phenyl)benzamide (116)

Compound 116 was prepared according to procedure C to afford 65 mg of white powder (83%). $^1$H NMR (500 MHz, CDCl$_3$) δ 2.73 (s, 3H), 3.09 (s, 3H), 3.26 (s, 3H), 7.36 (d, J=8.7 Hz, 2H), 7.55-7.62 (m, 4H), 7.82 (d, J=8.7 Hz, 2H), 7.88 (d, J=8.7 Hz, 2H), 8.19-8.20 (m, 2H), 9.24 (s, 1H). $^{13}$C NMR (126 MHz, CDCl$_3$) δ 37.87, 43.60, 44.45, 121.37, 124.73, 126.40, 128.42, 129.67, 130.49, 132.58, 135.80, 136.74, 138.71, 140.24, 140.76, 146.00, 164.30. LCQ (M+H$^+$) calcd C$_{22}$H$_{22}$N$_2$O$_6$S$_3$ 506. found 506.

N-(5-cyanopyridin-2-yl)-3-(N-methyl-N-(4-(methylsulfonyl)phenyl)sulfamoyl)benzamide (118)

Compound 118 was prepared according to procedure C to afford 50 mg of white powder (69%). $^1$H NMR (500 MHz, CDCl$_3$) δ 3.08 (s, 3H), 3.28 (s, 3H), 7.38 (d, J=8.8 Hz, 2H), 7.69 (t, 7.8 Hz, 1H), 7.76 (dt, J=1.3, 8.1 Hz, 1H), 7.93 (d, J=8.8 Hz, 2H), 8.04 (dd, J=2.2, 8.7 Hz, 1H), 8.11 (s, 1H), 8.17 (dd, J=1.3, 7.8 Hz, 1H). 8.49 (dd, J=0.6, 8.7 Hz, 1H), 8.63 (dd, J=0.6, 2.1 Hz, 1H), 8.67 (s, 1H). $^{13}$C NMR (126 MHz, CDCl$_3$) δ 37.87, 44.49, 105.90, 113.80, 116.48, 126.29, 126.40, 128.54, 130.15, 131.39, 131.89, 134.51, 137.47, 141.92, 145.90, 151.72, 153.32, 163.61. LCQ (M+H$^+$) calcd C$_{21}$H$_{18}$N$_4$O$_5$S$_2$ 471. found 471.

N-(4-cyanophenyl)-3-(N-(4-cyanophenyl)-N-methylsulfamoyl)-4-methoxybenzamide (119)

Compound 119 was prepared according to procedure C to afford 37 mg of white powder (54%). $^1$H NMR (500 MHz, DMSO) δ 3.33 (s, 3H), 3.76 (s, 3H), 7.37 (d, J=8.8 Hz, 2H), 7.47 (d, J=8.7 Hz, 2H), 7.80-7.85 (m, 4H), 7.97 (d, J=8.7 Hz, 2H), 8.28 (dd, J=2.1, 8.8 Hz, 1H), 8.43 (s, 1H), 10.75 (s, 1H). $^{13}$C NMR (126 MHz, CDCl$_3$) δ 41.38, 60.17, 110.68, 112.72, 116.39, 122.20, 122.90, 124.37, 128.14, 129.45, 130.64, 134.88, 136.75, 137.03, 139.72, 146.72, 149.67, 163.26, 168.73. LCQ (M+H$^+$) calcd C$_{22}$H$_{17}$N$_5$O$_4$S 448. found 448.

3-(N-(4-cyanophenyl)-N-methylsulfamoyl)-4-methoxy-N-(4-(methylsulfinyl)phenyl)benzamide (120)

Compound 120 was prepared according to procedure C to afford 64 mg of white powder (86%). $^1$H NMR (500 MHz, CDCl$_3$) δ 2.76 (s, 3H), 3.38 (s, 3H), 3.76 (s, 3H), 7.08 (d, J=8.8 Hz, 2H), 7.40 (d, J=8.2 Hz, 2H), 7.61-7.65 (m, 2H), 7.91 (d, J=8.4 Hz, 1H), 8.23 (d, J=8.7 Hz, 1H), 8.47 (s, 1H). $^{13}$C NMR (126 MHz, CDCl$_3$) δ 43.57, 50.28, 53.45, 99.99, 108.94, 112.20, 112.74, 118.30, 121.14, 124.02, 124.56, 124.81, 125.50, 126.84, 130.50, 132.68, 135.78, 139.53, 141.27, 141.36, 145.71, 159.22, 164.35. LCQ (M+H$^+$) calcd C$_{22}$H$_{17}$N$_5$O$_4$S 448. found 448. LCQ (M+H$^+$) calcd C$_{22}$H$_{20}$N$_4$O$_5$S$_2$ 485. found 485.

3-(N-(4-acetylphenyl)-N-methylsulfamoyl)-N-(4-cyanophenyl)-4-methoxybenzamide (121)

Compound 121 was prepared according to procedure C to afford 51 mg of white powder (71%). $^1$H NMR (500 MHz, DMSO) δ 2.53 (s, 3H), 3.36 (s, 3H), 3.82 (s, 3H), 7.38 (d, J=9.0 Hz, 1H), 7.40 (d, J=8.3 Hz, 2H), 7.83 (d, J=8.3 Hz, 2H), 7.90 (d, J=8.3 Hz, 2H), 7.97 (d, J=8.3 Hz, 2H), 8.26 (d, J=8.7 Hz, 1H), 8.42 (s, 1H), 10.74 (s, 1H). $^{13}$C NMR (126 MHz, DMSO) δ 26.67, 56.46, 56.92, 105.41, 112.82, 115.23, 119.02, 120.32, 122.88, 123.28, 125.60, 125.93, 128.94, 131.04, 133.11, 133.46, 135.33, 143.28, 145.26, 159.09, 164.07, 196.83. LCQ (M+H$^+$) calcd C$_{24}$H$_{21}$N$_3$O$_5$S 464. found 464.

3-(N-(4-acetylphenyl)-N-methylsulfamoyl)-4-methoxy-N-(4-(methylsulfonyl)phenyl)benzamide (122)

Compound 122 was prepared according to procedure C to afford 59 mg of white powder (74%). $^1$H NMR (500 MHz, DMSO) δ 2.53 (s, 3H), 3.20 (s, 3H), 3.82 (s, 3H), 7.38 (d, J=9.1 Hz, 1H), 8.3 Hz, 2H), 7.90-7.93 (m, 4H), 8.02 (d, J=8.2 Hz, 2H), 8.28 (d, J=8.8 Hz, 1H), 8.44 (s, 1H), 10.76 (s, 1H). $^{13}$C NMR (126 MHz, DMSO) δ 26.68, 43.85, 56.46, 112.82, 113.24, 120.13, 122.89, 123.28, 125.60, 125.92, 128.00, 128.93, 130.84, 131.04, 133.47, 135.11, 143.53, 145.27, 159.08, 164.02, 196.84. LCQ (M+H$^+$) calcd C$_{24}$H$_{24}$N$_2$O$_7$S$_2$ 517. found 517.

N-(4-chlorophenyl)-3-(N-(5-chloropyridin-2-yl)-N-methylsulfamoyl)benzamide (123)

Compound 123 was prepared according to procedure C to afford 55 mg of white powder (82%). $^1$H NMR (500 MHz, CDCl$_3$) δ 3.27 (s, 3H), 7.64 (d, J=9.0 Hz, 2H), 7.72 (d, J=2.6 Hz, 1H), 7.72-7.78 (m, 3H), 8.13-8.16 (m, 2H), 8.28-8.30 (m, 2H), 8.34 (d, J=8.9 Hz, 1H), 8.57 (brs, 1H). $^{13}$C NMR (126 MHz, CDCl$_3$) δ 35.97, 114.83, 121.89, 126.14, 127.45, 129.86, 131.02, 131.86, 134.93, 137.73, 138.09, 138.22, 146.72, 146.94, 149.31, 151.69, 163.57. LCQ (M+H$^+$) calcd C$_{19}$H$_{15}$C$_{12}$N$_3$O$_3$S 436. found 436.

3-(N-(5-chloropyridin-2-yl)-N-methylsulfamoyl)-N-(4-cyanophenyl)benzamide (124)

Compound 124 was prepared according to procedure C to afford 46 mg of white powder (70%). $^1$H NMR (500 MHz, CDCl$_3$) δ 3.25 (s, 3H), 7.57-7.62 (m, 2H), 7.67-7.71 (m, 4H), 7.82 (d, J=8.8 Hz, 2H), 8.13-8.14 (m, 2H), 8.22 (dd, J=0.5, 2.6 Hz, 1H), 8.36 (s, 1H). $^{13}$C NMR (126 MHz, CDCl$_3$) δ 35.97, 107.79, 120.22, 121.65, 125.94, 129.83, 129.92, 130.85, 132.35, 133.37, 135.21, 137.70, 137.79, 141.63, 146.83, 151.50, 164.13. LCQ (M+H$^+$) calcd C$_{20}$H$_{15}$ClN$_4$O$_3$S 427. found 427.

3-(N-(5-chloropyridin-2-yl)-N-methylsulfamoyl)-N-(4-(methylsulfinyl)phenyl)benzamide (125)

Compound 125 was prepared according to procedure C to afford 49 mg of white powder (68%). $^1$H NMR (500 MHz, CDCl$_3$) δ 2.73 (s, 3H), 3.28 (s, 3H), 7.56-7.63 (m, 4H), 7.67-7.71 (m, 2H), 7.82 (d, J=8.7 Hz, 2H), 8.16 (dd, J=1.2, 7.8 Hz, 1H), 8.22-8.23 (m, 2H), 8.87 s, 1H). $^{13}$C NMR (126 MHz, CDCl$_3$) δ 35.94, 43.70, 121.25, 121.58, 124.76, 126.27, 129.67, 130.56, 132.36, 135.54, 137.66, 137.72, 140.49, 140.59, 146.77, 151.57, 164.27. LCQ (M+H$^+$) calcd C$_{20}$H$_{18}$ClN$_3$O$_4$S$_2$ 464. found 464.

N-(4-chlorophenyl)-3-(N-(4-(1-hydroxyethyl)phenyl)-N-methylsulfamoyl)benzamide (127)

127 was prepared according to procedure K from 155 (25 mg, 0.058 mmol) to afford 23 mg of 127 (89%). $^1$H NMR (500 MHz, CDCl$_3$) δ 1.44 (d, J=6.5 Hz, 3H), 3.21 (s, 3H), 4.84 (q, J=6.5 Hz, 1H), 7.05 (d, J=8.4 Hz, 2H), 7.31-7.34 (m, 4H), 7.60-7.65 (m, 3H), 7.71 (d, J=7.8 Hz, 1H), 8.01 (s, 1H), 8.18 (d, J=7.8 Hz, 1H). $^{13}$C NMR (126 MHz, CDCl$_3$) δ 24.97, 38.35, 69.21, 121.88, 121.98, 126.13, 126.71, 128.92, 129.44, 129.73, 130.56, 132.39, 135.59, 135.62, 136.73, 139.75, 145.84, 164.65. LCQ (M+H$^+$) calcd C$_{22}$H$_{21}$ClN$_2$O$_4$S 445. found 445.

N-(5-chloropyridin-2-yl)-3-(N-(4-(1-hydroxyethyl)phenyl)-N-methylsulfamoyl)benzamide (128)

128 was prepared according to procedure K from 155 (25 mg, 0.058 mmol) to afford 24 mg of 128 (91%). $^1$H NMR (500 MHz, CDCl$_3$) δ 1.48 (d, J=6.5 HZ, 3H), 3.19 (s, 3H), 4.93 (q, J=6.5 Hz, 1H), 7.08 (d, J=8.5 Hz, 2H), 7.31 (d, J=1.6 Hz, 1H), 7.42 (d, J=8.5 Hz, 2H), 7.70-7.76 (m, 3H), 7.98 (dt, J=1.3, 7.9 Hz, 1H), 8.19 (dt, J=1.3, 7.9 Hz, 1H), 8.28 (s, 1H), 8.29 (d, J=5.1 Hz, 1H). $^{13}$C NMR (126 MHz, CDCl$_3$) δ 24.98, 37.91, 69.39, 115.25, 125.63, 125.99, 126.71, 127.69, 129.80, 130.95, 132.62, 134.24, 135.70, 138.72, 140.02, 146.42, 146.86, 149.01, 163.93. LCQ (M+H$^+$) calcd C$_{21}$H$_{20}$ClN$_3$O$_4$S 446. found 446.

3-(azepan-1-ylsulfonyl)-N-(4-chloropyridin-2-yl)benzamide (129)

Compound 129 was prepared according to procedure C to afford 35 mg of white powder (57%). $^1$H NMR (500 MHz, CDCl$_3$) δ 1.61 (m. 4H), 1.74 (bs, 4H), 3.31 (t, J=5.9 Hz, 4H), 7.72 (dd, J=1.8, 5.4 Hz, 1H), 7.68 (t, J=7.8 Hz, 1H), 8.00 (dt, J=1.5, 6.6 Hz, 1H), 8.12 (dt, J=1.5, 6.6 Hz, 1H), 8.17 (d, J=5.4 Hz, 1H), 8.47 (d, J=1.8 Hz, 1H), 9.01 (s, 1H). $^{13}$C NMR (126 MHz, CDCl$_3$) δ 26.86, 29.17, 48.34, 114.57, 120.81, 125.56, 129.86, 130.46, 130.99, 134.93, 140.74, 146.12, 148.63, 152.09, 164.29. LCQ (M+H$^+$) calcd C$_{18}$H$_{20}$ClN$_3$O$_3$S 394. found 394.

3-(azepan-1-ylsulfonyl)-N-(4-bromopyridin-2-yl)benzamide (130)

Compound 130 was prepared according to procedure C to afford 35 mg of white powder (52%). $^1$H NMR (500 MHz, CDCl$_3$) δ 1.56 (m. 4H), 1.68 (bs, 4H), 3.25 (t, J=5.9 Hz, 4H), 7.61 (t, J=7.8 Hz, 1H), 7.90 (d, J=7.9 Hz, 1H), 8.01 (s, 1H), 8.18 (d, J=7.8 Hz, 1H), 8.34 (s, 1H), 8.42 (s, 1H), 8.60 (d, J=2.0 Hz, 1H), 9.93 (s, 1H). $^{13}$C NMR (126 MHz, CDCl$_3$) δ 26.81, 29.06, 48.31, 120.44, 125.54, 129.68, 129.97, 130.24, 132.04, 135.31, 139.81, 140.18, 146.09, 162.89, 165.25. LCQ (M+H$^+$) calcd C$_{18}$H$_{20}$BrN$_3$O$_3$S 438. found 438.

3-(azepan-1-ylsulfonyl)-N-(3-bromobenzyl)benzamide (131)

Compound 131 was prepared according to procedure C to afford 60 mg of white powder (86%). $^1$H NMR (500 MHz, CDCl$_3$) δ 1.59 (dd, J=2.7, 6.2 Hz, 4H), 1.71 (d, J=0.9 Hz, 4H), 3.28 (t, J=5.8 Hz, 4H), 4.64 (d, J=5.9 Hz, 2H), 6.99 (t, J=5.6 Hz, 1H), 7.24 (t, J=7.9 Hz, 1H), 7.32 (d, J=7.8 Hz, 1H), 7.44 (d, J=7.9 Hz, 1H), 7.53 (s, 1H), 7.61 (t, J=7.8 Hz, 1H), 7.92 (dt, J=1.4, 7.9 Hz, 1H), 8.08 (dt, J=1.4, 7.9 Hz, 1H), 8.21 (s, 1H). $^{13}$C NMR (126 MHz, CDCl$_3$) δ 26.85, 28.98, 43.66, 48.32, 122.77, 125.02, 126.64, 129.65, 130.36, 130.78, 130.93, 131.40, 135.19, 140.02, 140.27, 165.83. LCQ (M+H$^+$) calcd C$_{20}$H$_{23}$BrN$_2$O$_3$S 451. found 451.

3-(azepan-1-ylsulfonyl)-N-(3-chlorobenzyl)benzamide (132)

Compound 132 was prepared according to procedure C to afford 51 mg of white powder (81%). $^1$H NMR (500 MHz, CDCl$_3$) δ 1.55 (t, J=3.4 Hz, 4H), 1.67 (brs, 4H), 3.25 (t, J=5.9 Hz, 4H), 4.62 (d, J=5.9 Hz, 2H), 7.23-7.29 (m, 2H), 7.31 (t, J=5.9 Hz, 1H), 7.35 (s, 1H), 7.58 (t, J=7.8 Hz, 1H), 7.89 (dd, J=1.2, 7.9 Hz, 1H), 8.09 (dd, J=1.2, 7.9 Hz, 1H), 8.24 (s, 1H). $^{13}$C NMR (126 MHz, CDCl$_3$) δ 26.83, 29.06, 43.50, 48.30, 125.05, 126.11, 127.70, 127.95, 129.61, 129.99, 131.55, 134.45, 135.19, 139.81, 140.17, 165.86. LCQ (M+H$^+$) calcd C$_{20}$H$_{23}$ClN$_2$O$_3$S 407. found 407.

3-(azepan-1-ylsulfonyl)-N-(3-cyanophenyl)benzamide (133)

Compound 133 was prepared according to procedure C to afford 41 mg of white powder (70%). $^1$H NMR (500 MHz, CDCl$_3$) δ 1.53 (t, J=3.2 Hz, 4H), 1.64 (brs, 4H), 3.24 (t, J=6.0 Hz, 4H), 7.43-7.50 (m, 2H), 7.62 (t, J=7.8 Hz, 1H), 7.89 (d, J=7.8 Hz, 1H), 8.00 (d, J=7.8 Hz, 1H), 8.14-8.16 (m, 2H), 8.30 (s, 1H), 9.11 (s, 1H). $^{13}$C NMR (126 MHz, CDCl$_3$) δ 26.79, 28.99, 48.34, 112.76, 118.62, 123.94, 125.03, 125.28, 128.13, 129.84, 129.90, 129.95, 132.02, 135.48, 138.85, 139.66, 164.93. LCQ (M+H$^+$) calcd C$_{20}$H$_{21}$N$_3$O$_3$S 384. found 384.

3-(azepan-1-ylsulfonyl)-N-(6-chloropyridazin-3-yl)benzamide (134)

Compound 134 was prepared according to procedure C to afford 39 mg of white powder (64%). $^1$H NMR (500 MHz, CDCl$_3$) δ 1.63 (m, 4H), 1.77 (t, J=0.8 Hz, 4H), 3.34 (t, J=5.9 Hz, 4H), 7.62 (d, J=9.4 Hz, 1H), 7.73 (t, J=7.8 Hz, 1H), 8.06 (dt, J=1.2, 8.0 Hz, 1H), 8.20 (dt, J=1.2, 8.0 Hz, 1H), 8.39 (s, 1H), 8.67 (d, J=9.4 Hz, 1H). $^{13}$C NMR (126 MHz, CDCl$_3$) δ 26.87, 29.19, 48.36, 121.49, 125.93, 129.99, 130.16, 130.92, 131.03, 134.12, 140.98, 152.82, 154.37, 164.74. LCQ (M+H$^+$) calcd C$_{17}$H$_{19}$ClN$_4$O$_3$S 395. found 395.

3-(azepan-1-ylsulfonyl)-N-(5-chloropyridin-2-yl)benzamide (135)

Compound 135 was prepared according to procedure C to afford 36 mg of white powder (59%). $^1$H NMR (500 MHz, CDCl$_3$) δ 1.59 (m, 4H), 1.73 (brs, 4H), 3.30 (t, J=5.9 Hz, 4H), 7.42-7.47 (m, 2H), 7.61 (t, J=7.8 Hz, 1H), 7.73 (d, J=8.0 Hz, 1H), 7.81 (d, J=8.0 Hz, 1H), 7.98-8.00 (m, 1H), 8.25 (dt, J=1.3, 7.9 Hz, 1H), 8.47 (t, J=1.6 Hz, 1H). $^{13}$C NMR (126 MHz, CDCl$_3$) δ 26.85, 29.14, 48.31, 111.03, 117.17, 126.34, 126.75, 128.22, 129.27, 131.03, 131.50, 133.47, 140.08, 146.04, 167.40. LCQ (M+H$^+$) calcd C$_{18}$H$_{20}$ClN$_3$O$_3$S 394. found 394.

3-(azepan-1-ylsulfonyl)-N-(pyridin-2-ylmethyl)benzamide (136)

Compound 136 was prepared according to procedure C to afford 55 mg of white powder (95%). $^1$H NMR (500 MHz, CDCl$_3$) δ 1.58 (t, J=5.3 Hz, 4H), 1.72 (s, 4H), 3.27 (t, J=5.9 Hz, 4H), 4.76 (d, J=4.9 Hz, 2H), 7.23 (dd, J=5.2, 7.2 Hz, 1H), 7.33 (d, J=7.8 Hz, 1H), 7.59 (t, J=7.8 Hz, 1H), 7.70 (dt, J=1.6, 7.7 Hz, 1H), 7.91-7.94 (m, 2H), 8.07 (d, J=7.3 Hz, 1H), 8.28 (s, 1H), 8.55 (d, J=4.7 Hz, 1H). $^{13}$C NMR (126 MHz, CDCl$_3$) δ 26.85, 29.14, 44.87, 48.30, 122.22, 122.60, 125.43, 129.45, 129.57, 130.95, 135.48, 136.96, 140.13, 149.03, 155.78, 165.86. LCQ (M+H$^+$) calcd C$_{19}$H$_{23}$N$_3$O$_3$S 374. found 374.

3-(azepan-1-ylsulfonyl)-N-(3-(trifluoromethyl)phenyl)benzamide (137)

Compound 137 was prepared according to procedure C to afford 58 mg of white powder (88%). $^1$H NMR (500 MHz, CDCl$_3$) δ 1.57 (m, 4H), 1.70 (brs, 4H), 3.28 (t, J=5.9 Hz, 4H), 7.44 (d, J=7.8 Hz, 1H), 7.52 (t, J=7.9 Hz, 1H), 7.65 (t, 7.8 Hz, 1H), 7.89 (d, J=8.1 Hz, 1H), 7.93 (d, J=7.9 Hz, 1H), 8.03 (s, 1H), 8.12 (d, J=7.8 Hz, 1H), 8.25 (s, 1H), 8.37 (s, 1H). $^{13}$C NMR (126 MHz, CDCl$_3$) δ 26.81, 29.06, 48.32, 117.19, 117.22, 117.26, 117.29, 121.43, 121.46, 121.49, 121.52, 123.47, 125.00, 129.66, 129.91, 129.98, 131.37, 131.51, 135.58, 138.13, 140.17, 164.50. LCQ (M+H$^+$) calcd C$_{20}$H$_{21}$F$_3$N$_2$O$_3$S 427. found 427.

3-(azepan-1-ylsulfonyl)-N-(3-(methylsulfinyl)phenyl)benzamide (138)

Compound 138 was prepared according to procedure C to afford 53 mg of white powder (81%). $^1$H NMR (500 MHz, CDCl$_3$) δ 1.59 (m, 4H), 1.72 (s, 4H), 2.73 (s, 3H), 3.30 (t, J=5.9 Hz, 4H), 7.15 (d, J=7.8 Hz, 1H), 7.46 (t, J=8.0 Hz, 1H), 7.66 (t, J=7.9 Hz, 1H), 7.97 (d, J=7.9 Hz, 1H), 8.15 (s, 1H), 8.22 (d, J=7.8 Hz, 1H), 8.35 (dd, J=0.8, 8.2 HZ, 1H), 8.45 (s, 1H), 10.30 (s, 1H). $^{13}$C NMR (126 MHz, CDCl$_3$) δ 26.82, 29.12, 43.94, 48.34, 115.18, 119.04, 123.22, 125.70, 129.43, 129.71, 132.05, 136.15, 139.84, 140.36, 145.41, 165.17. LCQ (M+H$^+$) calcd C$_{20}$H$_{24}$N$_2$O$_4$S$_2$ 421. found 421.

3-(azepan-1-ylsulfonyl)-N-(3-(methylsulfonyl)phenyl)benzamide (139)

Compound 139 was prepared according to procedure C to afford 50 mg of white powder (74%). $^1$H NMR (500 MHz, CDCl$_3$) δ 1.54 (m, 4H), 1.66 (brs, 4H), 3.10 (s, 3H), 3.26 (t, J=5.9 Hz, 4H), 7.53 (t, J=8.0 Hz, 1H), 7.61 (t, J=7.8 Hz, 1H), 7.66 (d, J=7.9 Hz, 1H), 7.90 (d, J=7.9 Hz, 1H), 8.17 (d, J=7.8 Hz, 1H), 8.20 (d, J=8.2 Hz, 1H), 8.38 (s, 1H), 9.48 (s, 1H). $^{13}$C NMR (126 MHz, CDCl$_3$) δ 26.77, 29.03, 44.30, 48.30, 119.29, 122.80, 125.72, 125.86, 129.72, 129.90, 130.09, 131.72, 135.39, 139.25, 139.81, 140.73, 164.99. LCQ (M+H$^+$) calcd C$_{20}$H$_{24}$N$_2$O$_5$S$_2$ 437. found 437.

3-(azepan-1-ylsulfonyl)-N-(pyridin-3-ylmethyl)benzamide (140)

Compound 140 was prepared according to procedure C to afford 48 mg of white powder (83%). $^1$H NMR (500 MHz, CDCl$_3$) δ 1.55-1.56 (m, 4H), 1.67 (brs, 4H), 3.23 (t, J=6.0 Hz, 4H), 4.67 (d, J=5.9 Hz, 2H), 7.26-7.28 (m, 1H), 7.53 (t, J=5.7 Hz, 1H), 7.59 (t, J=7.8 Hz, 1H), 7.75 (dd, J=1.8, 6.1 Hz, 1H), 7.88 (d, J=7.9 Hz, 1H), 8.08 (d, J=7.9 Hz, 1H), 8.20 (s, 1H), 8.48 (dd, J=1.4, 4.8 Hz. 1H), 8.59 (d, J=1.8 Hz, 1H). $^{13}$C NMR (126 MHz, CDCl$_3$) δ 26.79, 29.06, 41.60, 48.28, 123.69, 125.07, 129.59, 129.62, 131.52, 133.86, 135.15, 136.04, 139.86, 148.87, 149.39, 166.01. LCQ (M+H$^+$) calcd C$_{19}$H$_{23}$N$_3$O$_3$S 374. found 374.

3-(azepan-1-ylsulfonyl)-N-(3-(methylsulfinyl)phenyl)benzamide (141)

Compound 141 was prepared according to procedure C to afford 43 mg of white powder (66%). $^1$H NMR (500 MHz, DMSO) δ 1.50 (m, 4H), 1.63 (brs, 4H), 3.20 (t, J=5.9 Hz, 4H), 7.64-7.69 (m, 2H), 7.78 (t, 1H), 8.00 (d, J=7.9 Hz, 1H), 8.04 (d, J=7.9 Hz, 1H), 8.14 (d, J=7.9 Hz, 1H), 8.28 (s, 1H). $^{13}$C NMR (126 MHz, DMSO) δ 26.27, 28.48, 47.74, 119.15, 122.79, 125.63, 126.28, 129.60, 129.77, 131.80, 132.29, 135.37, 139.33, 164.19. LCQ (M+H$^+$) calcd C$_{20}$H$_{24}$N$_2$O$_4$S$_2$ 421. found 421.

3-(azepan-1-ylsulfonyl)-N-(5-chlorothiazol-2-yl)benzamide (142)

Compound 142 was prepared according to procedure C to afford 55 mg of white powder (89%). $^1$H NMR (500 MHz, CDCl$_3$) δ 1.63 (m, 4H), 1.77 (m, 4H), 3.33 (t, 4H, J=5.9 Hz), 7.20 (s, 1H), 7.74 (t, 1H, J=7.9 Hz), 8.08 (dt, 1H, J=1.3, 7.9 Hz), 8.16 (dt, 1H, J-1.3, 7.9 Hz), 8.37 (t, 1H, J=1.7 Hz). $^{13}$C NMR (126 MHz, CDCl$_3$) δ 26.80, 29.28, 48.28, 121.51, 124.31, 125.77, 130.08, 130.98, 132.85, 134.71, 140.83, 156.12, 162.91. LCQ (M+H$^+$) calcd C$_{16}$H$_{18}$ClN$_3$O$_3$S$_2$ 400. found 400.

3-(azepan-1-ylsulfonyl)-N-(5-methylthiazol-2-yl)benzamide (143)

Compound 143 was prepared according to procedure C to afford 53 mg of white powder (90%). $^1$H NMR (500 MHz, CDCl$_3$) δ 1.61 (m, 4H), 1.74 (m, 4H), 2.08 (s, 3H), 3.28 (t, J=5.9 Hz, 4H), 6.61 (d, J=0.9 Hz, 1H), 7.64 (t, J=7.8 Hz, 1H), 8.02 (dd, J=1.1, 7.8 Hz, 1H), 8.10 (dd, J=1.1, 7.8 Hz, 1H), 8.37 (s, 1H). $^{13}$C NMR (126 MHz, CDCl$_3$) δ 16.54, 26.85, 29.21, 48.31, 108.95, 126.16, 129.77, 130.77, 131.18, 133.65, 140.91, 146.60, 158.89, 164.00. LCQ (M+H$^+$) calcd C$_{17}$H$_{21}$N$_3$O$_3$S$_2$ 380. found 380.

3-(azepan-1-ylsulfonyl)-N-(thiazol-2-ylmethyl)benzamide (144)

Compound 144 was prepared according to procedure C to afford 48 mg of white powder (82%). $^1$H NMR (500 MHz, CDCl$_3$) δ 1.56 (m, 4H), 1.67 (m, 4H), 3.23 (t, J=5.9 Hz, 4H), 4.94 (d, J=5.8 Hz, 2H), 7.31 (d, J=3.3 Hz, 1H), 7.57 (t, J=7.8 Hz, 1H), 7.69 (d, J=3.3 Hz, 1H), 7.89 (dt, J=1.3, 7.9 Hz, 1H), 8.08 (dt, 1.3, J=7.9 Hz, 1H), 8.14 (t, J=5.5 Hz, 1H), 8.27 (t, J=1.6 Hz, 1H). $^{13}$C NMR (126 MHz, CDCl$_3$) δ 26.82, 29.10, 41.43, 48.27, 119.86, 125.46, 129.52, 129.76, 131.32, 134.84, 140.03, 142.25, 162.66, 165.96, 167.23. LCQ (M+H$^+$) calcd C$_{17}$H$_{21}$N$_3$O$_3$S$_2$ 380. found 380.

3-(azepan-1-ylsulfonyl)-N-(thiazol-2-yl)benzamide (145)

Compound 145 was prepared according to procedure C to afford 42 mg of white powder (75%). $^1$H NMR (500 MHz, CDCl$_3$) δ 1.59 (m, 4H), 1.72 (bs, 4H), 3.29 (t, J=5.9 Hz, 4H), 6.93 (d, J=3.7 Hz, 1H), 6.98 (d, J=3.7 Hz, 1H), 7.68 (t, J=7.8 Hz, 1H), 8.05 (dt, J=1.1, 7.9 Hz, 1H), 8.02 (dt, J=1.1, 7.9 Hz, 1H), 8.45 (t, J=1.7 Hz, 1H). $^{13}$C NMR (126 MHz, CDCl$_3$) δ 26.85, 29.21, 48.35, 114.04, 126.61, 129.71, 130.68, 131.49, 134.11, 136.97, 140.87, 160.08, 164.65. LCQ (M+H$^+$) calcd C$_{16}$H$_{19}$N$_3$O$_3$S$_2$ 366. found 366.

3-(azepan-1-ylsulfonyl)-N-(2-methyloxazol-5-yl)benzamide (147)

Compound 147 was prepared according to procedure C to afford 24 mg of white powder (42%). $^1$H NMR (500 MHz, CDCl$_3$) δ 1.59 (m, 4H), 1.73 (brs, 4H), 3.30 (t, J=5.9 Hz, 4H), 7.40-7.48 (m, 2H), 7.61 (t, J=7.8 Hz, 1H), 7.71 (d, J=8.3 Hz, 1H), 7.84 (d, J=8.3 Hz, 1H), 7.98 (d, J=7.9 Hz, 1H), 8.24 (d, J=7.9 Hz, 1H), 8.46 (s, 1H). $^{13}$C NMR (126 MHz, CDCl$_3$) δ 26.87, 29.15, 48.34, 110.70, 117.64, 125.97, 126.86, 128.19, 128.28, 129.28, 130.95, 131.69, 133.47, 140.03, 167.25. LCQ (M+H$^+$) calcd C$_{17}$H$_{21}$N$_3$O$_4$S 364. found 364.

3-(azepan-1-ylsulfonyl)-N-(5-bromothiazol-2-yl)benzamide (148)

Compound 148 was prepared according to procedure C to afford 42 mg of white powder (62%). $^1$H NMR (500 MHz, CDCl$_3$) δ 1.60 (m, 4H), 1.75 (brs, 4H), 3.30 (t, J=5.9 Hz, 4H), 7.01 (s, 1H), 7.71 (t, J=7.8 Hz, 1H), 8.07 (d, J=8.0 Hz, 1H), 8.16 (d, J=9.0 Hz, 1H), 8.39 (s, 1H), 11.83 (s, 1H). $^{13}$C NMR (126 MHz, CDCl$_3$) δ 26.83, 29.21, 48.34, 104.24, 126.24, 129.94, 131.03, 131.29, 133.06, 137.82, 141.11, 159.52, 164.09. LCQ (M+H$^+$) calcd C$_{16}$H$_{18}$BrN$_3$O$_3$S$_2$ 444. found 444.

3-(azepan-1-ylsulfonyl)-N-(3,4-dimethylisoxazol-5-yl)benzamide (149)

Compound 149 was prepared according to procedure C to afford 16 mg of white powder (28%). $^1$H NMR (500 MHz, CDCl$_3$) δ 1.61 (m, 4H), 1.75 (brs, 4H), 1.99 (s, 3H), 2.26 (s, 3H), 3.32 (t, J=5.9 Hz, 4H), 7.69 (t, J=7.9 Hz, 1H), 8.01 (d, J=7.8 Hz, 1H), 8.16 (d, J=7.8 Hz, 1H), 8.34 (s, 1H). $^{13}$C NMR (126 MHz, CDCl$_3$) δ 7.44, 10.76, 26.86, 29.16, 48.37, 104.28, 125.78, 129.89, 130.55, 131.75, 133.85, 140.52, 155.70, 162.26, 163.08. LCQ (M+H$^+$) calcd C$_{18}$H$_{23}$N$_3$O$_4$S 378. found 378.

3-(azepan-1-ylsulfonyl)-N-(3-methylisoxazol-5-yl)benzamide (150)

Compound 150 was prepared according to procedure C to afford 22 mg of white powder (38%). $^1$H NMR (500 MHz, CDCl$_3$) δ 1.58-1.60 (m, 4H), 1.72 (brs, 4H), 2.32 (s, 3H), 3.31 (t, J=6.0 Hz, 4H), 6.41 (s, 1H), 7.67 (t, J=7.9 Hz, 1H), 7.99 (d, J=8.0 Hz, 1H), 8.18 (d, J=8.0 Hz, 1H), 8.41 (s, 1H), 10.31 (s, 1H). $^{13}$C NMR (126 MHz, CDCl$_3$) δ 11.92, 26.86, 29.13, 48.39, 90.60, 125.87, 129.84, 130.56, 131.89, 133.91, 140.42, 160.49, 161.73, 162.38. LCQ (M+H$^+$) calcd C$_{17}$H$_{21}$N$_3$O$_4$S 364. found 364.

3-(azepan-1-ylsulfonyl)-N-(3-bromophenyl)-4-methoxybenzamide (151)

Compound 151 was prepared according to procedure C to afford 51 mg of white powder (71%). $^1$H NMR (500 MHz, CDCl$_3$) δ 1.62 (brs, 4H), 1.72 (brs, 4H), 3.31 (t, J=5.8 Hz, 4H), 3.82 (s, 3H), 6.90 (d, J=8.7 Hz, 1H), 7.29-7.24 (m, 2H), 7.75 (d, J=7.9 Hz, 1H), 8.01 (d, J=2.1 Hz, 1H), 8.03 (s, 1H), 8.33 (d, J=2.0 Hz, 1H), 8.82 (s, 1H). $^{13}$C NMR (126 MHz, CDCl$_3$) δ 26.80, 28.98, 48.34, 118.85, 119.32, 122.64, 122.79, 123.23, 123.33, 126.64, 127.49, 130.32, 133.79, 139.15, 158.11, 164.12, 164.20. LCQ (M+H$^+$) calcd C$_{20}$H$_{23}$BrN$_2$O$_4$S 467. found 467.

3-(azepan-1-ylsulfonyl)-N-(3-bromophenyl)-4-hydroxybenzamide (152)

Compound 152 was prepared according to procedure J from 151 to afford 58 mg of white powder (83%). $^1$H NMR (500 MHz, CDCl$_3$) δ 1.62 (brs, 4H), 1.76 (brs, 4H), 3.37 (t, J=5.9 Hz, 4H), 7.15 (d, J=8.5 Hz, 1H), 7.33-7.25 (m, 2H), 7.56 (d, J=7.8 Hz, 1H), 7.87 (s, 1H), 7.98-7.95 (m, 2H), 8.10 (s, 1H), 9.41 (s, 1H). $^{13}$C NMR (126 MHz, CDCl$_3$) δ 26.81, 28.84, 48.36, 118.74, 119.46, 122.76, 122.98, 123.26, 126.79, 127.39, 127.78, 130.41, 133.41, 138.91, 158.07, 163.82. LCQ (M+H$^+$) calcd C$_{19}$H$_{21}$BrN$_2$O$_4$S 453. found 453.

4-(methylsulfinyl)aniline (155)

Compound 155 was prepared according to procedure D from 154 to afford 880 mg of brown powder (79%). $^1$H NMR (500 MHz, CDCl$_3$) δ 2.30 (s, 3H), 6.77 (d, J=8.6 Hz, 2H), 7.46 (d, J=8.6 Hz, 2H). $^{13}$C NMR (126 MHz, CDCl$_3$) δ 43.82, 115.06, 125.69, 133.23, 149.57. LCQ (M+H$^+$) calcd C$_7$H$_9$NOS 156. found 156.

4-(methylsulfinyl)aniline (156)

Compound 156 was prepared according to procedure D from 153 to afford 910 mg of brown powder (81%). %). $^1$H NMR (500 MHz, CDCl$_3$) δ 2.71 (s, 3H), 6.76 (ddd, J=0.8, 2.3, 8.0, 1H), 6.88-6.90 (m, 1H), 7.02 (t, J=1.9 Hz, 1H), 7.24-7.28 (m, 1H). $^{13}$C NMR (126 MHz, CDCl$_3$) δ 43.90, 109.02, 113.00, 117.29, 130.14, 146.68, 147.67. LCQ (M+H$^+$) calcd C$_7$H$_9$NOS 156. found 156.

4-(methylsulfonyl)aniline (157)

Compound 157 was prepared according to procedure E from 154 to afford 572 mg of brown powder (93%). $^1$H NMR (500 MHz, CDCl$_3$) δ 3.01 (s, 3H), 6.72 (d, J=8.7 Hz, 2H), 7.39 (d, J=8.7 Hz, 2H). $^{13}$C NMR (126 MHz, CDCl$_3$) δ 45.01, 114.10, 128.78, 129.49, 151.32. LCQ (M+H$^+$) calcd C$_7$H$_9$NO$_2$S 172. found 172.

4-(methylsulfonyl)aniline (158)

Compound 158 was prepared according to procedure E from 153 to afford 557 mg of brown powder (92%). $^1$H NMR (500 MHz, CDCl$_3$) δ 3.03 (s, 3H), 6.89 (ddd, J=0.8, 2.3, 8.0 Hz, 1H), 7.21 (t, J=2.1 Hz, 1H), 7.24 (dt, J=1.1, 7.7 Hz, 1H), 7.30 (t, 7.8 Hz, 1H). $^{13}$C NMR (126 MHz, CDCl$_3$) δ 44.40, 112.69, 116.37, 119.72, 130.30, 141.16, 147.69. LCQ (M+H$^+$) calcd C$_7$H$_9$NO$_2$S 172. found 172.

5-chloro-N-methylpyridin-2-amine (162)

Compound 162 was prepared according to procedure F from 160 to afford 73 mg of brown powder (42%). $^1$H NMR (500 MHz, CDCl$_3$) δ 2.90 (s, 3H), 4.79 (brs, 1H), 6.33 (d, J=8.9 Hz, 1H), 7.38 (dd, J=2.6, 8.9 Hz, 1H), 8.02 (d, J=2.6 Hz, 1H). $^{13}$C NMR (126 MHz, CDCl$_3$) δ 29.22, 106.90, 119.44, 137.27, 146.26, 157.88. LCQ (M+H$^+$) calcd C$_6$H$_7$ClN$_2$ 143. found 143.

N-methyl-4-(methylsulfinyl)aniline (164)

Compound 164 was prepared according to procedure D from 154 to afford 1045 mg of brown powder (86%). $^1$H NMR (500 MHz, CDCl$_3$) δ 2.69 (s, 3H), 2.85 (d, J=1.4 Hz, 3H), 6.95 (dd, J=0.7, 8.6 Hz, 2H), 7.47 (dd, J=0.7, 8.6 Hz, 2H). $^{13}$C NMR (126 MHz, CDCl$_3$) δ 30.22, 43.51, 112.26, 125.74, 130.88, 152.00. LCQ (M+H$^+$) calcd C$_8$H$_{11}$NOS 170. found 170.

3-((4-chlorobenzyl)thio)benzoic acid (165)

Compound 165 was prepared according to procedure G to afford 1819 mg of white powder (90%). $^1$H NMR (500 MHz, CDCl$_3$) δ 4.14 (s, 2H), 7.22-7.27 (m, 4H), 7.36 (t, J=7.8 Hz, 1H), 7.47 (dt, J=1.6, 7.9 Hz, 1H), 7.92 (dd, J=1.1, 7.8 Hz, 1H), 8.05 (t, J=1.6 Hz, 1H). $^{13}$C NMR (126 MHz, CDCl$_3$) δ 41.96, 131.69, 132.48, 132.66, 134.05, 134.73, 136.23, 136.88, 137.66, 139.59, 140.06, 173.24.

3-((4-methoxybenzyl)thio)benzoic acid (166)

Compound 166 was prepared according to procedure G to afford 1670 mg of white powder (84%). $^1$H NMR (500 MHz, CDCl$_3$) δ 3.78 (s, 3H), 4.13 (s, 2H), 6.82 (d, J=8.6 Hz, 2H), 7.23 (d, J=8.6 Hz, 2H), 7.34 (t, J=7.8 Hz, 1H), 7.48 (d, J=7.9 Hz, 1H), 7.89 (d, J=7.7 Hz, 1H), 8.05 (s, 1H). $^{13}$C NMR (126 MHz, CDCl$_3$) δ 38.03, 55.29, 113.99, 127.79, 128.66, 128.88, 130.02, 130.05, 130.58, 134.44, 137.59, 158.86, 171.31.

3-((4-(methylthio)benzyl)thio)benzoic acid (167)

Compound 167 was prepared according to procedure G to afford 1663 mg of white powder (79%). $^1$H NMR (500 MHz, CDCl$_3$) δ 2.47 (s, 3H), 4.14 (s, 2H), 7.17 (d, J=8.4 Hz, 2H), 7.23 (d, J=8.4 Hz, 2H), 7.36 (t, J=7.8 Hz, 1H), 7.49 (dd, J=0.7, 7.9 Hz, 1H), 7.91 (dt, J=1.3, 7.8 Hz, 1H), 8.06 (s, 1H). $^{13}$C NMR (126 MHz, CDCl$_3$) δ 15.82, 38.22, 126.66, 127.96, 128.96, 129.33, 129.87, 130.74, 133.54, 134.66, 137.27, 137.59, 171.04.

3-((4-chlorobenzyl)sulfonyl)benzoic acid (168)

Compound 168 was prepared according to procedure I from 165 to afford 510 mg of white powder (93%). $^1$H NMR (500 MHz, CDCl$_3$) δ 4.33 (s, 2H), 7.05 (d, J=8.4 Hz, 2H), 7.26 (d, J=8.4 Hz, 2H), 7.57 (t, J=7.8 Hz, 1H), 7.76 (d, J=7.9 Hz, 1H), 8.30 (d, J=7.9 Hz, 1H), 8.40 (s, 1H). $^{13}$C NMR (126 MHz, CDCl$_3$) δ 61.96, 126.17, 129.01, 129.30, 129.91, 132.08, 132.15, 132.58, 135.14, 135.33, 138.12, 166.75. LCQ (M+H$^+$) calcd C$_{14}$H$_{11}$ClO$_4$S 311. found 311.

3-((4-methoxybenzyl)sulfonyl)benzoic acid (169)

Compound 169 was prepared according to procedure I from 166 to afford 406 mg of white powder (74%). $^1$H NMR (500 MHz, CDCl$_3$) δ 3.79 (s, 3H), 4.30 (s, 2H), 6.89 (d, J=8.7 Hz, 2H), 7.00 (d, J=8.7 Hz, 2H), 7.53 (t, J=7.8 Hz, 1H), 7.73 (dt, J=1.5, 7.9 Hz, 1H), 8.28 (d, J=7.8 Hz, 1H), 8.39 (t, J=1.5 Hz, 1H). $^{13}$C NMR (126 MHz, CDCl$_3$) δ 55.29, 62.11, 114.15, 119.46, 129.06, 129.98, 131.60, 132.04, 132.75, 134.84, 138.40, 160.08, 166.75.

3-((4-(methylsulfonyl)benzyl)sulfonyl)benzoic acid (170)

Compound 170 was prepared according to procedure I from 165 to afford 520 mg of white powder (82%). $^1$H NMR (500 MHz, DMSO) δ 3.21 (s, 3H), 4.95 (s, 2H), 7.46 (d, J=8.4 Hz, 2H), 7.77 (t, J=7.8 Hz, 1H), 7.88 (d, J=8.4 Hz, 2H), 7.98 (dt, J=1.2, 8.4 Hz, 1H), 8.16 (s, 1H), 8.26 (dt, J=1.3, 7.9 Hz, 1H). $^{13}$C NMR (126 MHz, DMSO) δ 43.38, 59.83, 126.87, 128.82, 129.95, 131.68, 131.99, 132.12, 134.26, 134.50, 138.63, 140.72, 165.80. LCQ (M+H$^+$) calcd C$_{15}$H$_{14}$O$_6$S$_2$ 355. found 355.

3-((4-chlorobenzyl)sulfonyl)-N-(4-chlorophenyl)benzamide (171)

Compound 171 was prepared according to procedure C to afford 52 mg of white powder (80%). $^1$H NMR (500 MHz, CDCl$_3$) δ 4.35 (s, 2H), 7.05 (d, J=8.5 Hz, 2H), 7.28 (d, J=8.5 Hz, 2H), 7.34 (d, J=8.9 Hz, 2H), 7.60 (t, J=7.8 Hz, 1H), 7.64

(dd, J=2.2, 8.8 Hz, 1H), 7.71 (dd, J=1.4, 7.9 Hz, 1H), 8.18 (d, J=1.6 Hz, 1H), 8.22 (dd, J=1.2, 7.7 Hz, 1H). $^{13}$C NMR (126 MHz, CDCl$_3$) δ 61.87, 121.80, 125.94, 126.63, 129.03, 129.69, 129.83, 131.51, 132.15, 133.70, 135.43, 136.04, 136.43, 137.82, 164.17. LCQ (M+H$^+$) calcd C$_{20}$H$_{15}$C$_{12}$NO$_3$S 420. found 420.

N-(4-bromophenyl)-3-((4-chlorobenzyl)sulfonyl)benzamide (172)

Compound 172 was prepared according to procedure C to afford 58 mg of white powder (81%). $^1$H NMR (500 MHz, CDCl$_3$) δ 4.35 (s, 2H), 7.05 (d, J=8.4 Hz, 2H), 7.27 (d, J=8.4 Hz, 2H), 7.50 (d, J=8.8 Hz, 2H), 7.60-7.63 (m, 3H), 7.73 (d, J=7.9 Hz, 1H), 8.17 (s, 1H), 8.23 (d, J=7.9 Hz, 1H). $^{13}$C NMR (126 MHz, CDCl$_3$) δ 61.92, 117.54, 122.04, 125.97, 126.55, 129.04, 129.75, 131.57, 132.02, 132.16, 133.71, 135.45, 135.99, 136.89, 137.87, 164.01. LCQ (M+H$^+$) calcd C$_{20}$H$_{15}$BrClNO$_3$S 464. found 464.

3-((4-chlorobenzyl)sulfonyl)-N-(5-chloropyridin-2-yl)benzamide (173)

Compound 173 was prepared according to procedure C to afford 47 mg of white powder (73%). $^1$H NMR (500 MHz, CDCl$_3$) δ 4.36 (s, 2H), 7.08 (d, J=8.4 Hz, 2H), 7.30 (d, J=8.4 Hz, 2H), 7.67 (t, J=8.3 Hz, 1H), 7.78 (dd, J=2.6, 8.9 Hz, 1H), 7.82 (dt, J=1.4, 7.8 JHz, 1H), 8.22-8.24 (m, 2H), 8.32 (d, J=2.4 Hz, 1H), 8.36 (d, J=8.9 Hz, 1H), 8.56 (s, 1H). $^{13}$C NMR (126 MHz, CDCl$_3$) δ 62.09, 114.88, 126.10, 126.96, 127.58, 129.11, 129.91, 132.12, 132.19, 132.83, 135.06, 135.54, 138.25, 138.70, 146.80, 149.24, 163.32. LCQ (M+H$^+$) calcd C$_{19}$H$_{14}$C$_{12}$N$_2$O$_3$S 421. found 421.

3-((4-chlorobenzyl)sulfonyl)-N-(4-(methylsulfinyl)phenyl)benzamide (175)

Compound 175 was prepared according to procedure C to afford 62 mg of white powder (89%). $^1$H NMR (500 MHz, CDCl$_3$) δ 2.75 (s, 3H), 4.35 (s, 2H), 7.06 (d, J=8.4 Hz, 2H), 7.26 (d, 8.4 Hz, 2H), 7.57-7.60 (m, 3H), 7.72 (dt, J=1.3, 7.9 Hz, 1H), 7.81 (d, J=8.7 Hz, 2H), 8.22 (d, J=7.9 Hz, 1H), 8.27 (s, 1H), 8.94 (s, 1H). $^{13}$C NMR (126 MHz, CDCl$_3$) δ 43.64, 61.93, 121.36, 124.79, 126.04, 126.92, 129.03, 129.66, 131.73, 132.18, 133.49, 135.40, 135.71, 138.20, 140.47, 140.56, 164.10. LCQ (M+H$^+$) calcd C$_{21}$H$_{18}$ClNO$_4$S$_2$ 448. found 448.

3-((4-chlorobenzyl)sulfonyl)-N-(5-cyanopyridin-2-yl)benzamide (176)

Compound 176 was prepared according to procedure C to afford 62 mg of white powder (89%). $^1$H NMR (500 MHz, CDCl$_3$) δ 4.35 (s, 2H), 7.06 (d, J=8.5 Hz, 2H), 7.28 (d, J=8.5 Hz, 2H), 7.67 (t, J=7.8 Hz, 1H), 7.84 (dt, J=1.3, 8.0 Hz, 1H), 8.04 (dd, J=2.2, 8.7 Hz, 1H), 8.18 (t, J=1.6 Hz, 1H), 8.22 (dt, J=1.6, 7.8 Hz, 1H), 8.50 (dd, J=0.7, 8.6 Hz, 1H), 8.63 (dd, J=0.7, 8.6 Hz, 1H), 8.74 (brs, 1H). $^{13}$C NMR (126 MHz, CDCl$_3$) δ 62.08, 105.83, 113.86, 116.59, 126.07, 127.12, 129.13, 130.07, 132.13, 132.58, 133.01, 134.43, 135.60, 138.78, 141.89, 151.75, 153.44, 163.64. LCQ (M+H$^+$) calcd C$_{20}$H$_{14}$ClN$_3$O$_3$S 412. found 412.

3-((4-chlorobenzyl)sulfonyl)-N-(4-(methylsulfonyl)phenyl)benzamide (177)

Compound 177 was prepared according to procedure C to afford 59 mg of white powder (83%). $^1$H NMR (500 MHz, DMSO) δ 3.21 (s, 3H), 4.81 (s, 2H), 7.21 (d, J=7.9 Hz, 2H), 7.39 (d, J=7.9 Hz, 2H), 7.79 (t, J=7.8 Hz, 1H), 7.89 (d, J=7.7 Hz, 1H), 7.95 (d, J=8.3 Hz, 2H), 8.05 (d, J=8.3 Hz, 2H), 8.31 (d, J=7.7 Hz, 1H), 8.37 (s, 1H), 10.93 (s, 1H). $^{13}$C NMR (126 MHz, DMSO) δ 40.10, 59.59, 120.21, 127.38, 127.47, 127.55, 128.08, 128.18, 128.58, 132.54, 133.07, 133.39, 135.19, 135.41, 138.58, 143.31, 164.46. LCQ (M+H$^+$) calcd C$_{21}$H$_{18}$ClNO$_5$S$_2$ 464. found 464.

N-(4-acetylphenyl)-3-((4-chlorobenzyl)sulfonyl)benzamide (178)

Compound 178 was prepared according to procedure C to afford 48 mg of white powder (73%). $^1$H NMR (500 MHz, CDCl$_3$) δ 2.62 (s, 3H), 4.36 (s, 2H), 7.06 (d, J=8.4 Hz, 2H), 7.28 (d, J=8.4 Hz, 2H), 7.63 (t, J=7.8 Hz, 1H), 7.75 (d, J=7.8 Hz, 1H), 7.83 (d, J=8.7 Hz, 2H), 8.00 (d, J=8.7 Hz, 2H), 8.23 (s, 1H), 8.26 (d, J=7.8 Hz, 1H). $^{13}$C NMR (126 MHz, CDCl$_3$) δ 26.50, 61.89, 119.69, 119.78, 125.92, 126.73, 129.05, 129.73, 129.76, 131.72, 132.15, 133.16, 133.78, 135.47, 135.88, 137.90, 142.41, 164.35, 197.54. LCQ (M+H$^+$) calcd C$_{22}$H$_{18}$ClNO$_4$S 428. found 428.

3-((4-chlorobenzyl)sulfonyl)-N-(6-chloropyridazin-3-yl)benzamide (179)

Compound 179 was prepared according to procedure C to afford 42 mg of white powder (64%). $^1$H NMR (500 MHz, CDCl$_3$) δ 4.41 (s, 2H), 7.09 (d, J=8.5 Hz, 2H), 7.28 (d, J=8.5 Hz, 2H), 7.64-7.68 (m, 2H), 7.79 (d, J=7.8 Hz, 1H), 8.31 (d, J=7.8 Hz, 1H), 8.42 (s, 1H), 8.66 (d, J=9.4 Hz, 1H). $^{13}$C NMR (126 MHz, CDCl$_3$) δ 61.71, 122.14, 125.95, 127.80, 128.95, 129.62, 130.20, 132.09, 132.35, 133.23, 134.52, 135.31, 138.46, 152.40, 154.89, 165.07. LCQ (M+H$^+$) calcd C$_{18}$H$_{13}$Cl$_2$N$_3$O$_3$S 422. found 422.

N-(4-cyanophenyl)-3-((4-methoxybenzyl)sulfonyl)benzamide (180)

Compound 179 was prepared according to procedure C to afford 49 mg of white powder (79%). $^1$H NMR (500 MHz, CDCl$_3$) δ 3.76 (s, 3H), 4.35 (s, 2H), 6.81 (d, J=8.6 Hz, 2H), 7.02 (d, J=8.6 Hz, 2H), 7.62 (t, J=7.6 Hz, 1H), 7.68 (d, J=8.6 Hz, 2H), 7.74 (d, J=7.8 Hz, 1H), 7.90 (d, J=8.6 Hz, 2H), 8.19 (s, 1H), 8.24 (d, J=7.8 Hz, 1H). $^{13}$C NMR (126 MHz, CDCl$_3$) δ 55.34, 62.08, 107.24, 114.26, 119.02, 119.27, 120.48, 120.57, 127.07, 129.69, 131.95, 132.22, 133.28, 133.77, 135.57, 138.05, 142.58, 160.27, 165.01. LCQ (M+H$^+$) calcd C$_{22}$H$_{18}$N$_2$O$_4$S 407. found 407.

3-((4-chlorobenzyl)thio)-N-(4-cyanophenyl)benzamide (181)

Compound 181 was prepared according to procedure C to afford 45 mg of white powder (77%). $^1$H NMR (500 MHz, CDCl$_3$) δ 4.12 (s, 2H), 7.22 (d, J=8.6 Hz, 2H), 7.27 (d, J=8.6 Hz, 2H), 7.39 (t, J=7.8 Hz, 1H), 7.47 (dt, J=1.1, 6.7 Hz, 1H), 7.65-7.67 (m, 3H), 7.71 (t, J=1.8 Hz, 1H), 7.76 (d, J=8.8 Hz, 2H), 7.90 (s, 1H). $^{13}$C NMR (126 MHz, CDCl$_3$) δ 38.10, 107.52, 118.77, 119.91, 125.10, 128.31, 128.76, 129.45, 130.20, 133.24, 133.37, 133.57, 134.75, 135.45, 137.30, 141.75, 165.14. LCQ (M+H$^+$) calcd C$_{21}$H$_{15}$ClN$_2$OS 379. found 379.

3-((4-chlorobenzyl)thio)-N-(4-(methylsulfinyl)phenyl)benzamide (182)

Compound 182 was prepared according to procedure C to afford 51 mg of white powder (82%). $^1$H NMR (500 MHz, CDCl$_3$) δ 2.75 (s, 3H), 4.14 (s, 2H), 7.23 (d, J=8.7 Hz, 2H), 7.26 (d, J=8.7 Hz, 2H), 7.38 (t, J=7.8 Hz, 1H), 7.44 (dt, J=1.3, 8.0 HZ, 1H), 7.63 (d, J=8.7 Hz, 2H), 7.73 (d, J=7.7

Hz, 1H), 7.84-7.88 (m, 3H). $^{13}$C NMR (126 MHz, CDCl$_3$) δ 38.06, 43.56, 121.07, 121.17, 124.77, 125.45, 128.57, 128.75, 129.22, 130.23, 133.15, 133.19, 135.22, 135.24, 135.57, 136.94, 139.53, 141.22, 141.31, 165.95, 166.03. LCQ (M+H$^+$) calcd C$_{21}$H$_{18}$ClNO$_2$S$_2$416. found 416.

N-(4-cyanophenyl)-3-((4-(methylthio)benzyl)thio) benzamide (183)

Compound 183 was prepared according to procedure C to afford 40 mg of white powder (67%). $^1$H NMR (500 MHz, CDCl$_3$) δ 2.45 (s, 3H), 4.11 (s, 2H), 7.17 (d, J=8.4 Hz, 2H), 7.21 (d, J=8.4 Hz, 2H), 7.39 (t, J=7.8 Hz, 1H), 7.49 (dt, J=1.0, 8.1 Hz, 1H), 7.65-7.68 (m, 4H), 7.76 (d, J=8.8 Hz, 1H), 7.86 (s, 1H). $^{13}$C NMR (126 MHz, CDCl$_3$) δ 15.62, 38.38, 107.46, 118.79, 119.90, 125.16, 126.43, 128.16, 129.39, 129.43, 133.35, 133.58, 134.64, 137.56, 137.77, 141.79, 165.21. LCQ (M+H$^+$) calcd C$_{22}$H$_{18}$N$_2$OS$_2$391. found 391.

3-((4-chlorobenzyl)sulfinyl)benzoic acid (184)

Compound 184 was prepared according to procedure H from 165 to afford 454 mg of white powder (86%). $^1$H NMR (500 MHz, CDCl$_3$) δ 4.06 (q, J=12.9 Hz, 2H), 6.90 (d, J=8.3 Hz, 2H), 7.23 (d, J=8.3 Hz, 2H), 7.54 (m, 2H), 8.08 (s, 1H), 8.16-8.19 (m, 1H). $^{13}$C NMR (126 MHz, CDCl$_3$) δ 62.04, 125.82, 126.90, 128.71, 128.77, 129.27, 131.36, 131.67, 132.74, 134.68, 142.62, 167.42. LCQ (M–H$^+$) calcd C$_{14}$H$_{11}$ClO$_3$S 293. found 293.

3-((4-methoxybenzyl)sulfinyl)benzoic acid (185)

Compound 185 was prepared according to procedure H from 165 to afford 369 mg of white powder (71%). $^1$H NMR (500 MHz, CDCl$_3$) δ 3.77 (s, 2H), 4.10 (q, J=12.9 Hz, 2H), 6.78 (d, J=8.7 Hz, 2H), 6.90 (d, J=8.7 Hz, 2H), 7.55 (t, J=7.8 Hz, 1H), 7.58 (t, J=1.6, 7.8 Hz, 1H), 8.14 (s, 1H), 8.21 (dt, J=1.4, 7.5 Hz, 1H). $^{13}$C NMR (126 MHz, CDCl$_3$) δ 55.27, 62.45, 114.02, 120.16, 126.28, 129.16, 129.54, 130.56, 131.65, 132.72, 143.04, 159.83, 169.37. LCQ (M–H$^+$) calcd C$_{15}$H$_{14}$O$_4$S 289. found 289.

N-(4-cyanophenyl)-3-((4-chlorobenzyl)sulfinyl)benzamide (186)

Compound 186 was prepared according to procedure C to afford 36 mg of white powder (60%). $^1$H NMR (500 MHz, CDCl$_3$) δ 4.07 (dt, J=7.5, 12.9 Hz, 2H), 6.90 (d, J=8.4 Hz, 2H), 7.24 (d, J=8.4 Hz, 2H), 7.36 (d, J=7.8 Hz, 1H), 7.55 (t, J=7.8 Hz, 1H), 7.66 (d, J=8.8 Hz, 2H), 7.87 (d, J=8.8 Hz, 2H), 7.98 (s, 1H), 8.11 (d, J=7.8 Hz, 1H). $^{13}$C NMR (126 MHz, CDCl$_3$) δ 62.07, 107.27, 118.96, 120.23, 120.32, 122.49, 126.56, 128.01, 128.82, 129.45, 131.58, 131.74, 133.22, 134.97, 135.69, 135.73, 142.27, 142.33, 142.43, 164.85, 164.93. LCQ (M+H$^+$) calcd C$_{22}$H$_{18}$N$_2$O$_3$S 391. found 391.

3-((4-chlorobenzyl)sulfinyl)-N-(4-(methylsulfinyl)phenyl)benzamide (187)

Compound 187 was prepared according to procedure C to afford 55 mg of white powder (82%). $^1$H NMR (500 MHz, CDCl$_3$) δ 2.74 (s, 3H), 4.00 (dt, J=7.5, 12.9 Hz, 2H), 6.89 (d, J=8.4 Hz, 2H), 7.21 (d, J=8.4 Hz, 2H), 7.38 (d, J=7.7 Hz, 1H), 7.52 (t, J=7.8 Hz, 1H), 7.60 (d, J=8.4 Hz, 2H), 7.85 (d, J=8.4 Hz, 2H), 7.99 (d, J=1.5 Hz, 1H), 8.08 (dt, J=1.1, 7.9 Hz, 1H), 9.30 (d, J=4.9 Hz, 1H). $^{13}$C NMR (126 MHz, CDCl$_3$) δ 43.84, 62.08, 121.26, 122.93, 124.65, 126.86, 127.64, 128.74, 129.42, 131.16, 131.76, 134.80, 135.76, 140.29, 140.97, 142.72, 164.84. LCQ (M+H$^+$) calcd C$_{21}$H$_{18}$ClNO$_3$S$_2$432. found 432.

3-((4-chlorobenzyl)sulfonyl)-N-(4-(methylsulfinyl)phenyl)benzamide (188)

Compound 188 was prepared according to procedure C to afford 52 mg of white powder (75%). $^1$H NMR (500 MHz, CDCl$_3$) δ 3.09 (s, 3H), 4.09 (d, J=2.7 Hz, 2H), 6.92 (d, J=8.4 Hz, 2H), 7.25 (d, J=8.4 Hz, 2H), 7.38 (d, J=7.8 Hz, 1H), 7.57 (t, J=7.8 Hz, 1H), 7.92-7.98 (m, 4H), 8.04 (s, 1H), 8.13 (d, J=7.9 Hz, 1H). $^{13}$C NMR (126 MHz, CDCl$_3$) δ 44.68, 62.05, 120.44, 120.53, 122.66, 126.66, 128.14, 128.60, 128.85, 129.45, 131.61, 131.77, 134.95, 135.25, 135.69, 135.72, 142.26, 143.35, 165.12. LCQ (M+H$^+$) calcd C$_{21}$H$_{18}$ClNO$_4$S$_2$ 448. found 448.

N-(4-cyanophenyl)-3-((4-methoxybenzyl)sulfinyl)benzamide (189)

Compound 189 was prepared according to procedure C to afford 37 mg of white powder (62%). $^1$H NMR (500 MHz, CDCl$_3$) δ 3.74 (s, 3H), 4.00 (dt, J=5.5, 12.9 Hz, 2H), 6.78 (d, J=8.7 Hz, 2H), 6.85 (d, J=8.7 Hz, 2H), 7.39 (dt, J=1.2, 7.8 Hz, 1H), 7.53 (t, J=7.8 Hz, 1H), 7.66 (d, J=8.8 Hz, 2H), 7.73 (s, 1H), 7.81 (d, J=8.8 Hz, 2H), 8.05 (dt, J=1.4, 7.8 Hz, 1H), 8.68 (s, 1H). $^{13}$C NMR (126 MHz, CDCl$_3$) δ 55.25, 62.41, 107.47, 113.91, 118.85, 119.90, 120.12, 122.45, 127.79, 129.48, 131.27, 131.87, 133.23, 135.31, 142.01, 142.83, 159.86, 164.81. LCQ (M+H$^+$) calcd C$_{22}$H$_{18}$N$_2$O$_3$S 391. found 391.

Various aspects of the present invention can also be considered in conjunction with the following.

General Procedure of Synthesizing Compound 203:

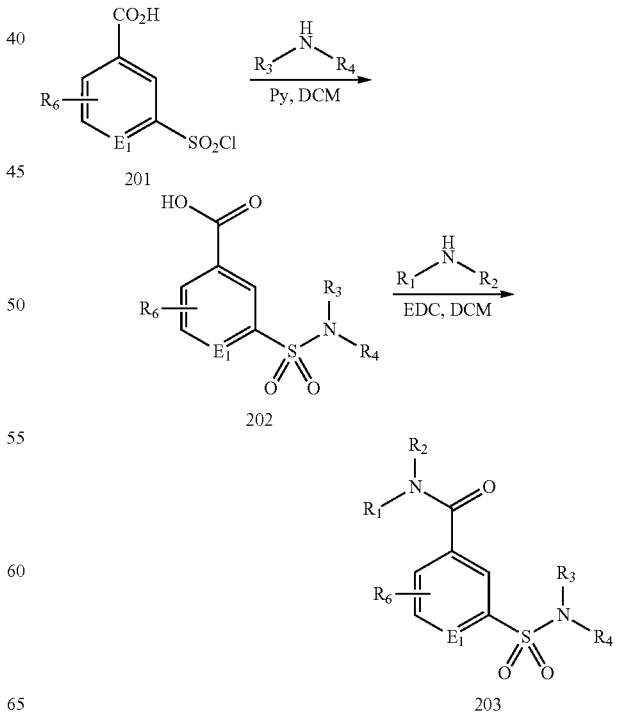

To a well stirred solution of 3-(Chlorosulfonyl) aromatic acid (201) (1 mmol) and amine/aniline (1.2 mmol) in DCM (5 mL) was added pyridine (1 mL) dropwisely at 0° C. The solution was stirred at room temperature for 5 hours until the completion of the reaction (monitored by TLC). Solvent was then removed under reduced pressure and the residue was dissolved in a mixture of Et$_2$O/NaOH (1N) (20 mL, 20 mL). The resulting mixture extracted three times with 20 mL of Et$_2$O, and the aqueous layer acidified (PH=2-3) with HCl (1 M) to give a white solid 202. The crude product 202 was filtered, washed with water, dried under vacuum, and used in next step without further purification.

To a solution of compound 202 (1 mmol) and substituted amine in DCM (5 mL) EDC (1.1 mmol) was added at 0° C. The solution was stirred for 12 hours at room temperature and then diluted with Et$_2$O (30 mL). The resulting mixture extracted 3 times with Et$_2$O (20 mL), the organic layers washed with HCl (0.5 N, 3×20 mL), NaHCO$_3$ (Sat. 1×20 mL), water, and brine, dried over Na$_2$SO$_4$, and concentrated under reduced pressure. Product 203 was purified by column chromatography and obtained as white solid.

General Procedure of Synthesizing Compound 207:

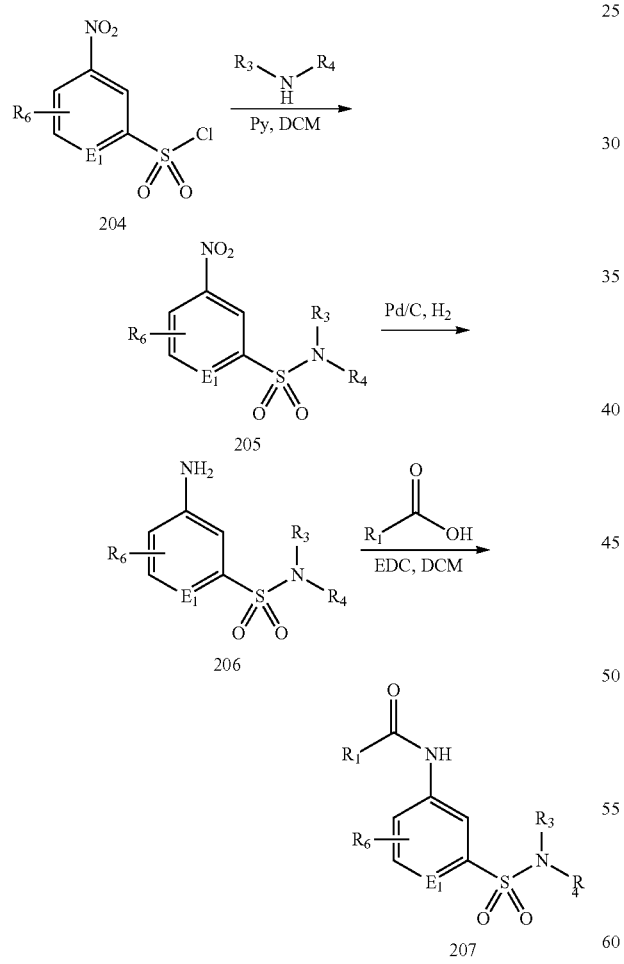

then removed under reduced pressure and the residue was dissolved in a mixture of Et$_2$O/NaOH (1N) (20 mL/20 mL). The resulting mixture extracted three times with 20 mL of Et$_2$O, and the aqueous layer acidified (PH=2-3) with HCl (1 M) to give a white solid 205. The crude product 205 was filtered, washed with water, dried under vacuum, and used in next step without further purification.

To a 25 mL flask containing compound 205 (1 mmol) a mixture of MeOH/THF (3 mL/3 mL) and Pd/C (10%) (0.1 mmol) was added. The flask purged three times with H$_2$ and the mixture stirred under H$_2$ gas (1 atm) over night at room temperature, then filtered over celite and concentrated under vacuum. The resulting residue was purified with column chromatography to provide compound 206.

To a solution of compound 206 (1 mmol), aromatic acid (1 mmol) in DCM was added EDC (1.1 mmol) at 0° C. The mixture was allowed to warm to room temperature and stirred for 12 hours. After the disappearance of the starting material as indicated by TLC, the solution was diluted with Et$_2$O (30 mL) and washed three times with HCl (1 M, 30 mL). The organic layers were dried over Na$_2$SO$_4$, concentrated, and the residue was purified by column chromatography to provide compound 207.

General Procedure of Synthesizing Compound 212:

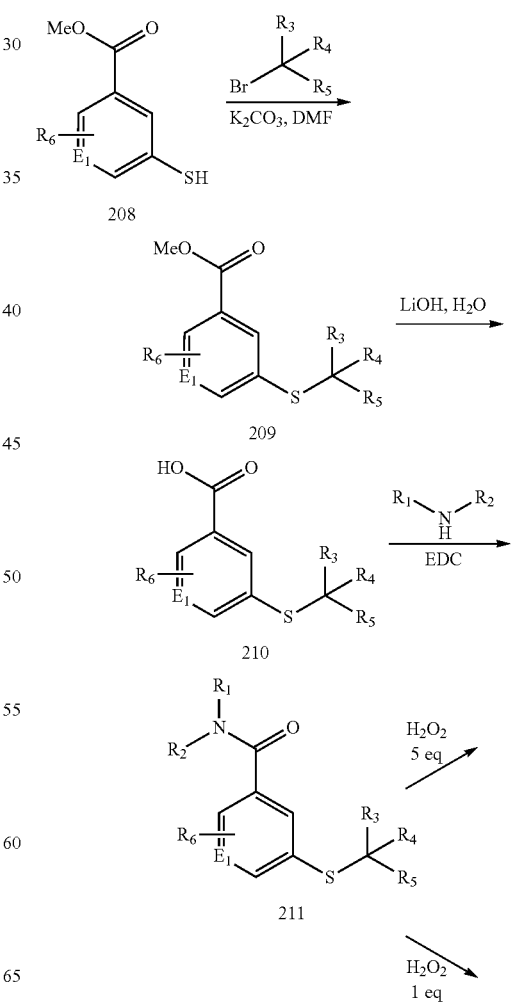

To a well stirred solution of 3-(Chlorosulfonyl) nitrobenzene (204) (1 mmol) and amine/aniline (1.2 mmol) in DCM (5 mL) was added pyridine (1 mL) dropwisely at 0° C. The solution was stirred at room temperature for 5 hours until the completion of the reaction (monitored by TLC). Solvent was

73

-continued

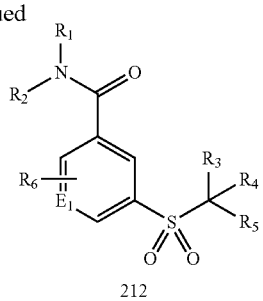

212

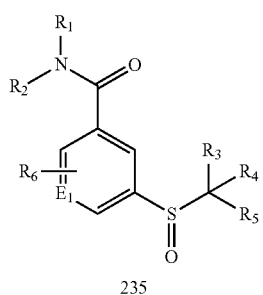

235

To a solution of compound 208 (1 mmol), Alkyl bromide (1 mmol) in DMF (10 mL) was added $K_2CO_3$ (3 mmol) at 0° C. The mixture was allowed to warm up to room temperature and stirred at ambient temperature for 12 hours until the reaction completion (monitored by TLC). Afterwards, the reaction mixture diluted with 50 mL water and extracted 3 times by EtOAc (50 mL). The organic layers was combined, washed three times with water, dried over $Na_2SO_4$, and concentrated under vacuum. The residue was purified by chromatography to provide compound 209.

To a solution of compound 209 (1 mmol) in MeOH/$H_2O$ (5 mL/5 mL) LiOH was added. The mixture was stirred at rt for 4 hours, and the mixture was concentrated to half volume and diluted with 20 mL of $H_2O$. Aqueous solution was then washed 3 times with $Et_2O$ (30 mL) and neutralized with HCl (1 M) and gave rise to white solid precipitate. The solid was collected to provide compound 210.

To a solution of compound 210 (1 mmol) and substituted amine in DCM (5 mL) EDC (1.1 mmol) was added at 0° C. The solution was stirred for 12 hours at room temperature and then diluted with $Et_2O$ (30 mL). The resulting mixture extracted 3 times with $Et_2O$ (20 mL), the organic layers washed with HCl (0.5 N, 3×20 mL), $NaHCO_3$ (Sat. 1×20 mL), water, and brine, dried over $Na_2SO_4$, and concentrated under reduced pressure. Product 211 was purified by column chromatography and obtained as white solid.

To a well stirred solution of compound 211 (1 mmol) in HOAc (5 mL) was added $H_2O_2$ (30%, 5 mmol). The mixture was stirred at 100° C. for 5 hours until the completion of the reaction (monitored by TLC). Upon the temperature cooled down to rt, the mixture was poured into 30 mL of ice water to give compound 212 as write solid.

To a well stirred solution of compound 211 (1 mmol) in HOAc (5 mL) was added $H_2O_2$ (30%, 1 mmol). The mixture was stiffed at room temperature for 12 hours until the completion of the reaction (monitored by TLC). Upon the temperature cooled down to rt, the mixture was poured into 30 mL of ice water to give compound 235 as write solid.

74

General Procedure of Synthesizing Compound 216:

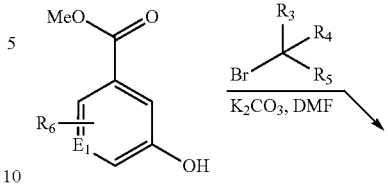

213

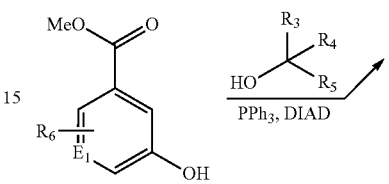

213

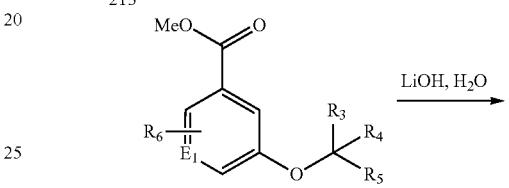

214

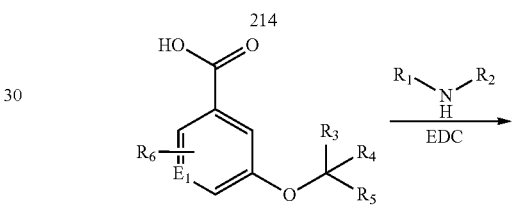

215

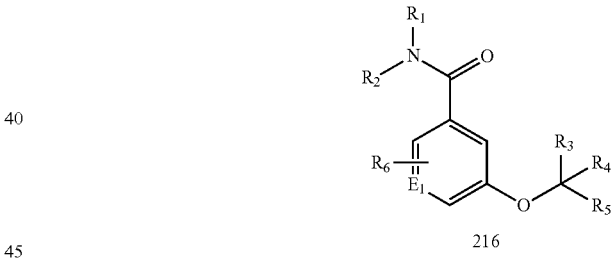

216

Compound 14 was synthesis by two different methods.
Method 1:

To a solution of compound 213 (1 mmol), and Alkyl bromide (1 mmol) in DMF (10 mL) was added $K_2CO_3$ (3 mmol). The mixture was stirred at ambient temperature overnight, and then diluted with 50 mL water. The resulting mixture extracted three times with EtOAc (50 mL). The organic layers was combined, washed three times with water, dried over $Na_2SO_4$, and concentrated under vacuum. The residue was purified by chromatography to provide compound 214.
Method 1:

To a solution of compound 213 (1 mmol), Alkyl alcohol (1 mmol), triphenylphosphine (1.05 mmol), in THF (10 mL) was added DIAD (1 mmol) dropwise over 5 min. The reaction mixture was stirred at room temperature overnight, and then was concentrated under vacuum. The residue was purified by column chromatography to provide compound 214.

To a solution of compound 214 (1 mmol) in MeOH/$H_2O$ (5 mL/5 mL) LiOH was added. The mixture was stiffed at rt for 4 hours, and the mixture was concentrated to half volume and diluted with 20 mL of $H_2O$. Aqueous solution was then washed 3 times with $Et_2O$ (30 mL) and neutralized with HCl (1 M) and gave rise to white solid precipitate. The solid was collected to provide compound 215.

To a solution of compound 215 (1 mmol) and substituted amine in DCM (5 mL) EDC (1.1 mmol) was added at 0° C. The solution was stirred for 12 hours at room temperature and then diluted with $Et_2O$ (30 mL). The resulting mixture extracted 3 times with $Et_2O$ (20 mL), the organic layers washed with HCl (0.5 N, 3×20 mL), $NaHCO_3$ (Sat. 1×20 mL), water, and brine, dried over $Na_2SO_4$, and concentrated under reduced pressure. Product 216 was purified by column chromatography and obtained as white solid.

General Procedure of Synthesizing Compound 221:

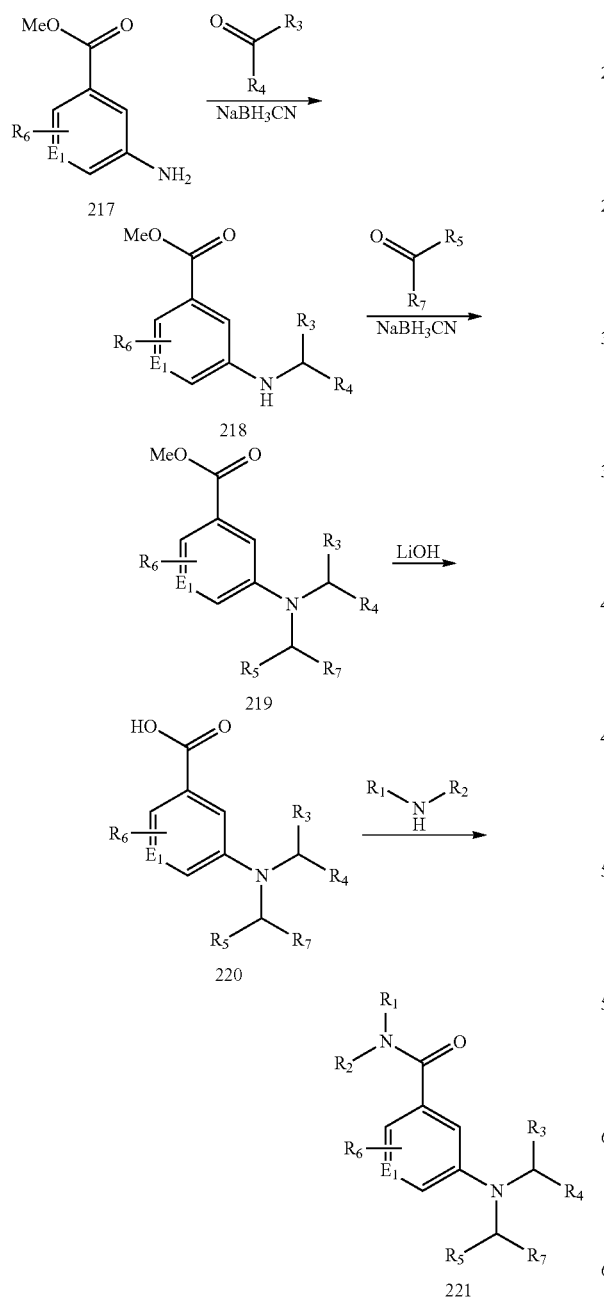

To a solution of compound 217 (1 mmol), Aldehyde/ketone (1 mmol), in THF was added $NaBH_3CN$ (2 mmol). The reaction mixture was stirred at room temperature overnight. After disappearance of the starting material as indicated by TLC, a solution of saturated $NH_4Cl$ solution (5 mL) was added dropwise at room temperature. The mixture was then diluted with $Et_2O$ (30 mL) and washed three times with water (30 mL), and brine (30 mL). Organic layer was dried over $Na_2SO_4$, concentrated under vacuum, and the residue was purified by column chromatography to provide compound 218.

To a solution of compound 218 (1 mmol), Aldehyde/ketone (1 mmol), in THF was added $NaBH_3CN$ (2 mmol). The reaction mixture was stirred at room temperature overnight. After disappearance of the starting material as indicated by TLC, a solution of saturated $NH_4Cl$ solution (5 mL) was added dropwise at room temperature. The mixture was then diluted with $Et_2O$ (30 mL) and washed three times with water (30 mL), and brine (30 mL). Organic layer was dried over $Na_2SO_4$, concentrated under vacuum, and the residue was purified by column chromatography to provide compound 219.

To a solution of compound 219 (1 mmol) in $MeOH/H_2O$ (5 mL/5 mL) LiOH was added. The mixture was stirred at rt for 4 hours, and the mixture was concentrated to half volume and diluted with 20 mL of $H_2O$. Aqueous solution was then washed 3 times with $Et_2O$ (30 mL) and neutralized with HCl (1 M) and gave rise to white solid precipitate. The solid was collected to provide compound 220.

To a solution of compound 220 (1 mmol) and substituted amine in DCM (5 mL) EDC (1.1 mmol) was added at 0° C. The solution was stirred for 12 hours at room temperature and then diluted with $Et_2O$ (30 mL). The resulting mixture extracted 3 times with $Et_2O$ (20 mL), the organic layers washed with HCl (0.5 N, 3×20 mL), $NaHCO_3$ (Sat. 1×20 mL), water, and brine, dried over $Na_2SO_4$, and concentrated under reduced pressure. Product 221 was purified by column chromatography and obtained as white solid.

General Procedure of Synthesizing Compound 225:

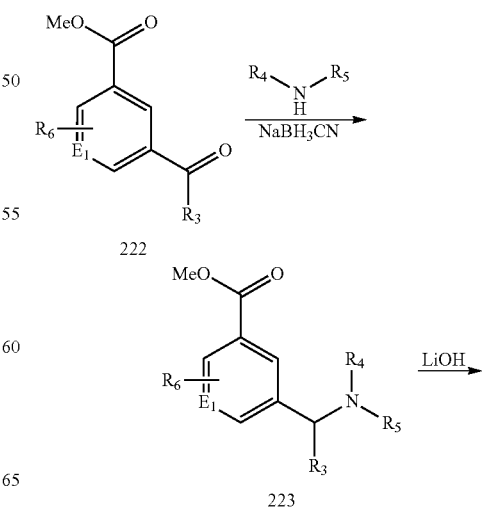

-continued

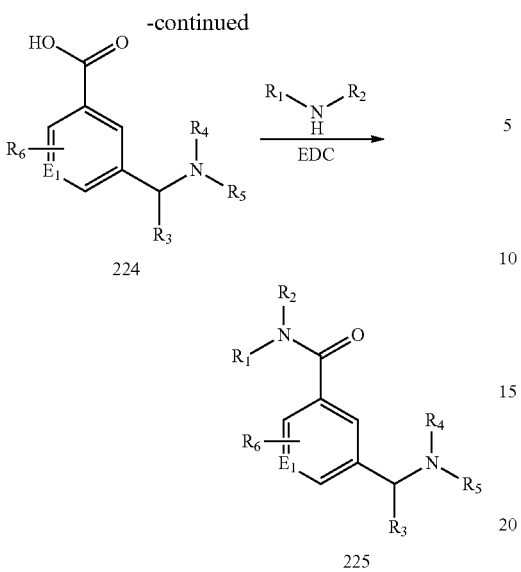

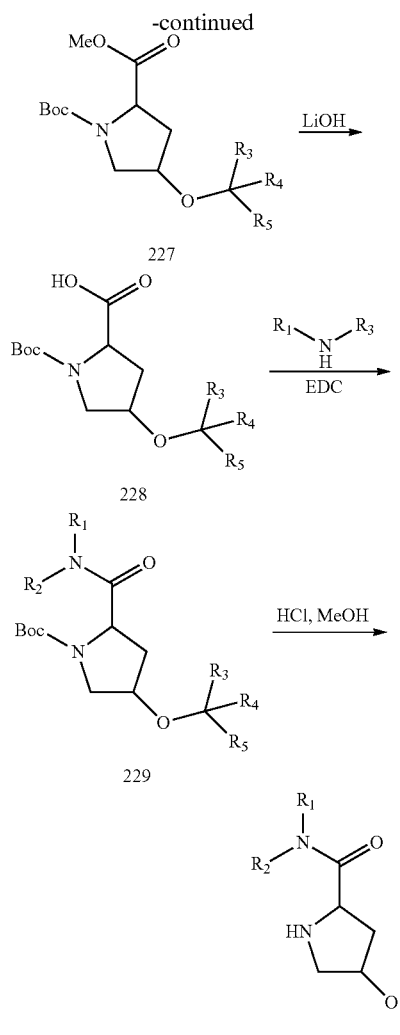

To a solution of compound 222 (1 mmol), Aldehyde/ketone (1 mmol), in THF was added NaBH₃CN (2 mmol). The reaction mixture was stirred at room temperature overnight. After disappearance of the starting material as indicated by TLC, a solution of saturated NH₄Cl solution (5 mL) was added dropwise at room temperature. The mixture was then diluted with Et₂O (30 mL) and washed three times with water (30 mL), and brine (30 mL). Organic layer was dried over Na₂SO₄, concentrated under vacuum, and the residue was purified by column chromatography to provide compound 223.

To a solution of compound 223 (1 mmol) in MeOH/H₂O (5 mL/5 mL) LiOH was added. The mixture was stiffed at rt for 4 hours, and the mixture was concentrated to half volume and diluted with 20 mL of H₂O. Aqueous solution was then washed 3 times with Et₂O (30 mL) and neutralized with HCl (1 M) and gave rise to white solid precipitate. The solid was collected to provide compound 224.

To a solution of compound 224 (1 mmol) and substituted amine in DCM (5 mL) EDC (1.1 mmol) was added at 0° C. The solution was stirred for 12 hours at room temperature and then diluted with Et₂O (30 mL). The resulting mixture extracted 3 times with Et₂O (20 mL), the organic layers washed with HCl (0.5 N, 3×20 mL), NaHCO₃ (Sat. 1×20 mL), water, and brine, dried over Na₂SO₄, and concentrated under reduced pressure. Product 225 was purified by column chromatography and obtained as white solid.

General Procedure of Synthesizing Compound 30:

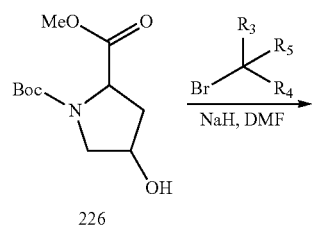

To a solution of compound 226 (1 mmol), alkyl bromide (1.1 mmol) in DMF (10 mL) was added NaH (1.1 mmol) at 0° C. The reaction mixture was stirred at 0° C. for 30 min and then allowed to warm up to room temperature and stirred overnight. After the completion of reaction (monitored by TLC), a solution of Sat. NH₄Cl was added at 0° C. to quench the reaction. The mixture was diluted with 40 mL of Et₂O and washed three times with water, and brine. The organic layer was combined, dried over Na₂SO₄, and concentrated under vacuum. The residue was purified by column chromatography to provide compound 227.

To a solution of compound 227 (1 mmol) in MeOH/H₂O (5 mL/5 mL) LiOH was added. The mixture was stiffed at rt for 4 hours, and the mixture was concentrated to half volume and diluted with 20 mL of H₂O. Aqueous solution was then washed 3 times with Et₂O (30 mL) and neutralized with HCl (1 M) and gave rise to white solid precipitate. The solid was collected to provide compound 228.

To a solution of compound 228 (1 mmol) and substituted amine in DCM (5 mL) EDC (1.1 mmol) was added at 0° C. The solution was stirred for 12 hours at room temperature and then diluted with Et₂O (30 mL). The resulting mixture extracted 3 times with Et₂O (20 mL), the organic layers washed with HCl (0.5 N, 3×20 mL), NaHCO₃ (Sat. 1×20 mL), water, and brine, dried over Na₂SO₄, and concentrated under reduced pressure. Product 229 was purified by column chromatography and obtained as white solid.

Compound 229 was dissolved in HCl (Conc.) (3 mL) and MeOH (3 mL), and the solution was stirred at room temperature for 3 hours until the disappearance of the starting material as indicated by TLC. Afterwards, the solution was concentrated to provide compound 230 as white solid.

General Procedure of Synthesizing Compound 231:

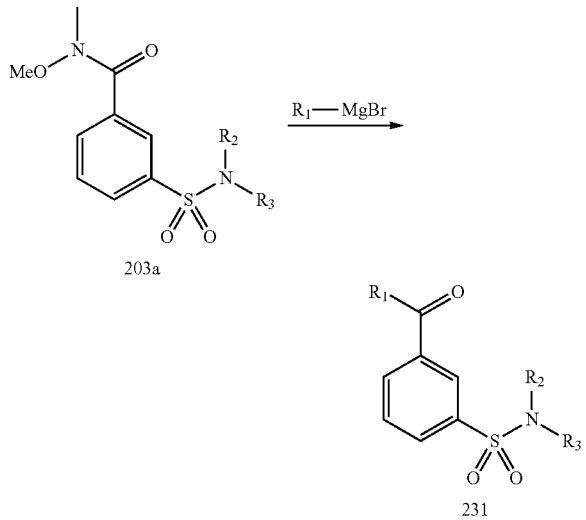

To a well stirred solution of compound 203a (1 mmol) in anhydrous THF (10 mL) was added Grignard reagent (1M, 1.1 mL) dropwise at −78° C. under argon atmosphere over 5 min. The mixture was stirred at same temperature for 3 hours. The solution allowed to warm to ambient temperature and stirred overnight. After the completion of the reaction as indicated by TLC, a solution of Sat. NH$_4$Cl (20 mL) was added to quench the reaction. The resulted mixture was extracted three times with Ethyl acetate (20 mL) and the organic layers was combined, dried over Na$_2$SO$_4$, and concentrated. The residue was purified by column chromatography to provide product 231.

General Procedure of Synthesizing Compound 233:

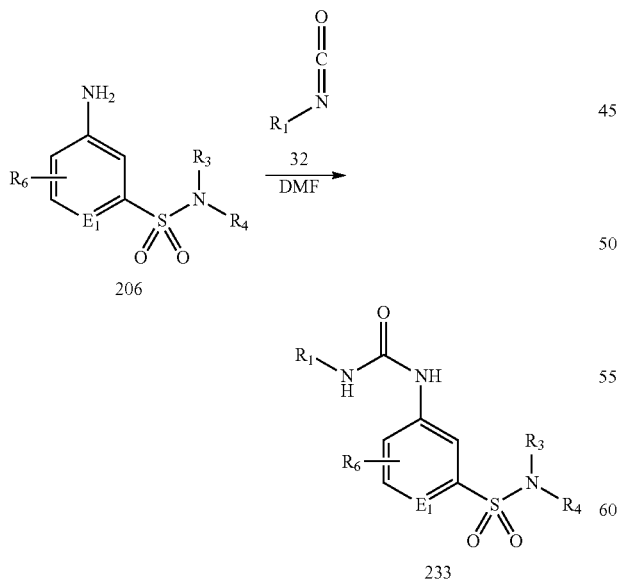

To a well stirred solution of compound 206 (1 mmol) in DMF was added a solution of isocyanides in DMF (1 M, 1.1 mL) dropwise at room temperature. The mixture was stirred overnight. After the disappearance of the starting material, the reaction mixture was diluted with 20 mL of Et$_2$O. The resulting solution was washed three times with water (20 mL), brine (20 mL), and the organic layer was dried over Na$_2$SO$_4$, and concentrated under vacuum. Compound 232 was purified by column chromatography.

General Procedure of Synthesizing Compound 234:

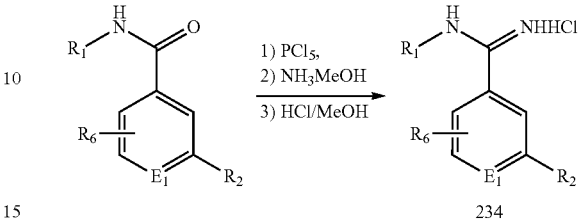

To a stirred suspension of benzamide (1 mmol) in Benzene (10 mL) was added PCl$_5$ (1.5 mmol). The mixture was heated to refluxing until the white solid dissolved completely. The mixture was then cooled to 0° C. and a solution of NH$_3$ in MeOH (1M, 5 mL) was added. The resulted mixture was stirred overnight, concentrated under vacuum, and purified by chromatography. The resulted pure compounds was dissolved in a solution of HCl in MeOH (3 mL) (1.25 M) and concentrated to provide compound 234.

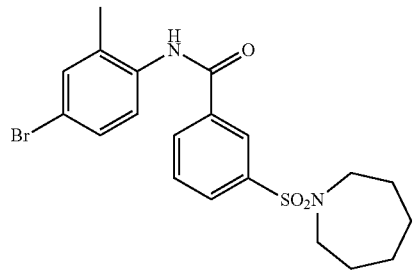

3-(azepan-1-ylsulfonyl)-N-(4-bromo-2-methylphenyl)benzamide (203b)

Compound 203b was synthesized following the general procedure of synthesizing compound 203. White Solid, Melting point: 177-179° C.; $^1$H NMR (500 MHz, CDCl$_3$) δ 8.26 (s, 1H), 8.08 (d, J=7.7 Hz, 1H), 7.94 (s, 1H), 7.86 (s, 1H), 7.75-7.57 (m, 2H), 7.45-7.32 (m, 1H), 3.28 (t, J=5.9 Hz, 4H), 2.31 (s, 3H), 1.76-1.68 (m, 4H), 1.63-1.49 (m, 4H); $^{13}$C NMR (126 MHz, CDCl$_3$) δ 164.3, 140.4, 135.6, 134.3, 133.4, 132.5, 131.1, 129.9, 129.8, 125.4, 125.3, 119.0, 48.3, 29.1, 26.8, 17.8; Mass Spectrum (ESI): C$_{20}$H$_{24}$BrN$_2$O$_3$ [M+H]$^+$452.1

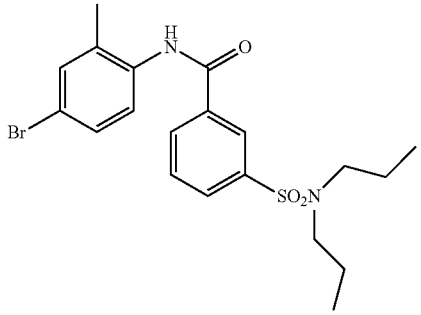

N-(4-bromo-2-methylphenyl)-3-(N,N-dipropylsulfamoyl)benzamide (203c)

Compound 203c was synthesized following the general procedure of synthesizing compound 203. White Solid, Melting point: 135-136° C.; $^1$H NMR (500 MHz, CDCl$_3$) δ 8.26 (s, 1H), 8.07 (d, J=7.6 Hz, 1H), 7.99 (d, J=7.9 Hz, 1H), 7.77 (d, J=8.1 Hz, 1H), 7.71-7.61 (m, 2H), 7.41-7.37 (m, 2H), 3.14-3.09 (m, 4H), 2.32 (s, 3H), 1.62-1.53 (m, 4H), 0.88 (t, J=7.4 Hz, 6H); $^{13}$C NMR (126 MHz, CDCl$_3$) δ 164.2, 141.3, 135.7, 134.3, 133.4, 132.0, 131.0, 130.1, 129.9, 129.9, 125.3, 125.0, 118.9, 50.0, 22.0, 17.7, 11.2; Mass Spectrum (ESI): C$_{20}$H$_{25}$BrN$_2$O$_3$SCl [M+Cl]$^-$ 488.7

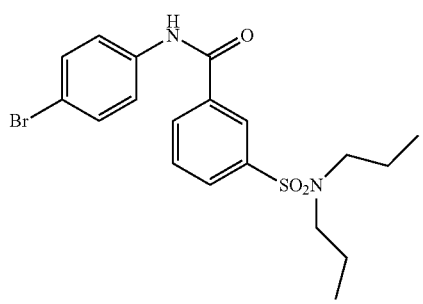

N-(4-bromophenyl)-3-(N,N-dipropylsulfamoyl)benzamide (203d)

Compound 203d was synthesized following the general procedure of synthesizing compound 203. White Solid, Melting point: 160-162° C.; $^1$H NMR (500 MHz, CDCl$_3$) δ 8.22 (s, 1H), 8.13-8.07 (m, 2H), 7.94 (d, J=8.0 Hz, 1H), 7.64 (t, J=7.8 Hz, 1H), 7.60 (d, J=8.8 Hz, 2H), 7.51 (d, J=8.8 Hz, 2H), 3.12-3.07 (m, 4H), 1.59-1.50 (m, 4H), 0.86 (t, J=7.4 Hz, 6H); $^{13}$C NMR (126 MHz, CDCl$_3$) δ 164.2, 140.9, 136.6, 135.7, 132.1, 131.4, 130.0, 129.8, 125.1, 121.9, 117.6, 50.0, 22.0, 11.2; Mass Spectrum (ESI): C$_{19}$H$_{23}$BrN$_2$O$_3$SCl [M+Cl]$^-$ 474.9

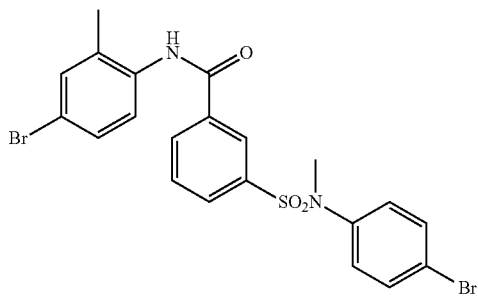

N-(4-bromo-2-methylphenyl)-3-(N-(4-bromophenyl)-N-methylsulfamoyl)benzamide (203e)

Compound 203e was synthesized following the general procedure of synthesizing compound 203. White foam; $^1$H NMR (500 MHz, CDCl$_3$) δ 8.18-8.13 (m, 1H), 7.93 (s, 1H), 7.76-7.68 (m, 2H), 7.64 (t, J=7.8 Hz, 1H), 7.53 (s, 1H), 7.45 (d, J=8.7 Hz, 2H), 7.41-7.35 (m, 2H), 6.99 (d, J=8.7 Hz, 2H), 3.19 (s, 3H), 2.25 (s, 3H); $^{13}$C NMR (126 MHz, CDCl$_3$) δ 163.8, 140.1, 136.9, 135.5, 134.1, 133.4, 132.2, 132.2, 132.2, 130.9, 129.9, 129.8, 128.2, 125.6, 125.1, 121.5, 119.1, 38.1, 17.6. Mass Spectrum (ESI): C$_{21}$H$_{17}$Br$_2$N$_2$O$_3$S [M−H]$^-$ 537.3

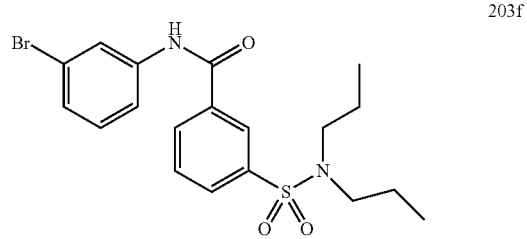 [SMILES: CCCN(CCC)S(=O)(=O)c1cccc(C(=O)Nc2cccc(Br)c2)c1]

N-(3-bromophenyl)-3-(N,N-dipropylsulfamoyl)benzamide (203f)

Compound 203f was synthesized following the general procedure of synthesizing compound 203. White Solid, Melting point: 105-107° C.; $^1$H NMR (500 MHz, CDCl$_3$) δ 8.73 (s, 1H), 8.22 (t, J=1.8 Hz, 1H), 8.08-8.02 (m, 1H), 7.96 (t, J=2.0 Hz, 1H), 7.84 (dt, J=8.0, 1.4 Hz, 1H), 7.64 (ddd, J=8.0, 2.2, 1.1 Hz, 1H), 7.55 (t, J=7.8 Hz, 1H), 7.29-7.26 (m, 1H), 7.21 (t, J=8.0 Hz, 1H), 3.08-3.00 (m, 4H), 1.55-1.44 (m, 4H), 0.82 (t, J=7.4 Hz, 6H); $^{13}$C NMR (126 MHz, CDCl$_3$) δ 164.7, 140.4, 139.1, 135.8, 131.6, 130.3, 129.8, 129.7, 127.8, 125.4, 123.5, 122.6, 119.1, 50.0, 22.0, 11.1; Mass Spectrum (ESI): C$_{19}$H$_{23}$BrN$_2$O$_3$SCl [M+Cl]$^-$ 474.8

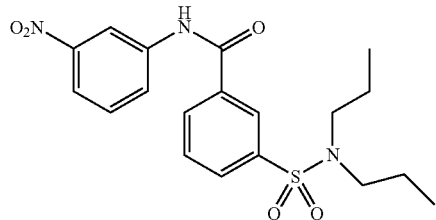

3-(N,N-dipropylsulfamoyl)-N-(3-nitrophenyl)benzamide (203h)

Compound 203h was synthesized following the general procedure of synthesizing compound 203. White Solid, Melting point: 126-128° C.; $^1$H NMR (500 MHz, CDCl$_3$) δ 9.26 (s, 1H), 8.63 (t, J=2.1 Hz, 1H), 8.29 (t, J=1.8 Hz, 1H), 8.17 (d, J=8.2 Hz, 1H), 8.13 (d, J=7.8 Hz, 1H), 8.01-7.94 (m, 1H), 7.91-7.84 (m, 1H), 7.58 (t, J=7.8 Hz, 1H), 7.52 (t, J=8.2 Hz, 1H), 3.10-3.00 (m, 4H), 1.54-1.43 (m, 4H), 0.81 (t, J=7.4 Hz, 6H); $^{13}$C NMR (126 MHz, CDCl$_3$) δ 165.1, 148.4, 140.4, 139.1, 135.4, 131.8, 130.0, 129.8, 126.5, 125.6, 119.3, 115.5, 50.1, 22.0, 11.1; Mass Spectrum (ESI): C$_{19}$H$_{22}$N$_3$O$_5$S [M−H]$^-$ 404.2

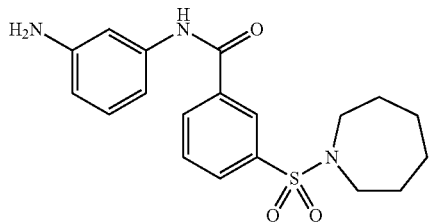

N-(3-aminophenyl)-3-(azepan-1-ylsulfonyl)benzamide (203i)

Compound 203i was synthesized following the general procedure of synthesizing compound 203. White foam; $^1$H NMR (500 MHz, CDCl$_3$) δ 8.20 (t, J=1.8 Hz, 1H), 8.10-8.03 (m, 2H), 7.92 (dt, J=7.8, 1.5 Hz, 1H), 7.62 (t, J=7.8 Hz, 1H), 7.26 (m, 1H), 7.13 (t, J=8.0 Hz, 1H), 6.92-6.85 (m, 1H), 6.52-6.46 (m, 1H), 3.32-3.23 (m, 4H), 1.74-1.66 (m, 4H), 1.61-1.55 (m, 4H); $^{13}$C NMR (126 MHz, CDCl$_3$) δ 164.2, 147.3, 140.1, 138.5, 136.2, 131.3, 129.8, 129.7, 129.7, 125.0, 111.7, 110.3, 107.0, 48.3, 29.1, 26.8. Mass Spectrum (ESI) [M–H]$^-$ C$_{19}$H$_{22}$N$_3$O$_3$S 372.1

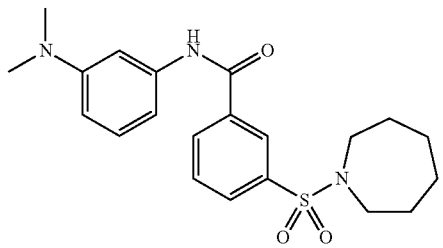

3-(azepan-1-ylsulfonyl)-N-(3-(dimethylamino)phenyl)benzamide (203j)

Compound 203j was synthesized following the general procedure of synthesizing compound 203. White Solid, Melting point: 178-180° C.; $^1$H NMR (500 MHz, CDCl$_3$) δ 8.23 (s, 1H), 8.09 (d, J=7.7 Hz, 1H), 7.92 (d, J=7.8 Hz, 1H), 7.62 (t, J=7.8 Hz, 1H), 7.29-7.13 (m, 2H), 6.96 (d, J=7.8 Hz, 1H), 6.55 (dd, J=8.4, 2.5 Hz, 1H), 3.27 (t, J=5.8 Hz, 4H), 2.98 (s, 6H), 1.77-1.65 (m, 4H), 1.63-1.48 (m, 4H); $^{13}$C NMR (126 MHz, CDCl$_3$) δ 164.2, 151.2, 140.1, 138.5, 136.4, 131.3, 129.7, 129.6, 129.6, 125.0, 109.3, 108.4, 104.4, 48.3, 40.6, 29.1, 26.7. Mass Spectrum (ESI) [2M–H]$^-$ C$_{42}$H$_{53}$N$_6$O$_6$S$_2$, 801.0.

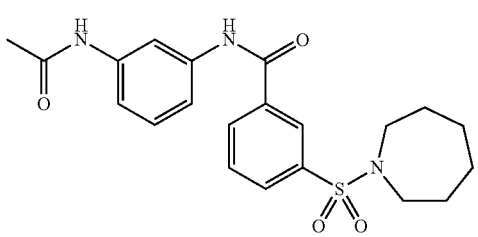

N-(3-acetamidophenyl)-3-(azepan-1-ylsulfonyl)benzamide (203k)

Compound 203k was synthesized following the general procedure of synthesizing compound 203. White Solid, Melting point: 117-120° C.; $^1$H NMR (500 MHz, CDCl$_3$) δ 8.24 (s, 1H), 8.17 (s, 1H), 8.08 (d, J=7.7 Hz, 1H), 7.98-7.93 (m, 2H), 7.65 (t, J=7.7 Hz, 1H), 7.50-7.46 (m, 1H), 7.36-7.27 (m, 2H), 3.30 (t, J=6.0 Hz, 4H), 2.18 (s, 3H), 1.78-1.68 (m, 4H), 1.64-1.57 (m, 4H). $^{13}$C NMR (126 MHz, CDCl$_3$) δ 168.6, 164.3, 140.4, 138.5, 138.2, 135.9, 131.2, 129.9, 129.7, 129.7, 125.1, 116.1, 111.7, 48.3, 29.1, 26.9, 24.7. Mass Spectrum (ESI) [M+Cl]$^-$ C$_{21}$H$_{25}$N$_3$O$_4$SCl, 450.0.

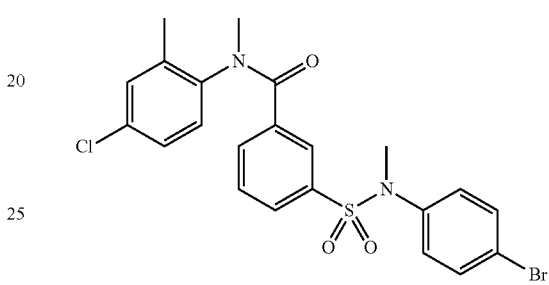

3-(N-(4-bromophenyl)-N-methylsulfamoyl)-N-(4-chloro-2-methylphenyl)-N-methylbenzamide (203l)

Compound 203l was synthesized following the general procedure of synthesizing compound 203. White Solid, Melting point: 124-125° C.; $^1$H NMR (500 MHz, CDCl$_3$) δ 7.59 (dt, J=7.5, 1.6 Hz, 1H), 7.52 (t, J=1.7 Hz, 1H), 7.43-7.39 (m, 2H), 7.31-7.24 (m, 2H), 7.17 (d, J=2.4 Hz, 1H), 7.08 (dd, J=8.4, 2.4 Hz, 1H), 6.95 (d, J=8.4 Hz, 1H), 6.85 (m, 2H), 3.36 (s, 3H), 2.92 (s, 3H), 2.20 (s, 3H); $^{13}$C NMR (126 MHz, CDCl$_3$) δ 168.7, 141.4, 140.1, 136.8, 136.5, 135.7, 133.8, 132.6, 132.1, 131.4, 129.9, 129.0, 128.7, 128.0, 127.4, 127.2, 121.2, 37.7, 37.6, 17.6; Mass Spectrum (ESI) [M+H]$^+$ C$_{22}$H$_{22}$BrClN$_2$O$_3$S: 509.4.

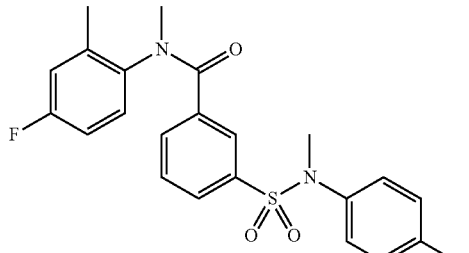

3-(N-(4-bromophenyl)-N-methylsulfamoyl)-N-(4-fluoro-2-methylphenyl)-N-methylbenzamide (203m)

Compound 203m was synthesized following the general procedure of synthesizing compound 203. White Solid, Melting point: 104-105° C.; $^1$H NMR (500 MHz, CDCl$_3$) δ 7.60-7.55 (m, 1H), 7.53-7.49 (m, 1H), 7.43-7.37 (m, 2H), 7.31-7.25 (m, 2H), 6.99 (dd, J=8.7, 5.2 Hz, 1H), 6.90-6.83

(m, 3H), 6.80 (dt, J=8.3, 4.2 Hz, 1H), 3.36 (s, 3H), 2.96 (s, 3H), 2.20 (s, 3H); $^{13}$C NMR (126 MHz, CDCl$_3$) δ 168.9, 161.6 (d, J=248.6 Hz), 140.2, 138.8 (d, J=3.2 Hz), 137.3 (d, J=8.5 Hz), 136.7, 135.7, 132.6, 132.1, 130.2 (d, J=8.9 Hz), 128.9, 128.6, 128.0, 127.3, 121.2, 118.1 (d, J=22.2 Hz), 114.2 (d, J=22.4 Hz), 37.85, 37.69, 17.85. Mass Spectrum (ESI) [M+H]$^+$ C$_{22}$H$_{21}$BrFN$_2$O$_3$S: 493.3.

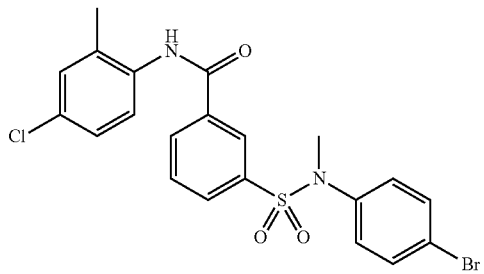

3-(N-(4-bromophenyl)-N-methylsulfamoyl)-N-(4-chloro-2-methylphenyl)benzamide (203n)

Compound 203n was synthesized following the general procedure of synthesizing compound 203. White Solid, Melting point: 163-164° C.; $^1$H NMR (500 MHz, CDCl$_3$) δ 8.11 (d, J=7.8 Hz, 1H), 7.94 (s, 1H), 7.87 (s, 1H), 7.66 (d, J=7.8 Hz, 1H), 7.59 (t, J=8.1 Hz, 2H), 7.42 (d, J=8.3 Hz, 2H), 7.24-7.13 (m, 2H), 6.94 (d, J=8.5 Hz, 2H), 3.14 (s, 3H), 2.21 (s, 3H); $^{13}$C NMR (126 MHz, CDCl$_3$) δ 164.1, 140.1, 136.6, 135.4, 133.6, 132.9, 132.3, 132.3, 131.4, 130.8, 130.5, 129.7, 128.2, 126.8, 125.8, 125.5, 121.5, 38.2, 17.8; Mass Spectrum (ESI) [M−H]$^-$ C$_{21}$H$_{17}$BrClN$_2$O$_3$S: 493.1.

132.4, 132.3, 130.7, 129.7, 126.5 (d, J=8.6 Hz), 125.8, 121.5, 117.3 (d, J=22.4 Hz), 113.4 (d, J=22.3 Hz), 38.2, 18.1. Mass Spectrum (ESI) [M−H]$^-$ C$_{21}$H$_{17}$BrFN$_2$O$_3$S: 477.0.

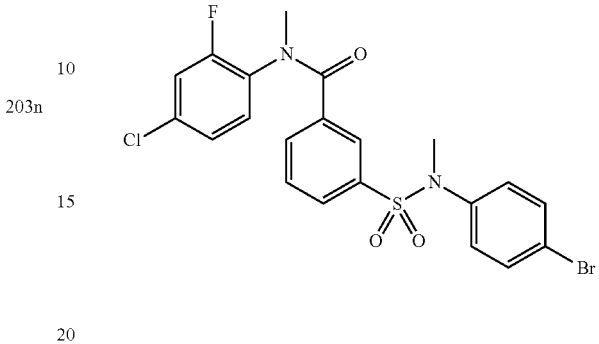

3-(N-(4-bromophenyl)-N-methylsulfamoyl)-N-(4-chloro-2-fluorophenyl)-N-methylbenzamide (203p)

Compound 203p was synthesized following the general procedure of synthesizing compound 203. White Solid, Melting point: 127-128° C.; $^1$H NMR (500 MHz, CDCl$_3$) δ 7.62 (s, 1H), 7.57 (s, 1H), 7.43 (d, J=5.0 Hz, 1H), 7.41 (d, J=5.0 Hz, 1H), 7.31 (m, 2H), 7.06 (m, 3H), 6.88 (d, J=5.0 Hz 2H), 3.41 (s, 3H), 3.00 (s, 3H). $^{13}$C NMR (126 MHz, CDCl$_3$) δ 169.5, 156.4 (d, J=253.5 Hz), 140.1, 136.2, 136.1, 134.5 (d, J=9.5 Hz), 132.3, 132.2, 130.0, 129.2, 128.8, 128.0, 127.1, 125.5 (d, J=3.7 Hz), 121.2, 117.6 (d, J=23.4 Hz), 37.9, 37.6. HRMS (ESI) (M+H$^+$) calcd for C$_{21}$H$_{18}$BrClFN$_2$O$_3$S 510.9894. found 510.9867.

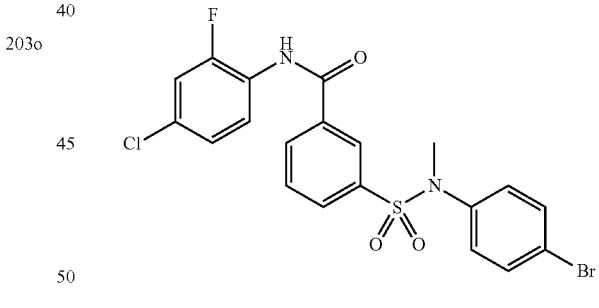

3-(N-(4-bromophenyl)-N-methylsulfamoyl)-N-(4-chloro-2-fluorophenyl)benzamide (203q)

Compound 203q was synthesized following the general procedure of synthesizing compound 203. White Solid, Melting point: 117-118° C.; $^1$H NMR (500 MHz, CDCl$_3$) δ 8.29 (t, J=8.7 Hz, 1H), 8.12 (dd, J=7.7, 1.6 Hz, 1H), 8.01 (m, 2H), 7.67 (m, 1H), 7.62 (t, J=7.8 Hz, 1H), 7.44 (d, J=8.7 Hz, 2H), 7.19 (m, 2H), 6.98 (d, J=8.8 Hz, 2H), 3.18 (s, 3H); $^{13}$C NMR (126 MHz, CDCl$_3$) δ 163.6, 152.6 (d, J=247.7 Hz), 140.0, 137.1, 135.1, 132.3, 131.8, 131.0, 129.9 (d, J=9.9 Hz), 129.8, 128.1, 126.0, 124.9 (d, J=3.6 Hz), 124.6 (d, J=10.2 Hz), 123.0, 121.5, 115.9 (d, J=22.6 Hz), 38.2; Mass Spectrum (ESI) [M−H]$^-$ C$_{20}$H$_{14}$BrClFN$_2$O$_3$S: 496.9

3-(N-(4-bromophenyl)-N-methylsulfamoyl)-N-(4-fluoro-2-methylphenyl)benzamide (203o)

Compound 203o was synthesized following the general procedure of synthesizing compound 203. White Solid, Melting point: 163-165° C.; $^1$H NMR (500 MHz, CDCl$_3$) δ 8.14 (d, J=7.6 Hz, 1H), 7.94 (s, 1H), 7.76 (s, 1H), 7.68 (d, J=7.8 Hz, 1H), 7.61 (t, J=7.8 Hz, 1H), 7.56-7.50 (m, 1H), 7.45-7.40 (m, 2H), 6.99-6.88 (m, 4H), 3.16 (s, 3H), 2.23 (s, 3H); $^{13}$C NMR (126 MHz, CDCl$_3$) δ 164.3, 160.7 (d, J=245.6 Hz), 140.1, 136.6, 135.5, 134.2 (d, J=8.0 Hz),

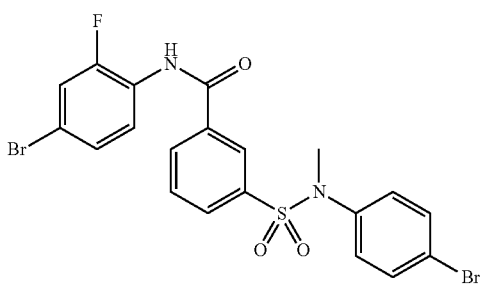

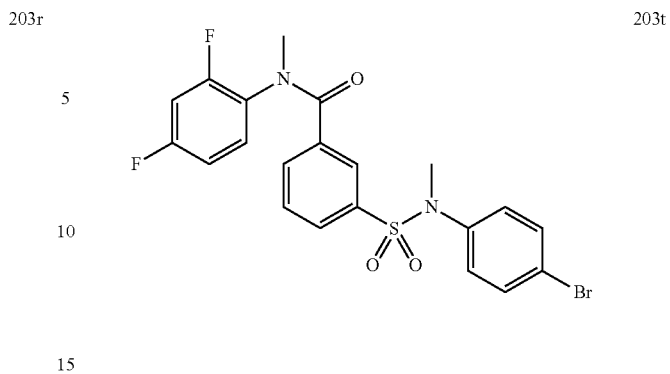

N-(4-bromo-2-fluorophenyl)-3-(N-(4-bromophenyl)-N-methylsulfamoyl)benzamide (203r)

Compound 203r was synthesized following the general procedure of synthesizing compound 203. White Solid, Melting point: 1114-115° C.; $^1$H NMR (500 MHz, CDCl$_3$) δ 8.25 (t, J=8.4 Hz, 1H), 8.12 (d, J=7.7 Hz, 1H), 8.01 (m, 2H), 7.67 (m, 1H), 7.62 (t, J=7.8 Hz, 1H), 7.44 (d, J=8.8 Hz, 2H), 7.33 (m, 2H), 6.98 (m, 2H), 3.18 (s, 3H); $^{13}$C NMR (126 MHz, CDCl$_3$) δ 163.6, 152.6 (d, J=248.7 Hz), 140.0, 137.1, 135.1, 132.3, 131.8, 131.1, 129.8, 128.1, 127.9 (d, J=3.6 Hz), 126.0, 125.1 (d, J=10.2 Hz), 123.3, 121.5, 118.7 (d, J=22.4 Hz), 117.0 (d, J=9.0 Hz), 38.2; Mass Spectrum (ESI) [M−H]$^-$ C$_{20}$H$_{14}$Br$_2$FN$_2$O$_3$S: 540.9

3-(N-(4-bromophenyl)-N-methylsulfamoyl)-N-(2,4-difluorophenyl)-N-methyl-benzamide (203t)

Compound 203t was synthesized following the general procedure of synthesizing compound 203. White foam; $^1$H NMR (500 MHz, CDCl$_3$) δ 7.63-7.51 (m, 2H), 7.42 (d, J=8.7 Hz, 2H), 7.35-7.28 (m, 2H), 7.13-7.05 (q, J=8.0, 7.6 Hz, 1H), 6.92-6.86 (d, J=8.4 Hz, 2H), 6.83-6.74 (m, 2H), 3.41 (s, 3H), 3.93 (s, 3H); $^{13}$C NMR (126 MHz, CDCl$_3$) δ 169.2, 161.8 (dd, J=252.0, 11.0 Hz), 157.4 (dd, J=252.6, 12.1 Hz), 140.1, 136.4, 136.1, 132.2, 132.1, 130.2 (d, J=9.8 Hz), 129.0, 128.7, 128.0, 127.0, 121.3, 112.3 (dd, J=22.3, 3.8 Hz), 105.2 (dd, J=26.3, 23.8 Hz), 38.0, 37.6; Mass Spectrum (ESI) [M+H]$^+$ C$_{21}$H$_{18}$BrF$_2$N$_2$O$_3$S: 495.3

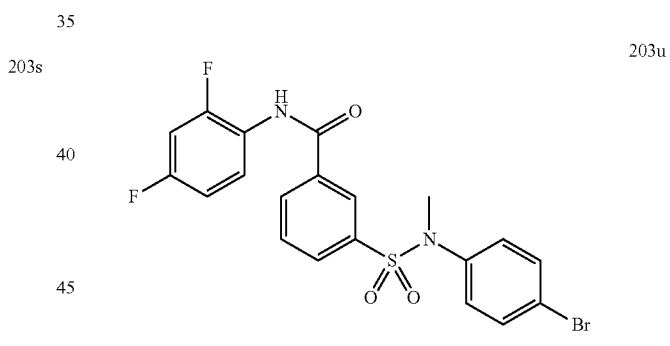

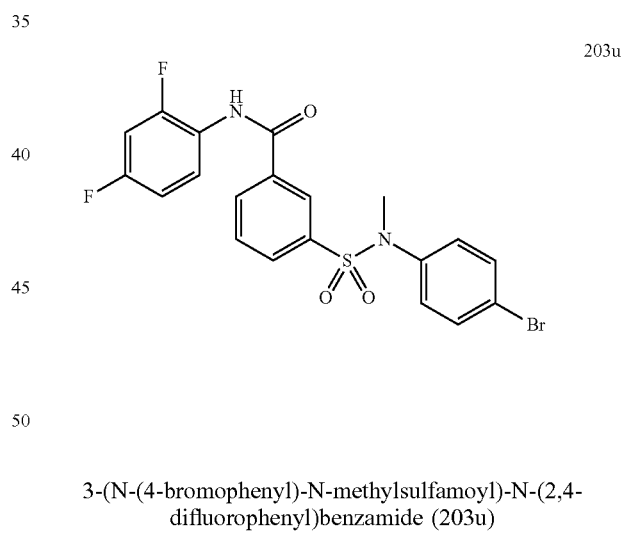

N-(4-bromo-2-fluorophenyl)-3-(N-(4-bromophenyl)-N-methylsulfamoyl)-N-methylbenzamide (203s)

Compound 203s was synthesized following the general procedure of synthesizing compound 203. White Solid, Melting point: 136-137° C.; $^1$H NMR (500 MHz, CDCl$_3$) δ 7.62 (s, 1H), 7.60-7.55 (m, 1H), 7.44-7.40 (m, 2H), 7.35-7.29 (m, 1H), 7.22 (d, J=8.3 Hz, 2H), 7.06-6.99 (t, J=7.7 Hz, 1H), 6.88 (d, J=8.2 Hz, 2H), 3.40 (s, 3H), 3.0 (s, 3H); $^{13}$C NMR (126 MHz, CDCl$_3$) δ 169.0, 156.9 (d, J=254.7 Hz), 140.1, 136.2, 136.0, 132.3, 132.1, 130.3, 129.2, 128.8, 128.4 (d, J=3.9 Hz), 127.0, 121.8 (d, J=8.8 Hz), 120.5 (d, J=23.1 Hz), 37.9, 37.5. Mass Spectrum (ESI) [M+H]$^+$ C$_{21}$H$_{16}$Br$_2$FN$_2$O$_3$S: 556.9

3-(N-(4-bromophenyl)-N-methylsulfamoyl)-N-(2,4-difluorophenyl)benzamide (203u)

Compound 203u was synthesized following the general procedure of synthesizing compound 203. White Solid, Melting point: 119-120° C.; $^1$H NMR (500 MHz, CDCl$_3$) δ 8.19-8.06 (m, 3H), 8.04 (t, J=1.8 Hz, 1H), 7.66-7.57 (m, 2H), 7.43 (d, J=8.8 Hz, 2H), 6.96 (d, J=8.8 Hz, 2H), 6.91 (t, J=8.5 Hz, 2H), 3.16 (s, 3H); $^{13}$C NMR (126 MHz, CDCl$_3$) δ 163.9, 159.3 (dd, J=247.6, 11.4 Hz), 153.5 (dd, J=247.8, 12.0 Hz), 140.1, 137.0, 135.2, 132.3, 132.0, 130.9, 129.7, 128.2, 126.1, 124.1 (dd, J=9.0, 2.3 Hz), 121.9 (d, J=10.8, 3.8 Hz), 121.54, 111.4 (dd, J=21.8, 3.7 Hz), 103.9 (dd, J=26.6, 23.3 Hz), 38.2; Mass Spectrum (ESI) [M+Cl]$^-$ C$_{20}$H$_{16}$BrClF$_2$N$_2$O$_3$S: 516.7

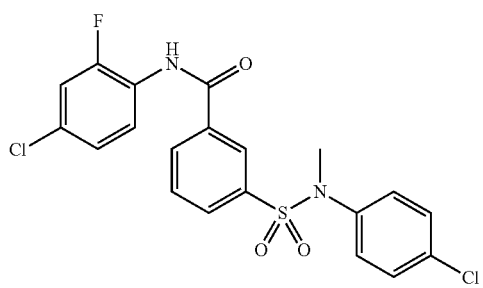

203v

N-(4-chloro-2-fluorophenyl)-3-(N-(4-chlorophenyl)-N-methylsulfamoyl)benzamide (203v)

Compound 203v was synthesized following the general procedure of synthesizing compound 203. White Solid, Melting point: 119-120° C.; $^1$H NMR (500 MHz, CDCl$_3$) δ 8.26 (t, J=8.6 Hz, 1H), 8.11 (dt, J=7.6, 1.6 Hz, 1H), 8.02 (q, J=2.7, 1.7 Hz, 2H), 7.69-7.57 (m, 2H), 7.31-7.24 (m, 2H), 7.16 (s, 2H), 7.03 (d, J=8.7 Hz, 2H), 3.17 (s, 3H); $^{13}$C NMR (126 MHz, CDCl$_3$) δ 163.7, 152.7 (d, J=247.8 Hz), 139.5, 137.1, 135.2, 133.6, 131.9, 131.1, 130.0 (d, J=9.9 Hz), 129.8, 129.3, 127.9, 126.0, 124.9 (d, J=3.6 Hz), 124.6 (d, J=10.3 Hz), 123.1 (d, J=1.6 Hz), 116.1, 115.9, 38.3; Mass Spectrum (ESI) [M−H]$^-$ C$_{20}$H$_{14}$Cl$_2$FN$_2$O$_3$S: 451.0

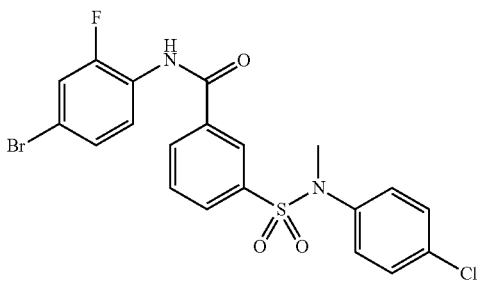

203w

N-(4-bromo-2-fluorophenyl)-3-(N-(4-chlorophenyl)-N-methylsulfamoyl)benzamide (203w)

Compound 203w was synthesized following the general procedure of synthesizing compound 203. White Solid, Melting point: 126-127° C.; $^1$H NMR (500 MHz, CDCl$_3$) δ 8.27 (t, J=8.4 Hz, 1H), 8.12 (d, J=7.8 Hz, 1H), 8.01 (t, J=1.8 Hz, 1H), 7.94 (d, J=3.2 Hz, 1H), 7.72-7.60 (m, 2H), 7.33 (d, J=8.6 Hz, 2H), 7.29 (d, J=8.7 Hz, 2H), 7.04 (d, J=8.8 Hz, 2H), 3.19 (s, 3H); $^{13}$C NMR (126 MHz, CDCl$_3$) δ 163.6, 152.5 (d, J=248.7 Hz), 139.5, 137.2, 135.1, 133.6, 131.8, 131.1, 129.8, 129.3, 127.9 (d, J=3.7 Hz), 127.8, 125.9, 125.1 (d, J=10.1 Hz), 123.2, 118.7 (d, J=22.4 Hz), 116.9 (d, J=9.1 Hz), 38.2; Mass Spectrum (ESI) [M−H]$^-$ C$_{20}$H$_{14}$BrClFN$_2$O$_3$S: 496.9

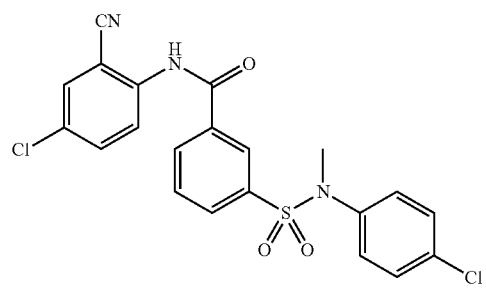

203x

N-(4-chloro-2-cyanophenyl)-3-(N-(4-chlorophenyl)-N-methylsulfamoyl)benzamide (203x)

Compound 203x was synthesized following the general procedure of synthesizing compound 203. White Solid, Melting point: 157-158° C.; $^1$H NMR (500 MHz, CDCl$_3$) δ 8.51 (s, 1H), 8.32 (d, J=9.0 Hz, 1H), 8.21 (s, 1H), 8.13 (d, J=7.5 Hz, 1H), 7.72-7.56 (m, 4H), 7.28 (d, J=8.6 Hz, 2H), 7.03 (d, J=8.5 Hz, 2H), 3.19 (s, 3H); $^{13}$C NMR (126 MHz, CDCl$_3$) δ 163.9, 139.4, 138.5, 137.5, 134.5, 133.6, 131.8, 131.5, 130.5, 129.9, 129.4, 127.9, 126.7, 123.9, 115.2, 105.2, 38.3; Mass Spectrum (ESI) [M−H]$^-$ C$_{21}$H$_{14}$Cl$_2$N$_3$O$_3$S: 458.1

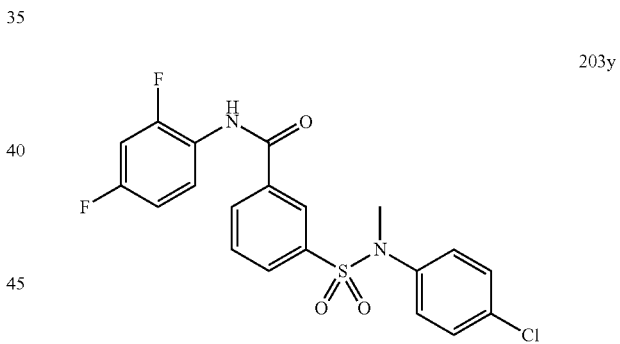

203y

3-(N-(4-chlorophenyl)-N-methylsulfamoyl)-N-(2,4-difluorophenyl)benzamide (203y)

Compound 203y was synthesized following the general procedure of synthesizing compound 203. White foam; $^1$H NMR (500 MHz, CDCl$_3$) δ 8.26-7.95 (m, 4H), 7.75-7.52 (m, 2H), 7.39-7.19 (m, 2H), 7.14-6.78 (m, 4H), 3.16 (s, 1H); $^{13}$C NMR (126 MHz, CDCl$_3$) δ 164.0, 159.4 (dd, J=247.7, 11.4 Hz), 153.6 (dd, J=248.0, 11.9 Hz), 139.5, 136.9, 135.2, 133.5, 132.0, 130.9, 129.7, 129.3, 127.9, 126.1, 124.3 (d, J=9.2 Hz), 121.9 (dd, J=10.4, 4.2 Hz), 111.4 (dd, J=21.7, 4.0 Hz), 103.9 (dd, J=26.9, 23.1 Hz), 38.2; Mass Spectrum (ESI) [M−H]$^-$ C$_{20}$H$_{14}$ClF$_2$N$_2$O$_3$S: 435.0

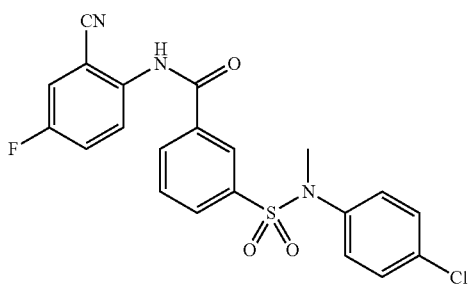

3-(N-(4-chlorophenyl)-N-methylsulfamoyl)-N-(2-cyano-4-fluorophenyl)benzamide (203z)

Compound 203z was synthesized following the general procedure of synthesizing compound 203. White foam; $^1$H NMR (500 MHz, CDCl$_3$) δ 8.66-8.47 (m, OH), 8.36-8.03 (m, 3H), 7.78-7.52 (m, 2H), 7.49-7.17 (m, 4H), 7.12-6.93 (m, 2H), 3.18 (s, 3H); $^{13}$C NMR (126 MHz, CDCl$_3$) δ 164.1, 158.8 (d, J=249.0 Hz), 139.5, 137.3, 136.2 (d, J=3.3 Hz), 134.5, 133.5, 131.7, 131.4, 129.8, 129.4, 127.9, 126.6, 125.5 (d, J=8.1 Hz), 121.8 (d, J=22.1 Hz), 119.0 (d, J=25.7 Hz), 115.3 (d, J=3.0 Hz), 106.0 (d, J=9.2 Hz), 38.3; Mass Spectrum (ESI) [M–H]$^-$ C$_{21}$H$_{14}$ClFN$_3$O$_3$S: 442.0

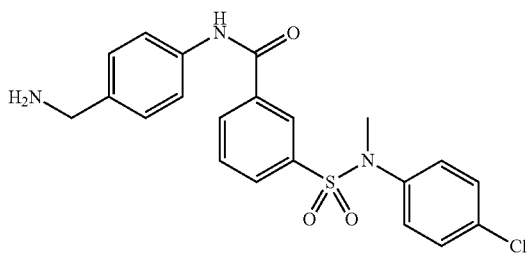

N-(4-(aminomethyl)phenyl)-3-(N-(4-chlorophenyl)-N-methylsulfamoyl)benzamide (203Aa)

Compound 203Aa was synthesized following the general procedure of synthesizing compound 203. White foam; $^1$H NMR (500 MHz, CDCl$_3$) δ 8.14-8.04 (m, 2H), 7.59-7.43 (m, 4H), 7.28-7.13 (m, 4H), 7.04-6.92 (m, 2H), 3.12 (s, 2H); $^{13}$C NMR (126 MHz, CDCl$_3$) δ 164.4, 139.5, 136.7, 136.4, 135.9, 133.4, 132.4, 130.4, 129.4, 129.2, 128.1, 127.9, 126.1, 121.2, 45.1, 38.2; Mass Spectrum (ESI) [M+H]$^+$ C$_{21}$H$_{21}$ClN$_3$O$_3$S: 430.0

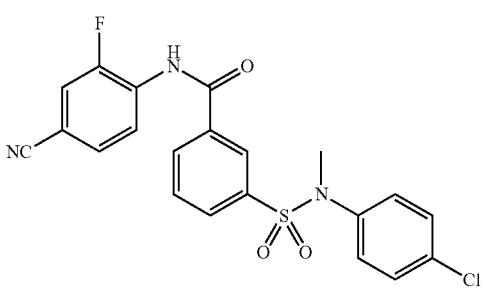

3-(N-(4-chlorophenyl)-N-methylsulfamoyl)-N-(4-cyano-2-fluorophenyl)benzamide (203Ab)

Compound 203Ab was synthesized following the general procedure of synthesizing compound 203. White Solid, Melting point: 158-159° C.; $^1$H NMR (500 MHz, CDCl$_3$) δ 8.60 (t, J=8.1 Hz, 1H), 8.30-8.25 (m, 1H), 8.13 (dt, J=7.5, 1.5 Hz, 1H), 8.04-8.01 (m, 1H), 7.70 (dd, J=7.6, 1.7 Hz, 1H), 7.65 (t, J=7.7 Hz, 1H), 7.53 (d, J=8.6 Hz, 1H), 7.46 (dd, J=10.4, 1.7 Hz, 1H), 7.29 (dd, J=8.7, 1.6 Hz, 2H), 7.04 (dd, J=8.6, 1.6 Hz, 2H), 3.19 (s, 3H). $^{13}$C NMR (126 MHz, CDCl$_3$) δ 163.9, 151.6 (d, J=247.4 Hz), 139.4, 137.3, 134.7, 131.9 (d, J=15.2 Hz), 130.7 (d, J=9.6 Hz), 129.6, 129.1, 128.1, 126.2, 122.3, 122.0, 118.9 (d, J=21.9 Hz), 118.5 (d, J=23.6 Hz), 117.6, 107.8 (d, J=9.2 Hz), 38.1. Mass Spectrum (ESI) [M–H]$^-$ C$_{21}$H$_{14}$ClFN$_3$O$_3$S: 442.0.

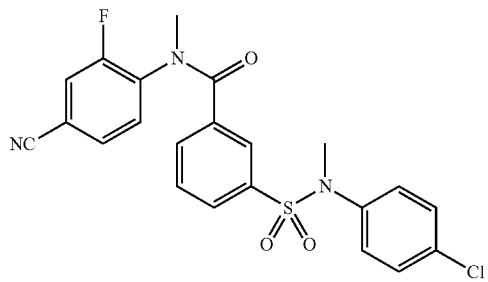

3-(N-(4-chlorophenyl)-N-methylsulfamoyl)-N-(4-cyano-2-fluorophenyl)-N-methylbenzamide (203Ac)

Compound 203Ac was synthesized following the general procedure of synthesizing compound 203. White Solid, Melting point: 169-170° C.; $^1$H NMR (500 MHz, CDCl$_3$) δ 7.61 (t, J=1.8 Hz, 1H), 7.55 (dt, J=7.6, 1.5 Hz, 1H), 7.44-7.39 (m, 2H), 7.39-7.34 (m, 2H), 7.29-7.25 (m, 3H), 6.99-6.95 (m, 2H), 3.44 (s, 3H), 3.06 (s, 3H). $^{13}$C NMR (126 MHz, CDCl$_3$) δ 168.8, 156.5 (d, J=253.9 Hz), 139.5, 136.5, 135.7, 133.3, 132.3, 130.1, 129.6, 129.2, 129.2, 129.0, 127.7, 127.3, 120.7 (d, J=23.7 Hz), 116.6 (d, J=2.7 Hz), 112.7 (d, J=9.0 Hz), 38.0, 37.8. Mass Spectrum (ESI) [M+H]$^+$ C$_{22}$H$_{18}$ClFN$_3$O$_3$S: 458.0.

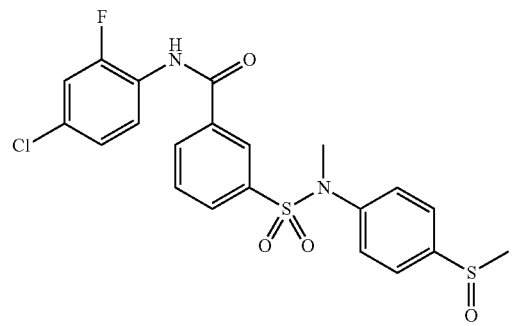

N-(4-chloro-2-fluorophenyl)-3-(N-methyl-N-(4-(methylsulfinyl)phenyl)sulfamoyl)-benzamide (203Ad)

Compound 203Ad was synthesized following the general procedure of synthesizing compound 203. White foam; $^1$H NMR (500 MHz, CDCl$_3$) δ 8.48 (d, J=2.7 Hz, 1H), 8.18-8.09 (m, 3H), 7.66-7.62 (m, 1H), 7.61 (d, J=7.7 Hz, 1H), 7.57 (d, J=8.6 Hz, 2H), 7.28 (d, J=8.6 Hz, 2H), 7.18-7.13 (m, 2H), 3.23 (s, 3H), 2.71 (s, 3H); $^{13}$C NMR (126 MHz, CDCl$_3$) δ 163.86, 153.1 (d, J=248.4 Hz), 144.46, 143.58, 137.01, 135.28, 130.81, 130.2 (d, J=9.9 Hz), 129.70, 127.12, 126.44, 124.9 (d, J=3.6 Hz), 124.46, 123.8 (d, J=2.1 Hz), 116.0 (d, J=22.7 Hz), 43.74, 38.08. Mass Spectrum (ESI) [M−H]$^-$ C$_{21}$H$_{17}$ClFN$_2$O$_4$S$_2$: 479.0.

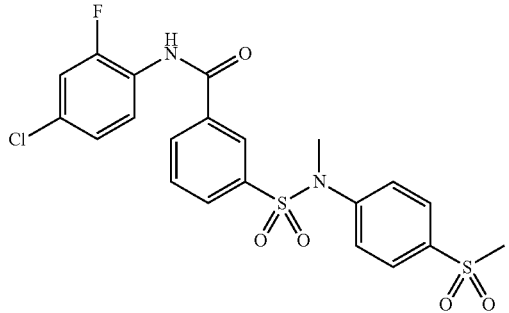

N-(4-chloro-2-fluorophenyl)-3-(N-methyl-N-(4-(methylsulfonyl)phenyl)sulfamoyl)-benzamide
(203Ae)

Compound 203Ae was synthesized following the general procedure of synthesizing compound 203. White Solid, Melting point: 182-183° C.; $^1$H NMR (500 MHz, CDCl$_3$) δ 8.27-8.19 (m, 2H), 7.98-7.90 (m, 3H), 7.75-7.64 (m, 2H), 7.47-7.42 (m, 2H), 7.28-7.20 (m, 2H), 3.33 (s, 3H), 3.15 (s, 3H); $^{13}$C NMR (126 MHz, CDCl$_3$) δ 168.72, 158.4 (d, J=250.3 Hz), 136.26, 134.9 (d, J=9.8 Hz), 134.50, 133.61, 132.27, 130.76, 130.36, 129.51, 128.6 (d, J=3.2 Hz), 128.1 (d, J=11.2 Hz), 120.3 (d, J=23.1 Hz), 48.1, 41.6. Mass Spectrum (ESI) [M−H]$^-$ C$_{21}$H$_{17}$ClFN$_2$O$_5$S$_2$: 495.0

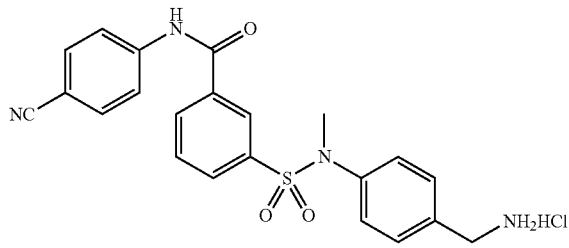

3-(N-(4-(aminomethyl)phenyl)-N-methylsulfamoyl)-N-(4-cyanophenyl)benzamide hydrochloride
(203Af)

Compound 203Af was synthesized following the general procedure of synthesizing compound 203. White Solid, Melting point: 169-171° C.; $^1$H NMR (500 MHz, DMSO) δ 8.30-8.11 (m, 2H), 8.10-8.04 (m, 1H), 7.90 (m, 2H), 7.76 (dd, J=8.7, 1.5 Hz, 2H), 7.69-7.63 (m, 1H), 7.59 (dt, J=8.7, 3.5 Hz, 1H), 7.40-7.31 (m, 2H), 7.11 (dd, J=8.6, 2.3 Hz, 2H), 3.94-3.87 (m, 2H), 3.10 (s, 3H); $^{13}$C NMR (126 MHz, DMSO) δ 164.5, 143.1, 140.9, 136.7, 135.2, 133.2, 132.6, 130.5, 129.7, 129.6, 126.6, 126.4, 120.4, 119.0, 105.8, 41.6, 38.1. Mass Spectrum (ESI) [M−Cl]$^+$ C$_{23}$H$_{22}$N$_4$O$_3$S 421.0

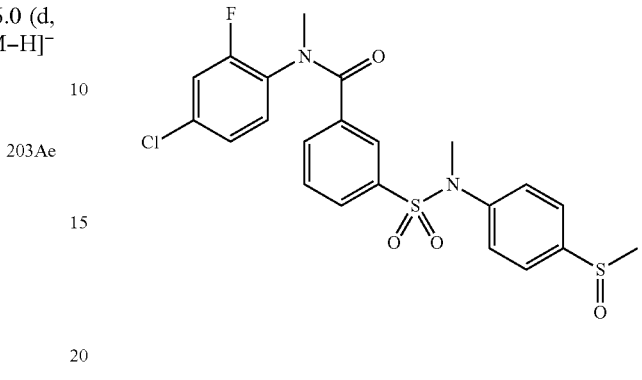

N-(4-chloro-2-fluorophenyl)-N-methyl-3-(N-methyl-N-(4-(methylsulfinyl)phenyl)-sulfamoyl)benzamide
(203Ag)

Compound 203Ag was synthesized following the general procedure of synthesizing compound 203. White Solid, Melting point: 104-106° C.; $^1$H NMR (500 MHz, CDCl$_3$) δ 7.65-7.52 (m, 4H), 7.38-7.28 (m, 2H), 7.24-7.17 (m, 2H), 7.12-7.04 (m, 3H), 3.41 (s, 3H), 3.06 (s, 3H), 2.75 (s, 3H); $^{13}$C NMR (126 MHz, CDCl$_3$) δ 168.95, 156.9 (d, J=253.5 Hz), 144.49, 143.59, 136.35, 136.05, 134.6 (d, J=9.5 Hz), 132.37, 130.66, 130.02, 129.02, 128.87, 127.15, 126.98, 125.6 (d, J=3.7 Hz), 124.37, 117.6 (d, J=23.4 Hz), 43.89, 37.79, 37.58; Mass Spectrum (ESI) [M+H]$^+$ C$_{22}$H$_{21}$ClFN$_2$O$_4$S$_2$: 495.1.

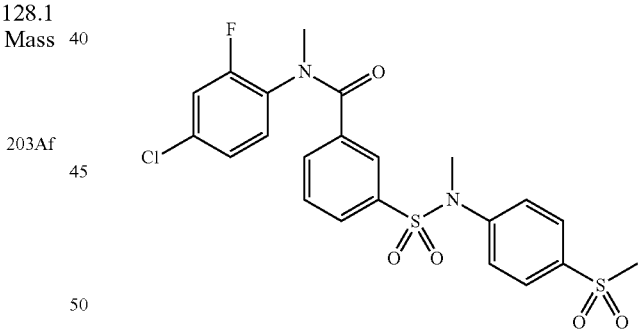

N-(4-chloro-2-fluorophenyl)-N-methyl-3-(N-methyl-N-(4-(methylsulfonyl)phenyl)-sulfamoyl)benzamide
(203Ah)

Compound 203Ah was synthesized following the general procedure of synthesizing compound 203. White Solid, Melting point: 159-160° C.; $^1$H NMR (500 MHz, CDCl$_3$) δ 7.89 (d, J=8.6 Hz, 2H), 7.63-7.51 (m, 2H), 7.42-7.23 (m, 4H), 7.12-7.02 (m, 3H). 3.40 (s, 3H), 3.09 (s, 3H), 3.08 (s, 3H); $^{13}$C NMR (126 MHz, CDCl$_3$) δ 168.8, 156.9 (d, J=253.6 Hz), 146.0, 138.6, 136.5, 136.0, 134.6 (d, J=9.6 Hz), 132.5, 130.6, 130.0, 129.0, 128.9, 127.1, 125.6 (d, J=3.7 Hz), 117.6 (d, J=23.4 Hz), 44.5, 37.6, 37.5; Mass Spectrum (ESI) [M+H]$^+$ C$_{22}$H$_{21}$ClFN$_2$O$_5$S$_2$: 511.2

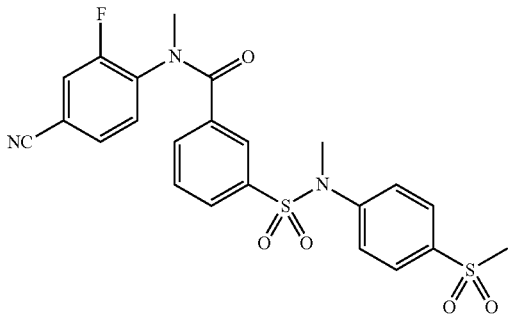

203Ai

N-(4-cyano-2-fluorophenyl)-3-(N-methyl-N-(4-(methylsulfonyl)phenyl)-sulfamoyl)benzamide (203Ai)

Compound 203Ai was synthesized following the general procedure of synthesizing compound 203. White Solid, Melting point: 188-189° C.; $^1$H NMR (500 MHz, CDCl$_3$) δ 9.84-9.58 (m, 1H), 8.40-8.10 (m, 3H), 7.97-7.80 (m, 2H), 7.72-7.57 (m, 2H), 7.57-7.22 (m, 4H), 3.35-3.17 (s, 2H), 3.10-3.01 (s, 2H); $^{13}$C NMR (126 MHz, CDCl$_3$) δ 164.4 (d, J=4.5 Hz), 153.0 (d, J=229.0 Hz), 145.9, 138.7, 136.8, 135.0, 132.8 (d, J=8.3 Hz), 130.9 (d, J=11.0 Hz), 130.7, 129.6, 129.0, 128.3, 127.9 (d, J=3.9 Hz), 126.3, 124.3, 119.1 (d, J=23.0 Hz), 117.6, 108.2 (d, J=9.1 Hz), 44.4, 37.8; Mass Spectrum (ESI) [M–H]$^-$ C$_{22}$H$_{17}$FN$_3$O$_5$S$_2$: 486.0.

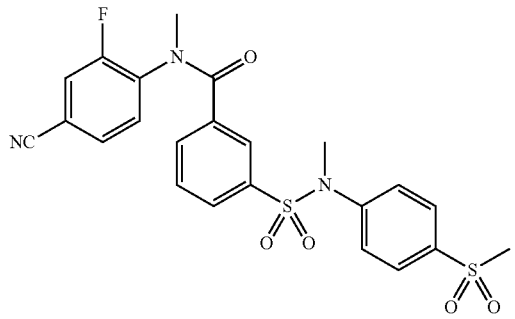

203Ak

N-(4-cyano-2-fluorophenyl)-N-methyl-3-(N-methyl-N-(4-(methylsulfonyl)phenyl)-sulfamoyl)benzamide (203Ak)

Compound 203Ak was synthesized following the general procedure of synthesizing compound 203. White Solid, Melting point: 156-157° C.; $^1$H NMR (500 MHz, CDCl$_3$) δ 7.90 (d, J=8.7 Hz, 2H), 7.58 (t, J=1.7 Hz, 1H), 7.53 (d, J=7.6 Hz, 1H), 7.47-7.41 (m, 2H), 7.39-7.34 (m, 2H), 7.33-7.28 (m, 3H), 3.42 (s, 3H), 3.14 (s, 3H), 3.10 (s, 3H); $^{13}$C NMR (126 MHz, CDCl$_3$) δ 168.5, 156.5 (d, J=253.8 Hz), 145.91, 138.73, 136.40, 135.86, 132.47, 130.08, 129.31, 129.28, 129.25, 129.17, 128.40, 127.36, 126.21, 120.8 (d, J=23.7 Hz), 116.6 (d, J=2.7 Hz), 112.8 (d, J=9.0 Hz), 44.5, 37.8, 37.6; Mass Spectrum (ESI) [M+H]$^+$ C$_{23}$H$_{21}$FN$_3$O$_5$S$_2$: 502.0.

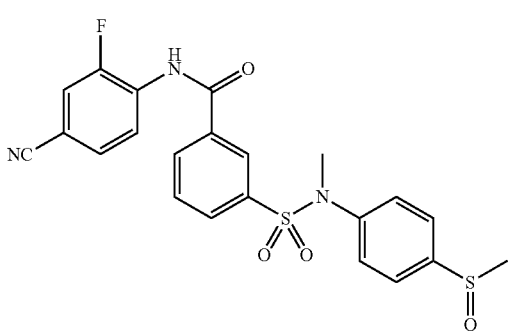

203Aj

N-(4-cyano-2-fluorophenyl)-3-(N-methyl-N-(4-(methylsulfinyl)phenyl)sulfamoyl)-benzamide (203Aj)

Compound 203Aj was synthesized following the general procedure of synthesizing compound 203. White Solid, Melting point: 192-194° C.; $^1$H NMR (500 MHz, CDCl$_3$) δ 9.75 (s, 1H), 8.21-8.05 (m, 3H), 7.55-7.42 (m, 4H), 7.41-7.25 (m, 2H), 7.23-7.09 (m, 2H), 3.11 (s, 2H), 2.60 (s, 3H), 2.59 (s, 3H); $^{13}$C NMR (126 MHz, CDCl$_3$) δ 164.5, 153.1 (d, J=249.7 Hz), 144.5, 143.5, 136.6, 134.9, 132.7, 131.0 (d, J=10.9 Hz), 130.8, 129.4, 128.8 (d, J=3.6 Hz), 127.0, 124.7, 124.3, 119.1 (d, J=23.1 Hz), 117.6 (d, J=2.9 Hz), 108.1 (d, J=8.9 Hz), 43.8, 38.0. Mass Spectrum (ESI) [M–H]$^-$ C$_{22}$H$_{17}$FN$_3$O$_4$S$_2$: 470.1

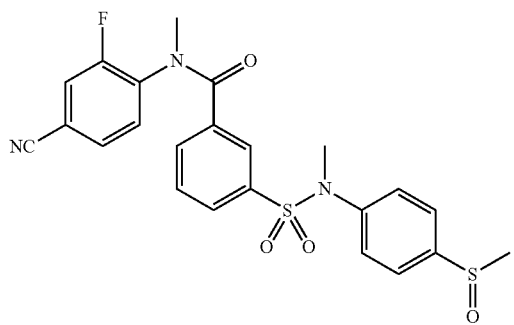

203Al

N-(4-cyano-2-fluorophenyl)-N-methyl-3-(N-methyl-N-(4-(methylsulfinyl)phenyl)-sulfamoyl)benzamide (203Al)

Compound 203Al was synthesized following the general procedure of synthesizing compound 203. White Solid, Melting point: 148-150° C.; $^1$H NMR (500 MHz, CDCl$_3$) δ 7.63-7.58 (m, 3H), 7.55-7.52 (m, 1H), 7.44-7.40 (m, 2H), 7.38-7.34 (m, 2H), 7.28-7.21 (m, 3H), 3.43 (s, 3H), 3.11 (s, 3H), 2.76 (s, 3H); $^{13}$C NMR (126 MHz, CDCl$_3$) δ 168.7, 156.5 (d, J=253.9 Hz), 144.6, 143.5, 136.5, 135.8, 132.3, 130.1, 129.4, 129.2 (d, J=4.1 Hz), 129.1, 127.4, 127.0, 124.5, 120.8 (d, J=23.7 Hz), 116.6 (d, J=2.7 Hz), 112.8 (d, J=9.0 Hz), 43.9, 37.9, 37.8; Mass Spectrum (ESI) [M+H]$^+$ C$_{23}$H$_{21}$FN$_3$O$_4$S$_2$: 486.3.

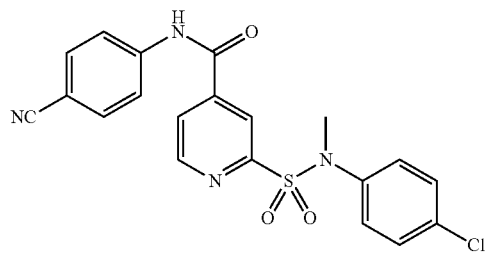

203Am

2-(N-(4-chlorophenyl)-N-methylsulfamoyl)-N-(4-cyanophenyl)isonicotinamide (203Am)

Compound 203Am was synthesized following the general procedure of synthesizing compound 203. White solid; m.p. 195-197° C.; $^1$H NMR (500 MHz, CDCl$_3$/DMSO-d6) δ 10.82 (s, 1H), 8.92 (s, 1H), 8.48 (s, 1H), 8.14 (s, 1H), 8.03-7.94 (m, 2H), 7.69-7.61 (m, 2H), 7.33-7.19 (m, 4H), 3.50 (s, 3H); $^{13}$C NMR (126 MHz, CDCl$_3$/DMSO-d6) δ 162.9, 157.4, 150.6, 143.8, 142.4, 139.5, 133.0, 132.8, 129.1, 128.4, 125.6, 120.7, 120.6, 118.8, 107.1, 40.0; HRMS (ESI) (M+H$^+$) calcd for C$_{20}$H$_{16}$ClN$_4$O$_3$S 427.0632. Found 427.0623.

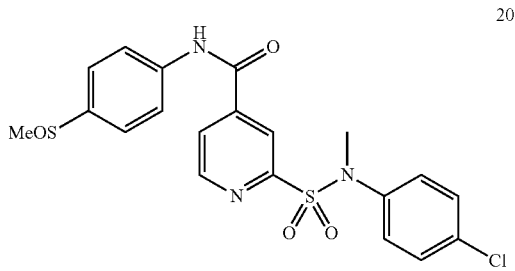

203An

2-(N-(4-chlorophenyl)-N-methylsulfamoyl)-N-(4-(methylsulfinyl)phenyl)-isonicotinamide (203An)

Compound 203An was synthesized following the general procedure of synthesizing compound 203. White solid; m.p. 172-174° C.; $^1$H NMR (500 MHz, CDCl$_3$) δ 9.91 (s, 1H), 8.82 (d, J=4.9 Hz, 1H), 8.33 (s, 1H), 8.02 (d, J=6.4 Hz, 1H), 7.84 (d, J=8.7 Hz, 2H), 7.53 (d, J=8.7 Hz, 2H), 7.23 (d, J=8.8 Hz, 2H), 7.18 (d, J=8.8 Hz, 2H), 3.46 (s, 3H), 2.42 (s, 3H); $^{13}$C NMR (126 MHz, CDCl$_3$) δ 162.9, 157.4, 150.9, 143.9, 140.7, 140.2, 139.5, 133.5, 129.4, 128.5, 125.4, 124.8, 121.6, 120.6, 43.5, 40.1; HRMS (ESI) (M+H$^+$) calcd for C$_{20}$H$_{19}$ClN$_3$O$_4$S$_2$ 464.0506. Found 464.0505.

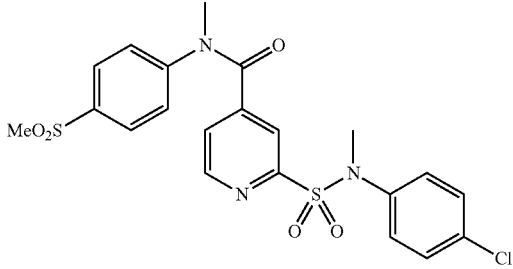

203Ao

2-(N-(4-chlorophenyl)-N-methylsulfamoyl)-N-methyl-N-(4-(methylsulfonyl)phenyl)-isonicotinamide (203Ao)

Compound 203Ao was synthesized following the general procedure of synthesizing compound 203. White foam; $^1$H NMR (500 MHz, CDCl$_3$) δ 8.69 (d, J=4.9 Hz, 1H), 7.86 (d, J=8.5 Hz, 2H), 7.51 (dd, J=4.9, 1.6 Hz, 1H), 7.40 (s, 1H), 7.30-7.23 (m, 2H), 7.22 (d, J=8.1 Hz, 2H), 7.11 (d, J=8.7 Hz, 2H), 3.52 (s, 3H), 3.34 (s, 3H), 3.03 (s, 3H); $^{13}$C NMR (126 MHz, CDCl$_3$) δ 166.1, 156.8, 150.7, 147.7, 144.6, 139.6, 139.4, 133.4, 129.3, 129.2, 128.3, 127.5, 125.8, 121.9, 44.6, 39.9, 38.2; Mass Spectrum (ESI) [M+H]$^+$ C$_{21}$H$_{21}$ClN$_3$O$_5$S$_2$: 494.4

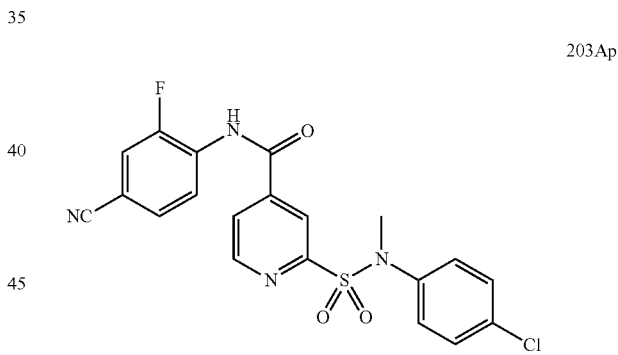

203Ap

2-(N-(4-chlorophenyl)-N-methylsulfamoyl)-N-(4-cyano-2-fluorophenyl)-isonicotinamide (203Ap)

Compound 203Ap was synthesized following the general procedure of synthesizing compound 203. White solid; m.p. 186-188° C.; $^1$H NMR (500 MHz, CDCl$_3$) δ 8.95 (d, J=4.9 Hz, 1H), 8.59 (t, J=8.1 Hz, 1H), 8.28 (m, 1H), 8.11 (m, 1H), 7.97 (dd, J=4.9, 1.6 Hz, 1H), 7.55 (d, J=8.6 Hz, 1H), 7.48 (dd, J=10.3, 1.7 Hz, 1H), 7.27 (m, 3H), 7.18 (d, J=8.8 Hz, 2H), 3.51 (s, 3H); $^{13}$C NMR (126 MHz, CDCl$_3$) δ 162.1, 158.3, 151.6 (d, J=246.2 Hz), 151.3, 142.8, 139.2, 133.6, 130.0 (d, J=9.9 Hz), 129.6 (d, J=3.7 Hz), 129.4, 128.4, 124.6, 122.2, 119.8, 118.8 (d, J=22.7 Hz), 117.3 (d, J=2.8 Hz), 108.6 (d, J=9.3 Hz), 40.2; HRMS (ESI) (M+H$^+$) calcd for C$_{20}$H$_{15}$ClFN$_4$O$_3$S 445.0537. found 445.0544.

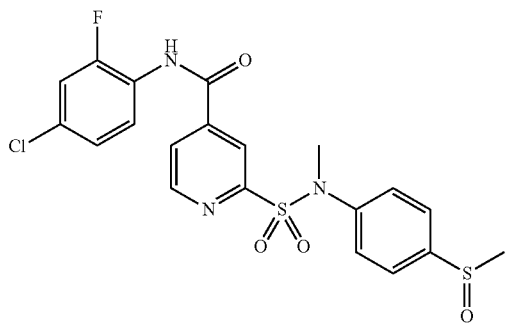

203Aq

N-(4-chloro-2-fluorophenyl)-2-(N-methyl-N-(4-(methylsulfinyl)phenyl)sulfamoyl)-isonicotinamide (203Aq)

Compound 203Aq was synthesized following the general procedure of synthesizing compound 203. White solid; m.p. 178-179° C.; $^1$H NMR (500 MHz, CDCl$_3$) δ 8.90 (s, 1H), 8.53 (s, 1H), 8.22 (s, 1H), 8.16 (t, J=10.0 Hz, 1H), 7.98 (s, 1H), 7.56 (d, J=7.3 Hz, 2H), 7.46 (d, J=7.3 Hz, 2H), 7.18 (d, J=8.6 Hz, 2H), 3.53 (s, 3H), 2.70 (s, 3H); $^{13}$C NMR (126 MHz, CDCl$_3$) δ 162.1, 157.8, 153.1 (d, J=248.7 Hz), 151.1, 144.2, 143.6 (d, J=14.9 Hz), 130.8 (d, J=9.9 Hz), 127.5, 125.0 (d, J=3.6 Hz), 124.9, 124.6, 123.9 (d, J=10.7 Hz), 123.8, 120.2, 116.2 (d, J=22.6 Hz), 43.7, 39.8; HRMS (ESI) (M+H$^+$) calcd for C$_{20}$H$_{18}$ClFN$_3$O$_4$S$_2$ 482.0411. Found 482.0232.

203Ar

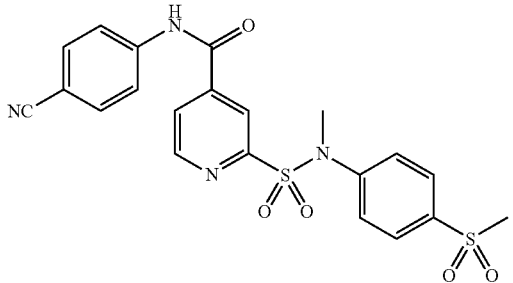

N-(4-cyanophenyl)-2-(N-methyl-N-(4-(methylsulfinyl)phenyl)sulfamoyl)-isonicotinamide (203Ar)

Compound 203Ar was synthesized following the general procedure of synthesizing compound 203. White solid; m.p. 243-245° C. (decompose); $^1$H NMR (500 MHz, CDCl$_3$/CD$_3$OD) δ 8.78 (s, 1H), 8.22 (s, 1H), 7.95 (s, 1H), 7.79 (d, J=7.8 Hz, 2H), 7.56 (d, J=7.8 Hz, 2H), 7.49 (d, J=7.6 Hz, 2H), 7.39 (d, J=7.6 Hz, 2H), 3.89 (s, 3H), 3.42 (s, 3H); $^{13}$C NMR (126 MHz, CDCl$_3$/CD$_3$OD) δ 167.2, 161.2, 154.9, 148.0, 147.8, 147.2, 146.1, 137.1, 131.5, 129.3, 128.5, 124.7, 124.6, 122.7, 111.5, 47.2, 43.5; HRMS (ESI) (M+H$^+$) calcd for C$_{21}$H$_{19}$N$_4$O$_4$S$_2$ 455.0848. Found 455.0850.

203As

N-(4-cyanophenyl)-2-(N-methyl-N-(4-(methylsulfonyl)phenyl)sulfamoyl)-isonicotinamide (203As)

Compound 203As was synthesized following the general procedure of synthesizing compound 203. White solid; m.p. 224-226° C.; $^1$H NMR (500 MHz, CDCl$_3$/CD$_3$OD) δ 8.78 (d, J=4.9 Hz, 1H), 8.27 (s, 1H), 7.97 (dd, J=4.9, 1.7 Hz, 1H), 7.80 (d, J=6.6 Hz, 2H), 7.79 (d, J=6.6 Hz, 2H), 7.57 (d, J=8.8 Hz, 2H), 7.47 (d, J=8.8 Hz, 1H), 3.71 (s, 3H), 2.97 (s, 3H); $^{13}$C NMR (126 MHz, CDCl$_3$/CD$_3$OD) δ 163.1, 157.0, 151.0, 146.1, 144.1, 142.0, 138.2, 133.1, 128.3, 126.5, 125.4, 120.7, 120.6, 118.7, 107.5, 44.22, 39.13. HRMS (ESI) (M+H$^+$) calcd for C$_{21}$H$_{19}$N$_4$O$_5$S$_2$ 471.0797. Found 471.0797.

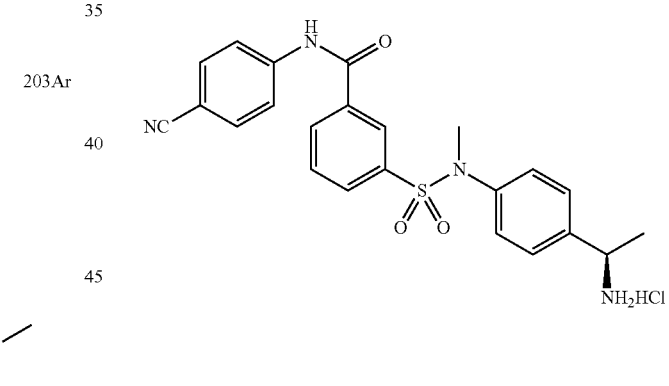

203At

(R)-3-(N-(4-(1-aminoethyl)phenyl)-N-methylsulfamoyl)-N-(4-cyanophenyl)-benzamide hydrochloride (203At)

Compound 203At was synthesized following the general procedure of synthesizing compound 203. White Solid, decomposed at 180° C.; $^1$H NMR (500 MHz, CDCl$_3$) δ 10.98 (s, 1H), 8.48 (s, 3H), 8.28 (d, J=7.6 Hz, 1H), 8.05 (s, 1H), 7.93 (d, J=8.5 Hz, 2H), 7.75 (d, J=8.3 Hz, 2H), 7.66 (t, J=7.7 Hz, 1H), 7.58 (d, J=7.8 Hz, 1H), 7.41 (d, J=8.2 Hz, 2H), 7.10 (d, J=8.2 Hz, 2H), 4.34-4.22 (m, 1H), 3.09 (s, 3H), 1.37 (d, J=6.8 Hz, 3H); $^{13}$C NMR (126 MHz, CDCl$_3$) δ 169.8, 148.4, 146.0, 143.7, 141.9, 140.4, 138.4, 137.9, 135.7, 134.9, 132.8, 132.0, 131.7, 125.7, 124.2, 110.9, 60.1, 54.6, 25.9; Mass Spectrum (ESI) [M−Cl]$^+$ C$_{23}$H$_{23}$ClN$_4$O$_3$S: 435.0.0

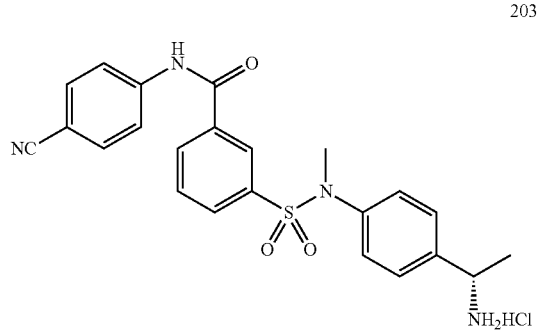

(S)-3-(N-(4-(1-aminoethyl)phenyl)-N-methylsulfamoyl)-N-(4-cyanophenyl)benzamide hydrochloride (203Au)

Compound 203Au was synthesized following the general procedure of synthesizing compound 203. White solid, decomposed at 180° C.; $^1$H NMR (500 MHz, CDCl$_3$) δ 10.98 (s, 1H), 8.48 (s, 3H), 8.28 (d, J=7.6 Hz, 1H), 8.05 (s, 1H), 7.93 (d, J=8.5 Hz, 2H), 7.75 (d, J=8.3 Hz, 2H), 7.66 (t, J=7.7 Hz, 1H), 7.58 (d, J=7.8 Hz, 1H), 7.41 (d, J=8.2 Hz, 2H), 7.10 (d, J=8.2 Hz, 2H), 4.34-4.22 (m, 1H), 3.09 (s, 3H), 1.37 (d, J=6.8 Hz, 3H); $^{13}$C NMR (126 MHz, CDCl$_3$) δ 169.8, 148.4, 146.0, 143.7, 141.9, 140.4, 138.4, 137.9, 135.7, 134.9, 132.8, 132.0, 131.7, 125.7, 124.2, 110.9, 60.1, 54.6, 25.9; Mass Spectrum (ESI) [M–H]$^-$ C$_{23}$H$_{23}$N$_4$O$_3$S: 435.0

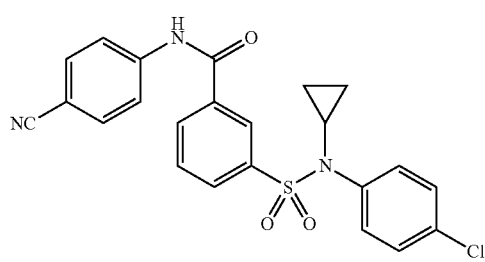

3-(N-(4-chlorophenyl)-N-cyclopropylsulfamoyl)-N-(4-cyanophenyl)benzamide (203Av)

Compound 203Av was synthesized following the general procedure of synthesizing compound 203. White Solid, Melting point: 180-182° C.; $^1$H NMR (500 MHz, CDCl$_3$) δ 8.19 (dt, J=7.9, 1.4 Hz, 1H), 8.00 (m, 2H), 7.82-7.75 (m, 3H), 7.72-7.64 (m, 3H), 7.30 (d, J=8.7 Hz, 2H), 7.02 (d, J=8.7 Hz, 2H), 1.60 (s, 4H); $^{13}$C NMR (126 MHz, CDCl$_3$) δ 164.1, 141.4, 139.7, 137.3, 135.1, 133.5, 133.4, 132.5, 131.4, 130.0, 129.1, 128.3, 125.6, 120.1, 118.7, 108.0, 31.7, 9.2; Mass Spectrum (ESI) [M–H]$^-$ C$_{23}$H$_{17}$ClN$_3$O$_3$S: 450.2.

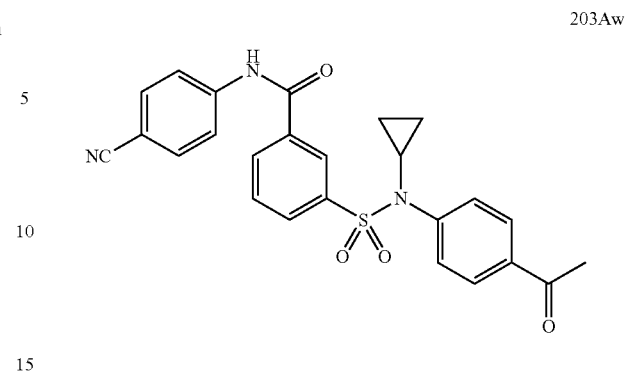

3-(N-(4-acetylphenyl)-N-cyclopropylsulfamoyl)-N-(4-cyanophenyl)benzamide (203Aw)

Compound 203Aw was synthesized following the general procedure of synthesizing compound 203. White Solid, Melting point: 185-186° C.; $^1$H NMR (500 MHz, CDCl$_3$) δ 8.17 (d, J=7.8 Hz, 1H), 8.04 (t, J=1.9 Hz, 1H), 7.93 (d, J=8.3 Hz, 2H), 7.88 (s, 1H), 7.80-7.75 (m, 3H), 7.70 (d, J=8.4 Hz, 2H), 7.66 (t, J=7.8 Hz, 1H), 7.25 (d, J=8.3 Hz, 2H), 2.60 (s, 1H), 2.57 (m, 1H), 0.89 (m, 4H); Mass Spectrum (ESI) [M–H]$^-$ C$_{25}$H$_{20}$N$_3$O$_4$S: 458.3

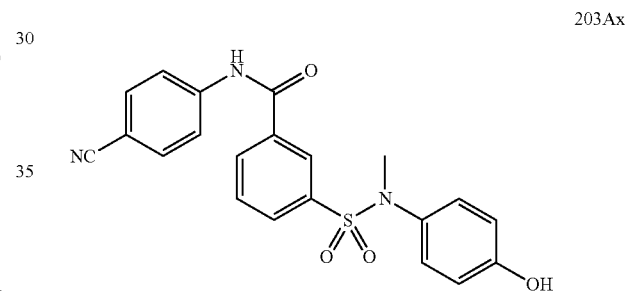

N-(4-cyanophenyl)-3-(N-(4-hydroxyphenyl)-N-methylsulfamoyl)benzamide (203Ax)

Compound 203Ax was synthesized following the general procedure of synthesizing compound 203. White foam; $^1$H NMR (500 MHz, DMSO) δ 10.52 (s, 1H), 9.14 (d, J=8.2 Hz, 1H), 8.28-8.13 (m, 2H), 7.98-7.88 (m, 2H), 7.61-7.45 (m, 4H), 6.79-6.60 (m, 4H), 3.09 (s, 1H); $^{13}$C NMR (126 MHz, DMSO) δ 164.5, 156.6, 142.7, 136.7, 135.0, 132.3, 132.0, 131.7, 130.4, 128.5, 127.6, 126.4, 120.3, 118.6, 115.3, 106.1, 38.4; Mass Spectrum (ESI) [M–H]$^-$ C$_{21}$H$_{14}$FN$_2$O$_2$ C$_{21}$H$_{16}$N$_3$O$_4$S: 406.1

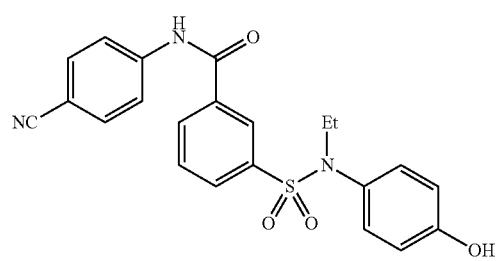

N-(4-cyanophenyl)-3-(N-ethyl-N-(4-hydroxyphenyl)sulfamoyl)benzamide (203Ay)

Compound 203Ay was synthesized following the general procedure of synthesizing compound 203. White Solid, Melting point: 102-104° C.; $^1$H NMR (500 MHz, CDCl$_3$) δ 8.29 (s, 1H), 8.18 (dt, J=7.8, 1.3 Hz, 1H), 7.96 (s, 1H), 7.83 (m, 3H), 7.70-7.64 (m, 3H), 6.87 (d, J=8.8 Hz, 2H), 6.78 (d, J=8.8 Hz, 2H), 3.59 (q, J=7.1 Hz, 2H), 1.09 (t, J=7.1 Hz, 3H); $^{13}$C NMR (126 MHz, CDCl$_3$) δ 164.5, 155.8, 141.6, 138.9, 135.0, 133.4, 132.2, 130.9, 130.5, 130.4, 129.9, 125.5, 120.3, 118.8, 116.0, 107.8, 46.1, 14.0; Mass Spectrum (ESI) [M–H]$^-$ C$_{22}$H$_{19}$N$_3$O$_4$S: 419.9

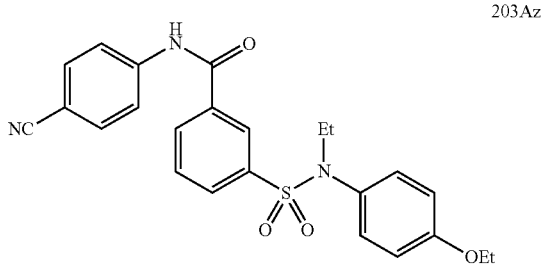 [SMILES: CCOc1ccc(N(CC)S(=O)(=O)c2cccc(C(=O)Nc3ccc(C#N)cc3)c2)cc1]

203Az

N-(4-cyanophenyl)-3-(N-(4-ethoxyphenyl)-N-ethylsulfamoyl)benzamide (203Az)

Compound 203Az was synthesized following the general procedure of synthesizing compound 203. White Solid, Melting point: 168-169° C.; $^1$H NMR (500 MHz, CDCl$_3$) δ 8.21-8.13 (m, 2H), 7.94 (d, J=1.9 Hz, 1H), 7.86-7.79 (m, 3H), 7.70 (d, J=8.7 Hz, 2H), 7.66 (t, J=7.8 Hz, 1H), 6.93 (d, J=8.9 Hz, 2H), 6.84 (d, J=8.9 Hz, 2H), 4.02 (q, J=7.0 Hz, 2H), 3.60 (q, J=7.1 Hz, 2H), 1.43 (t, J=6.9 Hz, 3H), 1.09 (t, J=7.1 Hz, 3H); $^{13}$C NMR (126 MHz, CDCl$_3$) δ 164.3, 158.8, 141.6, 138.9, 134.9, 133.4, 132.2, 130.9, 130.4, 130.2, 129.9, 125.4, 120.1, 118.7, 114.8, 107.8, 63.7, 46.1, 14.8, 14.0; Mass Spectrum (ESI) [M–H]$^-$ C$_{24}$H$_{22}$N$_3$O$_4$S: 448.2

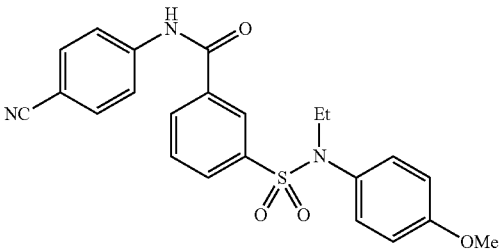

203Ba

N-(4-cyanophenyl)-3-(N-ethyl-N-(4-methoxyphenyl)sulfamoyl)benzamide (203Ba)

Compound 203Ba was synthesized following the general procedure of synthesizing compound 203. White Solid, Melting point: 168-169° C.; $^1$H NMR (500 MHz, CDCl$_3$) δ 8.21-8.16 (m, 1H), 8.09 (s, 1H), 7.96 (t, J=1.7 Hz, 1H), 7.85-7.80 (m, 3H), 7.71 (d, J=8.7 Hz, 2H), 7.67 (t, J=7.8 Hz, 1H), 6.95 (d, J=8.9 Hz, 2H), 6.86 (d, J=8.9 Hz, 2H), 3.82 (s, 3H), 3.61 (q, J=7.1 Hz, 2H), 1.11 (t, J=7.1 Hz, 3H); $^{13}$C NMR (126 MHz, CDCl$_3$) δ 164.3, 159.3, 141.6, 139.1, 134.9, 133.4, 132.2, 131.0, 130.6, 130.3, 129.9, 125.3, 120.1, 118.7, 114.4, 107.9, 55.5, 46.1, 14.1; Mass Spectrum (ESI) [M–H]$^-$ C$_{23}$H$_{20}$N$_3$O$_4$S: 434.2

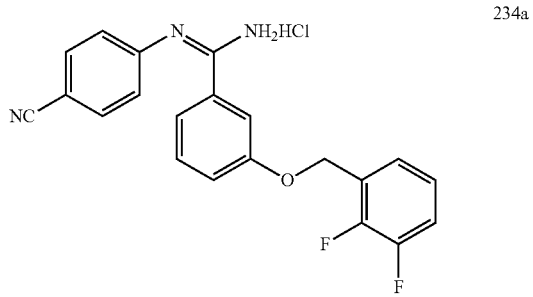

234a

N'-(4-cyanophenyl)-3-((2,3-difluorobenzyl)oxy)benzimidamide hydrochloride (234a)

Compound 234a was synthesized following the general procedure of synthesizing compound 234. Whiter solid; $^1$H NMR (500 MHz, MeOD) δ 7.99 (d, J=8.1 Hz, 2H), 7.72 (d, J=8.1 Hz, 2H), 7.68-7.60 (m, 2H), 7.57-7.49 (m, 2H), 7.39 (t, J=6.8 Hz, 1H), 7.35-7.29 (m, 1H), 7.27-7.20 (m, 1H), 5.33 (s, 1H); $^{13}$C NMR (126 MHz, MeOD) δ 166.1, 160.4, 151.7 (d, J=230.0 Hz), 149.9 (d, J=217.1 Hz), 140.0, 135.5, 132.0, 131.3, 127.4, 126.4 (t, J=3.0 Hz), 125.9 (d, J=5.6 Hz), 122.2, 121.8, 118.9, 118.5 (d, J=17.2 Hz), 116.0, 113.7, 65.1. Mass Spectrum (ESI) [M+H]$^+$ C$_{21}$H$_{16}$F$_2$N$_3$O: 364.2.

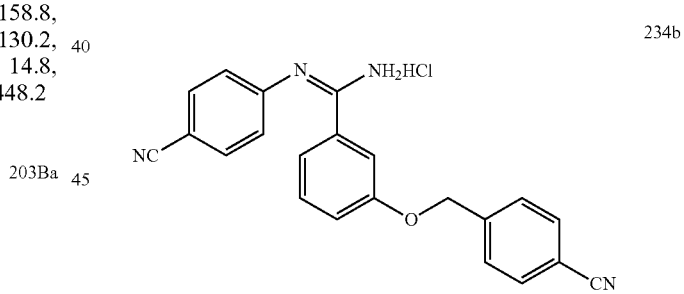

234b

3-((4-cyanobenzyl)oxy)-N'-(4-cyanophenyl)benzimidamide hydrochloride (234b)

Compound 234b was synthesized following the general procedure of synthesizing compound 34. White solid; $^1$H NMR (500 MHz, MeOD) δ 7.99 (d, J=8.0 Hz, 2H), 7.81 (d, J=8.0 Hz, 2H), 7.71 (t, J=8.2 Hz, 4H), 7.64 (dd, J=15.4, 7.0 Hz, 2H), 7.58-7.47 (m, 2H), 5.35 (s, 2H); $^{13}$C NMR (126 MHz, MeOD) δ 166.1, 160.3, 143.7, 140.0, 135.5, 133.6, 132.1, 129.1, 127.4, 122.2, 121.8, 119.5, 118.7, 116.1, 113.8, 112.9, 101.4, 70.4; Mass Spectrum (ESI) [M+H]$^+$ C$_{22}$H$_{17}$N$_4$O: 353.2.

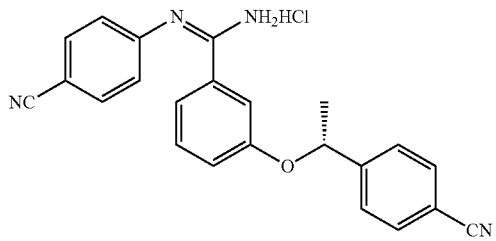

(R)—N'-(4-cyanophenyl)-3-(1-(4-cyanophenyl)
ethoxy)benzimidamide hydrochloride (234c Compound 234c was synthesized following the general procedure of synthesizing compound 234. White Solid $^1$H NMR (500 MHz, MeOD) δ 7.97 (d, J=7.5 Hz, 2H), 7.78-7.64 (m, 6H), 7.57-7.44 (m, 3H), 7.33 (d, J=7.9 Hz, 1H), 5.72 (d, J=5.6 Hz, 0H), 1.69 (d, J=5.6 Hz, 2H); $^{13}$C NMR (126 MHz, MeOD) δ 166.0, 159.4, 149.5, 140.0, 135.5, 133.8, 132.0, 131.3, 128.0, 127.4, 122.4, 122.1, 119.5, 118.9, 117.5, 113.7, 112.7, 76.9, 24.3; Mass Spectrum (ESI) [M+H]$^+$ $C_{23}H_{19}N_4O$: 367.2

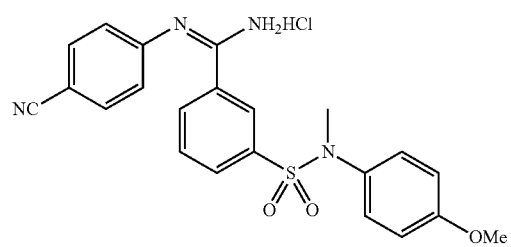

N'-(4-cyanophenyl)-3-(N-(4-methoxyphenyl)-N-methylsulfamoyl)benzimidamide hydrochloride (234d)

Compound 234d was synthesized following the general procedure of synthesizing compound 234. White Solid; $^1$H NMR (500 MHz, MeOD) δ 8.20 (s, 2H), 8.00 (d, J=8.1 Hz, 2H), 7.85 (d, J=4.5 Hz, 2H), 7.73 (d, J=7.9 Hz, 2H), 7.07 (d, J=8.4 Hz, 2H), 6.92-6.83 (m, 2H), 3.81 (s, 3H), 3.28 (s, 3H); $^{13}$C NMR (126 MHz, MeOD) δ 165.3, 160.7, 139.8, 135.6, 134.9, 134.2, 133.9, 131.4, 129.4, 128.9, 127.4, 118.8, 115.3, 114.0, 101.4, 56.0, 39.3; Mass Spectrum (ESI) [M+H]$^+$ $C_{22}H_{21}N_4O_3S$: 421.3

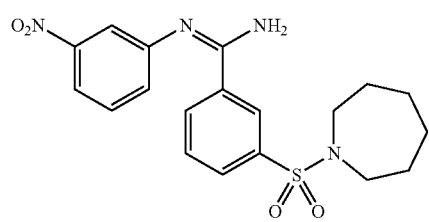

3-(azepan-1-ylsulfonyl)-N'-(3-nitrophenyl)benzimidamide (234e)

Compound 234e was synthesized following the general procedure of synthesizing compound 234. White Solid; $^1$H NMR (500 MHz, CDCl$_3$) δ 8.27 (t, J=1.8 Hz, 1H), 8.17 (dt, J=7.7, 1.4 Hz, 1H), 7.98-7.93 (m, 2H), 7.88 (t, J=2.1 Hz, 1H), 7.66 (t, J=7.8 Hz, 1H), 7.57 (t, J=8.0 Hz, 1H), 7.35 (ddd, J=7.9, 1.9, 1.1 Hz, 1H), 5.06 (s, 2H), 3.39-3.24 (m, 4H), 1.81-1.71 (m, 4H), 1.70-1.57 (m, 4H). $^{13}$C NMR (126 MHz, CDCl$_3$) δ 154.0, 150.6, 149.3, 140.2, 136.2, 130.9, 130.5, 129.6, 129.2, 128.2, 125.1, 118.2, 116.5, 48.4, 29.2, 26.9; Mass Spectrum (ESI) [M+H]$^+$ $C_{19}H_{23}N_4O_4S$: 403.4

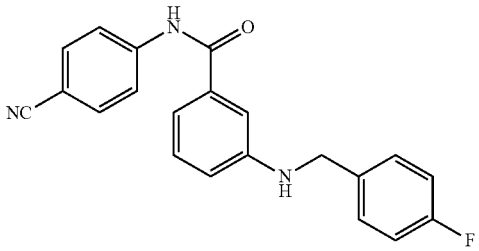

N-(4-cyanophenyl)-3-((4-fluorobenzyl)amino)benzamide (221a)

Compound 221a was synthesized following the general procedure of synthesizing compound 221. White Solid Melting point: 173-174° C.; $^1$H NMR (500 MHz, CDCl$_3$) δ 7.89 (s, 1H), 7.76 (d, J=8.7 Hz, 2H), 7.66 (d, J=8.7 Hz, 2H), 7.34 (dd, J=8.4, 5.6 Hz, 2H), 7.29-7.25 (m, 1H), 7.15 (t, J=2.1 Hz, 1H), 7.10-7.07 (m, 1H), 7.05 (t, J=8.6 Hz, 2H), 6.81-6.78 (m, 1H), 4.37 (d, J=4.9 Hz, 2H), 4.30 (t, J=5.1 Hz, 1H); $^{13}$C NMR (126 MHz, CDCl$_3$) δ 166.2, 162.1 (d, J=245.5 Hz), 148.4, 142.0, 135.3, 134.2 (d, J=3.2 Hz), 133.4, 129.8, 129.0 (d, J=8.1 Hz), 119.7, 118.8, 116.7, 115.6 (d, J=21.4 Hz), 115.0, 111.6, 107.3, 47.4; Mass Spectrum (ESI) [M-H]$^-$ $C_{21}H_{15}FN_3O$: 346.9.

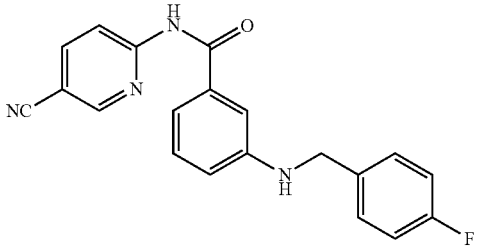

N-(5-cyanopyridin-2-yl)-3-((4-fluorobenzyl)amino)benzamide (221b)

Compound 221b was synthesized following the general procedure of synthesizing compound 221. White foam; $^1$H NMR (500 MHz, CDCl$_3$) δ 8.70 (s, 1H), 8.56 (d, J=2.2 Hz, 1H), 8.52 (d, J=8.8 Hz, 1H), 7.99 (dd, J=8.7, 2.2 Hz, 1H), 7.34 (dd, J=8.4, 5.6 Hz, 2H), 7.29 (t, J=7.9 Hz, 1H), 7.20-7.14 (m, 2H), 7.05 (t, J=8.6 Hz, 2H), 6.84-6.80 (m, 1H), 4.37 (s, 2H), 4.31 (s, 1H); $^{13}$C NMR (126 MHz, CDCl$_3$)

δ 166.15, 162.1 (d, J=245.8 Hz), 153.98, 151.66, 148.44, 141.62, 134.42, 134.2 (d, J=3.2 Hz), 129.84, 129.0 (d, J=8.0 Hz), 117.14, 116.79, 115.6 (d, J=21.4 Hz), 115.49, 113.60, 111.55, 105.01, 47.35; Mass Spectrum (ESI) [M+H]$^+$ C$_{20}$H$_{16}$FN$_4$O: 347.4.

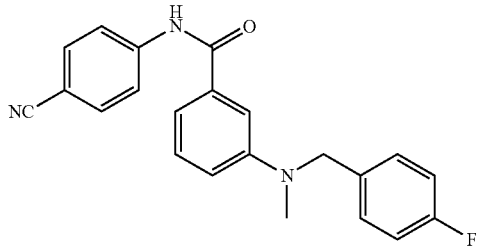

N-(4-cyanophenyl)-3-((4-fluorobenzyl)(methyl)amino)benzamide (221c)

Compound 221c was synthesized following the general procedure of synthesizing compound 221. White Solid Melting point: 176-177° C.; $^1$H NMR (500 MHz, CDCl$_3$) δ 7.90 (s, 1H), 7.76 (d, J=8.8 Hz, 2H), 7.68-7.63 (d, J=8.8 Hz, 2H), 7.31 (t, J=7.9 Hz, 1H), 7.18 (dd, J=8.6, 5.4 Hz, 3H), 7.06 (d, J=7.6 Hz, 2H), 7.01 (t, J=8.7 Hz, 2H), 6.90 (dd, J=8.3, 2.6 Hz, 1H), 4.58 (s, 2H), 3.10 (s, 3H); $^{13}$C NMR (126 MHz, CDCl$_3$) δ 166.5, 161.9 (d, J=245.1 Hz), 149.9, 142.0, 135.2, 133.7 (d, J=3.0 Hz), 133.3, 129.7, 128.1 (d, J=8.0 Hz), 119.7, 118.8, 116.0, 115.6 (d, J=21.6 Hz), 113.8, 111.2, 107.2, 55.7, 38.8; Mass Spectrum (ESI) [M+H]$^+$ C$_{22}$H$_{19}$FN$_3$O: 360.3

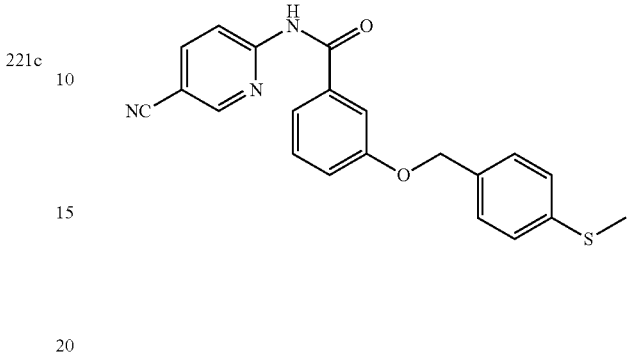

N-(4-cyanophenyl)-3-((4-(methylthio)benzyl)oxy)benzamide (216a)

Compound 216a was synthesized following the general procedure of synthesizing compound 216. White Solid, Melting point: 147-148° C.; $^1$H NMR (500 MHz, CDCl$_3$) δ 7.95 (s, 1H), 7.78 (d, J=8.8 Hz, 2H), 7.66 (d, J=8.7 Hz, 2H), 7.49 (m, 1H), 7.41 (m, 2H), 7.36 (d, J=8.3 Hz, 2H), 7.27 (d, J=4.2 Hz, 2H), 7.18 (dt, J=6.9, 2.6 Hz, 1H), 5.09 (s, 2H), 2.50 (s, 3H); $^{13}$C NMR (126 MHz, CDCl$_3$) δ 165.5, 159.1, 141.9, 138.8, 135.5, 133.4, 132.9, 130.1, 128.2, 126.6, 119.8, 119.3, 119.0, 118.8, 113.7, 107.4, 69.9, 15.7; Mass Spectrum (ESI) [M−H]$^-$ C$_{22}$H$_{17}$N$_2$O$_2$S: 373.1.

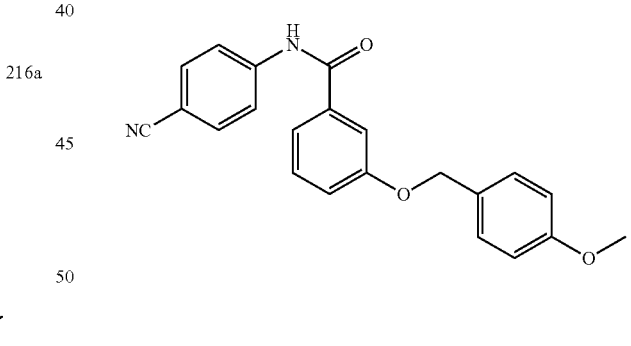

N-(5-cyanopyridin-2-yl)-3-(4-(methylthio)benzyl)oxy)benzamide (216b)

Compound 216b was synthesized following the general procedure of synthesizing compound 216. White Solid, Melting point: 146-147° C.; $^1$H NMR (500 MHz, CDCl$_3$) δ 8.71 (s, 1H), 8.58 (d, J=2.4 Hz, 1H), 8.53 (d, J=9.0 Hz, 1H), 8.00 (dd, J=8.7, 2.3 Hz, 1H), 7.54 (t, J=2.1 Hz, 1H), 7.47-7.41 (m, 2H), 7.37 (d, J=8.3 Hz, 2H), 7.28 (d, J=8.3 Hz, 2H), 7.23-7.17 (m, 1H), 5.10 (s, 2H), 2.50 (s, 3H); $^{13}$C NMR (126 MHz, CDCl$_3$) δ 165.5, 159.2, 153.9, 151.7, 141.7, 138.8, 134.7, 132.8, 130.1, 128.2, 126.6, 119.8, 119.2, 116.7, 113.7, 113.6, 105.2, 69.9, 15.7; Mass Spectrum (ESI) [M−]$^-$ C$_{21}$H$_{16}$N$_3$O$_2$S: 374.0

N-(4-cyanophenyl)-3-((4-methoxybenzyl)oxy)benzamide (216c)

Compound 216c was synthesized following the general procedure of synthesizing compound 216. White Solid, Melting point: 147-148° C.; $^1$H NMR (500 MHz, CDCl$_3$) δ 7.95 (s, 1H), 7.78 (d, J=8.8 Hz, 2H), 7.66 (d, J=8.8 Hz, 2H), 7.51-7.47 (m, 1H), 7.45-7.34 (m, 4H), 7.18 (dt, J=6.9, 2.6 Hz, 1H), 6.93 (d, J=8.6 Hz, 2H), 5.06 (s, 2H), 3.83 (s, 3H); $^{13}$C NMR (126 MHz, CDCl$_3$) δ 165.6, 159.6, 159.2, 141.9, 135.5, 133.4, 130.1, 129.4, 128.2, 119.8, 119.3, 118.9, 118.8, 114.1, 113.6, 107.4, 70.1, 55.3; Mass Spectrum (ESI) [M−H]$^-$ C$_{22}$H$_{17}$N$_2$O$_3$: 357.1.

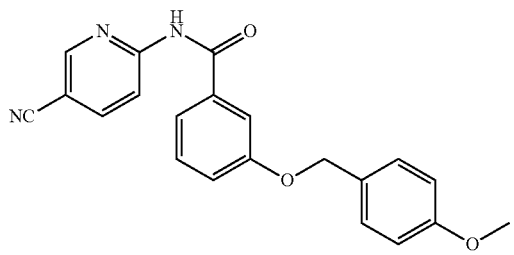

216d

N-(5-cyanopyridin-2-yl)-3-((4-methoxybenzyl)oxy)benzamide (216d)

Compound 216d was synthesized following the general procedure of synthesizing compound 216. White Solid, Melting point: 132-134° C.; $^1$H NMR (500 MHz, CDCl$_3$) δ 8.70 (s, 1H), 8.60-8.57 (m, 1H), 8.55-8.49 (m, 1H), 8.00 (dd, J=8.8, 2.3 Hz, 1H), 7.56-7.53 (m, 1H), 7.49-7.34 (m, 4H), 7.23-7.18 (m, 1H), 6.94 (d, J=8.6 Hz, 1H), 5.07 (s, 2H), 3.83 (s, 3H); $^{13}$C NMR (126 MHz, CDCl$_3$) δ 165.5, 159.6, 159.3, 153.9, 151.7, 141.7, 134.7, 130.1, 129.4, 128.2, 119.9, 119.1, 116.8, 114.1, 113.7, 113.6, 105.2, 70.1, 55.3; Mass Spectrum (ESI) [M−H]$^−$ C$_{21}$H$_{16}$N$_3$O$_3$: 358.1.

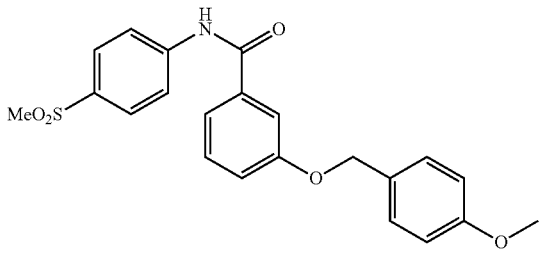

216f

3-((4-methoxybenzyl)oxy)-N-(4-(methylsulfonyl)phenyl)benzamide (216f)

Compound 216f was synthesized following the general procedure of synthesizing compound 216. White Solid, Melting point: 173-174° C.; $^1$H NMR (500 MHz, CDCl$_3$) δ 8.06 (s, 1H), 7.94 (d, J=8.8 Hz, 2H), 7.85 (d, J=8.8 Hz, 2H), 7.53-7.49 (m, 1H), 7.45-7.40 (m, 2H), 7.37 (d, J=8.6 Hz, 2H), 7.21-7.16 (m, 1H), 6.93 (d, J=8.6 Hz, 2H), 5.06 (s, 2H), 3.82 (s, 3H), 3.06 (s, 3H); $^{13}$C NMR (126 MHz, CDCl$_3$) δ 165.6, 159.6, 159.2, 142.8, 135.5, 135.5, 130.1, 129.4, 128.8, 128.2, 119.9, 119.3, 119.0, 114.1, 113.6, 70.1, 55.3, 44.7. Mass Spectrum (ESI) [M+H]$^+$ C$_{22}$H$_{20}$NO$_5$S: 434.5.

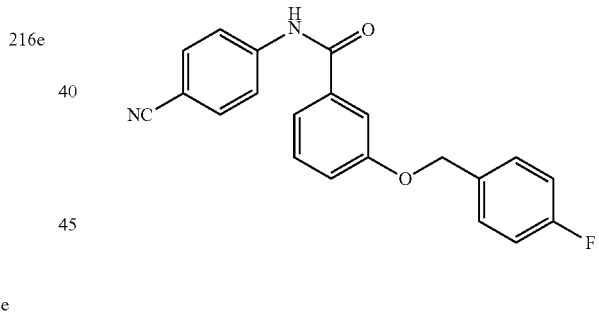

216g

N-(4-cyanophenyl)-3-((4-fluorobenzyl)oxy)benzamide (216g)

Compound 216g was synthesized following the general procedure of synthesizing compound 216. White Solid, Melting point: 149-150° C.; $^1$H NMR (500 MHz, CDCl$_3$) δ 7.98 (s, 1H), 7.78 (d, J=8.8 Hz, 2H), 7.66 (d, J=8.6 Hz, 2H), 7.52-7.48 (m, 1H), 7.46-7.37 (m, 4H), 7.18 (dt, J=6.7, 2.6 Hz, 1H), 7.09 (t, J=8.7 Hz, 2H), 5.09 (s, 2H); $^{13}$C NMR (126 MHz, CDCl$_3$) δ 165.5, 162.6 (d, J=246.9 Hz), 159.0, 141.8, 135.6, 133.4, 132.0 (d, J=3.2 Hz), 130.1, 129.4 (d, J=8.3 Hz), 119.8, 119.3, 119.0, 118.8, 115.7 (d, J=21.6 Hz), 113.6, 107.5, 69.6. Mass Spectrum (ESI) [M−H]$^−$ C$_{21}$H$_{14}$FN$_2$O$_2$: 345.7.

216e

N-(4-cyanophenyl)-3-((4-(methylsulfinyl)benzyl)oxy)benzamide (216e)

Compound 216e was synthesized following the general procedure of synthesizing compound 216. White Solid, Melting point: 174-175° C.; $^1$H NMR (500 MHz, CDCl$_3$) δ 8.51 (s, 1H), 7.84 (d, J=8.7 Hz, 2H), 7.68-7.61 (m, 4H), 7.59-7.52 (m, 3H), 7.48-7.38 (m, 2H), 7.20-7.13 (m, 1H), 5.16 (s, 2H), 2.72 (s, 3H); $^{13}$C NMR (126 MHz, CDCl$_3$) δ 165.7, 158.7, 145.2, 142.2, 139.8, 135.9, 133.3, 130.1, 128.2, 123.9, 120.0, 119.6, 119.1, 118.9, 113.7, 107.3, 69.3, 43.9; Mass Spectrum (ESI) [M−H]$^−$ C$_{22}$H$_{17}$N$_2$O$_3$S: 389.2.

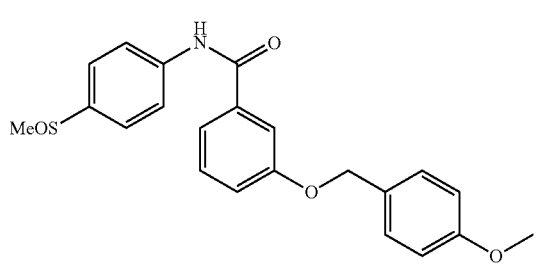

3-((4-methoxybenzyl)oxy)-N-(4-(methylsulfinyl)phenyl)benzamide (216h)

Compound 216h was synthesized following the general procedure of synthesizing compound 216. White Solid, Melting point: 135-136° C.; $^1$H NMR (500 MHz, CDCl$_3$) δ 8.13 (s, 1H), 7.83 (d, J=8.7 Hz, 2H), 7.65 (d, J=8.6 Hz, 2H), 7.53-7.50 (m, 1H), 7.45-7.34 (m, 4H), 7.19-7.14 (m, 1H), 6.93 (d, J=8.7 Hz, 2H), 5.06 (s, 2H), 3.82 (s, 3H), 2.72 (s, 3H); $^{13}$C NMR (126 MHz, CDCl$_3$) δ 165.7, 159.6, 159.2, 140.6, 140.6, 135.8, 129.9, 129.4, 128.3, 124.7, 120.6, 119.1, 119.0, 114.1, 113.6, 70.1, 55.3, 44.0; Mass Spectrum (ESI) [M+Na]$^+$ C$_{22}$H$_{22}$NO$_4$SNa: 418.4.

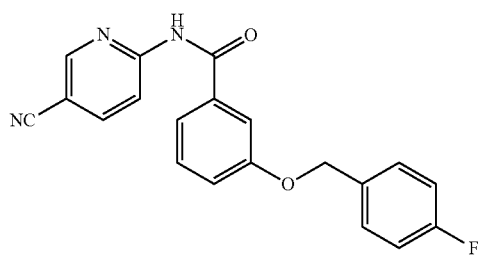

N-(5-cyanopyridin-2-yl)-3-((4-fluorobenzyl)oxy)benzamide (216i)

Compound 216i was synthesized following the general procedure of synthesizing compound 216. White Solid, Melting point: 170-171° C.; $^1$H NMR (500 MHz, CDCl$_3$) δ 8.74 (s, 1H), 8.58 (d, J=2.3 Hz, 1H), 8.55-8.50 (m, 1H), 8.01 (dd, J=8.8, 2.2 Hz, 1H), 7.57-7.53 (m, 1H), 7.49-7.39 (m, 4H), 7.21 (ddd, J=7.7, 2.6, 1.4 Hz, 1H), 7.10 (t, J=8.6 Hz, 2H), 5.10 (s, 2H); $^{13}$C NMR (126 MHz, CDCl$_3$) δ 165.44, 162.6 (d, J=246.8 Hz), 159.09, 153.85, 151.68, 141.70, 134.75, 131.94 (d, J=3.2 Hz), 130.18, 129.43 (d, J=8.2 Hz), 119.82, 119.32, 116.72, 115.7 (d, J=21.6 Hz), 113.66, 105.23, 69.59; Mass Spectrum (ESI) [M+H]$^+$ C$_{20}$H$_{13}$FN$_3$O$_2$: 348.5.

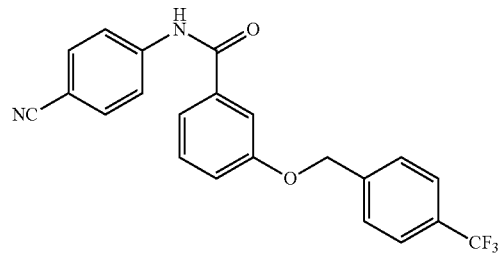

N-(4-cyanophenyl)-3-((4-(trifluoromethyl)benzyl)oxy)benzamide (216j)

Compound 216j was synthesized following the general procedure of synthesizing compound 216. White Solid, Melting point: 167-168° C.; $^1$H NMR (500 MHz, CDCl$_3$) δ 7.95 (s, 1H), 7.79 (d, J=8.8 Hz, 2H), 7.70-7.63 (m, 4H), 7.57 (d, J=7.9 Hz, 2H), 7.52 (dd, J=2.8, 1.4 Hz, 1H), 7.48-7.39 (m, 2H), 7.23-7.14 (m, 1H), 5.21 (s, 2H); $^{13}$C NMR (126 MHz, CDCl$_3$) δ 165.4, 158.9, 141.8, 140.3, 135.7, 133.4, 130.4 (q, J=32.8 Hz), 130.2, 127.4, 125.7 (q, J=3.7 Hz), 123.0 (q, J=272.0 Hz) 119.8, 119.3, 119.2, 118.7, 113.7, 107.5, 69.3. Mass Spectrum (ESI) [M–H]$^-$ C$_{22}$H$_{14}$F$_3$N$_2$O$_2$: 395.1.

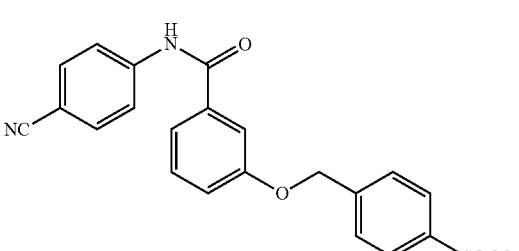

N-(4-cyanophenyl)-3-((4-(methylsulfonyl)benzyl)oxy)benzamide (216k)

Compound 216k was synthesized following the general procedure of synthesizing compound 216. White Solid, Melting point: 209-210° C.; $^1$H NMR (500 MHz, CDCl$_3$) δ 10.01 (s, 1H), 7.85-7.66 (m, 4H), 7.50-7.32 (m, 6H), 7.21-7.14 (m, 1H), 6.99-6.86 (m, 1H), 5.03 (s, 2H), 2.85 (s, 3H); $^{13}$C NMR (126 MHz, CDCl$_3$) δ 171.1, 162.9, 148.2, 147.7, 144.8, 141.1, 137.6, 134.4, 132.6, 132.4, 125.6, 125.2, 123.9, 123.4, 118.9, 111.0, 73.6, 49.2; Mass Spectrum (ESI) [M+H]$^+$ C$_{22}$H$_{19}$N$_2$O$_4$S: 407.4

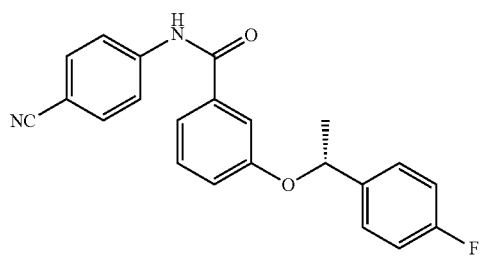

(R)—N-(4-cyanophenyl)-3-(1-(4-fluorophenyl)ethoxy)benzamide (216l)

Compound 216l was synthesized following the general procedure of synthesizing compound 216. White foam; $^1$H NMR (500 MHz, CDCl$_3$) δ 7.93 (s, 1H), 7.75 (d, J=8.7 Hz, 2H), 7.64 (d, J=8.7 Hz, 2H), 7.40-7.30 (m, 5H), 7.07-6.99 (m, 3H), 5.38 (q, J=6.4 Hz, 1H), 1.64 (d, J=6.4 Hz, 3H); $^{13}$C NMR (126 MHz, CDCl$_3$) δ 165.5, 162.1 (d, J=245.8 Hz), 158.2, 141.9, 138.1 (d, J=3.1 Hz), 135.4, 133.3, 129.9, 127.3 (d, J=8.1 Hz), 120.0, 119.8, 118.8, 115.8 (d, J=21.5 Hz), 114.9, 107.4, 75.7, 24.4; Mass Spectrum (ESI) [M−H]$^-$ C$_{22}$H$_{16}$FN$_2$O$_2$: 359.1.

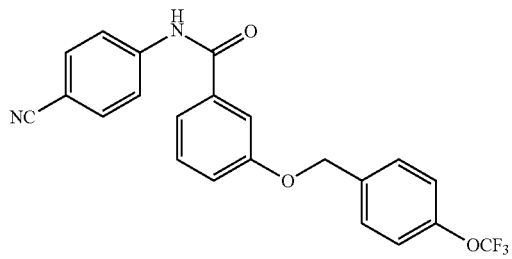

216m

N-(4-cyanophenyl)-3-((4-(trifluoromethoxy)benzyl)oxy)benzamide (216m)

Compound 216m was synthesized following the general procedure of synthesizing compound 216. White Solid, Melting point: 138-139° C.; $^1$H NMR (500 MHz, CDCl$_3$) δ 7.95 (s, 1H), 7.79 (d, J=8.7 Hz, 2H), 7.67 (d, J=8.8 Hz, 2H), 7.53-7.40 (m, 5H), 7.28-7.24 (m, 2H), 7.19 (dt, J=7.3, 2.3 Hz, 1H), 5.13 (s, 2H); $^{13}$C NMR (126 MHz, CDCl$_3$) δ 165.4, 159.0, 149.0, 141.8, 135.6, 134.9, 133.4, 130.2, 128.9, 121.2, 120.3 (q, J=257.7 Hz), 119.8, 119.2 (q, J=17.4 Hz), 118.8, 113.6, 107.5, 69.3; Mass Spectrum (ESI) [M−H]$^-$ C$_{22}$H$_{14}$F$_3$N$_2$O$_3$: 411.1

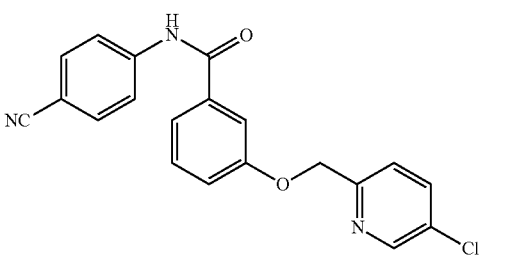

216n

3-((5-chloropyridin-2-yl)methoxy)-N-(4-cyanophenyl)benzamide (216n)

Compound 216n was synthesized following the general procedure of synthesizing compound 216. White Solid, Melting point: 168-169° C.; $^1$H NMR (500 MHz, CDCl$_3$) δ 8.58 (d, J=2.5 Hz, 1H), 8.05 (s, 1H), 7.79 (d, J=8.7 Hz, 2H), 7.72 (dd, J=8.4, 2.4 Hz, 1H), 7.67 (d, J=8.7 Hz, 2H), 7.53-7.46 (m, 2H), 7.46-7.40 (m, 2H), 7.18 (dt, J=6.5, 2.6 Hz, 1H), 5.23 (s, 2H); $^{13}$C NMR (126 MHz, CDCl$_3$) δ 165.4, 158.6, 154.6, 148.3, 141.9, 136.7, 135.7, 133.4, 131.3, 130.2, 122.3, 119.9, 119.5, 118.9, 118.8, 113.8, 107.5, 70.2; Mass Spectrum (ESI) [M+H]$^+$ C$_{20}$H$_{15}$ClN$_3$O$_2$: 364.4.

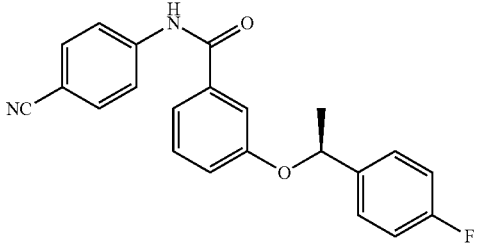

216o

(S)—N-(4-cyanophenyl)-3-(1-(4-fluorophenyl)ethoxy)benzamide (216o)

Compound 216o was synthesized following the general procedure of synthesizing compound 216. White foam; $^1$H NMR (500 MHz, CDCl$_3$) δ 7.93 (s, 1H), 7.75 (d, J=8.7 Hz, 2H), 7.64 (d, J=8.7 Hz, 2H), 7.40-7.30 (m, 5H), 7.07-6.99 (m, 3H), 5.38 (q, J=6.4 Hz, 1H), 1.64 (d, J=6.4 Hz, 3H); $^{13}$C NMR (126 MHz, CDCl$_3$) δ 165.5, 162.1 (d, J=245.8 Hz), 158.2, 141.9, 138.1 (d, J=3.1 Hz), 135.4, 133.3, 129.9, 127.3 (d, J=8.1 Hz), 120.0, 119.8, 118.8, 115.8 (d, J=21.5 Hz), 114.9, 107.4, 75.7, 24.4; Mass Spectrum (ESI) [M−H]$^-$ C$_{22}$H$_{16}$FN$_2$O$_2$: 359.3.

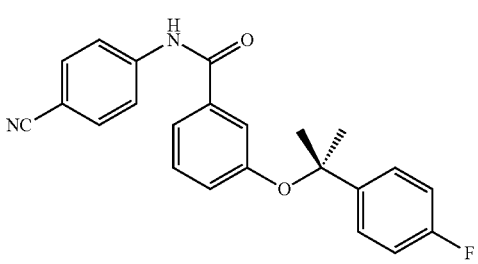

216p

N-(4-cyanophenyl)-3-((2-(4-fluorophenyl)propan-2-yl)oxy)benzamide (216p)

Compound 216p was synthesized following the general procedure of synthesizing compound 216. White foam; $^1$H NMR (500 MHz, CDCl$_3$) δ 7.81 (s, 1H), 7.72 (d, J=8.7 Hz, 2H), 7.64 (d, J=8.7 Hz, 2H), 7.44 (dd, J=8.8, 5.2 Hz, 2H), 7.35 (dd, J=1.6, 0.9 Hz, 1H), 7.22 (t, J=8.0 Hz, 1H), 7.15 (t, J=2.1 Hz, 1H), 7.06 (t, J=8.7 Hz, 2H), 6.79 (ddd, J=8.3, 2.5, 1.0 Hz, 1H), 1.74 (s, 6H); $^{13}$C NMR (126 MHz, CDCl$_3$) δ 165.5, 161.9 (d, J=246.3 Hz), 156.3, 141.9, 141.6 (d, J=3.2 Hz), 135.0, 133.4, 129.5, 127.1 (d, J=7.9 Hz), 123.6, 118.8, 118.7, 115.5 (d, J=21.2 Hz), 107.3, 80.5, 29.4; Mass Spectrum (ESI) [M−H]$^-$ C$_{23}$H$_{18}$FN$_2$O$_2$: 373.0

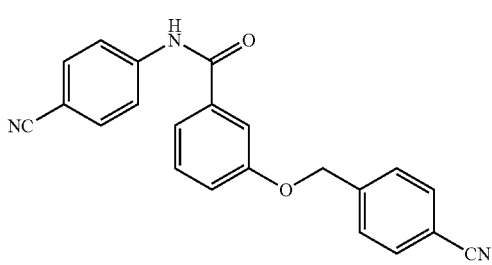

3-((4-cyanobenzyl)oxy)-N-(4-cyanophenyl)benz-amide (216q)

Compound 216q was synthesized following the general procedure of synthesizing compound 216. White Solid, Melting point: 205-207° C.; $^1$H NMR (500 MHz, CDCl$_3$) δ 7.94 (s, 1H), 7.80 (d, J=8.8 Hz, 2H), 7.72 (d, J=8.2 Hz, 2H), 7.69 (d, J=8.8 Hz, 2H), 7.58 (d, J=7.9 Hz, 2H), 7.54 (d, J=2.0 Hz, 1H), 7.49-7.41 (m, 2H), 7.20 (dt, J=7.4, 2.1 Hz, 1H), 5.22 (s, 2H); Mass Spectrum (ESI) [M–H]$^-$ C$_{22}$H$_{14}$N$_3$O$_2$: 352.1

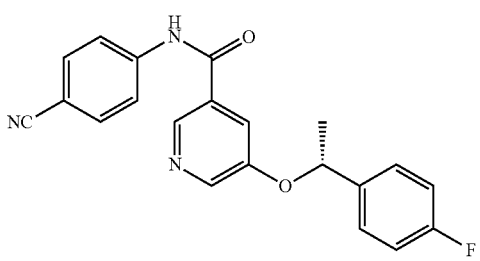

(R)—N-(4-cyanophenyl)-5-(1-(4-fluorophenyl)ethoxy)nicotinamide (216r)

Compound 216r was synthesized following the general procedure of synthesizing compound 216. White Solid, Melting point: 151-152° C.; $^1$H NMR (500 MHz, CDCl$_3$) δ 8.59 (s, 1H), 8.46 (d, J=2.9 Hz, 1H), 7.98 (s, 1H), 7.77 (d, J=8.7 Hz, 2H), 7.68 (d, J=8.8 Hz, 2H), 7.64 (s, 1H), 7.37 (dd, J=8.6, 5.1 Hz, 2H), 7.06 (t, J=8.5 Hz, 2H), 5.44 (q, J=6.4 Hz, 1H), 1.70 (d, J=6.3 Hz, 3H).); Mass Spectrum (ESI) [M–H]$^-$ C$_{21}$H$_{15}$FN$_3$O$_2$: 360.0

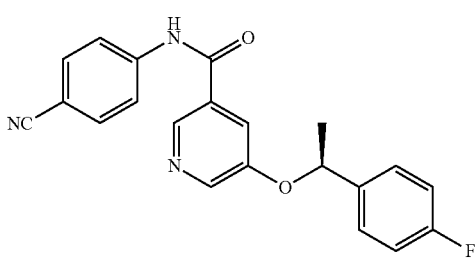

(S)—N-(4-cyanophenyl)-5-(1-(4-fluorophenyl)ethoxy)nicotinamide (216s)

Compound 216s was synthesized following the general procedure of synthesizing compound 216. White Solid, Melting point: 152-153° C.; $^1$H NMR (500 MHz, CDCl$_3$) δ 8.59 (s, 1H), 8.46 (d, J=2.9 Hz, 1H), 7.98 (s, 1H), 7.77 (d, J=8.4 Hz, 2H), 7.68 (d, J=8.4 Hz, 2H), 7.64 (s, 1H), 7.37 (dd, J=8.5, 5.6 Hz, 2H), 7.06 (t, J=8.5 Hz, 2H), 5.44 (q, J=6.4 Hz, 1H), 1.70 (d, J=6.4 Hz, 3H).); Mass Spectrum (ESI) [M–H]$^-$ C$_{21}$H$_{15}$FN$_3$O$_2$: 360.1

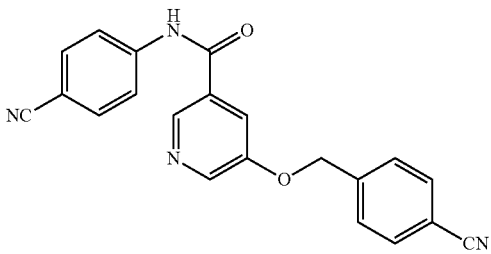

5-((4-cyanobenzyl)oxy)-N-(4-cyanophenyl)nicotina-mide (216t)

Compound 216t was synthesized following the general procedure of synthesizing compound 216. White Solid, Melting point: 266-268° C. (decomposed); $^1$H NMR (500 MHz, Acetone) δ 8.83 (d, J=1.8 Hz, 1H), 8.61 (d, J=2.8 Hz, 1H), 8.07 (dd, J=8.7, 1.7 Hz, 2H), 7.98 (dd, J=2.9, 1.8 Hz, 1H), 7.88 (d, J=8.3 Hz, 2H), 7.84-7.74 (m, 4H), 5.47 (s, 2H); $^{13}$C NMR (126 MHz, Acetone) δ 165.0, 155.4, 142.9, 142.4, 142.1, 134.0, 133.3, 129.1, 121.1, 121.1, 121.0, 119.4, 119.2, 112.7, 107.8, 70.1; Mass Spectrum (ESI) [M–H]$^-$ C$_{21}$H$_{13}$N$_4$O$_2$: 353.1

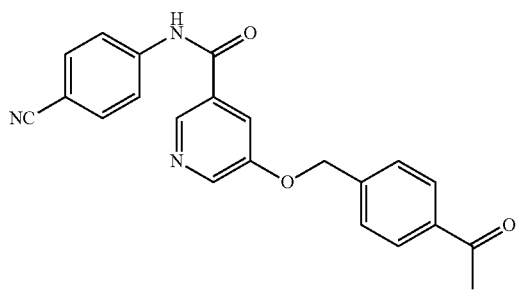

5-((4-acetylbenzyl)oxy)-N-(4-cyanophenyl)nicotina-mide (216u)

Compound 216u was synthesized following the general procedure of synthesizing compound 216. White Solid, Melting point: 228-229° C. (decomposed); $^1$H NMR (500 MHz, Acetone) δ 8.82 (d, J=1.7 Hz, 1H), 8.60 (d, J=2.8 Hz, 1H), 8.07 (d, J=8.1 Hz, 4H), 7.99 (d, J=0.9 Hz, 1H), 7.81 (d, J=8.7 Hz, 2H), 7.70 (d, J=8.0 Hz, 2H), 5.44 (s, 2H), 2.62 (s, 3H); $^{13}$C NMR (126 MHz, Acetone) δ 165.1, 155.6, 144.0, 142.5, 142.4, 141.9, 137.9, 134.0, 131.9, 129.4, 128.4, 121.1, 121.1, 121.0, 119.4, 107.7, 70.4, 26.8; Mass Spectrum (ESI) [M–H]$^-$ C$_{22}$H$_{17}$N$_3$O$_3$: 370.1

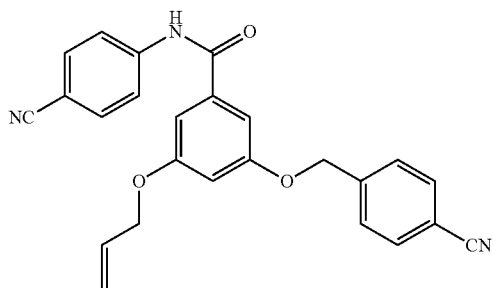

3-(allyloxy)-5-((4-cyanobenzyl)oxy)-N-(4-cyanophenyl)benzamide (216v)

Compound 216v was synthesized following the general procedure of synthesizing compound 216. White foam; $^1$H NMR (500 MHz, DMSO) δ 7.98 (d, J=8.7 Hz, 2H), 7.90 (d, J=8.3 Hz, 2H), 7.84 (d, J=8.7 Hz, 2H), 7.68 (d, J=8.3 Hz, 2H), 7.21 (dd, J=2.2, 1.3 Hz, 1H), 7.16 (dd, J=2.1, 1.3 Hz, 1H), 6.89 (t, J=2.2 Hz, 1H), 6.10-6.00 (m, 1H), 5.42 (dd, J=17.3, 1.7 Hz, 1H), 5.31 (s, 2H), 5.28 (dd, J=10.6, 1.6 Hz, 1H), 4.65 (d, J=5.2 Hz, 2H). $^{13}$C NMR (126 MHz, DMSO) δ 165.4, 159.3, 159.0, 143.3, 142.5, 136.4, 133.3, 133.1, 132.5, 128.1, 120.2, 119.0, 118.7, 117.7, 110.5, 107.0, 106.8, 105.4, 105.0, 68.6, 64.9; Mass Spectrum (ESI) [M−H]$^-$ C$_{25}$H$_{18}$N$_3$O$_3$: 408.4

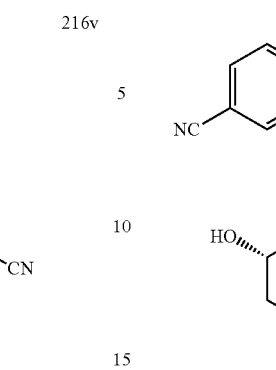

(S)-3-((4-cyanobenzyl)oxy)-N-(4-cyanophenyl)-5-(2,3-dihydroxypropoxy)benzamide (216x)

Compound 216x was synthesized following the general procedure of synthesizing compound 216. White foam; $^1$H NMR (500 MHz, Acetone) δ 8.08 (d, J=8.8 Hz, 2H), 7.85 (d, J=8.3 Hz, 2H), 7.78 (d, J=8.8 Hz, 2H), 7.75 (d, J=8.3 Hz, 2H), 7.27 (dd, J=2.4, 1.4 Hz, 1H), 7.22-7.20 (m, 1H), 6.88 (t, J=2.2 Hz, 1H), 5.335 (s, 1H), 4.24-3.98 (m, 4H), 3.93-3.86 (m, 1H), 3.74-3.63 (m, 2H), 2.11 (s, 1H); $^{13}$C NMR (126 MHz, Acetone) δ 166.3, 161.4, 160.6, 144.3, 143.6, 137.7, 133.9, 133.2, 128.9, 121.1, 121.0, 119.5, 119.3, 112.4, 107.6, 107.5, 107.4, 105.9, 71.3, 70.8, 69.8, 64.0; Mass Spectrum (ESI) [M+Cl]$^-$ C$_{25}$H$_{21}$N$_3$O$_5$Cl: 478.2

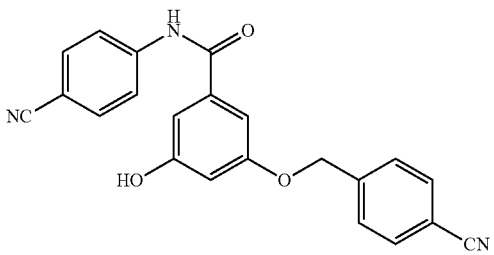

3-((4-cyanobenzyl)oxy)-N-(4-cyanophenyl)-5-hydroxybenzamide (216w)

Compound 216w was synthesized following the general procedure of synthesizing compound 216. White Solid, Melting point: 199-201° C.; $^1$H NMR (500 MHz, Acetone) δ 8.90 (s, 1H), 8.08 (d, J=8.8 Hz, 2H), 7.86 (d, J=8.3 Hz, 2H), 7.78 (d, J=8.7 Hz, 2H), 7.74 (d, J=8.5 Hz, 2H), 7.18 (t, J=1.7 Hz, 1H), 7.11 (t, J=1.7 Hz, 1H)), 6.75 (t, J=2.2 Hz, 2H), 5.31 (s, 2H); $^{13}$C NMR (126 MHz, Acetone) δ 166.5, 160.6, 159.6, 159.5, 144.4, 143.7, 137.9, 133.7, 133.2, 128.9, 121.0, 120.9, 119.5, 119.3, 112.4, 108.7, 106.4, 69.7; Mass Spectrum (ESI) [M−H]$^-$ C$_{22}$H$_{14}$N$_3$O$_3$: 369.0

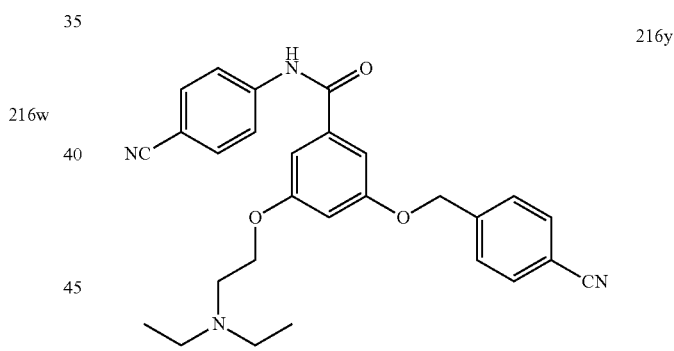

3-((4-cyanobenzyl)oxy)-N-(4-cyanophenyl)-5-(2-(diethylamino)ethoxy)benzamide (216y)

Compound 216y was synthesized following the general procedure of synthesizing compound 216. White foam; $^1$H NMR (500 MHz, Acetone) δ 8.07 (d, J=8.8 Hz, 2H), 7.84 (d, J=8.3 Hz, 2H), 7.77 (d, J=8.8 Hz, 2H), 7.75 (d, J=8.3 Hz, 2H), 7.26 (dd, J=2.2, 1.3 Hz, 1H), 7.20 (dd, J=2.1, 1.4 Hz, 1H), 6.85 (t, J=2.3 Hz, 1H), 5.33 (s, 2H), 4.11 (t, J=6.2 Hz, 2H), 2.85 (t, J=6.2 Hz, 2H), 2.61 (q, J=7.1 Hz, 4H), 1.03 (t, J=7.1 Hz, 6H); $^{13}$C NMR (126 MHz, Acetone) δ 166.3, 161.3, 160.6, 144.3, 143.6, 137.7, 133.9, 133.2, 128.9, 121.1, 121.0, 119.5, 119.3, 112.4, 107.6, 107.4, 105.8, 69.8, 68.2, 52.7, 48.4, 12.6; Mass Spectrum (ESI) [M−H]$^-$ C$_{28}$H$_{27}$N$_4$O$_3$: 467.4

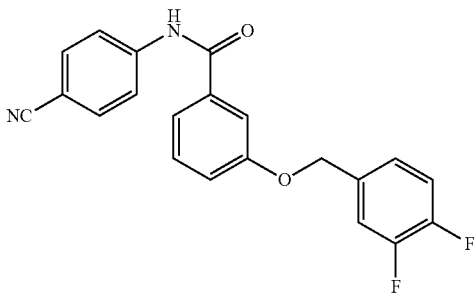

216z

N-(4-cyanophenyl)-3-((3,4-difluorobenzyl)oxy)benzamide (216z)

Compound 216z was synthesized following the general procedure of synthesizing compound 216. White Solid, Melting point: 173-174° C.; $^1$H NMR (500 MHz, MeOD) δ 7.97 (d, J=8.8 Hz, 2H), 7.74 (d, J=8.7 Hz, 2H), 7.59 (m, 2H), 7.45 (m, 2H), 7.34-7.21 (m, 3H), 5.17 (s, 2H); $^{13}$C NMR (126 MHz, MeOD) δ 168.6, 160.1, 153.0 (d, J=242.0 Hz), 151.1 (d, J=247.0 Hz), 144.5, 137.3, 136.0, 134.2, 131.0, 125.1 (d, J=3.8 Hz) 125.0 (d, J=3.6 Hz), 121.8, 121.4, 119.9, 119.8, 118.4 (d, J=17.4 Hz), 117.6 (d, J=18.0 Hz), 115.2, 108.0, 69.8; Mass Spectrum (ESI) [M−H]$^-$ $C_{21}H_{13}F_2N_2O_2$: 363.3.

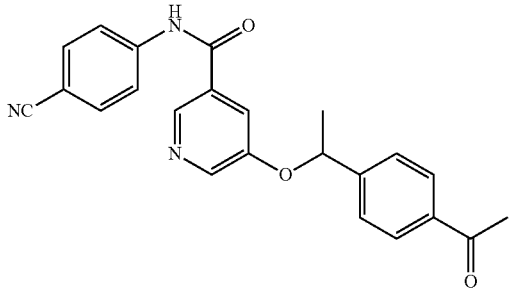

216Ab

5-(1-(4-acetylphenyl)ethoxy)-N-(4-cyanophenyl) nicotinamide (216Ab)

Compound 216Ab was synthesized following the general procedure of synthesizing compound 216. White Solid, Melting point: 181-183° C.; $^1$H NMR (500 MHz, CDCl$_3$) δ 8.61 (d, J=1.8 Hz, 1H), 8.46 (d, J=2.8 Hz, 1H), 8.19 (s, 1H), 7.96 (d, J=8.4 Hz, 2H), 7.78 (d, J=8.7 Hz, 2H), 7.68 (d, J=8.7 Hz, 2H), 7.64 (dd, J=2.8, 1.8 Hz, 1H), 7.49 (d, J=8.3 Hz, 2H), 5.50 (q, J=6.4 Hz, 1H), 2.60 (s, 3H), 1.73 (d, J=6.4 Hz, 3H). $^{13}$C NMR (126 MHz, CDCl$_3$) δ 197.7, 163.7, 154.1, 146.6, 143.0, 141.5, 139.3, 136.9, 133.4, 130.6, 129.1, 125.8, 121.2, 120.1, 118.7, 107.9, 76.5, 26.7, 24.1; Mass Spectrum (ESI) [M−H]$^-$ $C_{23}H_{18}N_3O_3$: 384.2

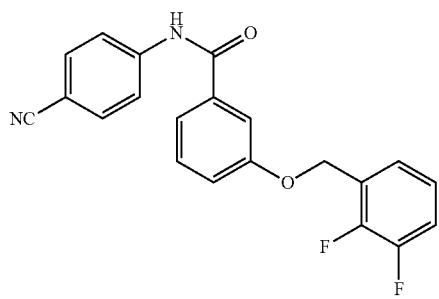

216Aa

N-(4-cyanophenyl)-3-((2,3-difluorobenzyl)oxy)benzamide (216Aa)

Compound 216Aa was synthesized following the general procedure of synthesizing compound 216. White Solid, Melting point: 149-150° C.; $^1$H NMR (500 MHz, MeOD) δ 7.97 (d, J=8.8 Hz, 2H), 7.74 (d, J=8.8 Hz, 2H), 7.62 (t, J=2.1 Hz, 1H), 7.61-7.57 (m, 1H), 7.49 (t, J=8.0 Hz, 1H), 7.38 (dd, J=7.7, 6.0 Hz, 1H), 7.32-7.26 (m, 2H), 7.24-7.19 (m, 1H), 5.28 (s, 2H); $^{13}$C NMR (126 MHz, MeOD) δ 168.6, 160.1, 151.7, (d, J=242.0 Hz), 147.8 (d, J=268.8 Hz), 144.5, 137.3, 134.2, 131.0, 127.9 (d, J=11.3 Hz), 126.2 (t, J=3.1 Hz), 125.7 (dd, J=6.5, 4.9 Hz), 121.8, 121.6, 119.8 118.2 (d, J=17.2 Hz), 115.1, 108.0, 64.8 (t, J=3.1 Hz); Mass Spectrum (ESI) [M−H]$^-$ $C_{21}H_{13}F_2N_2O_2$: 363.5

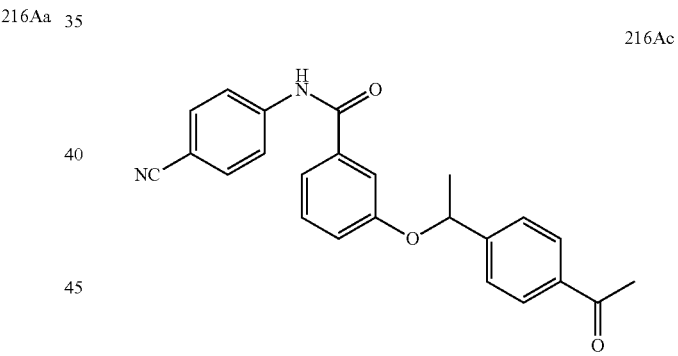

216Ac

3-(1-(4-acetylphenyl)ethoxy)-N-(4-cyanophenyl) benzamide (216Ac)

Compound 216Ac was synthesized following the general procedure of synthesizing compound 216. White Solid, Melting point: 79-81° C.; $^1$H NMR (500 MHz, CDCl$_3$) δ 7.97 (d, J=8.3 Hz, 2H), 7.91 (s, 1H), 7.77 (d, J=8.7 Hz, 2H), 7.68 (d, J=8.7 Hz, 2H), 7.50 (d, J=8.3 Hz, 2H), 7.41 (m, 1H), 7.35 (d, J=5.1 Hz, 2H), 7.09-7.02 (m, 1H), 5.48 (q, J=6.5 Hz, 1H), 2.61 (s, 2H), 1.70 (d, J=6.5 Hz, 2H); $^{13}$C NMR (126 MHz, CDCl$_3$) δ 197.7, 165.4, 158.1, 147.8, 141.8, 136.6, 135.5, 133.4, 130.0, 129.0, 125.8, 119.9, 119.8, 118.9, 118.8, 114.9, 107.5, 75.8, 26.7, 24.2; Mass Spectrum (ESI) [M−H]$^-$ $C_{24}H_{19}N_2O_3$: 383.2

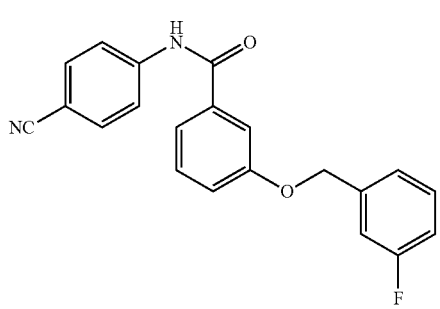

216Ad

N-(4-cyanophenyl)-3-((3-fluorobenzyl)oxy)benzamide (216Ad)

Compound 216Ad was synthesized following the general procedure of synthesizing compound 216. White Solid, Melting point: 142-143° C.; $^1$H NMR (500 MHz, CDCl$_3$) δ 8.02 (s, 1H), 7.81 (d, J=8.5 Hz, 2H), 7.69 (d, J=8.5 Hz, 2H), 7.52 (s, 1H), 7.47-7.35 (m, 3H), 7.25-7.16 (m, 3H), 7.09-7.03 (m, 1H), 5.15 (s, 2H); $^{13}$C NMR (126 MHz, CDCl$_3$) δ 165.5, 163.0 (d, J=246.4 Hz), 158.9, 141.9, 138.8 (d, J=7.4 Hz), 135.6, 133.4, 130.3 (d, J=8.4 Hz), 130.2, 122.8 (d, J=3.0 Hz), 119.9, 119.2, 115.1 (d, J=20.9 Hz), 114.3 (d, J=22.2 Hz), 113.7, 107.5, 69.4; Mass Spectrum (ESI) [M–H]$^-$ C$_{21}$H$_{14}$FN$_2$O$_2$: 345.2

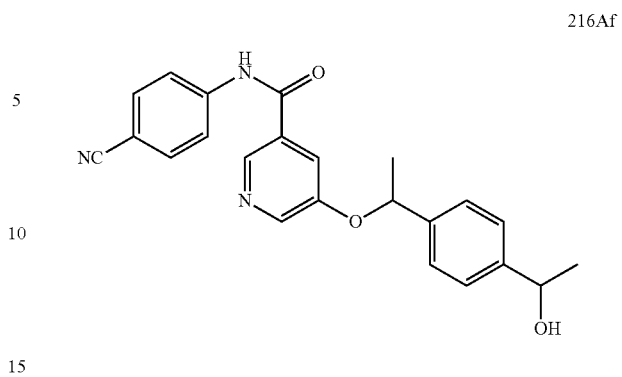

216Af

N-(4-cyanophenyl)-5-(1-(4-(1-hydroxyethyl)phenyl)ethoxy)nicotinamide (216Af)

Compound 216Af was synthesized following the general procedure of synthesizing compound 216. White Solid, Melting point: 179-181° C.; $^1$H NMR (500 MHz, CDCl$_3$) δ 8.56 (s, 1H), 8.43 (t, J=3.0 Hz, 1H), 8.22 (s, 1H), 7.78 (d, J=8.4 Hz, 2H), 7.68 (d, J=8.6 Hz, 2H), 7.63 (s, 1H), 7.36 (dd, J=3.6, 1.5 Hz, 4H), 5.43 (qd, J=6.4, 1.9 Hz, 1H), 4.89 (q, J=6.5 Hz, 1H), 1.71 (d, J=6.3 Hz, 3H), 1.49 (d, J=6.4 Hz, 3H); $^{13}$C NMR (126 MHz, CDCl$_3$) δ 163.9, 154.3, 145.8, 142.9, 141.5, 140.5, 139.0, 133.4, 130.6, 126.1, 125.8, 121.4, 120.1, 107.9, 70.0, 60.5, 25.2, 24.3; Mass Spectrum (ESI) [M–H]$^-$ C$_{23}$H$_{20}$N$_3$O$_3$: 386.4

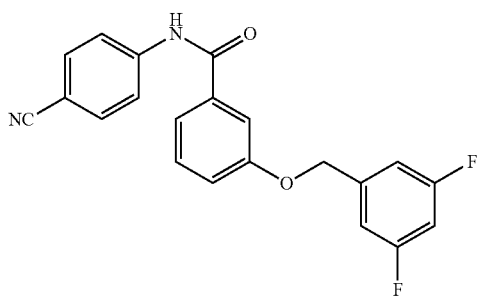

216Ae

N-(4-cyanophenyl)-3-((3,5-difluorobenzyl)oxy)benzamide (216Ae)

Compound 216Ae was synthesized following the general procedure of synthesizing compound 216. White Solid, Melting point: 185-187° C.; $^1$H NMR (500 MHz, CDCl$_3$) δ 7.99 (s, 1H), 7.82 (d, J=8.7 Hz, 2H), 7.70 (d, J=8.7 Hz, 2H), 7.53-7.42 (m, 3H), 7.20 (dt, J=6.8, 2.6 Hz, 1H), 7.01 (d, J=5.7 Hz, 1H), 6.81 (m, 1H), 5.15 (s, 2H); $^{13}$C NMR (126 MHz, CDCl$_3$) δ 165.4, 163.2 (dd, J=249.2, 12.6 Hz), 158.7, 141.8, 140.3 (t, J=9.0 Hz), 135.7, 133.4, 130.2, 119.9, 119.3, 119.2, 118.8, 113.67, 109.8 (dd, J=249.2, 12.6 Hz), 107.56, 103.5 (t, J=25.1 Hz), 68.82; Mass Spectrum (ESI) [M–H]$^-$ C$_{21}$H$_{13}$F$_2$N$_2$O$_2$: 363.4

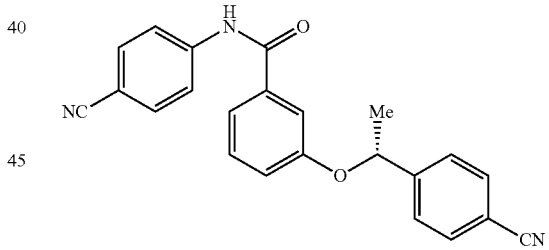

216Ag

(R)—N-(4-cyanophenyl)-3-(1-(4-cyanophenyl)ethoxy)benzamide (216Ag)

Compound 216Ag was synthesized following the general procedure of synthesizing compound 216. White foam; $^1$H NMR (500 MHz, CDCl$_3$) δ 8.24 (s, 1H), 7.79 (d, J=8.7 Hz, 2H), 7.63 (d, J=8.4 Hz, 4H), 7.51 (d, J=8.3 Hz, 2H), 7.43-7.30 (m, 3H), 7.06-7.01 (m, 1H), 5.46 (q, J=6.5 Hz, 1H), 1.67 (d, J=6.4 Hz, 3H); $^{13}$C NMR (126 MHz, CDCl$_3$) δ 165.6, 157.8, 147.9, 142.0, 135.6, 133.3, 132.7, 130.0, 126.3, 120.0, 119.9, 119.3, 118.9, 118.7, 115.0, 111.6, 107.3, 75.4, 24.1; Mass Spectrum (ESI) [M–H]$^-$ C$_{23}$H$_{17}$N$_3$O$_2$: 366.2

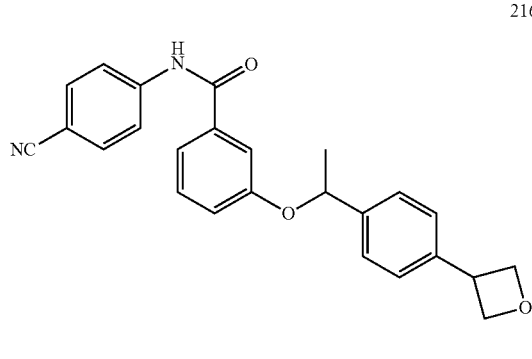

N-(4-cyanophenyl)-3-(1-(4-(oxetan-3-yl)phenyl)ethoxy)benzamide (216Ah)

Compound 216Ah was synthesized following the general procedure of synthesizing compound 216. White foam; $^1$H NMR (500 MHz, CDCl$_3$) δ 8.29 (s, 1H), 7.78 (d, J=8.3 Hz, 2H), 7.63 (d, J=8.3 Hz, 2H), 7.47-7.26 (m, 7H), 7.09-7.03 (m, 1H), 5.41 (q, J=6.4 Hz, 1H), 5.09-4.99 (m, 2H), 4.74 (q, J=6.8 Hz, 2H), 4.26-4.16 (m, 1H), 1.67 (d, J=6.4 Hz, 3H); $^{13}$C NMR (126 MHz, CDCl$_3$) δ 165.8, 158.3, 142.1, 141.3, 141.0, 135.5, 133.3, 129.9, 127.3, 126.0, 119.9, 119.9, 119.0, 118.9, 115.0, 107.2, 78.9, 76.0, 39.9, 24.4; Mass Spectrum (ESI) [M−H]$^-$ C$_{25}$H$_{21}$N$_2$O$_3$: 397.1

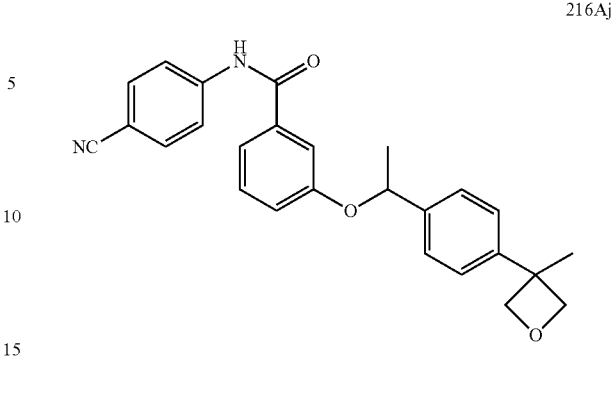

N-(4-cyanophenyl)-3-(1-(4-(3-methyloxetan-3-yl)phenyl)ethoxy)benzamide (216Aj)

Compound 216Aj was synthesized following the general procedure of synthesizing compound 216. White foam; $^1$H NMR (500 MHz, CDCl$_3$) δ 8.08 (s, 1H), 7.68 (d, J=8.6 Hz, 2H), 7.55 (d, J=8.5 Hz, 2H), 7.36-7.17 (m, 5H), 7.10 (d, J=7.8 Hz, 2H), 7.03-6.92 (m, 1H), 5.32 (q, J=6.4 Hz, 1H), 4.84 (dd, J=5.4, 2.4 Hz, 2H), 4.54 (d, J=5.5 Hz, 2H), 1.61 (s, 3H), 1.58 (d, J=6.4 Hz, 3H); $^{13}$C NMR (126 MHz, CDCl$_3$) δ 165.8, 158.3, 145.9, 142.1, 140.5, 135.5, 133.3, 129.9, 125.8, 125.5, 119.9, 118.9, 118.9, 114.9, 107.3, 83.8, 76.0, 43.2, 27.7, 24.3; Mass Spectrum (ESI) [M−H]$^-$ C$_{26}$H$_{23}$N$_2$O$_3$: 411.1.

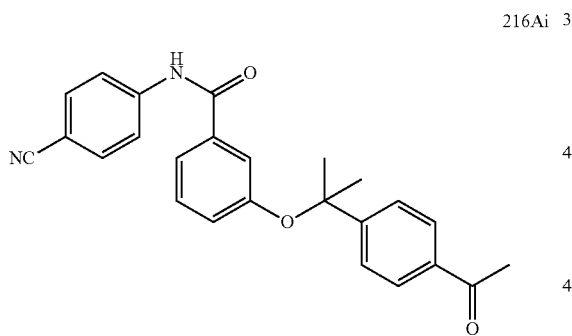

3-((2-(4-acetylphenyl)propan-2-yl)oxy)-N-(4-cyanophenyl)benzamide (216Al)

Compound 216Ai was synthesized following the general procedure of synthesizing compound 216. White foam; $^1$H NMR (500 MHz, CDCl$_3$) δ 8.38 (s, 1H), 7.95 (d, J=8.5 Hz, 2H), 7.78 (d, J=8.8 Hz, 2H), 7.60 (d, J=8.7 Hz, 2H), 7.57 (d, J=8.5 Hz, 2H), 7.38 (d, J=6.9 Hz, 1H), 7.29-7.25 (m, 1H), 7.18 (t, J=8.0 Hz, 1H), 6.75 (dd, J=7.9, 2.9 Hz, 1H), 2.60 (s, 3H), 1.75 (s, 6H); $^{13}$C NMR (126 MHz, CDCl$_3$) δ 165.8, 158.3, 145.9, 142.1, 140.5, 135.5, 133.3, 129.9, 125.8, 125.5, 119.9, 118.9, 118.9, 114.9, 107.3, 83.8, 76.0, 43.2, 27.7, 24.3. Mass Spectrum (ESI) [M−H]$^-$ C$_{25}$H$_{21}$N$_2$O$_3$: 397.0

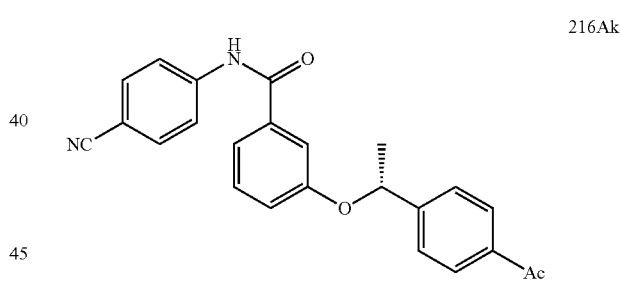

(R)-3-(1-(4-acetylphenyl)ethoxy)-N-(4-cyanophenyl)benzamide (216Ak)

Compound 216Ak was synthesized following the general procedure of synthesizing compound 216. $^1$H NMR (500 MHz, CDCl$_3$) δ 8.18 (s, 1H), 7.94 (d, J=8.3 Hz, 2H), 7.78 (d, J=8.8 Hz, 2H), 7.64 (d, J=8.8 Hz, 2H), 7.48 (d, J=8.3 Hz, 2H), 7.45-7.40 (m, 1H), 7.36 (dt, J=7.6, 1.3 Hz, 1H), 7.32 (t, J=7.9 Hz, 1H), 7.08-7.01 (m, 1H), 5.46 (q, J=6.4 Hz, 1H), 2.59 (s, 3H), 1.68 (d, J=6.4 Hz, 3H); $^{13}$C NMR (126 MHz, CDCl$_3$) δ 197.8, 165.6, 158.1, 147.9, 142.0, 136.6, 135.5, 133.3, 130.0, 129.0, 125.8, 119.9, 119.9, 119.1, 118.9, 114.9, 107.3, 75.8, 26.7, 24.2; Mass Spectrum (ESI) [M−H]$^-$ C$_{24}$H$_{19}$N$_2$O$_3$ 383.1

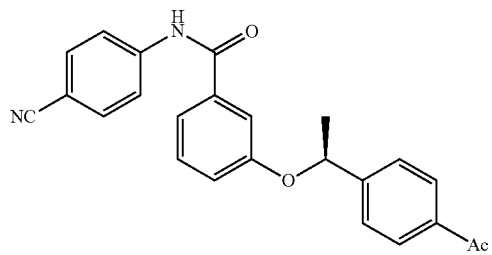

(S)-3-(1-(4-acetylphenyl)ethoxy)-N-(4-cyanophenyl)benzamide (216Al)

Compound 216Al was synthesized following the general procedure of synthesizing compound 216. $^1$H NMR (500 MHz, CDCl$_3$) δ 8.18 (s, 1H), 7.94 (d, J=8.3 Hz, 2H), 7.78 (d, J=8.8 Hz, 2H), 7.64 (d, J=8.8 Hz, 2H), 7.48 (d, J=8.3 Hz, 2H), 7.45-7.40 (m, 1H), 7.36 (dt, J=7.6, 1.3 Hz, 1H), 7.32 (t, J=7.9 Hz, 1H), 7.08-7.01 (m, 1H), 5.46 (q, J=6.4 Hz, 1H), 2.59 (s, 3H), 1.68 (d, J=6.4 Hz, 3H); $^{13}$C NMR (126 MHz, CDCl$_3$) δ 197.8, 165.6, 158.1, 147.9, 142.0, 136.6, 135.5, 133.3, 130.0, 129.0, 125.8, 119.9, 119.9, 119.1, 118.9, 114.9, 107.3, 75.8, 26.7, 24.2; Mass Spectrum (ESI) [M–H]$^-$ C$_{24}$H$_{19}$N$_2$O$_3$ 383.1.

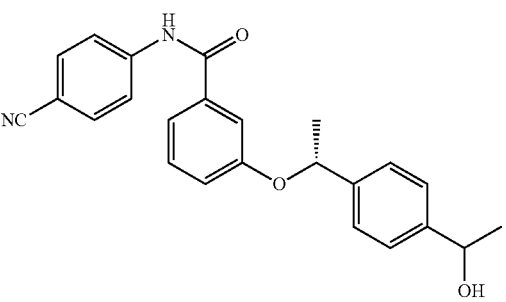

N-(4-cyanophenyl)-3-((1R)-1-(4-(1-hydroxyethyl)phenyl)ethoxy)benzamide (216Am)

Compound 216Am was synthesized following the general procedure of synthesizing compound 216. $^1$H NMR (500 MHz, CDCl$_3$) δ 7.86 (s, 1H), 7.66 (d, J=8.7 Hz, 2H), 7.56 (d, J=8.6 Hz, 2H), 7.32-7.21 (m, 6H), 7.01-6.95 (m, 1H), 5.32 (q, J=6.4 Hz, 1H), 4.83-4.74 (m, 1H), 1.58 (d, J=6.4 Hz, 3H), 1.41 (d, J=6.5 Hz, 3H); $^{13}$C NMR (126 MHz, CDCl$_3$) δ 165.7, 158.3, 145.3, 141.9, 141.6, 135.4, 133.4, 130.0, 125.9, 125.8, 120.0, 120.0, 119.8, 118.8, 114.8, 107.4, 76.1, 70.1, 70.1, 25.2, 24.4; Mass Spectrum (ESI) [M–H]$^-$ C$_{24}$H$_{21}$N$_2$O$_3$ 385.2.

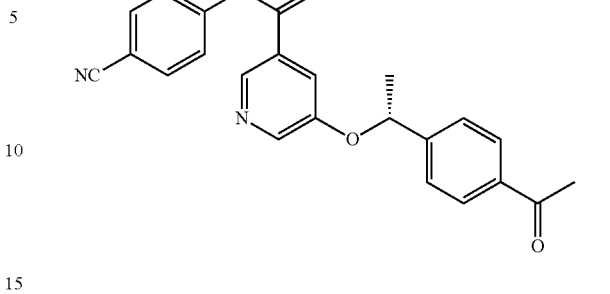

(R)-5-(1-(4-acetylphenyl)ethoxy)-N-(4-cyanophenyl)nicotinamide (216An)

Compound 216An was synthesized following the general procedure of synthesizing compound 216. $^1$H NMR (500 MHz, CDCl$_3$) δ 8.55 (s, 1H), 8.43-8.16 (m, 2H), 7.86 (d, J=7.7 Hz, 2H), 7.71 (d, J=8.3 Hz, 2H), 7.62-7.54 (m, 3H), 7.39 (d, J=7.9 Hz, 2H), 5.42 (q, J=6.1 Hz, 1H), 2.51 (s, 3H), 1.64 (d, J=6.0 Hz, 3H); $^{13}$C NMR (126 MHz, CDCl$_3$) δ 197.7, 146.6, 141.6, 136.9, 133.4, 129.1, 125.8, 120.2, 118.7, 107.9, 76.6, 26.7, 24.2. Mass Spectrum (ESI) [M–H]$^-$ C$_{23}$H$_{18}$N$_3$O$_3$ 384.2.

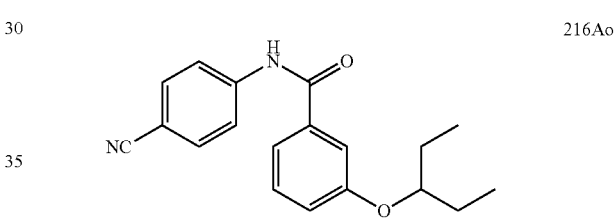

N-(4-cyanophenyl)-3-(pentan-3-yloxy)benzamide (216Ao)

Compound 216Ao was synthesized following the general procedure of synthesizing compound 216. $^1$H NMR (500 MHz, CDCl$_3$) δ 8.02 (s, 1H), 7.72 (d, J=8.7 Hz, 2H), 7.58 (d, J=8.7 Hz, 2H), 7.35-7.25 (m, 3H), 7.02 (ddd, J=7.6, 2.6, 1.6 Hz, 1H), 4.14 (p, J=5.8 Hz, 1H), 1.63 (qd, J=7.4, 5.7 Hz, 4H), 0.89 (t, J=7.4 Hz, 6H); $^{13}$C NMR (126 MHz, CDCl$_3$) δ 165.9, 159.3, 142.1, 135.5, 133.4, 130.0, 120.0, 119.9, 118.9, 118.4, 114.7, 107.3, 80.5, 26.0, 9.6; Mass Spectrum (ESI) [M–H]$^-$ C$_{19}$H$_{19}$N$_2$O$_2$ 307.3.

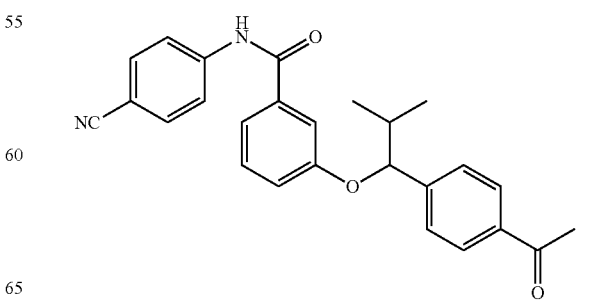

3-(1-(4-acetylphenyl)-2-methylpropoxy)-N-(4-cyanophenyl)benzamide (216Ap)

Compound 216Ap was synthesized following the general procedure of synthesizing compound 216. $^1$H NMR (500 MHz, CDCl$_3$) δ 8.71-8.57 (m, 1H), 7.88 (d, J=7.8 Hz, 2H), 7.80 (d, J=8.3 Hz, 2H), 7.61-7.51 (m, 2H), 7.45-7.37 (m, 3H), 7.35 (d, J=7.6 Hz, 1H), 7.22 (t, J=8.0 Hz, 1H), 6.98 (dd, J=8.2, 2.5 Hz, 1H), 4.96 (d, J=6.1 Hz, 1H), 2.54 (s, 3H), 2.16 (q, J=6.6 Hz, 1H), 1.05 (d, J=6.6 Hz, 3H), 0.92 (d, J=6.8 Hz, 3H); $^{13}$C NMR (126 MHz, CDCl$_3$) δ 198.2, 166.0, 166.0, 165.9, 158.6, 145.5, 142.3, 142.3, 142.3, 136.4, 135.5, 133.2, 129.8, 128.5, 127.0, 120.1, 119.7, 119.2, 119.0, 115.1, 107.0, 107.0, 84.7, 35.1, 26.7, 18.9, 18.0. Mass Spectrum (ESI) [M−H]$^-$ C$_{26}$H$_{23}$N$_2$O$_3$ 411.3.

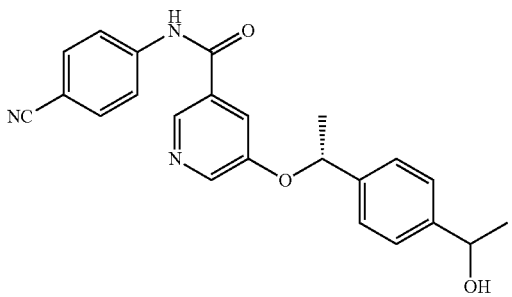

N-(4-cyanophenyl)-5-((1R)-1-(4-(1-hydroxyethyl)phenyl)ethoxy)nicotinamide (216Aq)

Compound 216Aq was synthesized following the general procedure of synthesizing compound 216. $^1$H NMR (500 MHz, CDCl$_3$) δ 8.49 (s, 1H), 8.36-8.29 (m, 1H), 8.25 (d, J=11.5 Hz, 1H), 7.70 (d, J=8.4 Hz, 2H), 7.61-7.52 (m, 3H), 7.31-7.22 (m, 4H), 5.34 (q, J=5.9 Hz, 1H), 4.80 (q, J=6.4 Hz, 1H), 1.62 (d, J=6.4 Hz, 3H), 1.40 (d, J=6.5 Hz, 3H); $^{13}$C NMR (126 MHz, CDCl$_3$) δ 163.9, 154.4, 145.8, 142.6, 142.6, 141.6, 140.4, 139.0, 133.4, 130.7, 126.1, 125.8, 125.7, 121.7, 121.6, 120.1, 118.7, 107.9, 70.1, 70.0, 25.2, 24.3. Mass Spectrum (ESI) [M−H]$^-$ C$_{23}$H$_{19}$N$_3$O$_3$ 386.4.

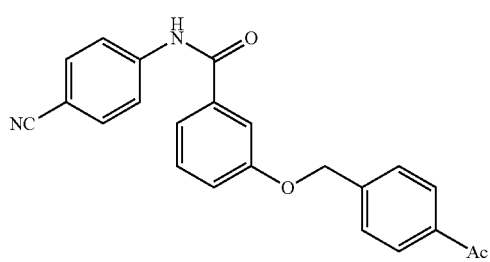

3-((4-acetylbenzyl)oxy)-N-(4-cyanophenyl)benzamide (216Ar)

Compound 216Ar was synthesized following the general procedure of synthesizing compound 216. $^1$H NMR (500 MHz, CDCl$_3$) δ 8.04-7.98 (m, 2H), 7.96-7.90 (m, 2H), 7.72-7.67 (m, 2H), 7.62-7.56 (m, 3H), 7.56-7.51 (m, 1H), 7.44 (t, J=8.0 Hz, 1H), 7.26-7.21 (m, 1H), 5.25 (s, 2H), 2.60 (s, 3H); $^{13}$C NMR (126 MHz, CDCl$_3$) δ 202.6, 171.1, 162.7, 147.1, 146.6, 140.4, 139.8, 136.7, 133.5, 132.3, 131.0, 124.3, 123.9, 122.4, 122.4, 117.7, 110.5, 72.9, 29.3. Mass Spectrum (ESI) [M−H]$^-$ C$_{23}$H$_{17}$N$_2$O$_3$ 369.3.

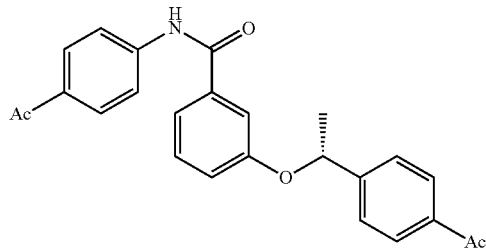

(R)—N-(4-acetylphenyl)-3-(1-(4-acetylphenyl)ethoxy)benzamide (216As)

Compound 216As was synthesized following the general procedure of synthesizing compound 216. $^1$H NMR (500 MHz, CDCl$_3$) δ 8.78 (s, 1H), 7.91 (d, J=8.7 Hz, 2H), 7.87 (s, 2H), 7.78 (d, J=8.8 Hz, 2H), 7.45-7.40 (m, 3H), 7.40-7.36 (m, 1H), 7.22 (t, J=8.0 Hz, 1H), 7.00-6.97 (m, 1H), 5.40 (q, J=6.4 Hz, 1H), 2.54 (d, J=9.6 Hz, 6H), 1.62 (d, J=6.4 Hz, 3H); $^{13}$C NMR (126 MHz, CDCl$_3$) δ 198.0, 197.3, 165.9, 157.9, 148.0, 142.7, 136.4, 135.9, 132.8, 129.8, 129.7, 128.9, 125.7, 119.6, 119.5, 119.4, 115.0, 75.6, 26.7, 26.5, 24.1; Mass Spectrum (ESI) [M−H]$^-$ C$_{25}$H$_{22}$NO$_4$ 400.1.

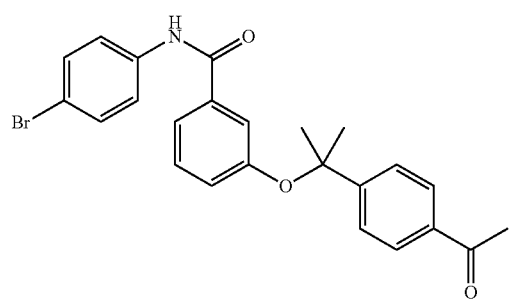

3-((2-(4-acetylphenyl)propan-2-yl)oxy)-N-(4-bromophenyl)benzamide (216At)

Compound 216At was synthesized following the general procedure of synthesizing compound 216 $^1$H NMR (500 MHz, CDCl$_3$) δ 7.91-7.84 (m, 2H), 7.76 (s, 1H), 7.54-7.45 (m, 2H), 7.44-7.32 (m, 4H), 7.31-7.24 (m, 1H), 7.15-7.05 (m, 2H), 6.66 (ddd, J=8.3, 2.5, 0.9 Hz, 1H), 2.52 (s, 3H), 1.67 (s, 6H). $^{13}$C NMR (126 MHz, CDCl$_3$): δ 197.8, 165.4, 156.1, 151.3, 137.0, 136.1, 135.7, 132.0, 129.3, 128.8, 125.5, 123.0, 121.6, 119.7, 118.8, 117.1, 80.5, 29.3, 26.7; m/z (ESI) 476.1 [M+Na]$^+$.

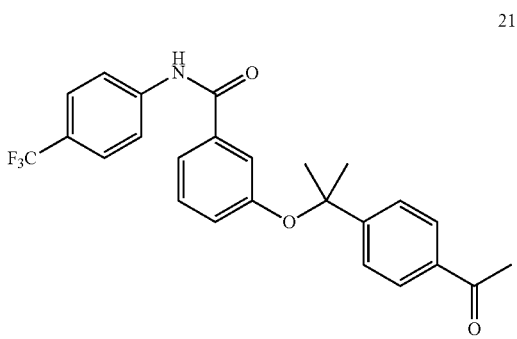

3-((2-(4-acetylphenyl)propan-2-yl)oxy)-N-(4-(trifluoromethyl)phenyl)benzamide (216Au)

Compound 216Au was synthesized following the general procedure of synthesizing compound 216 $^1$H NMR (500 MHz, CDCl$_3$) δ 8.03-7.96 (m, 2H), 7.83 (s, 1H), 7.73 (d, J=8.4 Hz, 2H), 7.66-7.57 (m, 4H), 7.39 (ddd, J=7.7, 1.8, 0.9 Hz, 1H), 7.27-7.20 (m, 2H), 6.79 (ddd, J=8.3, 2.5, 0.9 Hz, 1H), 2.63 (s, 3H), 1.79 (s, 6H). $^{13}$C NMR (126 MHz, CDCl$_3$) δ 197.7, 165.4, 156.2, 151.2, 140.9, 136.1, 135.5, 129.5, 128.9, 126.4, 126.4, 126.3, 125.5, 123.2, 119.7, 119.6, 118.7, 80.6, 29.3, 26.7; m/z (ESI) 464.1 [M+Na]$^+$.

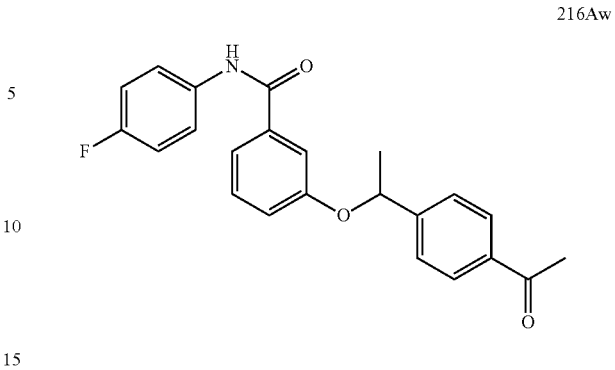

3-(1-(4-acetylphenyl)ethoxy)-N-(4-fluorophenyl)benzamide (216Aw)

Compound 216Aw was synthesized following the general procedure of synthesizing compound 216. $^1$H NMR (500 MHz, CDCl$_3$) δ 7.96 (s, 1H), 7.91 (d, J=6.5 Hz, 2H), 7.57-7.52 (m, 2H), 7.45 (dd, J=8.2, 3.9 Hz, 2H), 7.41-7.37 (m, 1H), 7.32 (d, J=7.7 Hz, 1H), 7.29-7.21 (m, 1H), 7.06-6.96 (m, 3H), 5.42 (q, J=7.1 Hz, 1H), 2.56 (d, J=1.7 Hz, 3H), 1.65 (d, J=6.5 Hz, 3H). $^{13}$C NMR (126 MHz, CDCl$_3$): δ=197.7, 165.4, 160.5, 158.0, 148.0, 136.5, 136.1, 133.9, 129.8, 128.9, 125.7, 122.1, 119.4, 119.0, 115.8, 114.8, 75.7, 26.6, 24.2; m/z (ESI) 400.1 [M+Na]$^+$; HRMS (pos. ion ESI) calcd for C$_{23}$H$_{20}$FNNaO$_3$ [M+Na]$^+$ 400.1319. found 400.1334.

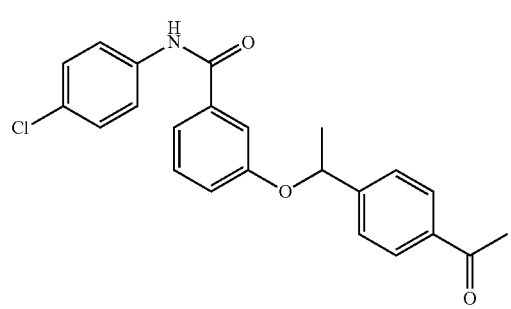

3-(1-(4-acetylphenyl)ethoxy)-N-(4-chlorophenyl)benzamide (216Av)

Compound 216Av was synthesized following the general procedure of synthesizing compound 216. $^1$H NMR (500 MHz, CDCl$_3$) δ 7.97 (d, J=8.4 Hz, 2H), 7.70 (s, 1H), 7.58 (d, J=8.8 Hz, 2H), 7.51 (d, J=1.8 Hz, 1H), 7.50 (d, J=2.6 Hz, 1H), 7.41 (d, J=2.4 Hz, 1H), 7.37-7.32 (m, 4H), 7.06-7.02 (m, 1H), 5.48 (q, J=6.5 Hz, 1H), 2.61 (s, 3H), 1.70 (d, J=6.5 Hz, 3H); $^{13}$C NMR (126 MHz, CDCl$_3$): δ 197.8, 165.4, 158.0, 147.9, 136.5, 136.4, 136.0, 129.8, 129.5, 129.1, 128.9, 125.7, 121.4, 119.5, 119.0, 114.8, 75.7, 26.7, 24.2; m/z (ESI) 416.1 [M+Na]$^+$; HRMS (pos. ion ESI) calcd for C$_{23}$H$_{20}$ClNNaO$_3$ [M+Na]$^+$ 416.1024. found 416.1044.

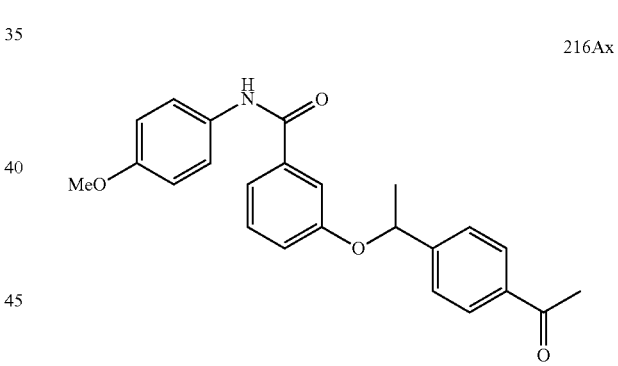

3-(1-(4-acetylphenyl)ethoxy)-N-(4-methoxyphenyl)benzamide (216Ax)

Compound 216Ax was synthesized following the general procedure of synthesizing compound 216. $^1$H NMR (500 MHz, CDCl$_3$): δ=7.91 (d, J=8.3 Hz, 2H), 7.87 (s, 1H), 7.49 (d, J=8.9 Hz, 2H), 7.45 (d, J=8.3 Hz, 2H), 7.39 (s, 1H), 7.32 (d, J=7.8 Hz, 1H), 7.26 (d, J=1.9 Hz, 1H), 6.97 (ddd, J=8.2, 2.6, 1.0 Hz, 1H), 6.89-6.84 (m, 2H), 5.41 (q, J=6.5 Hz, 1H), 3.79 (s, 3H), 2.55 (s, 3H), 1.64 (d, J=6.4 Hz, 3H). $^{13}$C NMR (126 MHz, CDCl$_3$): δ=197.7, 171.2, 165.3, 157.9, 156.6, 148.0, 136.5, 131.0, 129.7, 128.9, 125.8, 122.0, 119.2, 119.0, 114.7, 114.2, 75.6, 55.5, 26.6, 24.2; m/z (ESI) 412.1 [M+Na]$^+$; HRMS (pos. ion ESI) calcd for C$_{24}$H$_{23}$NNaO$_4$ [M+Na]$^+$ 412.1519. found 412.1530.

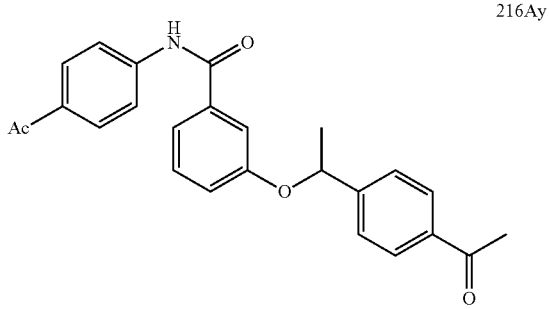

N-(4-acetylphenyl)-3-(1-(4-acetylphenyl)ethoxy) benzamide (216Ay)

Compound 216Ay was synthesized following the general procedure of synthesizing compound 216. $^1$H NMR (500 MHz, CDCl$_3$): δ=8.18 (s, 1H), 7.95 (d, J=8.7 Hz, 2H), 7.92 (d, J=8.3 Hz, 2H), 7.73 (d, J=8.7 Hz, 2H), 7.46 (d, J=8.3 Hz, 2H), 7.42-7.39 (m, 1H), 7.35 (dt, J=7.6, 1.3 Hz, 1H), 7.29 (d, J=8.0 Hz, 1H), 7.01 (ddd, J=8.2, 2.6, 1.1 Hz, 1H), 5.42 (q, J=6.5 Hz, 1H), 2.58 (s, 3H), 2.56 (s, 3H), 1.65 (d, J=6.4 Hz, 3H). $^{13}$C NMR (126 MHz, CDCl$_3$): δ=197.8, 197.0, 165.6, 158.0, 147.9, 142.3, 136.5, 135.9, 133.0, 129.9, 129.8, 129.0, 125.8, 119.7, 119.3, 119.1, 114.9, 75.7, 26.7, 26.5, 24.19; m/z (ESI) 424.1 [M+Na]$^+$; HRMS (pos. ion ESI) calcd for C$_{25}$H$_{23}$NNaO$_4$ [M+Na]$^+$424.1519. found 424.1527.

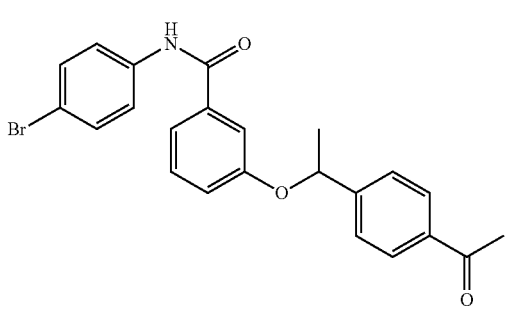

3-(1-(4-acetylphenyl)ethoxy)-N-(4-bromophenyl) benzamide (216Ba)

Compound 216Ba was synthesized following the general procedure of synthesizing compound 216. $^1$H NMR (500 MHz, CDCl$_3$): δ=7.94 (d, J=8.3 Hz, 2H), 7.69 (s, 1H), 7.49 (dtt, J=11.0, 6.5, 2.4 Hz, 6H), 7.38 (s, 1H), 7.33-7.28 (m, 2H), 7.01 (dq, J=5.7, 2.4, 1.7 Hz, 1H), 5.45 (q, J=6.4 Hz, 1H), 2.58 (s, 3H), 1.67 (d, J=6.5 Hz, 3H). $^{13}$C NMR (126 MHz, CDCl$_3$): (δ=197.7, 165.2, 158.0, 147.9, 143.7, 136.9, 136.1, 132.1, 129.9, 129.0, 125.8, 121.6, 119.6, 118.8, 117.2, 114.8, 75.8, 26.7, 24.2; m/z (ESI) 460.0 [M+Na]$^+$; HRMS (pos. ion ESI) calcd for C$_{23}$H$_{20}$BrNNaO$_3$ [M+Na]$^+$ 460.0519. found 460.0525.

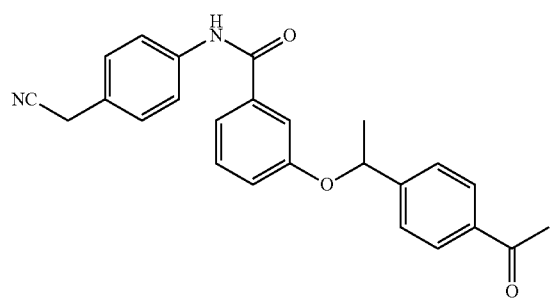

3-(1-(4-acetylphenyl)ethoxy)-N-(4-(cyanomethyl) phenyl)benzamide (216Az)

Compound 216Az was synthesized following the general procedure of synthesizing compound 216. $^1$H NMR (500 MHz, CDCl$_3$): δ 8.14 (s, 1H), 7.90 (d, J=8.2 Hz, 2H), 7.62 (d, J=8.5 Hz, 2H), 7.44 (d, J=8.1 Hz, 2H), 7.41-7.38 (m, 1H), 7.33 (d, J=7.6 Hz, 1H), 7.28-7.22 (m, 3H), 6.99 (dd, J=8.2, 2.5 Hz, 1H), 5.41 (q, J=6.4 Hz, 1H), 3.71 (s, 2H), 2.54 (s, 3H), 1.63 (d, J=6.4 Hz, 3H). $^{13}$C NMR (126 MHz, CDCl$_3$) δ 197.8, 165.6, 158.0, 148.0, 137.8, 136.5, 136.1, 129.8, 128.9, 128.6, 125.8, 125.7, 120.8, 119.5, 119.1, 118.0, 114.8, 75.6, 26.7, 24.2, 23.1; m/z (ESI) 421.2 [M+Na]$^+$; HRMS (pos. ion ESI) calcd for C$_{25}$H$_{22}$N$_2$NaO$_3$ [M+Na]$^+$421.1523. found 421.1526.

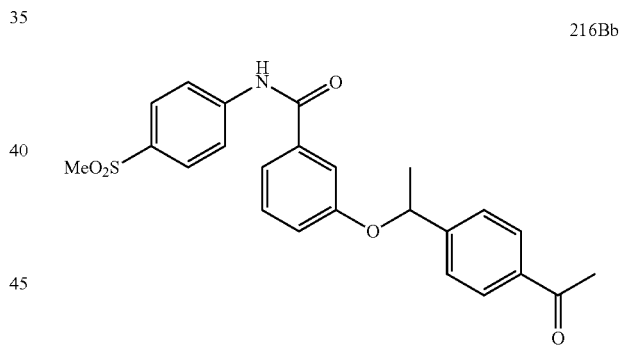

3-(1-(4-acetylphenyl)ethoxy)-N-(4-(methylsulfonyl) phenyl)benzamide (216Bb)

Compound 216Bb was synthesized following the general procedure of synthesizing compound 216. $^1$H NMR (500 MHz, CDCl$_3$): δ=7.98 (s, 1H), 7.96-7.91 (m, 4H), 7.82 (d, J=8.7 Hz, 2H), 7.48 (d, J=8.3 Hz, 2H), 7.41 (dd, J=2.8, 1.4 Hz, 1H), 7.37-7.30 (m, 2H), 7.04 (dt, J=7.1, 2.3 Hz, 1H), 5.46 (q, J=6.4 Hz, 1H), 3.05 (s, 3H), 2.58 (s, 3H), 1.68 (d, J=6.4 Hz, 3H). $^{13}$C NMR (126 MHz, CDCl$_3$): δ=197.9, 165.8, 158.0, 147.9, 143.0, 136.5, 135.5, 135.3, 129.9, 129.0, 128.7, 125.8, 120.13, 119.9, 119.3, 115.0, 75.7, 44.7, 26.7, 24.18; m/z (ESI) 460.1 [M+Na]$^+$; HRMS (pos. ion ESI) calcd for C$_{24}$H$_{23}$NNaO$_5$S [M+Na]$^+$460.1189. found 460.1201.

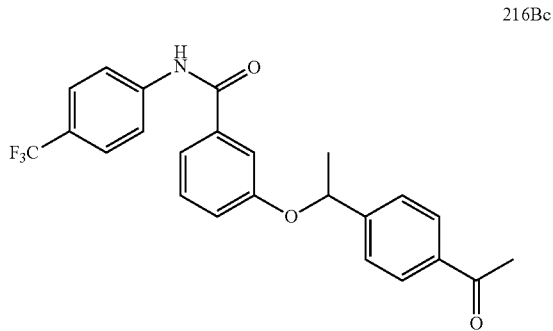 [SMILES: CC(=O)c1ccc(C(C)(C)Oc2cccc(C(=O)Nc3ccc(C(F)(F)F)cc3)c2)cc1]

216Bc

3-(1-(4-acetylphenyl)ethoxy)-N-(4-(trifluoromethyl)phenyl)benzamide (216Bc)

Compound 216Bc was synthesized following the general procedure of synthesizing compound 216. $^1$H NMR (500 MHz, Chloroform-d) δ 8.21 (s, 1H), 7.93 (d, J=8.3 Hz, 2H), 7.76 (d, J=8.4 Hz, 2H), 7.60 (d, J=8.4 Hz, 2H), 7.47 (d, J=8.3 Hz, 2H), 7.42 (dd, J=2.7, 1.6 Hz, 1H), 7.36 (d, J=7.9 Hz, 1H), 7.31-7.26 (m, 1H), 7.03 (ddd, J=8.3, 2.7, 1.0 Hz, 1H), 5.44 (q, J=6.4 Hz, 1H), 2.57 (s, 3H), 1.67 (d, J=6.4 Hz, 3H). $^{13}$C NMR (126 MHz, CDCl$_3$) δ 197.9, 165.7, 158.0, 147.9, 141.0, 136.5, 135.8, 129.9, 128.9, 126.3, 125.7, 125.1, 123.0, 119.8, 119.7, 119.1, 114.9, 75.7, 26.7, 24.2. m/z (ESI) 450.1 [M+Na]$^+$; HRMS (pos. ion ESI) calcd for C$_{24}$H$_{20}$F$_3$NNaO$_3$ [M+Na]$^+$ 450.1287. found 450.1298.

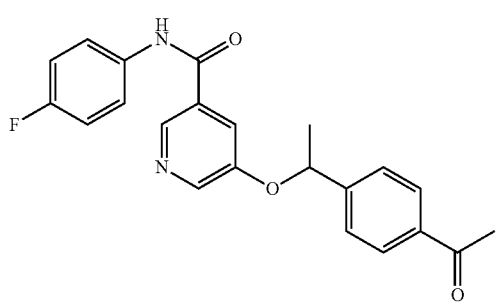

216Bd

5-(1-(4-acetylphenyl)ethoxy)-N-(4-fluorophenyl)nicotinamide (216Bd)

Compound 216Bd was synthesized following the general procedure of synthesizing compound 216. $^1$H NMR (500 MHz, CDCl$_3$) δ 8.59 (s, 1H), 8.42 (d, J=2.8 Hz, 1H), 8.18 (s, 1H), 7.98-7.92 (m, 2H), 7.67-7.60 (m, 1H), 7.58 (dd, J=8.9, 4.6 Hz, 2H), 7.51-7.44 (m, 2H), 7.11-7.02 (m, 2H), 5.48 (q, J=6.4 Hz, 1H), 2.59 (s, 3H), 1.71 (d, J=6.4 Hz, 3H). $^{13}$C NMR (126 MHz, CDCl$_3$) δ 197.7, 163.6, 160.7, 158.8, 154.1, 146.7, 142.4, 139.3, 136.8, 133.4, 131.2, 129.1, 125.8, 122.4, 121.3, 116.0, 26.7, 24.1; m/z (ESI) 377.1 [M−H]$^-$.

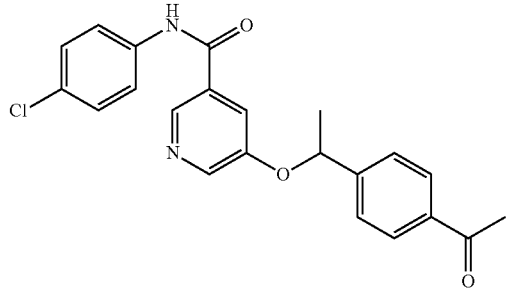

216Be

5-(1-(4-acetylphenyl)ethoxy)-N-(4-chlorophenyl)nicotinamide (216Be)

Compound 216Be was synthesized following the general procedure of synthesizing compound 216. $^1$H NMR (500 MHz, CDCl$_3$) δ 8.58 (s, 1H), 8.42-8.34 (m, 2H), 7.97-7.89 (m, 2H), 7.66-7.54 (m, 3H), 7.49-7.43 (m, 2H), 7.36-7.24 (m, 2H), 5.46 (q, J=6.4 Hz, 1H), 2.58 (s, 3H), 1.70 (d, J=6.4 Hz, 3H). $^{13}$C NMR (126 MHz, CDCl$_3$) δ 197.72, 163.63, 154.06, 146.73, 142.45, 139.36, 136.81, 136.07, 131.15, 130.04, 129.16, 129.10, 125.75, 121.68, 121.26, 76.4, 26.69, 24.10; m/z (ESI) 393.1 [M−H]$^-$.

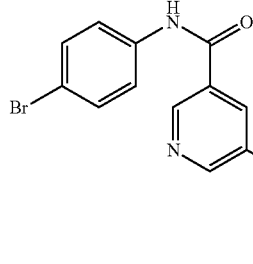

216Bf

5-(1-(4-acetylphenyl)ethoxy)-N-(4-bromophenyl)nicotinamide (216Bf)

Compound 216Bf was synthesized following the general procedure of synthesizing compound 216. $^1$H NMR (500 MHz, CDCl$_3$) δ 8.63 (s, 1H), 8.44 (d, J=2.8 Hz, 1H), 8.05 (s, 1H), 7.99-7.94 (m, 2H), 7.67 (s, 1H), 7.54 (d, J=8.9 Hz, 2H), 7.52-7.47 (m, 4H), 5.50 (q, J=6.4 Hz, 1H), 2.60 (s, 3H), 1.73 (d, J=6.4 Hz, 3H). $^{13}$C NMR (126 MHz, CDCl$_3$) δ 197.6, 163.3, 154.2, 146.6, 142.3, 139.0, 136.9, 136.5, 132.2, 131.2, 129.1, 125.8, 121.9, 121.5, 117.8, 76.5, 26.7, 24.1; m/z (ESI) 461.0 [M+Na]$^+$.

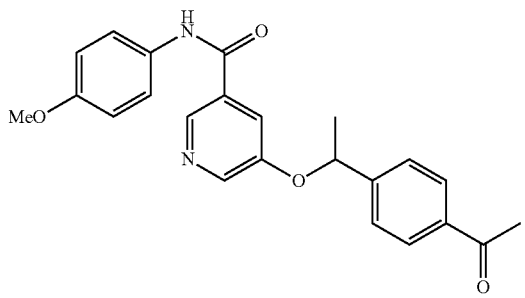

216Bg

5-(1-(4-acetylphenyl)ethoxy)-N-(4-methoxyphenyl) nicotinamide (216Bg)

Compound 216Bg was synthesized following the general procedure of synthesizing compound 216. $^1$H NMR (500 MHz, DMSO-d$_6$) δ 10.24 (s, 1H), 8.65 (d, J=1.8 Hz, 1H), 8.45 (d, J=2.8 Hz, 1H), 8.01-7.92 (m, 2H), 7.78 (dd, J=2.8, 1.7 Hz, 1H), 7.67-7.57 (m, 4H), 6.98-6.89 (m, 2H), 5.84 (q, J=6.3 Hz, 1H), 3.75 (s, 3H), 2.56 (s, 3H), 1.63 (d, J=6.3 Hz, 3H). $^{13}$C NMR (126 MHz, DMSO) δ 197.4, 163.0, 155.7, 153.2, 147.1, 141.1, 140.8, 136.2, 131.7, 131.2, 128.7, 126.0, 121.9, 121.3, 113.7, 75.1, 55.1, 26.7, 23.6; m/z (ESI) 413.2 [M+Na]$^+$.

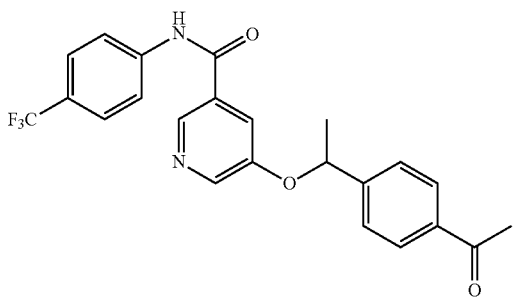

216Bi

5-(1-(4-acetylphenyl)ethoxy)-N-(4-(trifluoromethyl) phenyl)nicotinamide (216Bi)

Compound 216Bi was synthesized following the general procedure of synthesizing compound 216. $^1$H NMR (500 MHz, CDCl$_3$) δ 8.64 (d, J=1.8 Hz, 1H), 8.50 (s, 1H), 8.42 (d, J=2.8 Hz, 1H), 7.97-7.93 (m, 2H), 7.78 (d, J=8.3 Hz, 2H), 7.66 (dd, J=2.8, 1.6 Hz, 1H), 7.63 (d, J=8.5 Hz, 2H), 7.49-7.44 (m, 2H), 5.48 (q, J=6.5 Hz, 1H), 2.59 (s, 3H), 1.71 (d, J=6.4 Hz, 3H). $^{13}$C NMR (126 MHz, CDCl$_3$) δ 197.7, 163.8, 154.1, 146.7, 142.5, 140.6, 139.3, 136.9, 131.0, 129.1, 126.4, 126.4, 126.3, 125.8, 121.4, 120.0, 76.5, 26.7, 24.1. m/z (ESI) 451.0 [M+Na]$^+$.

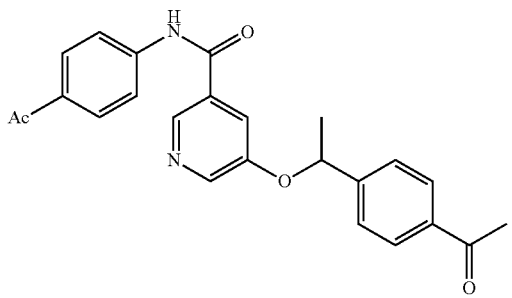

216Bh

N-(4-acetylphenyl)-5-(1-(4-acetylphenyl)ethoxy) nicotinamide (216Bh)

Compound 216Bh was synthesized following the general procedure of synthesizing compound 216. $^1$H NMR (500 MHz, CDCl$_3$) δ 8.66 (s, 1H), 8.46-8.41 (m, 2H), 8.01-7.94 (m, 4H), 7.79-7.74 (m, 2H), 7.68 (t, J=2.2 Hz, 1H), 7.51-7.45 (m, 2H), 5.50 (d, J=6.5 Hz, 1H), 2.61 (s, 3H), 2.60 (s, 3H), 1.72 (d, J=6.4 Hz, 3H). $^{13}$C NMR (126 MHz, CDCl$_3$) δ 197.7, 197.0, 163.6, 154.1, 146.6, 142.5, 141.8, 139.3, 136.9, 133.4, 131.1, 129.8, 129.1, 125.8, 121.5, 119.5, 76.5, 26.7, 26.5, 24.1; m/z (ESI) 425.2 [M+Na]$^+$.

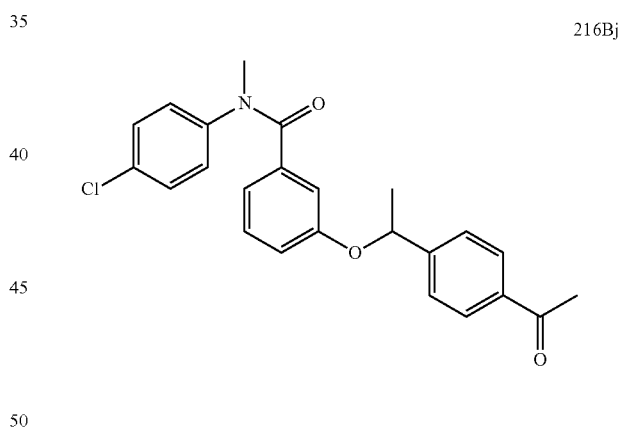

216Bj

3-(1-(4-acetylphenyl)ethoxy)-N-(4-chlorophenyl)-N-methylbenzamide (216Bj)

Compound 216Bj was synthesized following the general procedure of synthesizing compound 216. $^1$H NMR (500 MHz, CDCl$_3$) δ 7.97-7.92 (m, 2H), 7.39-7.35 (m, 2H), 7.17-7.13 (m, 2H), 7.04 (td, J=7.4, 1.8 Hz, 1H), 6.90-6.85 (m, 2H), 6.81 (dt, J=7.5, 1.3 Hz, 1H), 6.78-6.75 (m, 2H), 5.20 (q, J=6.4 Hz, 1H), 3.43 (s, 3H), 2.61 (s, 3H), 1.57 (d, J=6.5 Hz, 3H). $^{13}$C NMR (126 MHz, CDCl$_3$) δ 197.7, 170.2, 157.1, 148.1, 143.3, 136.8, 136.5, 132.0, 129.3, 129.1, 128.8, 127.9, 125.6, 121.3, 117.7, 115.9, 75.6, 38.3, 26.7, 24.2. m/z (ESI) 430.1 [M+Na]$^+$.

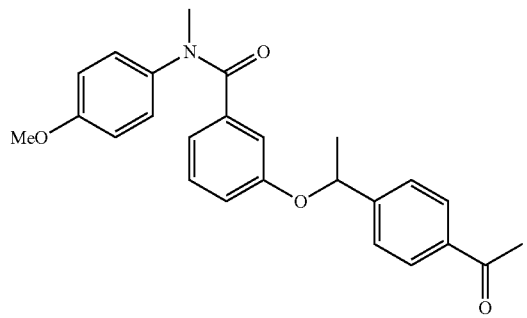

216Bk

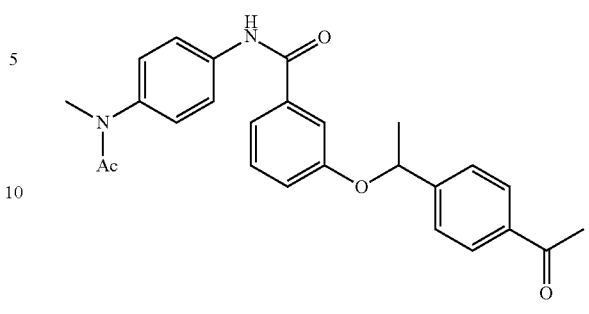

216Bm

3-(1-(4-acetylphenyl)ethoxy)-N-(4-methoxyphenyl)-N-methylbenzamide (216Bk)

Compound 216Bk was synthesized following the general procedure of synthesizing compound 216. $^1$H NMR (500 MHz, CDCl$_3$) δ 7.95-7.91 (m, 2H), 7.37 (d, J=8.0 Hz, 2H), 7.00 (t, J=8.1 Hz, 1H), 6.89-6.83 (m, 2H), 6.83-6.78 (m, 2H), 6.75-6.67 (m, 3H), 5.20 (q, J=6.5 Hz, 1H), 3.76 (s, 3H), 3.41 (s, 3H), 2.61 (s, 3H), 1.56 (d, J=6.4 Hz, 3H). $^{13}$C NMR (126 MHz, CDCl$_3$) δ 197.7, 170.4, 157.8, 156.9, 148.2, 137.6, 137.4, 136.4, 128.8, 128.8, 127.9, 125.7, 121.3, 117.4, 115.9, 114.3, 75.5, 55.4, 38.5, 26.7, 24.1; m/z (ESI) 426.2 [M+Na]$^+$.

3-(1-(4-acetylphenyl)ethoxy)-N-(4-(N-methylacetamido)phenyl)benzamide (216Bm)

Compound 216Bm was synthesized following the general procedure of synthesizing compound 216. $^1$H NMR (500 MHz, Chloroform-d) δ 8.56 (s, 1H), 7.94-7.89 (m, 2H), 7.75-7.70 (m, 2H), 7.50-7.42 (m, 3H), 7.40 (d, J=8.1 Hz, 1H), 7.31-7.25 (m, 1H), 7.16-7.11 (m, 2H), 7.01 (dd, J=8.2, 2.5 Hz, 1H), 5.45 (q, J=6.4 Hz, 1H), 3.22 (s, 3H), 2.56 (s, 3H), 1.84 (s, 3H), 1.66 (d, J=6.4 Hz, 3H). m/z (ESI) 453.2 [M+Na]$^+$.

216Bl

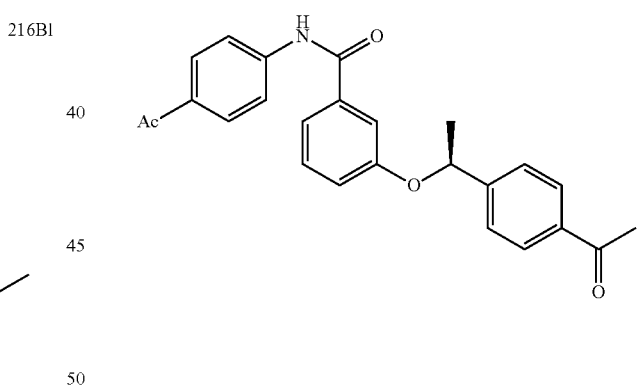

216Bn

3-((2-(4-acetylphenyl)propan-2-yl)oxy)-N-(4-(methylsulfonyl)phenyl)benzamide (216Bl)

Compound 216Bl was synthesized following the general procedure of synthesizing compound 216. $^1$H NMR (500 MHz, CDCl$_3$) δ 8.30 (s, 1H), 8.00-7.94 (m, 2H), 7.90-7.86 (m, 2H), 7.85-7.79 (m, 2H), 7.60-7.56 (m, 2H), 7.43-7.39 (m, 1H), 7.28 (dd, J=4.1, 2.0 Hz, 1H), 7.20 (t, J=7.9 Hz, 1H), 6.77 (dd, J=8.3, 2.4 Hz, 1H), 3.05 (s, 3H), 2.61 (s, 3H), 1.77 (s, 6H). $^{13}$C NMR (126 MHz, CDCl$_3$) δ 197.7, 165.7, 156.1, 151.3, 143.0, 136.1, 135.3, 135.2, 129.4, 128.9, 128.7, 125.5, 123.3, 120.0, 119.9, 118.9, 80.6, 44.7, 29.3, 26.7; m/z (ESI) 474.1 [M+Na]$^+$.

(S)—N-(4-acetylphenyl)-3-(1-(4-acetylphenyl)ethoxy)benzamide (216Bn)

Compound 216Bn was synthesized following the general procedure of synthesizing compound 216. $^1$H NMR (500 MHz, Chloroform-d) δ 8.25 (s, 1H), 7.99-7.95 (m, 2H), 7.95-7.91 (m, 2H), 7.78-7.74 (m, 2H), 7.50-7.45 (m, 2H), 7.43 (dd, J=2.6, 1.6 Hz, 1H), 7.39-7.35 (m, 1H), 7.32-7.27 (m, 1H), 7.03 (ddd, J=8.3, 2.5, 1.0 Hz, 1H), 5.45 (q, J=6.4 Hz, 1H), 2.60 (s, 3H), 2.58 (s, 3H), 1.67 (d, J=6.4 Hz, 3H). $^{13}$C NMR (126 MHz, CDCl$_3$) δ 197.8, 197.1, 165.6, 158.0, 147.9, 142.3, 136.5, 135.9, 133.0, 129.9, 129.8, 129.0, 125.7, 119.3, 119.1, 114.9, 75.7, 26.7, 26.5, 24.2; m/z (ESI) 424.1 [M+Na]$^+$.

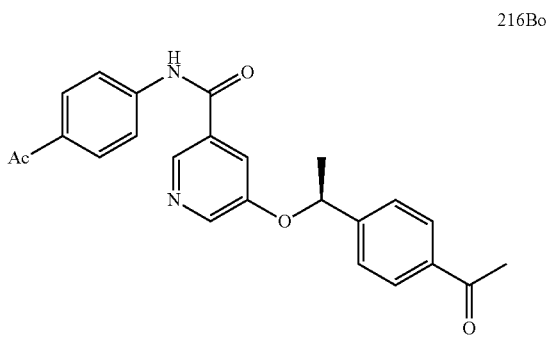 [SMILES: CC(=O)c1ccc(NC(=O)c2cncc(O[C@@H](C)c3ccc(C(C)=O)cc3)c2)cc1]

(S)—N-(4-acetylphenyl)-5-(1-(4-acetylphenyl)ethoxy)nicotinamide (216Bo)

Compound 216Bo was synthesized following the general procedure of synthesizing compound 216. $^1$H NMR (500 MHz, CDCl$_3$) δ 8.67 (s, 1H), 8.56 (d, J=1.8 Hz, 1H), 8.32 (d, J=2.8 Hz, 1H), 7.89-7.82 (m, 4H), 7.70-7.65 (m, 2H), 7.58 (dd, J=2.9, 1.7 Hz, 1H), 7.39-7.34 (m, 2H), 5.39 (q, J=6.4 Hz, 1H), 2.51 (s, 3H), 2.49 (s, 3H), 1.61 (d, J=6.4 Hz, 3H). $^{13}$C NMR (126 MHz, CDCl$_3$) δ 197.8, 197.1, 163.9, 154.0, 146.7, 142.5, 142.1, 139.6, 136.8, 133.3, 131.0, 129.8, 129.1, 125.8, 121.4, 119.6, 76.4, 26.7, 26.5, 24.1; m/z (ESI) 425.2 [M+Na]$^+$.

(S)—N-(4-acetylphenyl)-3-(1-(4-fluorophenyl)ethoxy)benzamide (216Bq)

Compound 216Bq was synthesized following the general procedure of synthesizing compound 216. $^1$H NMR (500 MHz, CDCl$_3$) δ 8.51 (s, 1H), 7.96-7.92 (m, 2H), 7.80-7.75 (m, 2H), 7.43 (dd, J=2.5, 1.6 Hz, 1H), 7.37 (dt, J=7.8, 1.2 Hz, 1H), 7.33 (dd, J=8.5, 5.4 Hz, 2H), 7.25 (t, J=7.9 Hz, 1H), 7.04-6.97 (m, 3H), 5.36 (q, J=6.4 Hz, 1H), 2.57 (s, 3H), 1.62 (d, J=6.4 Hz, 3H). $^{13}$C NMR (126 MHz, CDCl$_3$) δ 197.26, 165.86, 163.08, 161.13, 158.06, 142.54, 138.22, 135.77, 132.90, 129.75, 127.28, 119.79, 119.41, 119.12, 115.72, 115.01, 75.57, 26.48, 24.31; m/z (ESI) 400.2 [M+Na]$^+$.

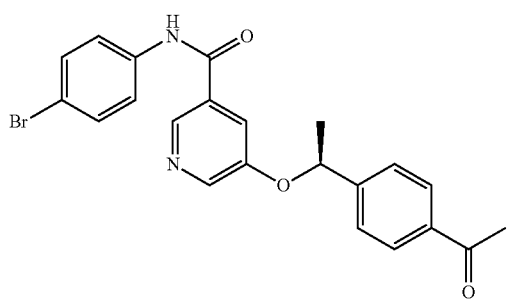

(S)-5-(1-(4-acetylphenyl)ethoxy)-N-(4-bromophenyl)nicotinamide (216 Bp)

Compound 216 Bp was synthesized following the general procedure of synthesizing compound 216. $^1$H NMR (500 MHz, CDCl$_3$) δ 8.85 (s, 1H), 8.58 (d, J=1.8 Hz, 1H), 8.35 (d, J=2.8 Hz, 1H), 7.93-7.87 (m, 2H), 7.61 (dd, J=2.9, 1.7 Hz, 1H), 7.54-7.49 (m, 2H), 7.44-7.39 (m, 4H), 5.42 (d, J=6.4 Hz, 1H), 2.56 (s, 3H), 1.67 (d, J=6.4 Hz, 3H). $^{13}$C NMR (126 MHz, CDCl$_3$) δ 197.9, 163.8, 154.0, 146.8, 142.2, 139.6, 136.8, 136.7, 132.0, 131.2, 129.1, 125.7, 122.1, 121.3, 117.6, 76.4, 26.7, 24.1; m/z (ESI) 461.1 [M+Na]$^+$.

(R)—N-(4-acetylphenyl)-5-(1-(4-acetylphenyl)ethoxy)nicotinamide (216Br)

Compound 216Br was synthesized following the general procedure of synthesizing compound 216. $^1$H NMR (500 MHz, CDCl$_3$) δ 8.66 (s, 1H), 8.46-8.41 (m, 2H), 8.01-7.94 (m, 4H), 7.79-7.74 (m, 2H), 7.68 (t, J=2.2 Hz, 1H), 7.51-7.45 (m, 2H), 5.50 (d, J=6.5 Hz, 1H), 2.61 (s, 3H), 2.60 (s, 3H), 1.72 (d, J=6.4 Hz, 3H). $^{13}$C NMR (126 MHz, CDCl$_3$) δ 197.7, 197.0, 163.6, 154.1, 146.6, 142.5, 141.8, 139.3, 136.9, 133.4, 131.1, 129.8, 129.1, 125.8, 121.5, 119.5, 76.5, 26.7, 26.5, 24.1; m/z (ESI) 425.2 [M+Na]$^+$.

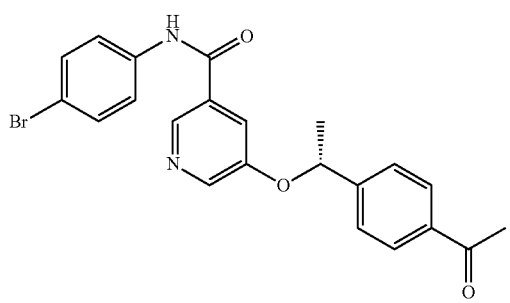

(R)-5-(1-(4-acetylphenyl)ethoxy)-N-(4-bromophenyl)nicotinamide (216Bs)

Compound 216Bs was synthesized following the general procedure of synthesizing compound 216. $^1$H NMR (500 MHz, CDCl$_3$) δ 8.85 (s, 1H), 8.58 (d, J=1.8 Hz, 1H), 8.35 (d, J=2.8 Hz, 1H), 7.93-7.87 (m, 2H), 7.61 (dd, J=2.9, 1.7 Hz, 1H), 7.54-7.49 (m, 2H), 7.44-7.39 (m, 4H), 5.42 (d, J=6.4 Hz, 1H), 2.56 (s, 3H), 1.67 (d, J=6.4 Hz, 3H). $^{13}$C NMR (126 MHz, CDCl$_3$) δ 197.9, 163.8, 154.0, 146.8, 142.2, 139.6, 136.8, 136.7, 132.0, 131.2, 129.1, 125.7, 122.1, 121.3, 117.6, 76.4, 26.7, 24.1; m/z (ESI) 461.1 [M+Na]$^+$.

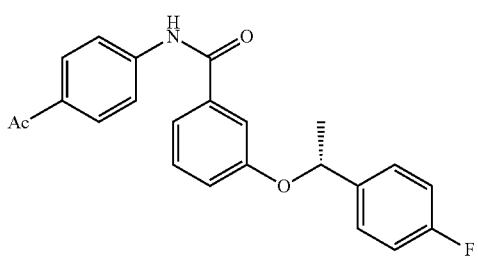

(R)—N-(4-acetylphenyl)-3-(1-(4-fluorophenyl)ethoxy)benzamide (216Bt)

Compound 216Bt was synthesized following the general procedure of synthesizing compound 216. $^1$H NMR (500 MHz, CDCl$_3$) δ 8.51 (s, 1H), 7.96-7.92 (m, 2H), 7.80-7.75 (m, 2H), 7.43 (dd, J=2.5, 1.6 Hz, 1H), 7.37 (dt, J=7.8, 1.2 Hz, 1H), 7.33 (dd, J=8.5, 5.4 Hz, 2H), 7.25 (t, J=7.9 Hz, 1H), 7.04-6.97 (m, 3H), 5.36 (q, J=6.4 Hz, 1H), 2.57 (s, 3H), 1.62 (d, J=6.4 Hz, 3H). $^{13}$C NMR (126 MHz, CDCl$_3$) δ 197.26, 165.86, 163.08, 161.13, 158.06, 142.54, 138.22, 135.77, 132.90, 129.75, 127.28, 119.79, 119.41, 119.12, 115.72, 115.01, 75.57, 26.48, 24.31; m/z (ESI) 400.2 [M+Na]$^+$.

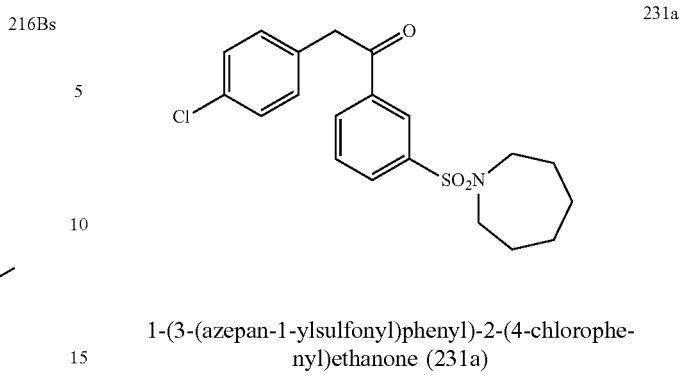

1-(3-(azepan-1-ylsulfonyl)phenyl)-2-(4-chlorophenyl)ethanone (231a)

Compound 231a was synthesized following the general procedure of synthesizing compound 231. White Solid, Melting point: 135-136° C.; $^1$H NMR (500 MHz, CDCl$_3$) δ 8.34 (s, 1H), 8.17 (dt, J=7.8, 1.4 Hz, 1H), 7.98 (dt, J=7.7, 1.5 Hz, 1H), 7.63 (t, J=7.8 Hz, 1H), 7.31 (d, J=8.3 Hz, 2H), 7.20 (d, J=8.3 Hz, 2H), 4.34-4.24 (s, 2H), 3.29-3.13 (m, 4H), 1.76-1.65 (qt, J=5.1, 2.8 Hz, 4H), 1.63-1.52 (dq, J=5.4, 2.7 Hz, 4H); $^{13}$C NMR (126 MHz, CDCl$_3$) δ 195.6, 140.4, 136.8, 133.2, 132.3, 131.9, 131.1, 130.8, 129.7, 129.0, 127.0, 48.2, 45.1, 29.1, 26.8; Mass Spectrum (ESI) [M+H]$^+$ C$_{20}$H$_{23}$ClNO$_3$S: 392.6.

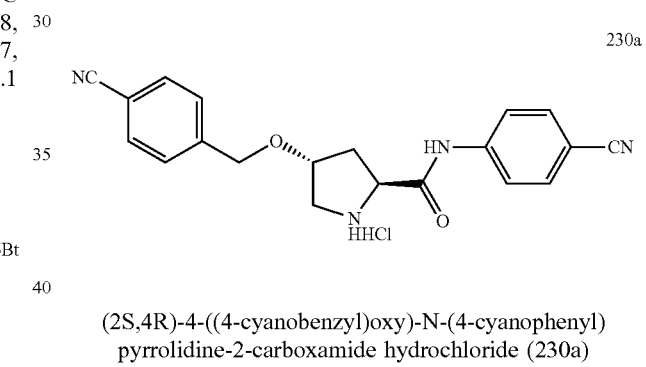

(2S,4R)-4-((4-cyanobenzyl)oxy)-N-(4-cyanophenyl)pyrrolidine-2-carboxamide hydrochloride (230a)

Compound 230a was synthesized following the general procedure of synthesizing compound 230. White foam; $^1$H NMR (500 MHz, MeOD) δ 7.85 (d, J=8.8 Hz, 1H), 7.79-7.73 (m, 4H), 7.62 (d, J=8.3 Hz, 2H), 4.74 (d, J=2.0 Hz, 2H), 4.65 (dd, J=10.8, 7.4 Hz, 1H), 4.54 (t, J=3.7 Hz, 1H), 3.68 (d, J=12.6 Hz, 1H), 3.58 (dd, J=12.7, 3.8 Hz, 1H), 2.92-2.82 (m, 1H), 2.24 (ddd, J=13.9, 10.8, 4.2 Hz, 1H); $^{13}$C NMR (126 MHz, MeOD) δ 168.1, 144.7, 143.4, 134.4, 133.4, 129.3, 121.1, 119.6, 119.5, 112.6, 108.7, 79.3, 71.0, 60.9, 52.7, 36.9; Mass Spectrum (ESI) [M–Cl]$^+$ C$_{19}$H$_{20}$N$_3$O$_2$: 347.3.

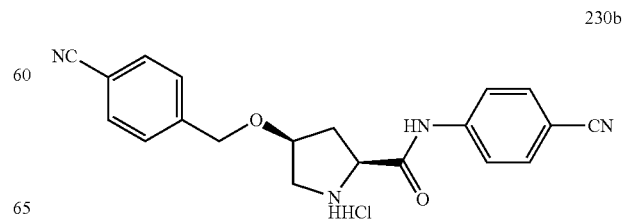

(2S,4S)-4-((4-cyanobenzyl)oxy)-N-(4-cyanophenyl) pyrrolidine-2-carboxamide hydrochloride (230b)

Compound 230b was synthesized following the general procedure of synthesizing compound 230. White foam; $^1$H NMR (500 MHz, MeOD) δ 7.79 (d, J=8.8 Hz, 2H), 7.72 (d, J=8.8 Hz, 2H), 7.60 (d, J=8.3 Hz, 2H), 7.45 (d, J=8.0 Hz, 2H), 4.71-4.62 (m, 2H), 4.58 (d, J=12.8 Hz, 1H), 4.48 (t, J=4.1 Hz, 1H), 3.76 (d, J=12.5 Hz, 1H), 3.51 (dd, J=12.6, 4.1 Hz, 1H), 2.75-2.58 (m, 2H); $^{13}$C NMR (126 MHz, MeOD) δ 168.3, 144.8, 143.5, 134.4, 133.2, 129.0, 121.1, 119.6, 112.3, 108.5, 78.4, 70.8, 60.8, 52.2, 36.9; Mass Spectrum (ESI) [[M–Cl]$^+$ C$_{19}$H$_{20}$N$_3$O$_2$: 347.3.

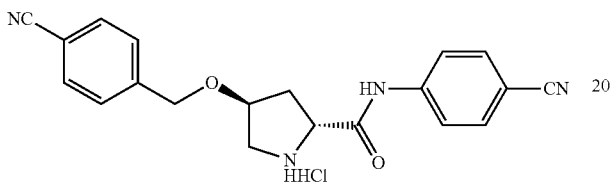

(2R,4S)-4-((4-cyanobenzyl)oxy)-N-(4-cyanophenyl) pyrrolidine-2-carboxamide hydrochloride (230c)

Compound 230c was synthesized following the general procedure of synthesizing compound 230. White foam; $^1$H NMR (500 MHz, MeOD) δ 7.85 (d, J=8.8 Hz, 1H), 7.79-7.73 (m, 4H), 7.62 (d, J=8.3 Hz, 2H), 4.74 (d, J=2.0 Hz, 2H), 4.65 (dd, J=10.8, 7.4 Hz, 1H), 4.54 (t, J=3.7 Hz, 1H), 3.68 (d, J=12.6 Hz, 1H), 3.58 (dd, J=12.7, 3.8 Hz, 1H), 2.92-2.82 (m, 1H), 2.24 (ddd, J=13.9, 10.8, 4.2 Hz, 1H); $^{13}$C NMR (126 MHz, MeOD) δ 168.1, 144.7, 143.4, 134.4, 133.4, 129.3, 121.1, 119.6, 119.5, 112.6, 108.7, 79.3, 71.0, 60.9, 52.7, 36.9; Mass Spectrum (ESI) [M–Cl]$^+$ C$_{19}$H$_{20}$N$_3$O$_2$: 347.3.

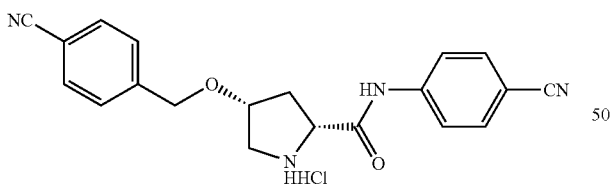

(2R,4R)-4-((4-cyanobenzyl)oxy)-N-(4-cyanophenyl) pyrrolidine-2-carboxamide hydrochloride (230d)

Compound 230d was synthesized following the general procedure of synthesizing compound 230. White foam; $^1$H NMR (500 MHz, MeOD) δ 7.79 (d, J=8.8 Hz, 2H), 7.72 (d, J=8.8 Hz, 2H), 7.60 (d, J=8.3 Hz, 2H), 7.45 (d, J=8.0 Hz, 2H), 4.71-4.62 (m, 2H), 4.58 (d, J=12.8 Hz, 1H), 4.48 (t, J=4.1 Hz, 1H), 3.76 (d, J=12.5 Hz, 1H), 3.51 (dd, J=12.6, 4.1 Hz, 1H), 2.75-2.58 (m, 2H); $^{13}$C NMR (126 MHz, MeOD) δ 168.3, 144.8, 143.5, 134.4, 133.2, 129.0, 121.1, 119.6, 112.3, 108.5, 78.4, 70.8, 60.8, 52.2, 36.9; Mass Spectrum (ESI) [M–Cl]$^+$ C$_{19}$H$_{20}$N$_3$O$_2$: 347.3.

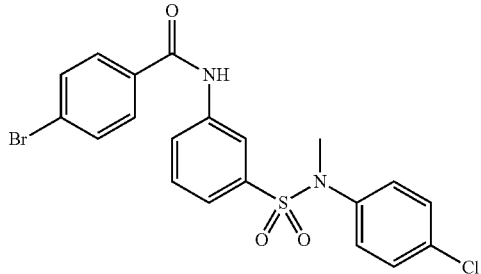

4-bromo-N-(3-(N-(4-chlorophenyl)-N-methylsulfamoyl)phenyl)benzamide (207a)

Compound 207a was synthesized following the general procedure of synthesizing compound 207. White solid; m.p. 187-189° C.; $^1$H NMR (500 MHz, CDCl$_3$) δ 8.72 (s, 1H), 8.35 (d, J=8.3 Hz, 1H), 7.84 (d, J=8.4 Hz, 2H), 7.71 (s, 1H), 7.64 (d, J=8.5 Hz, 2H), 7.48 (t, J=8.0 Hz, 1H), 7.24-7.18 (m, 3H), 6.96 (d, J=8.7 Hz, 2H), 3.11 (s, 3H); $^{13}$C NMR (126 MHz, CDCl$_3$) δ 165.3, 139.6, 139.0, 136.4, 133.5, 132.9, 132.1, 130.0, 129.2, 129.1, 128.0, 127.1, 124.9, 123.3, 119.0, 38.3; HRMS (ESI) (M+H$^+$) calcd for C$_{20}$H$_{17}$BrClN$_2$O$_3$S 478.9832. Found 478.9823.

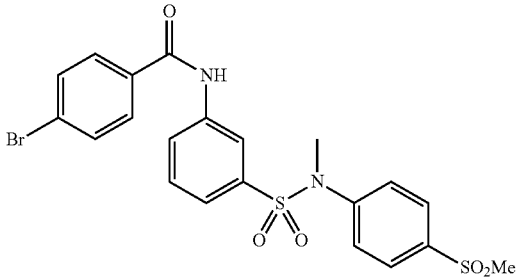

4-bromo-N-(3-(N-methyl-N-(4-(methylsulfonyl) phenyl)sulfamoyl)phenyl)benzamide (207b)

Compound 207b was synthesized following the general procedure of synthesizing compound 207. White solid; m.p. 216-218° C.; $^1$H NMR (500 MHz, DMSO) δ 10.64 (s, 1H), 8.14-8.10 (m, 2H), 7.91 (d, J=9.7 Hz, 4H), 7.77 (d, J=8.5 Hz, 2H), 7.60-7.55 (m, 1H), 7.47 (d, J=8.7 Hz, 2H), 7.25 (d, J=7.6 Hz, 1H), 3.23 (s, 3H), 3.22 (s, 3H); $^{13}$C NMR (126 MHz, DMSO) δ 164.9, 145.4, 139.8, 138.5, 136.1, 133.3, 131.5, 129.9, 129.8, 127.9, 125.9, 125.8, 124.5, 122.2, 118.4, 43.4, 37.5; HRMS (ESI) (M+H$^+$) calcd for C$_{21}$H$_{20}$BrN$_2$O$_5$S$_2$ 522.9997. Found 522.9996.

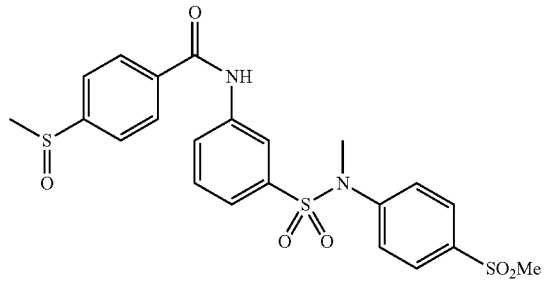

N-(3-(N-methyl-N-(4-(methylsulfonyl)phenyl)sulfamoyl)phenyl)-4-(methylsulfinyl)benzamide (207c)

Compound 207c was synthesized following the general procedure of synthesizing compound 207. White solid; m.p. 184-186° C.; $^1$H NMR (500 MHz, DMSO) δ 10.72 (s, 1H), 8.16-8.10 (m, 4H), 7.91 (d, J=8.6 Hz, 2H), 7.85 (d, J=8.4 Hz, 2H), 7.59 (t, J=8.3 Hz, 1H), 7.47 (d, J=8.7 Hz, 2H), 7.26 (d, J=7.6 Hz, 1H), 3.24 (s, 3H), 3.22 (s, 3H), 2.81 (s, 3H); $^{13}$C NMR (126 MHz, DMSO) δ 165.1, 150.2, 145.4, 139.8, 138.5, 136.3, 136.1, 129.9, 128.5, 127.9, 125.9, 124.5, 123.7, 122.2, 118.4, 43.4, 43.0, 37.5; HRMS (ESI) (M+H$^+$) calcd for $C_{22}H_{23}N_2O_6S_3$ 507.0718. Found 507.0717.

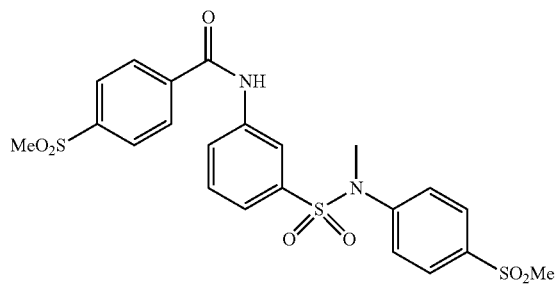

N-(3-(N-methyl-N-(4-(methylsulfonyl)phenyl)sulfamoyl)phenyl)-4-(methylsulfonyl)benzamide (207d)

Compound 207d was synthesized following the general procedure of synthesizing compound 207. White solid; m.p. 213-215° C. (decompose); $^1$H NMR (500 MHz, DMSO) δ 10.82 (s, 1H), 8.20-8.08 (m, 6H), 7.92 (d, J=8.3 Hz, 2H), 7.61 (t, J=8.3 Hz, 1H), 7.47 (d, J=8.3 Hz, 2H), 7.28 (d, J=7.8 Hz, 1H), 3.31 (s, 3H), 3.24 (s, 3H), 3.22 (s, 3H); $^{13}$C NMR (126 MHz, DMSO) 6 $^{13}$C NMR (126 MHz, DMSO) δ 164.7, 145.4, 143.4, 139.6, 138.8, 138.5, 136.1, 130.0, 128.7, 127.9, 127.1, 125.9, 124.6, 122.4, 118.5, 43.4, 43.2, 37.5; HRMS (ESI) (M+H$^+$) calcd for $C_{22}H_{23}N_2O_7S_3$ 523.0667. Found 523.0669.

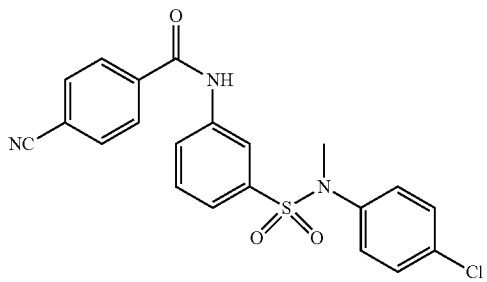

N-(3-(N-(4-chlorophenyl)-N-methylsulfamoyl)phenyl)-4-cyanobenzamide (207e)

Compound 207e was synthesized following the general procedure of synthesizing compound 207. White solid; m.p. 196-198° C.; $^1$H NMR (500 MHz, CDCl$_3$) δ 8.60 (s, 1H), 8.35 (d, J=8.2 Hz, 1H), 8.08 (d, J=8.3 Hz, 2H), 7.83 (d, J=8.3 Hz, 2H), 7.69 (s, 1H), 7.53 (t, J=8.0 Hz, 1H), 7.29 (d, J=8.1 Hz, 1H), 7.24 (d, J=10.5 Hz, 2H), 6.97 (d, J=8.6 Hz, 2H), 3.13 (s, 3H). $^{13}$C NMR (126 MHz, CDCl$_3$) δ 164.3, 139.5, 138.6, 137.9, 136.4, 133.6, 132.7, 130.1, 129.6, 128.1, 128.0, 124.9, 123.7, 119.0, 117.9, 115.7, 38.3; HRMS (ESI) (M+H$^+$) calcd for $C_{21}H_{16}ClN_3NaO_3S$ 448.0499 found 448.0500.

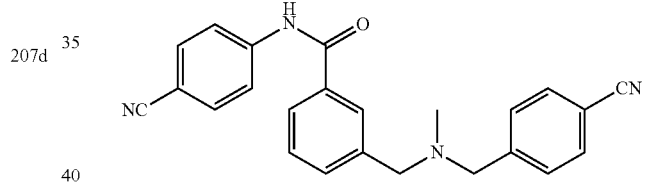

3-(((4-cyanobenzyl)(methyl)amino)methyl)-N-(4-cyanophenyl)benzamide (225a)

Compound 225a was synthesized following the general procedure of synthesizing compound 225. White foam; $^1$H NMR (500 MHz, CDCl$_3$) δ 8.02-7.91 (m, 1H), 7.91-7.74 (m, 4H), 7.74-7.58 (m, 5H), 7.58-7.47 (m, 3H), 3.66 (s, 4H), 2.25 (s, 3H); $^{13}$C NMR (126 MHz, CDCl$_3$) δ 165.8, 144.5, 142.1, 140.1, 134.4, 133.4, 132.m9, 132.3, 129.5, 129.1, 127.9, 125.9, 119.9, 118.9, 111.1, 107.4, 61.6, 61.4, 42.3; Mass Spectrum (ESI) [M+H]$^+$ $C_{24}H_{21}N_4O$: 381.2.

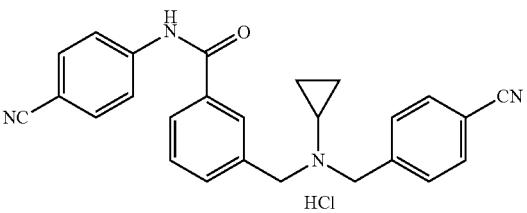

3-(((4-cyanobenzyl)(cyclopropyl)amino)methyl)-N-(4-cyanophenyl)benzamide hydrochloride (225b)

Compound 225b was synthesized following the general procedure of synthesizing compound 225. $^1$H NMR (500 MHz, CDCl$_3$) δ 8.21 (s, 1H), 7.82 (d, J=8.6 Hz, 2H), 7.79 (s, 1H), 7.73 (s, 1H), 7.64 (d, J=8.7 Hz, 2H), 7.55 (d, J=8.2 Hz, 2H), 7.49-7.44 (m, 1H), 7.42 (t, J=7.6 Hz, 1H), 7.36 (d, J=7.9 Hz, 2H), 3.74 (s, 2H), 3.71 (s, 2H), 1.89-1.82 (m, 1H), 0.47-0.39 (m, 2H), 0.31-0.26 (m, 2H); $^{13}$C NMR (126 MHz, CDCl$_3$) δ 165.9, 144.5, 142.1, 139.6, 134.0, 133.3, 131.9, 129.8, 128.6, 128.4, 125.4, 119.9, 119.0, 118.8, 110.6, 107.2, 58.9, 58.7, 37.0, 7.7. Mass Spectrum (ESI) [M–Cl]$^+$ C$_{26}$H$_{23}$N$_4$O: 407.3; HRMS (ESI) [M–Cl]$^+$ calcd for C$_{26}$H$_{23}$N$_4$O: 407.1866. found 407.1844.

MHz, CDCl$_3$) δ 8.21 (s, 1H), 7.83-7.79 (m, 2H), 7.76 (t, J=1.8 Hz, 1H), 7.72 (dt, J=7.7, 1.5 Hz, 1H), 7.65-7.59 (m, 2H), 7.49-7.45 (m, 1H), 7.41 (t, J=7.6 Hz, 1H), 7.10-7.01 (m, 2H), 6.98-6.91 (m, 1H), 3.71 (s, 2H), 3.61 (s, 2H), 1.83 (tt, J=6.6, 3.6 Hz, 1H), 0.47-0.37 (m, 2H), 0.31-0.23 (m, 2H); $^{13}$C NMR (126 MHz, CDCl$_3$) δ 166.0, 149.9 (dd, J=249.1, 12.7 Hz), 149.2 (dd, J=249.1, 12.7 Hz), 142.1, 139.8, 135.7 (t, J=4.4 Hz), 133.9, 133.3, 133.2, 128.6, 128.1, 125.5, 124.9 (dd, J=6.1, 3.4 Hz), 119.9, 118.9, 117.8 (d, J=16.9 Hz), 116.7 (d, J=17.0 Hz), 107.1, 58.4, 57.9, 36.7, 7.6. Mass Spectrum (ESI) [M–Cl]$^+$ C$_{26}$H$_{22}$F$_2$N$_3$O: 418.1; HRMS (ESI) [M–Cl]$^+$ calcd for C$_{26}$H$_{22}$F$_2$N$_3$O: 418.1725. found 418.1733.

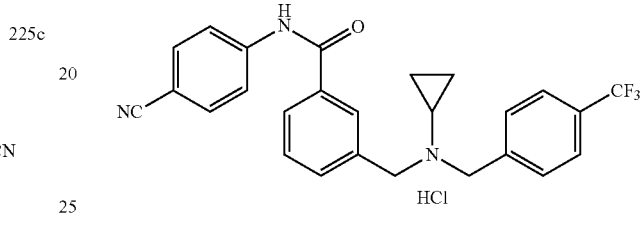

225c

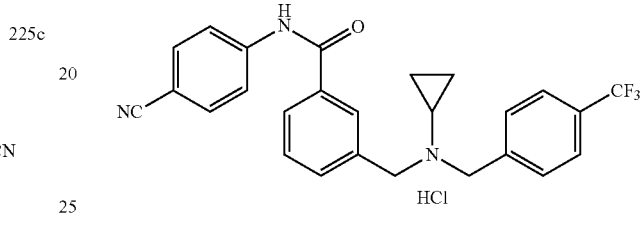

3-(((4-cyano-2-fluorobenzyl)(cyclopropyl)amino)methyl)-N-(4-cyanophenyl)-benzamide hydrochloride (225c)

Compound 225c was synthesized following the general procedure of synthesizing compound 225. $^1$H NMR (500 MHz, MeOD) δ 7.95-7.92 (m, 2H), 7.84 (t, J=1.8 Hz, 1H), 7.80 (dt, J=7.7, 1.5 Hz, 1H), 7.70 (d, J=8.8 Hz, 2H), 7.54-7.49 (m, 2H), 7.46-7.40 (m, 3H), 3.81 (s, 2H), 3.79 (s, 2H), 1.90 (dq, J=7.0, 3.5 Hz, 1H), 0.42 (dt, J=6.4, 3.2 Hz, 2H), 0.27 (dt, J=6.4, 3.2 Hz, 2H); $^{13}$C NMR (126 MHz, MeOD) δ 168.8, 162.1 (d, J=248.7 Hz), 144.5, 140.7, 135.5, 134.4 (d, J=5.2 Hz), 134.1, 133.5, 133.4, 129.7, 129.4, 129.0 d, J=3.7 Hz), 127.4, 121.8, 120.0, 119.8 (d, J=4.6 Hz), 118.6 (d, J=2.8 Hz), 113.3 (d, J=9.7 Hz), 107.9, 60.7, 52.7, 38.1, 8.1; Mass Spectrum (ESI) [M–Cl]$^+$ C$_{26}$H$_{22}$FN$_4$O: 425.1; HRMS (ESI) [M–Cl]$^+$ calcd for C$_{26}$H$_{22}$FN$_4$O: 425.1772. found 425.1775.

N-(4-cyanophenyl)-3-((cyclopropyl(4-(trifluoromethyl)benzyl)amino)methyl)-benzamide hydrochloride (225e)

Compound 225e was synthesized following the general procedure of synthesizing compound 225. $^1$H NMR (500 MHz, CDCl$_3$) δ 8.15 (s, 1H), 7.81 (d, J=8.6 Hz, 2H), 7.77 (t, J=1.8 Hz, 1H), 7.73-7.69 (m, 1H), 7.66-7.61 (m, 2H), 7.53 (d, J=7.9 Hz, 2H), 7.50-7.47 (m, 1H), 7.42 (t, J=7.6 Hz, 1H), 7.37 (d, J=7.8 Hz, 2H), 3.74 (s, 2H), 3.73 (s, 2H), 1.86 (dt, J=6.4, 3.0 Hz, 1H), 0.47-0.37 (m, 2H), 0.36-0.24 (m, 2H); $^{13}$C NMR (126 MHz, CDCl$_3$) δ 166.0, 142.7, 142.1, 139.9, 133.9, 133.4, 133.3, 129.4, 128.6, 128.2, 125.4, 124.9 (q, J=3.8 Hz), 124.2 (d, J=271.9 Hz), 119.9, 118.8, 107.2, 58.6, 58.5, 36.8, 7.7; Mass Spectrum (ESI) [M–Cl]$^+$ C$_{26}$H$_{23}$F$_3$N$_3$O: 450.2

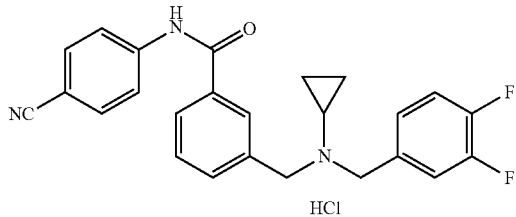

225d

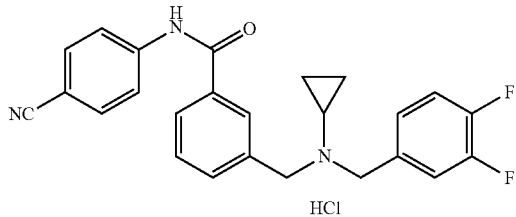

225f

N-(4-cyanophenyl)-3-((cyclopropyl(3,4-difluorobenzyl)amino)methyl)benzamide hydrochloride (225d)

Compound 225d was synthesized following the general procedure of synthesizing compound 225. $^1$H NMR (500

N-(4-cyanophenyl)-3-((cyclopropyl(3,5-difluorobenzyl)amino)methyl)benzamide hydrochloride (225f)

Compound 225f was synthesized following the general procedure of synthesizing compound 225. $^1$H NMR (500 MHz, CDCl$_3$) δ 8.09 (s, 1H), 7.84-7.78 (m, 2H), 7.77-7.70 (m, 2H), 7.65 (d, J=8.7 Hz, 2H), 7.50-7.46 (m, 1H), 7.44 (t, J=7.5 Hz, 1H), 6.85-6.76 (m, 2H), 6.70-6.64 (m, 1H), 3.74 (s, 2H), 3.65 (s, 2H), 1.91-1.83 (m, 1H), 0.50-0.41 (m, 2H), 0.34-0.27 (m, 2H); $^{13}$C NMR (126 MHz, CDCl$_3$) δ 165.9, 162.8 (dd, J=248.1, 12.7 Hz), 143.0 (t, J=8.4 Hz), 142.0, 139.6, 133.9, 133.4, 133.3, 128.7, 128.0, 125.7, 119.9, 118.8, 111.7 (dd, J=19.1, 5.8 Hz), 107.3, 102.3 (t, J=25.4 Hz), 58.6, 58.3, 36.8, 7.7. Mass Spectrum (ESI) [M−Cl]$^+$ $C_{26}H_{22}F_2N_3O$: 418.2; HRMS (ESI) [M−Cl]$^+$ calcd for $C_{26}H_{22}F_2N_3O$: 418.1725. found 418.1732.

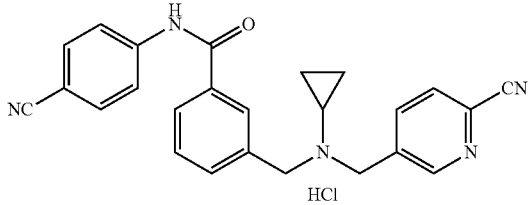

N-(4-cyanophenyl)-3-((((6-cyanopyridin-3-yl)methyl)(cyclopropyl)amino)-methyl)benzamide hydrochloride (225g)

Compound 225g was synthesized following the general procedure of synthesizing compound 225. $^1$H NMR (500 MHz, CDCl$_3$) δ 8.54 (d, J=2.3 Hz, 1H), 8.22 (s, 1H), 7.84 (d, J=8.8 Hz, 2H), 7.75 (s, 1H), 7.71-7.62 (m, 4H), 7.58 (dd, J=7.9, 0.9 Hz, 1H), 7.46-7.38 (m, 2H), 3.78 (s, 2H), 3.74 (s, 2H), 1.91 (dt, J=6.5, 3.0 Hz, 1H), 0.50-0.44 (m, 2H), 0.32-0.24 (m, 2H); $^{13}$C NMR (126 MHz, CDCl$_3$) δ 165.9, 151.8, 142.1, 139.3, 138.8, 137.4, 134.2, 133.3, 133.1, 132.1, 128.8, 128.3, 127.9, 125.6, 120.0, 118.8, 117.3, 107.2, 59.4, 56.2, 37.3, 7.9; Mass Spectrum (ESI) [M−Cl]$^+$ $C_{25}H_{22}N_4O$: 408.2; HRMS (ESI) [M−Cl]$^+$ calcd for ]$^+$ $C_{25}H_{22}N_4O$: 408.1819. found 408.1821.

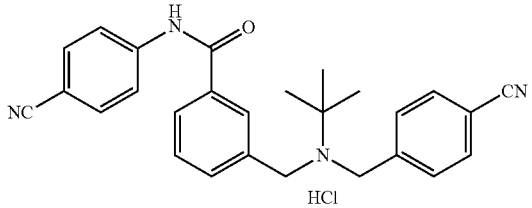

3-((tert-butyl(4-cyanobenzyl)amino)methyl)-N-(4-cyanophenyl)benzamide hydrochloride (225h)

Compound 225h was synthesized following the general procedure of synthesizing compound 225. $^1$H NMR (500 MHz, CDCl$_3$) δ 8.13 (s, 1H), 7.80 (d, J=8.7 Hz, 2H), 7.72 (t, J=1.7 Hz, 1H), 7.62 (d, J=8.7 Hz, 2H), 7.56-7.51 (m, 1H), 7.46 (d, J=7.8 Hz, 1H), 7.36 (d, J=8.3 Hz, 2H), 7.30 (d, J=8.3 Hz, 2H), 7.25 (t, J=7.8 Hz, 1H), 3.77 (s, 2H), 3.75 (s, 2H), 1.17 (s, 9H); $^{13}$C NMR (126 MHz, CDCl$_3$) δ 165.9, 148.5, 142.8, 142.1, 133.6, 133.2, 132.6, 131.5, 128.6, 128.2, 127.9, 124.7, 119.9, 119.1, 118.9, 109.6, 107.1, 55.9, 54.7, 54.3, 27.3; Mass Spectrum (ESI) [M−Cl]$^+$ $C_{27}H_{27}N_4O$: 423.2; HRMS (ESI) [M−Cl]$^+$ calcd for $C_{27}H_{27}N_4O$: 423.2179. found 423.2186.

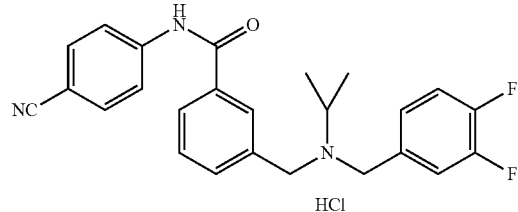

N-(4-cyanophenyl)-3-(((3,4-difluorobenzyl)(isopropyl)amino)methyl)benzamide hydrochloride (225i)

Compound 225i was synthesized following the general procedure of synthesizing compound 225. $^1$H NMR (500 MHz, CDCl$_3$) δ 8.17 (s, 1H), 7.87-7.78 (m, 3H), 7.71 (dt, J=7.7, 1.5 Hz, 1H), 7.67-7.63 (m, 2H), 7.61 (dt, J=7.7, 1.3 Hz, 1H), 7.44 (t, J=7.7 Hz, 1H), 7.26-7.16 (m, 1H), 7.10-7.02 (m, 2H), 3.62 (s, 2H), 3.53 (s, 2H), 2.92 (p, J=6.6 Hz, 1H), 1.10 (d, J=6.6 Hz, 6H); $^{13}$C NMR (126 MHz, CDCl$_3$) δ 166.1, 150.1 (dd, J=247.3, 12.7 Hz)), 148.2 (dd, J=246.5, 12.8 Hz), 142.0 (d, J=33.3 Hz), 137.8 (t, J=4.2 Hz), 134.0, 133.3, 132.6, 128.9, 127.3, 125.4, 124.0 (dd, J=5.9, 3.3 Hz), 119.9, 118.9, 116.9 (t, J=16.4 Hz), 107.2, 53.1, 52.6, 48.9, 17.7. Mass Spectrum (ESI) [M−Cl]$^+$ $C_{25}H_{23}F_2N_4O$ 420.2.

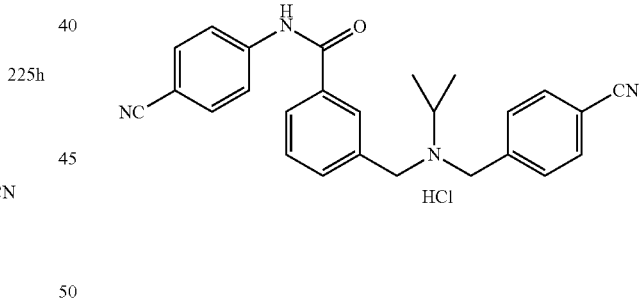

3-(((4-cyanobenzyl)(isopropyl)amino)methyl)-N-(4-cyanophenyl)benzamide hydrochloride (225j)

Compound 225j was synthesized following the general procedure of synthesizing compound 225. $^1$H NMR (500 MHz, CDCl$_3$) δ 8.39 (s, 1H), 7.85 (t, J=1.8 Hz, 1H), 7.82 (d, J=8.8 Hz, 2H), 7.71-7.66 (m, 1H), 7.61-7.55 (m, 3H), 7.51 (d, J=8.2 Hz, 2H), 7.45 (d, J=8.3 Hz, 2H), 7.39 (t, J=7.7 Hz, 1H), 3.60 (s, 4H), 2.86 (p, J=6.6 Hz, 1H), 1.08 (s, 3H), 1.07 (s, 3H); $^{13}$C NMR (126 MHz, CDCl$_3$) δ 166.1, 146.6, 142.2, 141.4, 134.0, 133.2, 132.4, 131.9, 128.9, 128.6, 127.6, 125.4, 120.0, 119.0, 118.9, 110.2, 106.9, 53.2, 49.1, 17.6; Mass Spectrum (ESI) [M−H]$^-$ $C_{26}H_{24}ClN_4O$: 443.0; HRMS (ESI) [M−Cl]$^+$ calcd for $C_{26}H_{25}N_4O$: 409.2023. found 409.2020.

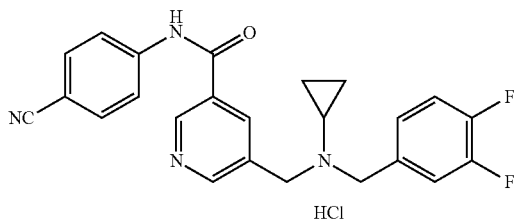

225k

HCl

N-(4-cyanophenyl)-5-((cyclopropyl(3,4-difluorobenzyl)amino)methyl)nicotinamide hydrochloride (225k)

Compound 225k was synthesized following the general procedure of synthesizing compound 225. $^1$H NMR (500 MHz, CDCl$_3$) δ 9.14-9.07 (m, 1H), 8.97 (d, J=2.2 Hz, 1H), 8.55 (d, J=2.0 Hz, 1H), 8.07 (t, J=2.1 Hz, 1H), 7.85 (d, J=8.7 Hz, 2H), 7.61 (d, J=8.6 Hz, 2H), 7.07-6.99 (m, 2H), 6.94-6.90 (m, 1H), 3.68 (s, 2H), 3.61 (s, 2H), 1.82 (dt, J=6.4, 3.0 Hz, 1H), 0.42 (dt, J=6.4, 3.2 Hz, 2H), 0.26-0.18 (m, 2H); $^{13}$C NMR (126 MHz, CDCl$_3$) δ 164.4, 153.2, 149.9 (dd, J=248.7, 12.6 Hz), 149.2 (dd, J=248.7, 12.6 Hz), 146.3, 142.1, 136.5, 135.2 (t, J=4.3 Hz), 134.8, 133.2, 129.8, 124.8 (dd, J=6.0, 3.3 Hz), 120.2, 118.8, 117.7 (d, J=16.8 Hz), 116.8 (d, J=16.9 Hz), 107.2, 58.3, 55.7, 36.7, 7.7; Mass Spectrum (ESI) [M–Cl]$^+$ C$_{24}$H$_{20}$ClF$_2$N$_4$O: 453.0; HRMS (ESI) [M–Cl]$^+$ calcd for C$_{24}$H$_{20}$ClF$_2$N$_4$O: 419.1678. found 419.1687.

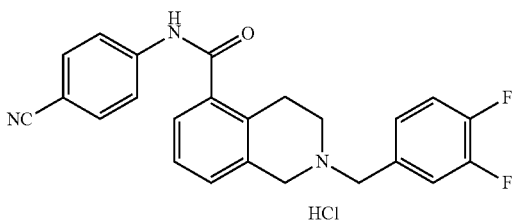

225m

HCl

N-(4-cyanophenyl)-2-(3,4-difluorobenzyl)-1,2,3,4-tetrahydroisoquinoline-5-carboxamide hydrochloride (225m)

Compound 225m was synthesized following the general procedure of synthesizing compound 225. $^1$H NMR (500 MHz, CDCl$_3$) δ 7.81-7.71 (m, 3H), 7.64 (d, J=8.2 Hz, 2H), 7.36 (d, J=7.5 Hz, 1H), 7.26-7.18 (m, 2H), 7.16-7.06 (m, 3H), 3.66 (s, 2H), 3.64 (s, 2H), 3.11 (t, J=5.9 Hz, 2H), 2.75 (t, J=5.9 Hz, 2H); $^{13}$C NMR (126 MHz, CDCl$_3$) δ 167.8, 150.3 (dd, J=248.0, 12.6 Hz), 149.6 (dd, J=248.0, 12.6 Hz), 141.9, 136.2, 135.3, 135.0 (t, J=4.5 Hz), 133.4, 133.0, 129.5, 125.9, 124.7, 124.6 (dd, J=5.6, 3.7 Hz), 119.6, 118.8, 117.6 (d, J=17.1 Hz), 117.0 (d, J=17.1 Hz), 107.4, 61.4, 56.0, 50.3, 27.1; Mass Spectrum (ESI) [M–Cl]$^+$ C$_{24}$H$_{20}$F$_2$N$_3$O: 404.1; HRMS (ESI) [M–Cl]$^+$ calcd for C$_{24}$H$_{20}$F$_2$N$_3$O: 404.1569. found 404.1576.

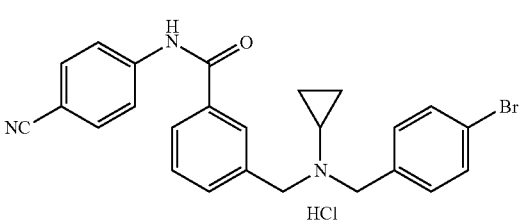

225l

HCl

3-(((4-bromobenzyl)(cyclopropyl)amino)methyl)-N-(4-cyanophenyl)benzamide hydrochloride (225l)

Compound 225l was synthesized following the general procedure of synthesizing compound 225. $^1$H NMR (500 MHz, CDCl$_3$) δ 8.19 (s, 1H), 7.81 (d, J=8.6 Hz, 2H), 7.76-7.69 (m, 2H), 7.63 (d, J=8.6 Hz, 2H), 7.49-7.44 (m, 1H), 7.41 (dd, J=8.5, 6.8 Hz, 3H), 7.13 (d, J=8.3 Hz, 2H), 3.70 (s, 2H), 3.62 (s, 2H), 1.83 (tt, J=6.7, 3.7 Hz, 1H), 0.42 (dt, J=6.4, 3.2 Hz, 2H), 0.29 (p, J=3.9 Hz, 2H); $^{13}$C NMR (126 MHz, CDCl$_3$) δ 166.0, 142.1, 140.0, 137.4, 133.8, 133.3, 133.2, 131.0, 128.6, 128.1, 125.5, 120.7, 119.9, 118.9, 107.1, 58.4, 58.2, 36.7, 7.6; Mass Spectrum (ESI) [M–Cl]$^+$ C$_{25}$H$_{23}$BrN$_3$O: 460.4; HRMS (ESI) [M–Cl]$^+$ calcd for C$_{25}$H$_{23}$BrN$_3$O: 460.1019. found 460.1018.

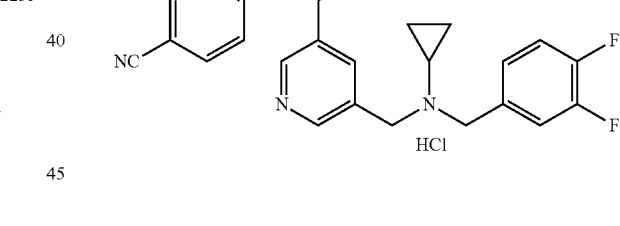

225n

HCl

N-(4-cyanophenyl)-5-((cyclopropyl(3,4-difluorobenzyl)amino)methyl)-N-methylnicotinamide hydrochloride (225n)

Compound 225n was synthesized following the general procedure of synthesizing compound 225. $^1$H NMR (500 MHz, CDCl$_3$) δ 8.39 (d, J=2.1 Hz, 1H), 8.38 (d, J=2.0 Hz, 1H), 7.55 (d, J=8.5 Hz, 2H), 7.46 (t, J=2.1 Hz, 1H), 7.15 (d, J=8.5 Hz, 2H), 7.09 (dt, J=10.1, 8.2 Hz, 1H), 7.02 (ddd, J=11.2, 7.7, 2.0 Hz, 1H), 6.94-6.88 (m, 1H), 3.54 (s, 3H), 3.53 (s, 2H), 3.51 (s, 2H), 1.69 (dq, J=6.5, 3.3 Hz, 1H), 0.42-0.33 (m, 2H), 0.12-0.06 (m, 2H); $^{13}$C NMR (126 MHz, CDCl$_3$) δ 168.1, 151.8, 150.2 (dd, J=246.5, 12.7 Hz), 149.5 (dd, J=246.5, 12.7 Hz), 148.4, 148.3, 136.9, 135.4 (t, J=4.5 Hz), 133.7, 133.4, 130.5, 127.3, 124.8 (dd, J=6.1, 3.4 Hz), 117.8, 117.6 (d, J=16.9 Hz), 116.9 (d, J=17.0 Hz), 110.5, 58.3, 55.4, 38.2, 36.5, 7.7; Mass Spectrum (ESI) [M–Cl]$^+$ C$_{25}$H$_{23}$F$_2$N$_4$O: 433.4; HRMS (ESI) [M–Cl]$^+$ calcd for C$_{25}$H$_{23}$F$_2$N$_4$O: 433.1834. found 433.1839.

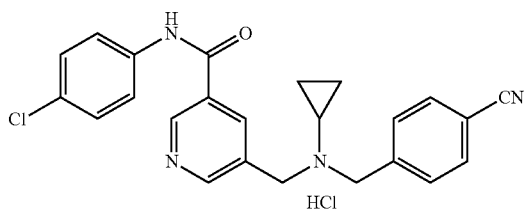

N-(4-chlorophenyl)-5-(((4-cyanobenzyl)(cyclopropyl)amino)methyl)nicotinamide hydrochloride (225o)

Compound 225o was synthesized following the general procedure of synthesizing compound 225. $^1$H NMR (500 MHz, CDCl$_3$) δ 8.96 (d, J=2.2 Hz, 1H), 8.64 (d, J=2.1 Hz, 1H), 8.19 (s, 1H), 8.11 (t, J=2.1 Hz, 1H), 7.70-7.63 (m, 2H), 7.62-7.56 (m, 2H), 7.39 (dd, J=10.3, 8.5 Hz, 4H), 3.78 (s, 4H), 1.93-1.88 (m, 1H), 0.54-0.43 (m, 2H), 0.34-0.27 (m, 2H); $^{13}$C NMR (126 MHz, CDCl$_3$) δ 163.8, 153.4, 146.1, 144.1, 136.5, 136.1, 134.4, 132.1, 130.1, 129.8, 129.2, 121.7, 118.9, 111.0, 59.1, 56.3, 37.1, 7.9. Mass Spectrum (ESI) [M–Cl]$^+$ C$_{24}$H$_{23}$ClN$_4$O: 417.4.

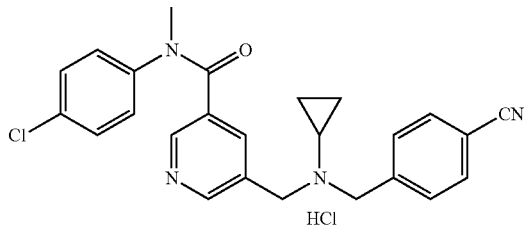

N-(4-chlorophenyl)-5-(((4-cyanobenzyl)(cyclopropyl)amino)methyl)-N-methylnicotinamide hydrochloride (225p)

Compound 225p was synthesized following the general procedure of synthesizing compound 225. $^1$H NMR (500 MHz, CDCl$_3$) δ 8.38 (d, J=30.1 Hz, 1H), 7.60 (d, J=7.9 Hz, 2H), 7.48 (s, 1H), 7.32 (d, J=7.9 Hz, 2H), 7.20 (d, J=8.6 Hz, 2H), 6.98 (d, J=8.2 Hz, 2H), 3.59 (s, 2H), 3.51 (s, 2H), 3.48 (s, 3H), 1.66 (dt, J=6.3, 3.1 Hz, 1H), 0.37 (dt, J=6.7, 3.3 Hz, 2H), 0.14 (m, 2H); $^{13}$C NMR (126 MHz, CDCl$_3$) δ 168.1, 151.3, 148.4, 144.0, 142.8, 136.9, 132.9, 132.1, 129.7, 128.3, 118.9, 111.0, 58.6, 55.7, 38.4, 36.5, 7.8. Mass Spectrum (ESI) [M–Cl]$^+$ C$_{25}$H$_{24}$ClN$_4$O: 431.3.

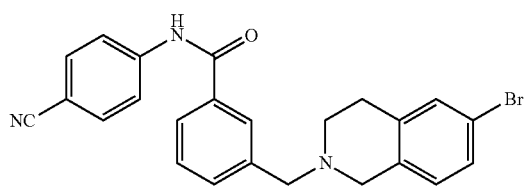

3-((6-bromo-3,4-dihydroisoquinolin-2(1H)-yl)methyl)-N-(4-cyanophenyl)benzamide hydrochloride (225q)

Compound 225q was synthesized following the general procedure of synthesizing compound 225. $^1$H NMR (500 MHz, CDCl$_3$) δ 8.29 (s, 1H), 7.93 (s, 1H), 7.85-7.79 (m, 3H), 7.65 (d, J=8.8 Hz, 2H), 7.60-7.56 (m, 1H), 7.49 (t, J=7.6 Hz, 1H), 7.29-7.21 (m, 2H), 6.86 (d, J=8.2 Hz, 1H), 3.76 (s, 2H), 3.59 (s, 2H), 2.90 (t, J=5.9 Hz, 2H), 2.78 (t, J=5.9 Hz, 2H); $^{13}$C NMR (126 MHz, CDCl$_3$) δ 165.9, 142.1, 136.3, 134.5, 133.3, 133.1, 131.5, 129.1, 128.9, 128.3, 127.5, 126.6, 120.0, 119.9, 118.9, 107.3, 62.2, 55.5, 50.4, 28.7; Mass Spectrum (ESI) [M–Cl]$^+$ C$_{24}$H$_{21}$BrN$_3$O: 460.4; HRMS (ESI) [M–Cl]$^+$ calcd for C$_{24}$H$_{21}$BrN$_3$O: 446.0863. found 446.0850.

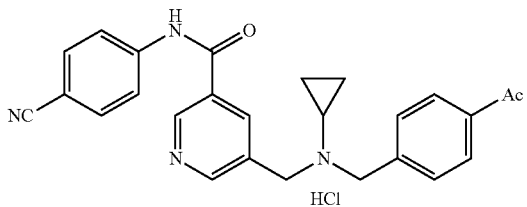

5-(((4-acetylbenzyl)(cyclopropyl)amino)methyl)-N-(4-cyanophenyl)nicotinamide hydrochloride (225r)

Compound 225r was synthesized following the general procedure of synthesizing compound 225. $^1$H NMR (500 MHz, MeOD) δ 8.95 (s, 1H), 8.62 (s, 1H), 8.20 (d, J=2.0 Hz, 1H), 7.97 (d, J=8.7 Hz, 2H), 7.93 (d, J=8.3 Hz, 2H), 7.77 (d, J=8.7 Hz, 2H), 7.44 (d, J=7.9 Hz, 2H), 3.87 (s, 2H), 3.86 (s, 2H), 2.59 (s, 3H), 2.02-1.92 (m, 1H), 0.51 (dd, J=6.4, 2.2 Hz, 2H), 0.35 (dd, J=3.7, 2.1 Hz, 2H); $^{13}$C NMR (126 MHz, MeOD) δ 200.2, 166.4, 153.8, 147.8, 145.9, 144.2, 138.3, 137.2, 136.8, 134.2, 131.7, 130.7, 129.4, 121.9, 119.8, 108.4, 60.6, 57.6, 38.4, 26.7, 8.4; Mass Spectrum (ESI) [M–Cl]$^+$ C$_{26}$H$_{25}$N$_4$O$_2$: 425.1; HRMS (ESI) [M–Cl]$^+$ calcd for C$_{26}$H$_{25}$N$_4$O$_2$: 425.1972. found 425.1980.

5-(((4-acetylbenzyl)(cyclopropyl)amino)methyl)-N-(4-cyanophenyl)-N-methylnicotinamide hydrochloride (225s)

Compound 225s was synthesized following the general procedure of synthesizing compound 225. $^1$H NMR (500 MHz, CDCl$_3$) δ 8.41-8.32 (m, 2H), 7.89 (d, J=8.2 Hz, 2H), 7.51 (d, J=8.6 Hz, 2H), 7.48 (t, J=2.1 Hz, 1H), 7.30 (d, J=8.1

Hz, 2H), 7.14 (d, J=8.6 Hz, 2H), 3.62 (s, 2H), 3.52 (s, 5H), 2.59 (s, 3H), 1.70 (dt, J=6.5, 3.0 Hz, 1H), 0.39-0.31 (m, 2H), 0.11 (dd, J=3.8, 2.1 Hz, 2H); $^{13}$C NMR (126 MHz, CDCl$_3$) δ 197.9, 168.1, 151.8, 148.3, 148.2, 143.8, 137.0, 136.2, 133.8, 133.4, 130.5, 129.2, 128.4, 127.3, 117.8, 110.4, 58.9, 55.6, 38.2, 36.6, 26.7, 7.7; Mass Spectrum (ESI) [M−Cl]$^+$ C$_{27}$H$_{27}$N$_4$O$_2$: 439.1

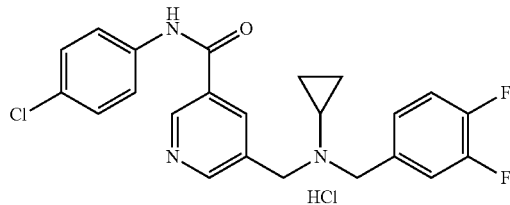

N-(4-chlorophenyl)-5-((cyclopropyl(3,4-difluorobenzyl)amino)methyl)nicotinamide hydrochloride (225t)

Compound 225t was synthesized following the general procedure of synthesizing compound 225. $^1$H NMR (500 MHz, CDCl$_3$) δ 8.92 (d, J=2.3 Hz, 1H), 8.58 (d, J=2.2 Hz, 1H), 8.27 (s, 1H), 8.05 (d, J=2.2 Hz, 1H), 7.61 (d, J=8.9 Hz, 2H), 7.33 (d, J=8.7 Hz, 2H), 7.12-7.01 (m, 2H), 6.95 (ddt, J=8.0, 3.7, 1.6 Hz, 1H), 3.71 (s, 2H), 3.64 (s, 2H), 1.83 (tt, J=6.6, 3.7 Hz, 1H), 0.49-0.37 (m, 2H), 0.34-0.21 (m, 2H); $^{13}$C NMR (126 MHz, CDCl$_3$) δ 164.0, 153.3, 150.1 (dd, J=248.2, 12.6 Hz), 149.5 (dd, J=247.4, 12.6 Hz), 146.2, 136.3, 136.1, 135.3, 134.6, 130.1 (d, J=3.0 Hz), 129.2, 124.9 (dd, J=6.2, 3.4 Hz), 121.7, 117.8 (d, J=16.9 Hz), 116.9 (d, J=17.1 Hz), 58.3, 55.8, 36.8, 7.8; Mass Spectrum (ESI) [M−Cl]$^+$ C$_{23}$H$_{21}$ClF$_2$N$_3$O: 428.1.

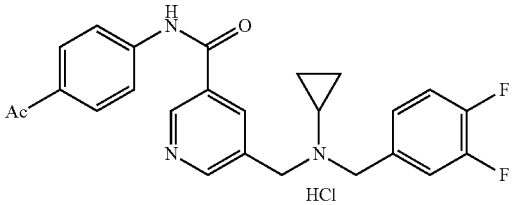

N-(4-acetylphenyl)-5-((cyclopropyl(3,4-difluorobenzyl)amino)methyl)nicotinamide hydrochloride (225u)

Compound 225u was synthesized following the general procedure of synthesizing compound 225. $^1$H NMR (500 MHz, CDCl$_3$) δ 8.97 (d, J=2.3 Hz, 1H), 8.66-8.41 (m, 2H), 8.09 (s, 1H), 7.98 (d, J=8.6 Hz, 2H), 7.79 (d, J=8.7 Hz, 2H), 7.13-6.99 (m, 2H), 6.95 (ddt, J=8.1, 3.6, 1.6 Hz, 1H), 3.72 (s, 2H), 3.64 (s, 2H), 2.59 (s, 3H), 1.84 (dq, J=6.6, 3.3 Hz, 1H), 0.45 (dt, J=6.4, 3.1 Hz, 2H), 0.27 (dd, J=3.8, 2.1 Hz, 2H); $^{13}$C NMR (126 MHz, CDCl$_3$) δ 197.1, 164.2, 153.5, 150.2 (dd, J=248.4, 12.7 Hz), 149.5 (dd, J=247.6, 12.6 Hz), 146.3, 142.0, 136.4, 135.3, 134.7, 133.4, 130.0, 129.8, 125.0 (dd, J=6.2, 3.4 Hz), 119.6, 117.8 (d, J=16.9 Hz), 116.9 (d, J=17.0 Hz), 58.4, 55.8, 36.8, 26.6, 7.8. Mass Spectrum (ESI) [M−Cl]$^+$ C$_{25}$H$_{24}$F$_2$N$_3$O: 436.3.

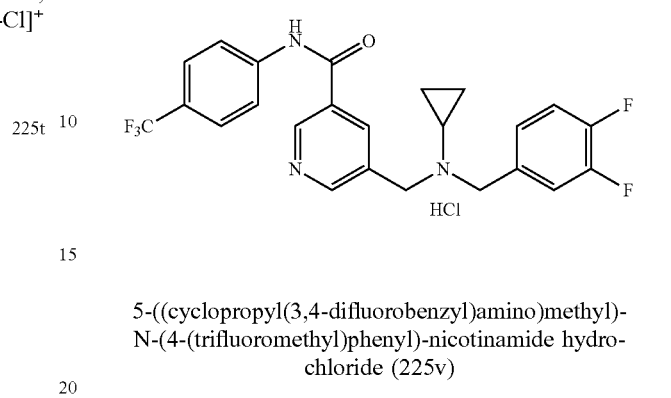

5-((cyclopropyl(3,4-difluorobenzyl)amino)methyl)-N-(4-(trifluoromethyl)phenyl)-nicotinamide hydrochloride (225v)

Compound 225v was synthesized following the general procedure of synthesizing compound 225. $^1$H NMR (500 MHz, CDCl$_3$) δ 8.95 (d, J=2.3 Hz, 1H), 8.59 (d, J=2.1 Hz, 1H), 8.49 (s, 1H), 8.07 (t, J=2.1 Hz, 1H), 7.80 (d, J=8.4 Hz, 2H), 7.63 (d, J=8.4 Hz, 2H), 7.10-7.02 (m, 2H), 6.95 (ddd, J=8.3, 4.4, 1.9 Hz, 1H), 3.72 (s, 2H), 3.64 (s, 2H), 1.84 (tt, J=6.7, 3.7 Hz, 1H), 0.48-0.41 (m, 2H), 0.30-0.23 (m, 2H); $^{13}$C NMR (126 MHz, CDCl$_3$) δ 164.2, 153.4, 150.2 (dd, J=248.2, 12.7 Hz), 149.5 (dd, J=247.5, 12.6 Hz), 146.2, 140.7, 136.4, 135.3, 134.8, 130.0, 126.9, 126.6, 126.4 (d, J=3.7 Hz), 125.1, 124.9 (d, J=2.6 Hz), 122.9, 120.1, 117.8 (d, J=16.8 Hz), 116.9 (d, J=17.0 Hz), 58.4, 55.8, 36.8, 7.8; Mass Spectrum (ESI) [M−Cl]$^+$ C$_{24}$H$_{21}$F$_5$N$_3$O: 462.2.

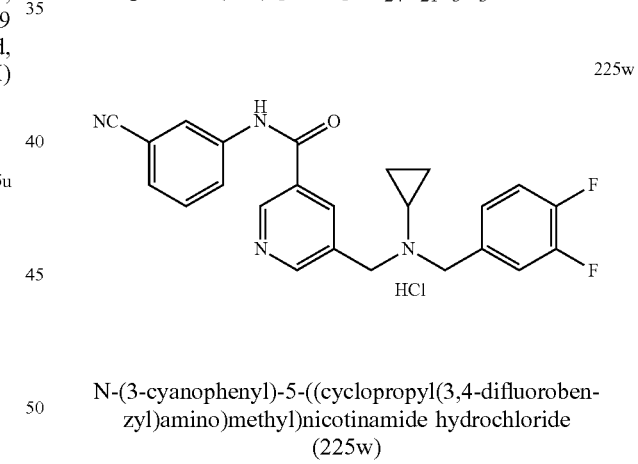

N-(3-cyanophenyl)-5-((cyclopropyl(3,4-difluorobenzyl)amino)methyl)nicotinamide hydrochloride (225w)

Compound 225w was synthesized following the general procedure of synthesizing compound 225. $^1$H NMR (500 MHz, CDCl$_3$) δ 8.90 (d, J=2.3 Hz, 1H), 8.54 (s, 1H), 8.52 (s, 1H), 8.06-7.98 (m, 2H), 7.88-7.82 (m, 1H), 7.46-7.36 (m, 2H), 7.05-6.95 (m, 2H), 6.92-6.85 (m, 1H), 3.67 (s, 2H), 3.59 (s, 2H), 1.79 (dt, J=6.4, 3.0 Hz, 1H), 0.39 (dd, J=6.5, 2.0 Hz, 2H), 0.24-0.14 (m, 2H); $^{13}$C NMR (126 MHz, CDCl$_3$) δ 164.3, 153.5, 150.1 (dd, J=248.1, 12.7 Hz), 149.5 (dd, J=247.5, 12.5 Hz), 146.3, 138.6, 136.5, 135.2, 134.8, 130.1, 129.7, 128.3, 125.0 (dd, J=6.1, 3.3 Hz), 124.6, 123.6, 118.5, 117.8 (d, J=16.9 Hz), 116.9 (d, J=17.0 Hz), 113.0, 58.4, 55.9, 36.8, 7.8; Mass Spectrum (ESI) [M−Cl]$^+$ C$_{24}$H$_{21}$F$_2$N$_4$O: 419.5; HRMS (ESI) [M−Cl]$^+$ calcd for C$_{24}$H$_{20}$ClF$_2$N$_4$O: 419.1678. found 419.1686.

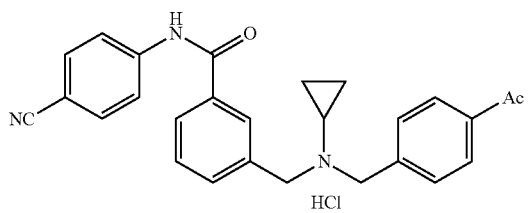

3-(((4-acetylbenzyl)(cyclopropyl)amino)methyl)-N-(4-cyanophenyl)benzamide hydrochloride (225x)

Compound 225x was synthesized following the general procedure of synthesizing compound 225. $^1$H NMR (500 MHz, CDCl$_3$) δ 8.07 (s, 1H), 7.90 (d, J=8.2 Hz, 2H), 7.84 (d, J=8.7 Hz, 2H), 7.78 (s, 1H), 7.76-7.66 (m, 3H), 7.54-7.48 (m, 1H), 7.45 (t, J=7.6 Hz, 1H), 7.38 (d, J=7.8 Hz, 2H), 3.77 (s, 2H), 3.76 (s, 2H), 2.61 (s, 3H), 1.95-1.84 (m, 1H), 0.47 (dd, J=6.5, 2.1 Hz, 2H), 0.40-0.28 (m, 2H); $^{13}$C NMR (126 MHz, CDCl$_3$) δ 198.1, 166.0, 144.3, 142.0, 140.0, 136.0, 134.0, 133.4, 133.4, 129.5, 128.7, 128.2, 125.4, 119.9, 118.9, 107.4, 58.8, 37.0, 26.7, 7.8; Mass Spectrum (ESI) [M−Cl]$^+$ C$_{27}$H$_{26}$N$_3$O$_2$: 424.2;

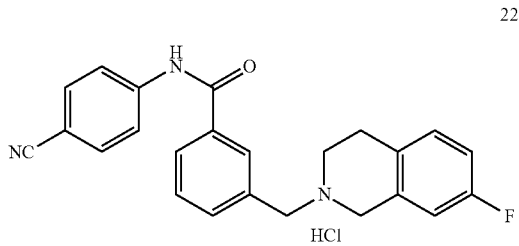

N-(4-cyanophenyl)-3-((7-fluoro-3,4-dihydroisoquinolin-2(1H)-yl)methyl)benzamide hydrochloride (225Ab)

Compound 225Ab was synthesized following the general procedure of synthesizing compound 225. $^1$H NMR (500 MHz, CDCl$_3$) δ 8.03 (s, 1H), 7.87 (dd, J=7.8, 4.7 Hz, 4H), 7.70-7.64 (m, 2H), 7.61 (d, J=7.6 Hz, 1H), 7.53 (t, J=7.6 Hz, 1H), 7.11 (dd, J=8.4, 5.6 Hz, 1H), 6.89 (td, J=8.5, 2.5 Hz, 1H), 6.72 (dd, J=9.3, 2.6 Hz, 1H), 3.83 (s, 2H), 3.70 (s, 2H), 2.98-2.89 (m, 2H), 2.89-2.81 (m, 2H); $^{13}$C NMR (126 MHz, CDCl$_3$) δ 165.8, 161.1 (d, J=244.2 Hz), 142.1, 134.5, 133.3, 133.1, 130.2 (d, J=8.0 Hz), 129.2, 127.7, 119.9, 118.9, 113.9, 113.0 (d, J=21.4 Hz), 107.3, 61.9, 55.6, 50.6, 27.9; Mass Spectrum (ESI) [M−Cl]$^+$ C$_{24}$H$_{21}$FN$_3$O: 386.5.

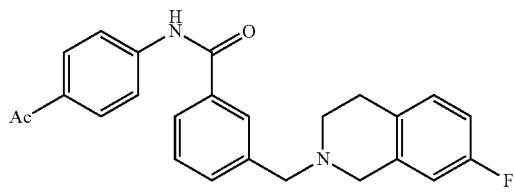

N-(4-acetylphenyl)-3-((7-fluoro-3,4-dihydroisoquinolin-2(1H)-yl)methyl)benzamide hydrochloride (225Ac)

Compound 225Ac was synthesized following the general procedure of synthesizing compound 225. $^1$H NMR (500 MHz, CDCl$_3$) δ 8.30 (s, 1H), 8.01 (d, J=8.7 Hz, 3H), 7.93-7.78 (m, 3H), 7.61 (d, J=7.5 Hz, 1H), 7.52 (t, J=7.6 Hz, 1H), 7.10 (t, J=6.9 Hz, 1H), 6.88 (t, J=8.1 Hz, 1H), 6.72 (d, J=9.0 Hz, 1H), 3.82 (s, 2H), 3.70 (s, 2H), 2.99-2.89 (m, 2H), 2.88-2.80 (m, 2H), 2.62 (s, 3H); $^{13}$C NMR (126 MHz, CDCl$_3$) δ 197.0, 165.7, 161.0 (d, J=244.1 Hz), 142.4, 134.8, 133.0, 132.9, 130.2 (d, J=7.7 Hz), 129.8, 129.1, 127.7, 126.7, 119.3, 113.8, 113.0 (d, J=21.2 Hz), 62.0, 55.6, 50.6, 28.0, 26.5. Mass Spectrum (ESI) [M−Cl]$^+$ C$_{25}$H$_{24}$FN$_2$O$_2$: 403.2.

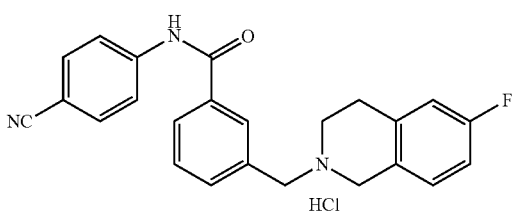

N-(4-cyanophenyl)-3-((6-fluoro-3,4-dihydroisoquinolin-2(1H)-yl)methyl)benzamide hydrochloride (225Ad)

Compound 225Ad was synthesized following the general procedure of synthesizing compound 225. $^1$H NMR (500 MHz, CDCl$_3$) δ 8.15 (s, 1H), 7.93 (s, 1H), 7.86-7.80 (m, 3H), 7.67 (d, J=8.6 Hz, 2H), 7.63 (d, J=7.7 Hz, 1H), 7.51 (t, J=7.7 Hz, 1H), 6.96 (dd, J=9.2, 5.8 Hz, 1H), 6.87-6.80 (m, 2H), 3.77 (s, 2H), 3.63 (s, 2H), 2.92 (t, J=6.0 Hz, 2H), 2.78 (t, J=5.9 Hz, 2H); $^{13}$C NMR (126 MHz, CDCl$_3$) δ 165.9, 161.3 (d, J=244.2 Hz), 142.0, 139.4, 136.2 (d, J=7.5 Hz), 134.3, 133.4, 133.2, 130.0, 129.1, 128.0 (d, J=8.1 Hz), 127.4, 126.4, 119.9, 118.9, 115.0 (d, J=20.7 Hz), 112.9 (d, J=21.5 Hz), 107.4, 62.3, 55.6, 50.4, 29.2. Mass Spectrum (ESI) [M−Cl]$^+$ C$_{24}$H$_{21}$FN$_3$O: 386.2.

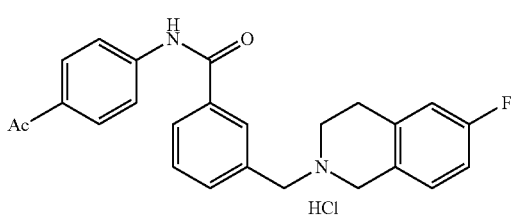

N-(4-acetylphenyl)-3-((6-fluoro-3,4-dihydroisoquinolin-2(1H)-yl)methyl)benzamide hydrochloride (225Ae)

Compound 225Ae was synthesized following the general procedure of synthesizing compound 225. $^1$H NMR (500 MHz, CDCl$_3$) δ 8.08-7.99 (m, 3H), 7.92 (d, J=1.8 Hz, 1H), 7.85 (d, J=7.9 Hz, 1H), 7.80 (d, J=8.7 Hz, 2H), 7.65-7.60 (m, 1H), 7.52 (t, J=7.6 Hz, 1H), 6.97 (dd, J=9.3, 5.6 Hz, 1H), 6.87-6.82 (m, 2H), 3.78 (s, 2H), 3.63 (s, 2H), 2.92 (t, J=5.9 Hz, 2H), 2.78 (t, J=5.9 Hz, 2H), 2.63 (s, 3H); $^{13}$C NMR (126 MHz, CDCl$_3$) δ 196.9, 165.7, 161.3 (d, J=243.9 Hz), 142.2, 139.5, 136.3 (d, J=7.3 Hz), 134.6, 133.1, 133.0, 130.1, 129.8, 129.1, 128.0 (d, J=8.1 Hz), 127.3, 126.2, 119.3, 115.0 (d, J=20.6 Hz), 112.9 (d, J=21.6 Hz), 62.4, 55.6, 50.4, 29.3, 26.5. Mass Spectrum (ESI) [M−Cl]$^+$ C$_{25}$H$_{24}$FN$_2$O$_2$: 403.3.

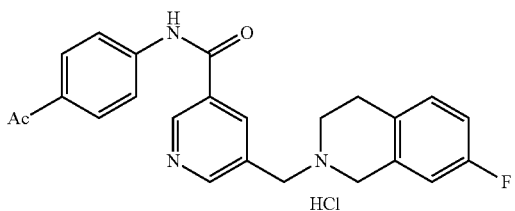

225Af

N-(4-acetylphenyl)-5-((7-fluoro-3,4-dihydroisoquinolin-2(1H)-yl)methyl)-nicotinamide hydrochloride (225Af)

Compound 225Af was synthesized following the general procedure of synthesizing compound 225. $^1$H NMR (500 MHz, CDCl$_3$) δ 9.08 (d, J=2.3 Hz, 1H), 8.80 (d, J=1.9 Hz, 1H), 8.27 (t, J=2.2 Hz, 1H), 8.18 (s, 1H), 8.09-7.98 (m, 2H), 7.87-7.76 (m, 2H), 7.09 (dd, J=8.4, 5.7 Hz, 1H), 6.88 (td, J=8.5, 2.6 Hz, 1H), 6.71 (dd, J=9.4, 2.6 Hz, 1H), 3.80 (s, 2H), 3.66 (s, 2H), 2.89 (t, J=5.9 Hz, 2H), 2.80 (t, J=5.9 Hz, 2H), 2.63 (s, 3H); $^{13}$C NMR (126 MHz, CDCl$_3$) δ 196.9, 164.0, 161.0 (d, J=243.8 Hz), 153.4, 147.3, 141.8, 135.9 (d, J=7.2 Hz), 135.4, 134.4, 133.5, 130.2, 130.1, 129.9, 129.5, 129.5, 119.6, 119.5, 113.6 (d, J=21.3 Hz), 112.9 (d, J=21.3 Hz), 59.3, 56.0, 50.7, 28.3, 26.6. Mass Spectrum (ESI) [M−Cl]$^+$ C$_{24}$H$_{23}$FN$_3$O$_2$: 404.3.

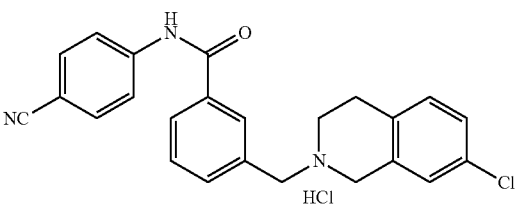

225Ag

3-((7-chloro-3,4-dihydroisoquinolin-2(1H)-yl)methyl)-N-(4-cyanophenyl)benzamide hydrochloride (225Ag)

Compound 225Ag was synthesized following the general procedure of synthesizing compound 225. $^1$H NMR (500 MHz, CDCl$_3$) δ 8.10 (s, 1H), 7.90 (s, 1H), 7.85-7.78 (m, 3H), 7.66 (d, J=8.6 Hz, 2H), 7.61-7.57 (m, 1H), 7.49 (t, J=7.6 Hz, 1H), 7.12-7.05 (m, 2H), 6.91 (d, J=8.1 Hz, 1H), 3.75 (s, 2H), 3.60 (s, 2H), 2.89 (t, J=5.9 Hz, 2H), 2.76 (t, J=5.9 Hz, 2H); $^{13}$C NMR (126 MHz, CDCl$_3$) δ 165.8, 142.0, 136.0, 134.4, 133.4, 133.1, 131.8, 129.1, 128.6, 127.9, 127.4, 126.4, 126.0, 119.9, 118.8, 107.4, 62.3, 55.6, 50.4, 29.7; Mass Spectrum (ESI) [M−Cl]$^+$ C$_{24}$H$_{21}$ClN$_3$O: 403.3.

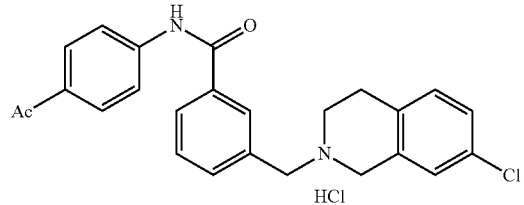

225Ah

N-(4-acetylphenyl)-3-((7-chloro-3,4-dihydroisoquinolin-2(1H)-yl)methyl)benzamide hydrochloride (225Ah)

Compound 225Ah was synthesized following the general procedure of synthesizing compound 225. $^1$H NMR (500 MHz, CDCl$_3$) δ 8.12 (s, 1H), 8.01 (d, J=8.8 Hz, 2H), 7.92 (s, 1H), 7.87-7.83 (m, 1H), 7.80 (d, J=8.8 Hz, 2H), 7.64-7.60 (m, 1H), 7.51 (t, J=7.6 Hz, 1H), 7.15-7.07 (m, 2H), 6.93 (d, J=8.1 Hz, 1H), 3.77 (s, 2H), 3.62 (s, 2H), 2.90 (t, J=6.0 Hz, 2H), 2.77 (t, J=5.9 Hz, 2H), 2.62 (s, 3H); $^{13}$C NMR (126 MHz, CDCl$_3$) δ 197.0, 165.8, 142.3, 139.4, 136.1, 134.7, 133.1, 133.0, 132.9, 131.7, 129.8, 129.1, 128.5, 127.9, 127.4, 126.2, 125.9, 119.3, 62.3, 55.6, 50.3, 29.0, 26.5; Mass Spectrum (ESI) [M−Cl]$^+$ C$_{25}$H$_{24}$ClN$_2$O$_2$: 420.2.

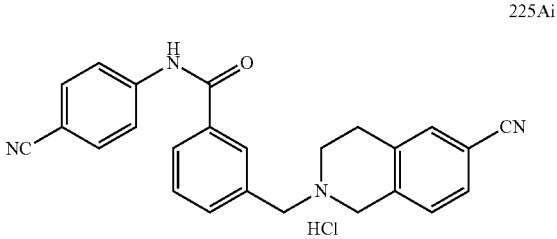 [SMILES: N#Cc1ccc(NC(=O)c2cccc(CN3CCc4cc(C#N)ccc4C3)c2)cc1 ; Cl]

225Ai

3-((6-cyano-3,4-dihydroisoquinolin-2(1H)-yl)methyl)-N-(4-cyanophenyl)benzamide hydrochloride (225Ai)

Compound 225Ai was synthesized following the general procedure of synthesizing compound 225. $^1$H NMR (500 MHz, CDCl$_3$) δ 8.28 (s, 1H), 7.93 (s, 1H), 7.86-7.80 (m, 3H), 7.70-7.64 (m, 2H), 7.62 (d, J=7.9 Hz, 1H), 7.51 (t, J=7.7 Hz, 1H), 7.43-7.38 (m, 2H), 7.09 (d, J=7.9 Hz, 1H), 3.78 (s, 2H), 3.69 (s, 2H), 2.95 (t, J=5.9 Hz, 2H), 2.81 (t, J=5.8 Hz, 2H); $^{13}$C NMR (126 MHz, CDCl$_3$) δ 165.9, 142.1, 140.1, 139.0, 135.7, 134.4, 133.3, 133.3, 133.1, 132.5, 129.2, 129.1, 127.7, 127.5, 126.4, 120.0, 119.06, 118.9, 110.0, 107.3, 62.2, 55.9, 50.1, 28.8; Mass Spectrum (ESI) [M−Cl]$^+$ C$_{25}$H$_{21}$N$_4$O: 393.4.

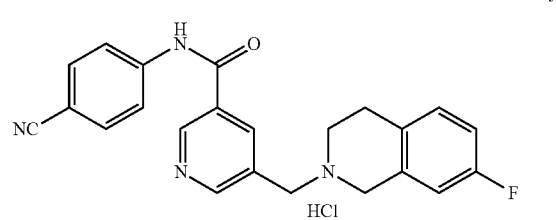

225Aj

N-(4-cyanophenyl)-5-((7-fluoro-3,4-dihydroisoquinolin-2(1H)-yl)methyl)nicotinamide hydrochloride (225Aj)

Compound 225Aj was synthesized following the general procedure of synthesizing compound 225. $^1$H NMR (500 MHz, CDCl$_3$) δ 9.08 (s, 1H), 8.81 (s, 1H), 7.85 (d, J=8.7 Hz, 2H), 7.71 (d, J=8.7 Hz, 2H), 7.11 (dd, J=8.5, 5.6 Hz, 1H), 6.92-6.86 (m, 1H), 6.72 (dd, J=9.5, 2.5 Hz, 1H), 3.83 (s, 2H), 3.69 (s, 2H), 2.92 (s, 2H), 2.84 (s, 2H); $^{13}$C NMR (126 MHz, CDCl$_3$) δ 164.0, 161.0 (d, J=245.2 Hz), 153.5, 147.5, 141.5, 135.5, 133.4, 130.2 (d, J=8.2 Hz), 129.8, 120.1, 119.2, 118.7, 113.8, 112.9 (d, J=21.5 Hz), 108.0, 59.2, 55.9, 50.7, 24.4. Mass Spectrum (ESI) [M–Cl]$^+$ C$_{23}$H$_{20}$FN$_4$O: 387.1.

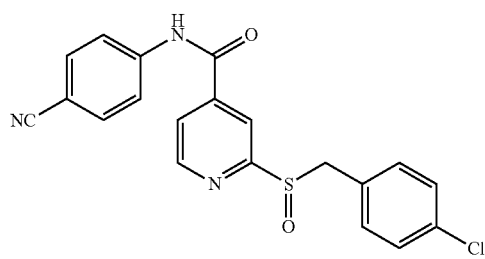

2-((4-chlorobenzyl)sulfinyl)-N-(4-cyanophenyl) isonicotinamide (235a)

Compound 235a was synthesized following the general procedure of synthesizing compound 235. White foam; $^1$H NMR (500 MHz, DMSO) δ 11.05 (s, 1H), 8.96 (d, J=5.0 Hz, 1H), 8.06 (s, 1H), 8.04 (dd, J=4.9, 1.7 Hz, 1H), 7.98 (d, J=8.8 Hz, 2H), 7.87 (d, J=8.8 Hz, 2H), 7.33 (d, J=8.5 Hz, 2H), 7.06 (d, J=8.4 Hz, 2H), 4.54 (d, J=13.2 Hz, 1H), 4.20 (d, J=13.1 Hz, 1H); $^{13}$C NMR (126 MHz, DMSO) δ 164.4, 163.5, 150.5, 143.2, 142.7, 133.2, 132.8, 132.1, 128.8, 128.1, 123.2, 120.6, 118.9, 118.0, 106.1, 58.0; Mass Spectrum (ESI) [M–H]$^-$ C$_{20}$H$_{13}$ClN$_3$O$_2$S: 394.3.

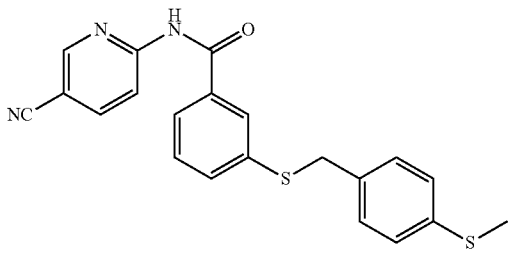

N-(5-cyanopyridin-2-yl)-3-((4-(methylthio)benzyl) thio)benzamide (211a)

Compound 211a was synthesized following the general procedure of synthesizing compound 211. White Solid, Melting point: 161-162° C.; $^1$H NMR (500 MHz, CDCl$_3$) δ 8.73 (s, 1H), 8.56 (d, J=2.3 Hz, 1H), 8.50 (d, J=8.8 Hz, 1H), 7.99 (dd, J=8.7, 2.2 Hz, 1H), 7.79 (t, J=1.8 Hz, 1H), 7.69 (d, J=7.8 Hz, 1H), 7.53-7.45 (m, 1H), 7.40 (t, J=7.8 Hz, 1H), 7.23 (d, J=8.4 Hz, 2H), 7.18 (d, J=8.4 Hz, 2H), 4.14 (s, 2H), 2.45 (s, 3H); $^{13}$C NMR (126 MHz, CDCl$_3$) δ 165.3, 153.9, 151.7, 141.7, 138.1, 137.8, 133.9, 133.7, 133.4, 129.4, 129.3, 128.2, 126.6, 125.0, 116.7, 113.7, 105.3, 38.2, 15.7; Mass Spectrum (ESI) [M-1-1]$^-$ C$_{21}$H$_{16}$N$_3$OS$_2$: 390.0.

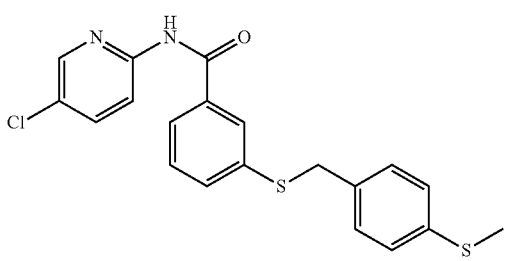

N-(5-chloropyridin-2-yl)-3-((4-(methylthio)benzyl) thio)benzamide (211b)

Compound 211b was synthesized following the general procedure of synthesizing compound 211. White Solid, Melting point: 159-161° C.; $^1$H NMR (500 MHz, CDCl$_3$) δ 8.44 (s, 1H), 8.35 (d, J=8.9 Hz, 1H), 8.27 (d, J=2.6 Hz, 1H), 7.81 (t, J=1.8 Hz, 1H), 7.73 (dd, J=8.9, 2.5 Hz, 1H), 7.71-7.66 (m, 1H), 7.50-7.44 (m, 1H), 7.38 (t, J=7.8 Hz, 1H), 7.23 (d, J=8.4 Hz, 2H), 7.18 (d, J=8.4 Hz, 2H), 4.14 (s, 2H), 2.46 (s, 3H); $^{13}$C NMR (126 MHz, CDCl$_3$) δ 164.9, 149.6, 146.6, 138.1, 137.8, 137.7, 134.5, 133.5, 133.3, 129.3, 128.9, 127.1, 126.6, 124.8, 114.7, 38.3, 15.7; Mass Spectrum (ESI) [M–H]$^-$ C$_{20}$H$_{16}$ClN$_2$OS$_2$: 399.9.

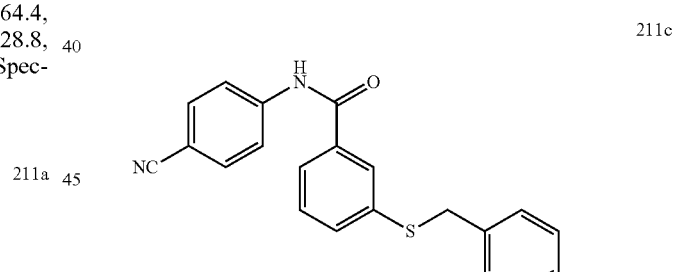

N-(4-cyanophenyl)-3-((4-methoxybenzyl)thio)benzamide (211c)

Compound 211c was synthesized following the general procedure of synthesizing compound 211. White Solid, Melting point: 167-169° C.; $^1$H NMR (500 MHz, CDCl$_3$) δ 7.75 (m, 3H), 7.67 (m, 3H), 7.61 (t, J=1.8 Hz, 1H), 7.52 (m, 1H), 7.41 (t, J=7.8 Hz, 1H), 7.21 (d, J=8.6 Hz, 2H), 6.84 (d, J=8.6 Hz, 2H), 4.11 (s, 2H), 3.77 (s, 3H); $^{13}$C NMR (126 MHz, CDCl$_3$) δ 165.2, 158.9, 141.8, 137.7, 134.6, 133.8, 133.4, 130.2, 129.4, 128.9, 128.3, 125.2, 119.8, 118.8, 114.0, 107.5, 55.3, 38.4; Mass Spectrum (ESI) [M–H]$^-$ C$_{22}$H$_{17}$N$_2$O$_2$S: 373.3.

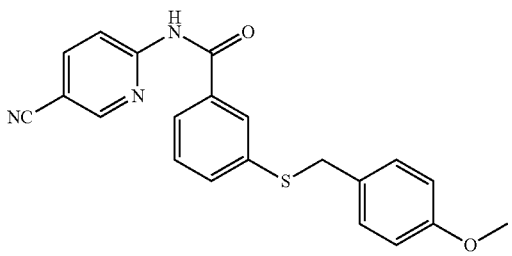

N-(5-cyanopyridin-2-yl)-3-((4-methoxybenzyl)thio)benzamide (211d)

Compound 211d was synthesized following the general procedure of synthesizing compound 211. White Solid, Melting point: 163-164° C.; $^1$H NMR (500 MHz, CDCl$_3$) δ 8.62-8.60 (m, 1H), 8.57 (s, 1H), 8.51 (dd, J=8.7, 0.9 Hz, 1H), 8.01 (dd, J=8.7, 2.3 Hz, 1H), 7.78 (t, J=1.8 Hz, 1H), 7.71-7.67 (m, 1H), 7.54-7.49 (m, 1H), 7.41 (t, J=7.8 Hz, 1H), 7.24 (d, J=8.7 Hz, 2H), 6.84 (d, J=8.6 Hz, 2H), 4.15 (s, 2H), 3.78 (s, 3H); $^{13}$C NMR (126 MHz, CDCl$_3$) δ 165.2, 158.9, 153.8, 151.7, 141.7, 138.4, 133.8, 133.7, 130.0, 129.4, 128.5, 128.0, 124.8, 116.7, 114.0, 113.7, 105.3, 55.2, 38.1; Mass Spectrum (ESI) [M−H]$^−$ C$_{21}$H$_{16}$N$_3$O$_2$S: 374.3.

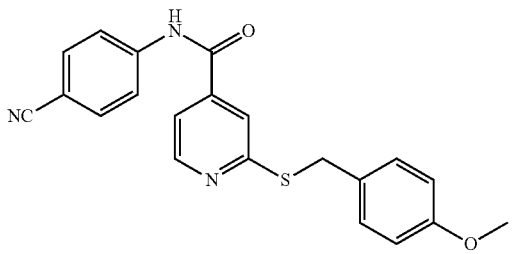

N-(4-cyanophenyl)-2-((4-methoxybenzyl)thio)isonicotinamide (211f)

Compound 211f was synthesized following the general procedure of synthesizing compound 211. White Solid, Melting point: 201-203° C.; $^1$H NMR (500 MHz, DMSO) δ 11.0 (s, 1H), 8.67 (d, J=5.2 Hz, 1H), 8.00 (d, J=8.7 Hz, 2H), 7.85 (d, J=8.7 Hz, 2H), 7.82-7.78 (m, 1H), 7.60 (dd, J=5.1, 1.6 Hz, 1H), 7.35 (d, J=8.6 Hz, 2H), 6.87 (d, J=8.6 Hz, 2H), 4.45 (s, 2H), 3.72 (s, 3H); $^{13}$C NMR (126 MHz, DMSO) δ 164.2, 159.3, 158.3, 150.0, 142.8, 141.9, 133.2, 130.1, 129.3, 120.4, 119.5, 118.9, 117.9, 113.8, 105.9, 55.0, 33.0; Mass Spectrum (ESI) [M+H]$^+$ C$_{21}$H$_{18}$N$_3$O$_2$S: 376.3.

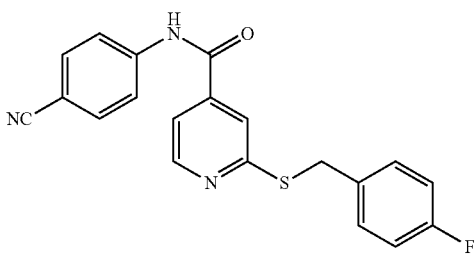

N-(4-cyanophenyl)-2-((4-fluorobenzyl)thio)isonicotinamide (211e)

Compound 211e was synthesized following the general procedure of synthesizing compound 211. White Solid, Melting point: 160-162° C.; $^1$H NMR (500 MHz, CDCl$_3$) δ 8.61 (d, J=5.2 Hz, 1H), 8.12 (s, 1H), 7.77 (d, J=8.4 Hz, 2H), 7.66 (d, J=8.3 Hz, 2H), 7.53 (s, 1H), 7.45-7.31 (m, 3H), 6.98 (t, J=8.7 Hz, 2H), 4.45 (s, 2H); $^{13}$C NMR (126 MHz, CDCl$_3$) δ 163.8, 162.0 (d, J=246.1 Hz) 160.5, 150.4, 141.3 (d, J=9.0 Hz), 133.5, 130.6 (d, J=8.1 Hz), 120.2, 119.3, 118.7, 116.7, 115.4 (d, J=21.5 Hz), 108.0, 33.7; Mass Spectrum (ESI) [M−H]$^−$ C$_{20}$H$_{13}$FN$_3$OS: 362.1

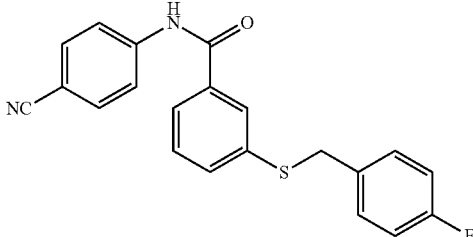

N-(4-cyanophenyl)-3-((4-fluorobenzyl)thio)benzamide (211g)

Compound 211g was synthesized following the general procedure of synthesizing compound 211. White Solid, Melting point: 148-150° C.; $^1$H NMR (500 MHz, CDCl$_3$) δ 7.90 (s, 1H), 7.77 (d, J=8.8 Hz, 2H), 7.74-7.70 (m, 1H), 7.69-7.64 (m, 3H), 7.50-7.46 (m, 1H), 7.39 (t, J=7.7 Hz, 1H), 7.29-7.23 (m, 2H), 6.99 (t, J=8.6 Hz, 2H), 4.14 (s, 2H); $^{13}$C NMR (126 MHz, CDCl$_3$) δ 165.17, 162.0 (d, J=246.6 Hz), 141.76, 137.52, 134.73, 133.52, 133.38, 132.6 (d, J=3.2 Hz), 130.5 (d, J=8.1 Hz), 129.42, 128.26, 124.99, 119.89, 118.76, 115.5 (d, J=21.5 Hz), 107.54, 38.01; Mass Spectrum (ESI) [M−H]$^−$ C$_{21}$H$_{14}$FN$_2$OS: 361.4.

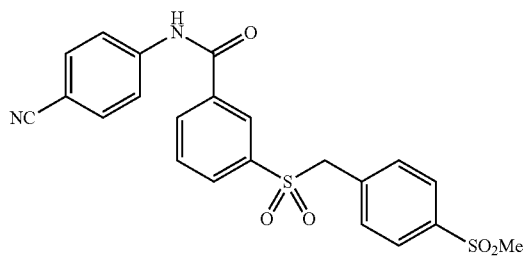

N-(4-cyanophenyl)-3-((4-(methylsulfonyl)benzyl)sulfonyl)benzamide (212a)

Compound 212a was synthesized following the general procedure of synthesizing compound 212. White foam; $^1$H NMR (500 MHz, CDCl$_3$) 8.34-8.23 (m, 1H), 8.23-8.08 (m, 1H), 7.89-7.75 (m, 2H), 7.70-7.60 (m, 3H), 7.53-7.39 (m, 3H), 7.32-7.20 (m, 2H), 4.42 (s, 2H), 2.89-2.87 (s, 3H); $^{13}$C NMR (126 MHz, CDCl$_3$) δ 169.2, 147.9, 145.7, 143.0, 140.6, 138.8, 138.6, 137.6, 136.7, 136.1, 134.2, 132.7, 132.3, 125.5, 123.8, 111.5, 66.4, 49.1. Mass Spectrum (ESI) [M+H]$^+$ C$_{22}$H$_{19}$N$_2$O$_5$S$_2$: 455.4.

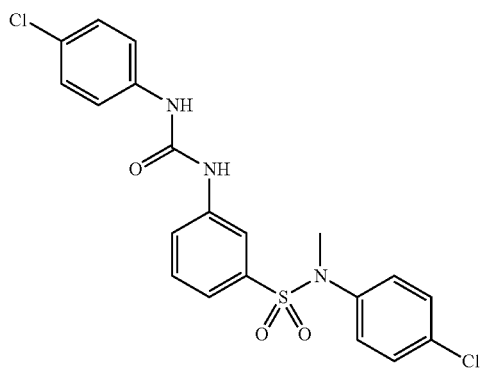

N-(4-chlorophenyl)-3-(3-(4-chlorophenyl)ureido)-N-methylbenzenesulfonamide (233a)

Compound 233a was synthesized following the general procedure of synthesizing compound 233. White foam; $^1$H NMR (500 MHz, DMSO) δ 9.14 (s, 1H), 8.89 (s, 1H), 7.82 (t, J=2.0 Hz, 1H), 7.72-7.66 (m, 1H), 7.53-7.47 (m, 3H), 7.44-7.39 (m, 2H), 7.34 (d, J=8.8 Hz, 2H), 7.19-7.13 (m, 2H), 7.09-7.05 (m, 1H), 3.15 (s, 3H); $^{13}$C NMR (126 MHz, DMSO) δ 152.2, 140.4, 139.9, 138.3, 136.0, 131.6, 129.7, 128.8, 128.6, 127.8, 125.7, 122.6, 120.5, 120.0, 116.5, 37.8. Mass Spectrum (ESI) [M+Cl]$^-$ C$_{20}$H$_{18}$Cl$_3$N$_3$O$_3$S 485.9.

TABLE 10

| | Bioactivity data: % of SIRT2 Inhibition at 10 μM | | |
|---|---|---|---|
| No. | Comp. No. | Comp. ID | % of SIRT2 Inhibition at 10 μM |
| 1 | 203e | HWI-12 | 0 |
| 2 | 203l | HWI-38 | 25 |
| 3 | 203m | HWI-39 | 28 |
| 4 | 203n | HWI-40 | 18 |
| 5 | 203o | HWI-41 | 14 |
| 6 | 203p | HWI-48D | 50 |
| 7 | 203q | HWI-48M | 29 |
| 8 | 203s | HWI-49D | 59 |
| 9 | 203r | HWI-49M | 30 |
| 10 | 203t | HWI-50D | 17 |
| 11 | 203u | HWI-50M | 22 |
| 12 | 203v | HWI-51 | 25 |
| 13 | 203w | HWI-52 | 31 |
| 14 | 203x | HWI-53 | 15 |
| 15 | 203Aa | HWI-67 | 15 |
| 16 | 233a | HWI-92 | 0 |
| 17 | 203Ab | HWI-97 | 45 |
| 18 | 203Ac | HWI-101 | 15 |
| 19 | 203Ad | HWI-108 | 0 |
| 20 | 203Ae | HWI-109 | 26 |
| 21 | 203Af | HWI-110 | 15 |
| 22 | 203Ag | HWI-112 | 14 |
| 23 | 203Ah | HWI-113 | 16 |
| 24 | 203Ai | HWI-115 | 16 |
| 25 | 203Aj | HWI-116 | 10 |
| 26 | 203Ak | HWI-119 | 0 |
| 27 | 203Al | HWI-120 | 0 |
| 28 | 207a | HWI-131 | 28 |
| 29 | 207b | HWI-134 | 57 |
| 30 | 207c | HWI-136 | 47 |
| 31 | 207d | HWI-137 | 26 |
| 32 | 203Am | HWI-158 | 64 |
| 33 | 203An | HWI-161 | 28 |
| 34 | 203Ao | HWI-163 | 0 |
| 35 | 203Ap | HWI-166 | 45 |
| 36 | 203Aq | HWI-170 | 14 |
| 37 | 203Ar | HWI-171 | 20 |
| 38 | 203As | HWI-174 | 33 |
| 39 | 203At | HWI-211 | 38 |
| 40 | 203Au | HWI-212 | 39 |
| 41 | 207e | HWI-238 | 69 |
| 42 | 203Av | HWI-303 | 51 |
| 43 | 203Aw | HWI-317 | 61 |
| 44 | 203Ax | HWI-485 | 51 |
| 45 | 203Ay | HWI-501 | 40 |
| 46 | 203Az | HWI-503 | 59 |
| 47 | 203Ba | HWI-504 | 53 |
| 48 | 234d | HWI-555 | 12 |
| 49 | 211a | HWI-207 | 63 |
| 50 | 211b | HWI-208 | 42 |
| 51 | 216a | HWI-209 | 60 |
| 52 | 216b | HWI-210 | 22 |
| 53 | 211c | HWI-215 | 69 |
| 54 | 211d | HWI-216 | 46 |
| 55- | 216c | HWI-217 | 40 |
| 56 | 216d | HWI-218 | 8 |
| 57 | 216e | HWI-221 | 32 |
| 58 | 216f | HWI-226 | 36 |
| 59 | 216g | HWI-227 | 64 |
| 60 | 211e | HWI-228 | 74 |
| 61 | 216h | HWI-232 | 50 |
| 62 | 216i | HWI-233 | 15 |
| 63 | 211f | HWI-234 | 68 |
| 64 | 211g | HWI-242 | 59 |
| 65 | 221a | HWI-251 | 41 |
| 66 | 221b | HWI-256 | 28 |
| 67 | 212a | HWI-262 | 19 |
| 68 | 221c | HWI-264 | 75 |
| 69 | 216j | HWI-274 | 67 |
| 70 | 216k | HWI-278 | 39 |
| 71 | 216l | HWI-282 | 88 |
| 72 | 216m | HWI-284 | 56 |
| 73 | 216n | HWI-286 | 34 |
| 74 | 216o | HWI-291 | 54 |
| 75 | 216p | HWI-297 | 55 |
| 76 | 216q | HWI-311 | 56 |
| 77 | 216r | HWI-323 | 69 |
| 78 | 216s | HWI-324 | 27 |
| 79 | 216t | HWI-369 | 0 |

TABLE 10-continued

Bioactivity data: % of SIRT2 Inhibition at 10 μM

| No. | Comp. No. | Comp. ID | % of SIRT2 Inhibition at 10 μM |
|---|---|---|---|
| 80 | 216u | HWI-371 | 0 |
| 81 | 216v | HWI-440 | 11 |
| 82 | 216w | HWI-442 | 15 |
| 83 | 216x | HWI-443 | 25 |
| 84 | 216y | HWI-444 | 19 |
| 85 | 216z | HWI-477 | 64 |
| 86 | 216Aa | HWI-478 | 56 |
| 87 | 216Ab | HWI-479 | 84 |
| 88 | 216Ac | HWI-480 | 93 |
| 89 | 216Ad | HWI-484 | 58 |
| 90 | 216Ae | HWI-486 | 57 |
| 91 | 216Af | HWI-487 | 12 |
| 92 | 216Ag | HWI-516 | 92 |
| 93 | 216Ah | HWI-518 | 41 |
| 94 | 216Ai | HWI-520 | 80 |
| 95 | 216Aj | HWI-523 | 43 |
| 96 | 216Ak | HWI-664 | 98 |
| 97 | 216Al | HWI-665 | 60 |
| 98 | 216Am | HWI-723 | 21 |
| 99 | 216An | HWI-742 | 95 |
| 100 | 216Ao | HWI-743 | 37 |
| 101 | 216Ap | HWI-744 | 44 |
| 102 | 216Aq | HWI-745 | 0 |
| 103 | 216Ar | HWI-794 | 27 |
| 104 | 216As | HWI-847 | 97 |
| 105 | 216At | AP-I-029 | 34 |
| 106 | 216Au | AP-I-031 | 27 |
| 107 | 216Av | AP-I-044 | 89 |
| 108 | 216Aw | AP-I-049 | 62 |
| 109 | 216Ax | AP-I-055 | 56 |
| 110 | 216Ay | AP-I-057 | 94 |
| 111 | 216Az | AP-I-058 | 58 |
| 112 | 216Ba | AP-I-059 | 85 |
| 113 | 216Bb | AP-I-062 | 70 |
| 114 | 216Bc | AP-I-063 | 77 |
| 115 | 216Bd | AP-I-066 | 28 (5 μM) |
| 116 | 216Be | AP-I-071 | 43 (5 μM) |
| 117 | 216Bf | AP-I-076 | 51 (5 μM) |
| 118 | 216Bg | AP-I-077 | 40 (5 μM) |
| 119 | 216Bh | AP-I-078 | 85 (5 μM) |
| 120 | 216Bi | AP-I-079 | 8 (5 μM) |
| 121 | 216Bj | AP-I-082 | 28 (5 μM) |
| 122 | 216Bk | AP-I-084 | 39 (5 μM) |
| 123 | 216Bl | AP-I-095 | 43 (5 μM) |
| 124 | 216Bm | AP-I-108 | 42 (5 μM) |
| 125 | 216Bn | AP-I-123 | 29 (5 μM) |
| 126 | 216Bo | AP-I-129 | 17 (5 μM) |
| 127 | 216Bp | AP-I-132 | 0 (5 μM) |
| 128 | 216Bq | AP-I-135 | 38 (5 μM) |
| 129 | 216Br | AP-I-136 | NA |
| 130 | 216Bs | AP-I-137 | NA |
| 131 | 216Bt | AP-I-140 | NA |
| 132 | 234a | HWI-550 | 12 |
| 133 | 234b | HWI-553 | 12 |
| 134 | 234c | HWI-554 | 39 |
| 135 | 203b | HWI-10 | 0 |
| 136 | 203c | HWI-15 | 0 |
| 137 | 203d | HWI-16 | 9 |
| 138 | 203l a | HWI-22 | 9 |
| 139 | 203f | HWI-25 | 60 |
| 140 | 203h | HWI-24 | 50 |
| 141 | 203i | HWI-27 | 43 |
| 142 | 203j | HWI-33 | 61 |
| 143 | 203k | HWI-35 | 59 |
| 144 | 234e | HWI-556 | 27 |
| 145 | 225a | HWI-574 | 63 |
| 146 | 225b | HWI-635 | NA |
| 147 | 225c | HWI-648 | NA |
| 148 | 225d | HWI-683 | 55 |
| 149 | 225e | HWI-684 | 49 |
| 150 | 225f | HWI-686 | 64 |
| 151 | 225g | HWI-692 | 44 |
| 152 | 225h | HWI-702 | 28 |
| 153 | 225i | HWI-719 | NA |
| 154 | 225j | HWI-720 | NA |
| 155 | 225k | HWI-722 | NA |
| 156 | 225l | HWI-741 | 37 |
| 157 | 225m | HWI-754 | 65 |
| 158 | 225n | HWI-764 | 0 |
| 159 | 225o | HWI-774 | 8 |
| 160 | 225p | HWI-775 | 0 |
| 161 | 225q | HWI-781 | 80 |
| 162 | 225r | HWI-782 | 10 |
| 163 | 225s | HWI-783 | 3 |
| 164 | 225t | HWI-786 | 9 |
| 165 | 225u | HWI-787 | 5 |
| 166 | 225v | HWI-788 | 3 |
| 167 | 225w | HWI-789 | 20 |
| 168 | 225x | HWI-796 | 24 |
| 169 | 225y | HWI-797 | 0 |
| 170 | 225z | HWI-798 | 0 |
| 171 | 225Aa | HWI-799 | 0 |
| 172 | 225Ab | HWI-863 | 94 (5 μM) |
| 173 | 225Ac | HWI-864 | 95 (5 μM) |
| 174 | 225Ad | HWI-873 | 69 (5 μM) |
| 175 | 225Ae | HWI-874 | 71 (5 μM) |
| 176 | 225Af | HWI-875 | 83 (5 μM) |
| 177 | 225Ag | HWI-879 | 81 (5 μM) |
| 178 | 225Ah | HWI-880 | 74 (5 μM) |
| 179 | 225Ai | HWI-883 | 46 (5 μM) |
| 180 | 225Aj | HWI-909 | NA |

NA = Not available

While the principles of this invention have been described in connection with specific embodiments, it should be understood clearly that these descriptions are added only by way of example and are not intended to limit, in any way, the scope of this invention. For instance, the present invention can be considered to include structural variations of the compounds described, such compound variations as would be understood by those skilled in the art made aware of this invention, such compounds available using synthetic techniques of the sort described herein or straightforward modifications thereof, as would also be understood by those skilled in the art made aware of this invention.

We claim:
1. A compound of a formula

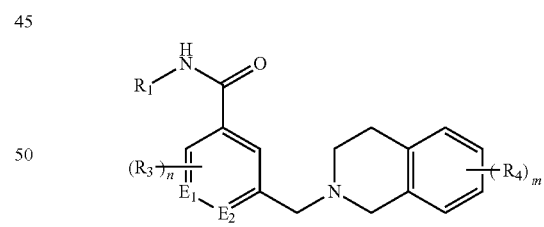

wherein $R_1$ is selected from phenyl, benzyl and heteroaryl moieties; each of $E_1$ and $E_2$ is independently selected from CH and N; and wherein each of $R_1$ and $R_2$ is optionally substituted with 1-5 substituents independently selected from but not limited to halo, cyano, nitro, hydroxy, amino, alkyl, cycloalkyl, cycloheteroalkyl, aryl, arylalkyl, alkoxy, alkenyl, haloalkyl, aminoalkyl, hydroxyalkyl, alkylsulfonyl, alkylsulfinyl, haloalkylsulfonyl, haloalkylsulfinyl, alkylamido, alkylsulfonamido, alkylthio, alkylcarbonyl, alkoxycarbonyl and combinations of such substituents; each of $R_3$ and $R_4$ is independently selected from said substituents and combinations thereof; and each of n and m is an integer independently selected from 0-4, providing where $R_1$ is a benzothiazolyl moiety, $E_1$ and $E_2$ are CH, n is 1 and m is 0, $R_3$ is not a phenyl substituent at $E_2$, and salts of said compounds.

2. The compound of claim 1 wherein m is 1-2.

3. The compound of claim 2 wherein $R_1$ is selected from phenyl and mono- and disubstituted phenyl moieties.

4. The compound of claim 3 wherein $E_2$ is CH, and $E_1$ is selected from CH and N.

5. The compound of claim 3 wherein n is 0.

* * * * *